US012788757B2

(12) United States Patent
Sahn et al.

(10) Patent No.: US 12,788,757 B2
(45) Date of Patent: Nov. 10, 2026

(54) SPIROCYCLIC PYRIDINE-1,5-DIONES EXHIBITING MNK INHIBITION AND THEIR METHOD OF USE

(71) Applicant: 4E Therapeutics, Inc., Austin, TX (US)

(72) Inventors: James J. Sahn, Austin, TX (US); Theodore J. Price, Austin, TX (US)

(73) Assignee: 4E Therapeutics, Inc., Austin, TX (US)

( * ) Notice: Subject to any disclaimer, the term of this patent is extended or adjusted under 35 U.S.C. 154(b) by 360 days.

(21) Appl. No.: 18/574,948

(22) PCT Filed: Jun. 30, 2022

(86) PCT No.: PCT/US2022/035703
§ 371 (c)(1),
(2) Date: Dec. 28, 2023

(87) PCT Pub. No.: WO2023/278686
PCT Pub. Date: Jan. 5, 2023

(65) Prior Publication Data
US 2025/0186436 A1 Jun. 12, 2025

Related U.S. Application Data

(60) Provisional application No. 63/217,264, filed on Jun. 30, 2021.

(51) Int. Cl.
*A61K 31/506* (2006.01)
*A61P 25/04* (2006.01)
(Continued)

(52) U.S. Cl.
CPC ............ *A61K 31/506* (2013.01); *A61P 25/04* (2018.01); *C07D 471/10* (2013.01); *C07D 471/20* (2013.01)

(58) Field of Classification Search
CPC ..... A61K 31/506; A61P 25/04; C07D 471/10; C07D 471/20
See application file for complete search history.

(56) References Cited

U.S. PATENT DOCUMENTS 8,153,803 B2 4/2012 Kazantsev
9,382,248 B2 7/2016 Reich et al.
(Continued)

FOREIGN PATENT DOCUMENTS

CN 101684098 A 3/2010
CN 102858782 A 1/2013
(Continued)

OTHER PUBLICATIONS

Megat et al., "Nociceptor Translational Profiling Reveals the Ragulator-Rag GTPase Complex as a Critical Generator of Neuropathic Pain," The Journal of Neuroscience, 2019, 39(3); 393-411.
(Continued)

*Primary Examiner* — Brandon J Fetterolf
(74) *Attorney, Agent, or Firm* — COOLEY LLP; John P. Rearick; Danielle Paglia

(57) ABSTRACT

Compounds having activity as inhibitors of MNK are provided, including compounds of Formula (I): or a pharmaceutically acceptable salt, stereoisomer, tautomer, or prodrug thereof, wherein $R^{1a}$, $R^{1b}$, $R^1$, $R^2$, $R^3$, $R^{4d}$, $R^{4c}$, $Z^1$, and n are as defined herein. Methods associated with preparation and use of such compounds, pharmaceutical compositions comprising such compounds and methods for treating neuropathic pain by modulating the activity of MNK are also provided.

(Continued)

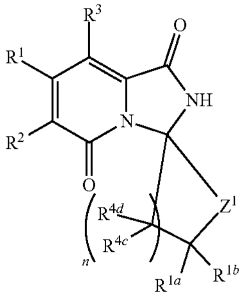

(I)

27 Claims, 15 Drawing Sheets

(51) Int. Cl.
*C07D 471/10* (2006.01)
*C07D 471/20* (2006.01)

(56) References Cited

U.S. PATENT DOCUMENTS

| | | | |
|---|---|---|---|
| 9,382,255 | B2 | 7/2016 | Klar et al. |
| 9,814,718 | B2 | 11/2017 | Reich et al. |
| 10,000,487 | B2 | 6/2018 | Sprengeler et al. |
| 11,083,727 | B2 | 8/2021 | Ernst et al. |
| 11,130,757 | B2 | 9/2021 | Reich et al. |
| 11,311,520 | B2 | 4/2022 | Klar et al. |
| 11,925,642 | B2 | 3/2024 | Dussor et al. |
| 2002/0111364 | A1 | 8/2002 | Campbell et al. |
| 2008/0039450 | A1 | 2/2008 | Jensen et al. |
| 2008/0085907 | A1 | 4/2008 | Guillemont et al. |
| 2009/0247526 | A1 | 10/2009 | Aicher et al. |
| 2015/0376181 | A1 | 12/2015 | Reich et al. |
| 2016/0303124 | A1 | 10/2016 | Webster et al. |
| 2017/0112832 | A1 | 4/2017 | Zanin-Zhorov et al. |
| 2017/0121339 | A1 | 5/2017 | Sprengeler et al. |
| 2017/0121346 | A1 | 5/2017 | Sprengeler et al. |
| 2017/0191136 | A1 | 7/2017 | Thompson et al. |
| 2018/0228803 | A1 | 8/2018 | Ernst et al. |
| 2018/0353545 | A1 | 12/2018 | Webster et al. |
| 2019/0100531 | A1 | 4/2019 | Zhang et al. |
| 2019/0209560 | A1 | 7/2019 | Reich et al. |
| 2019/0211020 | A1 | 7/2019 | Nacro et al. |
| 2019/0388425 | A1 | 12/2019 | Klar et al. |
| 2020/0131179 | A1 | 4/2020 | Reich et al. |
| 2020/0197400 | A1 | 6/2020 | Schneider et al. |
| 2020/0297696 | A1 | 9/2020 | Sverdrup et al. |
| 2021/0255170 | A1 | 8/2021 | Engelhardt et al. |
| 2022/0041602 | A1 | 2/2022 | Li |
| 2022/0110937 | A1 | 4/2022 | Dussor et al. |
| 2022/0193066 | A1 | 6/2022 | Wang et al. |
| 2022/0193067 | A1 | 6/2022 | Zhan et al. |
| 2022/0193204 | A1 | 6/2022 | Cruz et al. |
| 2022/0211693 | A1 | 7/2022 | Wang et al. |
| 2022/0226321 | A1 | 7/2022 | Price et al. |
| 2022/0289719 | A1 | 9/2022 | Kong et al. |
| 2022/0370463 | A1 | 11/2022 | Park-Min |
| 2022/0378821 | A1 | 12/2022 | Webster et al. |
| 2022/0401553 | A1 | 12/2022 | Paulsen et al. |
| 2023/0210902 | A1 | 7/2023 | Rezvani et al. |
| 2023/0286983 | A1 | 9/2023 | Price et al. |
| 2024/0092799 | A1 | 3/2024 | Mo et al. |
| 2025/0205244 | A1 | 6/2025 | Price et al. |

FOREIGN PATENT DOCUMENTS

| | | | | |
|---|---|---|---|---|
| CN | 103874496 | A | | 6/2014 |
| CN | 108495855 | A | | 9/2018 |
| CN | 110256432 | A | | 9/2019 |
| CN | 110563720 | A | | 12/2019 |
| CN | 111643503 | A | | 9/2020 |
| CN | 111840289 | A | | 10/2020 |
| CN | 111840585 | A | | 10/2020 |
| CN | 111956649 | A | | 11/2020 |
| CN | 111973747 | A | | 11/2020 |
| CN | 112043702 | A | | 12/2020 |
| CN | 112121048 | A | | 12/2020 |
| CN | 112294814 | A | | 2/2021 |
| CN | 113750096 | A | | 12/2021 |
| CN | 114469949 | A | | 5/2022 |
| CN | 114671869 | A | | 6/2022 |
| CN | 114736205 | A | | 7/2022 |
| CN | 114853756 | A | | 8/2022 |
| WO | WO-2013147711 | A1 | | 10/2013 |
| WO | WO-2014044691 | A1 | | 3/2014 |
| WO | WO-2015200481 | A1 | | 12/2015 |
| WO | WO-2016145383 | A1 | | 9/2016 |
| WO | WO-2017068064 | A1 | | 4/2017 |
| WO | WO-2017087808 | A1 | | 5/2017 |
| WO | WO-2017165908 | A1 | | 10/2017 |
| WO | WO-2018134148 | A1 | | 7/2018 |
| WO | WO-2018134335 | A1 | | 7/2018 |
| WO | WO-2018152117 | A1 | | 8/2018 |
| WO | WO2018218038 | A1 | * | 11/2018 |
| WO | WO-2020086713 | A1 | | 4/2020 |
| WO | WO-2020155842 | A1 | | 8/2020 |
| WO | WO-2020237167 | A1 | | 11/2020 |
| WO | WO-2020239123 | A1 | | 12/2020 |
| WO | WO-2021001743 | A1 | | 1/2021 |
| WO | WO-2021003192 | A1 | | 1/2021 |
| WO | WO-2021232050 | A1 | | 11/2021 |
| WO | WO-2021232066 | A1 | | 11/2021 |
| WO | WO-2022006331 | A2 | | 1/2022 |
| WO | WO-2022029334 | A1 | | 2/2022 |
| WO | WO-2022038563 | A1 | | 2/2022 |
| WO | WO-2022213076 | A1 | | 10/2022 |
| WO | WO-2022245977 | A2 | | 11/2022 |
| WO | WO-2022263673 | A1 | | 12/2022 |
| WO | WO-2023277594 | A1 | | 1/2023 |
| WO | WO-2023278686 | A1 | | 1/2023 |
| WO | WO-2023014943 | A1 | | 2/2023 |
| WO | WO-2023019093 | A2 | | 2/2023 |
| WO | WO-2023117768 | A1 | | 6/2023 |

OTHER PUBLICATIONS

Mihail et al., "MNK-eIF4E signalling is a highly conserved mechanism for sensory neuron axonal plasticity:evidence from Aplysia californica," Philos Trans R Soc Lond B Biol Sci. 2019;374(1785):20190289.

Moy et al., "The MNK-eIF4E Signaling Axis Contributes to Injury-Induced Nociceptive Plasticity and the Development of Chronic Pain," The Journal of Neuroscience, 2017, 37(31); 7481-7499.

PCT International Search Report and Written Opinion from PCT/US2021/039982, dated Dec. 23, 2021.

PCT International Search Report and Written Opinion from PCT/US2022/035703, dated Nov. 16, 2022.

PCT International Search Report and Written Opinion from PCT/US2022/039529, dated Dec. 28, 2022.

Pubchem CID 139317491 Create Date: Nov. 2, 2019 (Nov. 2, 2019) Date Accessed: Oct. 25, 2022 (Oct. 25, 2022); p. 2.

Pubchem—SID:440120553 Deposit Date; Feb. 17, 2021, 1-7.

Pubmed Compound Record for CID 118598717, 6-[(6-aminopyrimidin-4-yl)amino]-3-(3-fluorophenyl)-3,8-dimethyl-2H-imidazo[1,5-a]pyridine-1,5-dione, created Feb. 23, 2016, https://pubchem.ncbi.nlm.nih.gov/compound/118598717. Date Accessed: Jan. 17, 2024.

Pubmed Compound Record for CID 144985837, tert-butyl N-[6-[(8-methyl-1,5-dioxo-3,3-dipropyl-2H-imidazo[1,5-a]pyridin-6-yl)amino]pyrimidin-4-yl]carbamate, created Dec. 7, 2019, https://pubchem.ncbi.nlm.nih.gov/compound/144985837. Date Accessed: Jan. 17, 2024.

(56) References Cited

OTHER PUBLICATIONS

Reich et al., "Structure-based Design of Pyridone-Aminal eFT508 Targeting Dysregulated Translation by Selective Mitogen-activated Protein Kinase Interacting Kinases 1 and 2 (MNK1/2) Inhibition," J Med Chem. 2018;61(8):3516-3540.
Shiers et al. "Reversal of peripheral nerve injury-induced neuropathic pain and cognitive dysfunction via genetic and tomivosertib targeting of MNK," Neuropsychopharmacology (2020) 45:524-533.
Yousuf et al. "Pharmacological Manipulation of Translation as a Therapeutic Target for Chronic Pain," Pharmacol Rev 2021; 73: 59-88.
Biondi "Is Migraine a Neuropathic Pain Syndrome?" Current Pain And Headache Reports, (2006), 10(3):167-178, 12 pages.
Blackwood et al., "Escalated Oxycodone Self-Administration and Punishment: Differential Expression of Opioid Receptors and Immediate Early Genes in the Rat Dorsal Striatum and Prefrontal Cortex," Frontiers in Neuroscience, (Jan. 9, 2020), 13(1392):1-14, doi: 10.3389/fnins.2019.01392.
Blackwood et al., "Oxycodone Self-Administration Activates the Mitogen-Activated Protein Kinase/Mitogen- and Stress-Activated Protein Kinase (MAPK-MSK) Signaling Pathway in the Rat Dorsal Striatum," Scientific Reports, (2021), 11(2567):1-16, doi.org/10.1038/s41598-021-82206-3.
Caine et al., "Effects of Dopamine D-1 and D-2 Antagonists on Cocaine Self-Administration Under Different Schedules of Reinforcement in the Rat," Journal of Pharmacology and Experimental Therapeutics, (Mar. 29, 1994), 270(1):209-218.
CAS Registry No. 1849589-79-2, "Imidazo[1,5-a]pyridine-1,5-dione, 6-[(6-amino-4-pyrimidinyl)amino]-3-(3-chlorophenyl)-2,3-dihydro-3,8-dimethyl(," [chemical database, Chemical Abstracts Service, entered Jan. 20, 2016, 12 pages.
Fukui et al., "Significance of apoptosis induced by tumor necrosis factor-alpha and/or interferon-gamma against human gastric cancer cell lines and the role of the p53 gene," Surg Today, (Nov. 2003), 33(11):847-853.
Gopal et al., "A Phase 1-2 Dose-Escalation and Cohort- Expansion Study of eFT508, a Selective, Orally Bioavailable Inhibitor of MNK1 and MNK2, in Patients with Hematological Malignancies," Blood, (Dec. 8, 2017), 130(1):4624, 3 pages, doi.org/10.1182/blood.V130.Suppl_1.4624.4624.
Kimbrough et al., "Oxycodone Self-Administration and Withdrawal Behaviors in Male and Female Wistar Rats," Psychopharmacology (Berlin), (Epub Feb. 29, 2020), 237(5):1545-1555, doi.org/10.1007/s00213-020-05479-y.
Leite-Almeida et al., "The impact of age on emotional and cognitive behaviours triggered by experimental neuropathy in rats," Pain, (Jul. 2009), 144(1-2):57-65, doi:10.1016/j.pain.2009.02.024.
PCT Application No. PCT/US2021/039982, International Preliminary Report on Patentability mailed Jan. 12, 2023, Applicant 4E Therapeutics, Inc.. et al.; 8 pages.
PCT Application No. PCT/US2022/035703, International Preliminary Report on Patentability mailed Jan. 11, 2024, Applicant 4E Therapeutics, Inc.; 6 pages.
PCT Application No. PCT/US2022/039529, International Preliminary Report on Patentability mailed Feb. 15, 2024, A4E Therapeutics, Inc. et al.; 8 pages.
Valtcheva et al., "Surgical Extraction of Human Dorsal Root Ganglia From Organ Donors and Preparation of Primary Sensory Neuron Cultures," Nature Protocols, (Epub Sep. 8, 2016), 11(10):1877-1888, doi:10.1038/nprot.2016.111.
Wee et al., "Effects of Dose and Session Duration on Cocaine Self-Administration in Rats," Journal of Pharmacology and Experimental Therapeutics, (Dec. 2007), 320(3):1134-1143, doi:10.1124/jpet.106.113340.
Zorrilla et al., "Extended Access Cocaine Self-Administration Differentially Activates Dorsal Raphe and Amygdala Corticotropinreleasing Factor Systems in Rats," Addiction Biology, (2012), 17(2):300-308, doi:10.1111/j.1369-1600.2011.00329.x.

* cited by examiner

SPIROCYCLIC PYRIDINE-1,5-DIONES EXHIBITING MNK INHIBITION AND THEIR METHOD OF USE

CROSS REFERENCE TO RELATED APPLICATIONS

This application is a national stage filing under U.S.C. § 371 of PCT International Application No. PCT/US2022/035703, filed Jun. 30, 2022, which claims the benefit of U.S. Provisional Application No. 63/217,264 filed Jun. 30, 2021, the entirety of each of which is hereby incorporated by reference.

STATEMENT OF GOVERNMENT INTEREST

This invention was made with government support under grant No. 1U44NS115692-01 awarded by the National Institutes of Health. The government has certain rights in the invention.

TECHNICAL FIELD OF DISCLOSURE

The present disclosure describes compounds and methods useful as MNK inhibitors, useful for the treatment of neuropathic pain, Lupus, viral infection-induced pain, Covid19 related acute respiratory distress syndrome (ARDS), nonalcoholic fatty liver disease (NAFLD), high fat diet induced obesity, Alzheimer's disease, Fragile X syndrome and related conditions.

The present disclosure further describes a novel chemotype useful for the treatment of other disease types and other diseases that involve aberrant MNK activity.

BACKGROUND

Inadequate treatment of pain is a devastating health problem in the United States. One third of all Americans suffer from some form of chronic pain and a third of these have pain that is resistant to current medical therapies. The economic impact of pain is equally large at approximately $100 billion annually. Opioid or narcotic analgesics, typified by morphine, are the most effective treatments for acute and chronic severe pain. However, their clinical utility is often hampered by the development of analgesic tolerance which requires escalating doses to achieve equivalent pain relief. Furthermore, these drugs are often ineffective for neuropathic pain treatment. This complex pathophysiological cycle represents a critical barrier to the quality of life of these patients due to the resulting drug-induced sedation, reduced physical activity, constipation, respiratory depression, high potential for addiction, and other side effects.

Neuropathic pain typically develops over time and may benefit from therapies that interfere with pathways involved in its development and/or continuation.

Disease or damage causing neuropathic pain may affect the central nervous system (CNS), the peripheral nervous system, or both (as opposed to causes of nociceptive pain, which affect the peripheral nervous system only). Common causes of neuropathic pain include spinal cord injury, multiple sclerosis, central nervous system ischemia, spinal nerve disease, diabetes, other metabolic disorders, herpes zoster infection, HIV-related neuropathies, nutritional deficiencies, toxins, remote manifestations of malignancies, immune mediated disorders, physical trauma to a nerve trunk such as during surgery, peripheral ischemia, peripheral nerve lesions, nerve compression, chemotherapy or other drug-induced nerve damage, radiation injury, arthritis, autoimmune disease, and infection in an area near the affected nerves.

Neuropathic pain often involves abnormal nociceptor sensitivity. Nociceptors are specialized neurons that detect pain. Nociceptor sensitivity is not fixed; it can change over time. Some causes of neuropathic pain affect nociceptor sensitivity by inducing "peripheral sensitization." Peripheral sensitization includes spontaneous pathological activity, abnormal excitability, heightened sensitivity to chemical, stimuli, heightened sensitivity to thermal stimuli, heightened sensitivity to mechanical stimuli, and any combinations of these.

Disruption of peripheral sensitization, either by reducing or preventing such peripheral sensitization in the first place or by reducing the degree of already-developed peripheral sensitization, may therefore treat neuropathic pain. Although the disclosure is not limited to one mechanism of action, MNK inhibitors as disclosed herein may disrupt peripheral sensitization.

MNKs phosphorylate the eukaryotic translation initiation factor 4E (eIF4E) and factors that bind to AU-rich elements in the 3-untranslated region of certain messenger RNAs (mRNAs). MNKs are a subfamily of Ser/Thr kinases, phylogenetically considered $Ca^{2+}$/calmodulin-dependent kinases (CaMKs). MNKs are activated through phosphorylation by the growth factor-stimulated Ras/extracellular signal-regulated kinase pathway and the stress-induced p38 pathway.

Nociceptor sensitization may be blocked by inhibiting activity-dependent mRNA translation through mechanistic targeting of the mitogen-activated protein kinase (MAPK) pathway. The MAPK pathway signal to the eukaryotic translation initiation factor (eIF) 4F complex to regulate the sensitization of nociceptors. See, e.g., WO2020237167. There remains a need to further develop effective therapeutics for treating neuropathic pain.

BRIEF SUMMARY

The present disclosure is directed to small molecule MNK inhibitors, including peripherally-restricted MNK inhibitors, that may interrupt the MAPK pathway, thereby decreasing sensitization of nociceptors and achieving a therapeutic effect on neuropathic pain. One embodiment thus provides a compound of Formula (I'):

Formula (I')

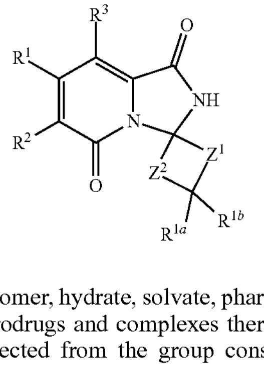

or a stereoisomer, hydrate, solvate, pharmaceutically acceptable salt, prodrugs and complexes thereof, wherein:

$R^1$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, cyano, $C_{1-6}$ alkoxyl, $C_{3-7}$ branched alkoxy, hydroxy, and $C_{3-6}$ cycloalkyl that is optionally substituted with 1 to 3 substituents selected from the groups consisting of halogen, $C_{1-6}$ alkyl, $C_{1-6}$ haloalkyl, and $C_{1-6}$ hydroxyalkyl:

$R^2$ is selected from the group consisting of

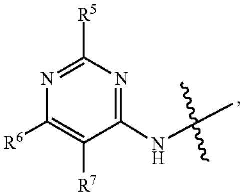,
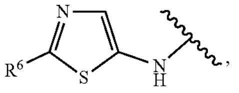,
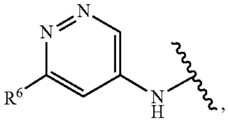,
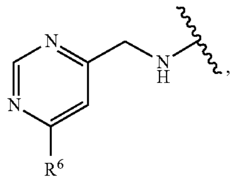,
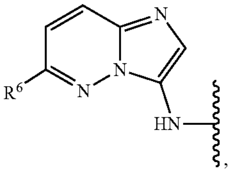,
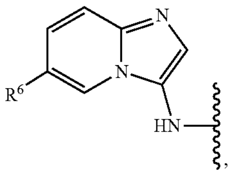,
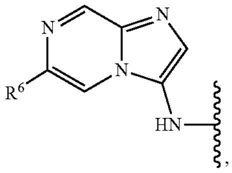,
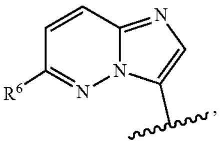,
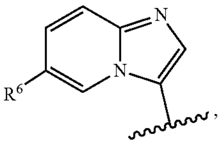,
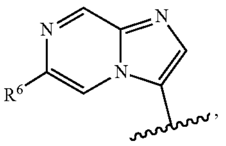,
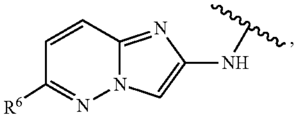,
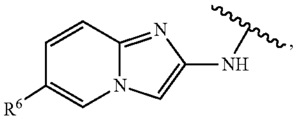,
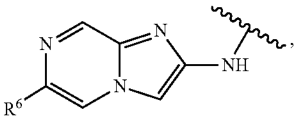,
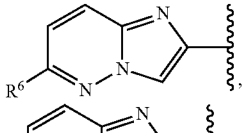,
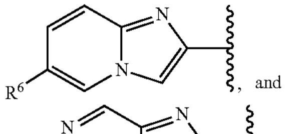, and
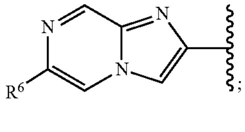;

$R^3$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, cyano, $C_{1-6}$ alkoxyl, $C_{3-7}$ branched alkoxy, hydroxy, and $C_{3-6}$ cycloakyl that is optionally substituted with 1 to 3 substituents selected from the groups consisting of halogen, $C_{1-6}$ alkyl, $C_{1-6}$ haloalkyl, and $C_{1-6}$ hydroxyalkyl;

$R^{1a}$ and $R^{1b}$ are taken together to form a 3- to 7-membered ring having 0-2 heteroatoms selected from the group consisting of N, O and S, wherein the 3- to 7-membered ring may be further optionally substituted with one or more substituents selected from the group consisting of halo, oxo, $C_{1-6}$ alkyl, $R^8$, and —C(═O)OR$^9$;

$Z^1$ and $Z^2$ are each independently a direct bond or —{C($R^{4a}$)($R^{4b}$)}$_p$—Y—; wherein p is 0, 1, 2, 3, 4, or 5, Y is a direct bond, —O—, or —N(R)—

$R^{4a}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, hydroxy, $C_{1-6}$ alkoxyl, $C_{3-7}$ branched alkoxy, NHCO($C_{1-6}$alkyl), NHCO($C_{3-7}$ branched alkyl), NHCO($C_{3-7}$ cycloalkyl), $NHSO_2$($C_{1-6}$alkyl), $NHSO_2$($C_{3-7}$ branched alkyl), and $NHSO_2$($C_{3-7}$ cycloalkyl); or two $R^{4a}$ attached to two adjacent carbons to form a direct bond;

$R^{4b}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, hydroxy, $C_{1-6}$ alkoxyl, $C_{3-7}$ branched alkoxy, NHCO($C_{1-6}$alkyl), NHCO($C_{3-7}$ branched alkyl), NHCO($C_{3-7}$ cycloalkyl), $NHSO_2$($C_{1-6}$alkyl), $NHSO_2$($C_{3-7}$ branched alkyl), and $NHSO_2$($C_{3-7}$ cycloalkyl); $R^5$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ alkoxyl, $C_{3-7}$ branched alkoxy, and hydroxy: $R^6$ is selected from the group consisting of hydrogen, $NH_2$, NHR$^{6a}$, $NHCH_2CH_2OH$, $NHCH_2CH_2NHSO_2Me$, $C_{1-6}$ alkoxyl, $C_{3-7}$ branched alkoxy, and hydroxy; $R^{6a}$ is selected from the group consisting of —(CO)$C_{1-6}$ alkyl, —(CO)$C_{3-7}$ branched alkyl, —(CO)$C_{1-6}$ hydroxyalkyl,

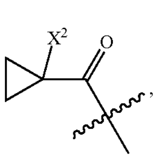,
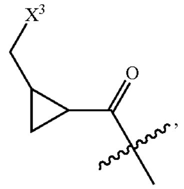,
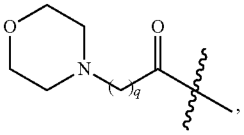,
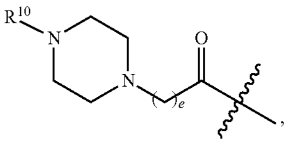,
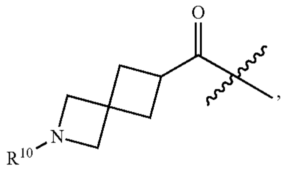,
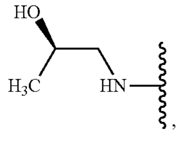,

-continued

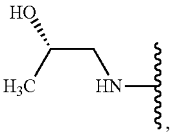
,
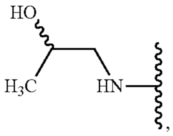
,

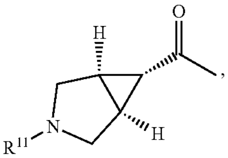
, and
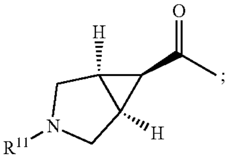
;

q is 1, 2, 3, 4, 5, or 6;

e is 1, 2, 3, 4, 5, or 6;

$X^2$ is selected from the group consisting of hydrogen, halogen, $C_{1-6}$alkyl, $C_{3-7}$ branched alkyl, $C_{1-6}$haloalkyl, $C_{3-7}$ branched haloalkyl, hydroxy, $C_{1-6}$hydroxyalkyl, $C_{3-7}$ branched hydroxyalkyl, $C_{1-6}$alkoxy, $C_{3-7}$ branched alkoxy, $C_{1-6}$haloalkoxy, $C_{3-7}$ branched haloalkoxy, $NH_2$, $NH(C_{1-6}alkyl)$, $N(C_{1-6}alkyl)_2$, $C_{1-5}(COOH)$, $C_{1-6}(NHSO_2Me)$; $X^3$ is selected from the group consisting of hydrogen, halogen, $C_{1-5}$ alkyl, $C_{3-7}$ branched alkyl, $C_{1-5}$ haloalkyl, $C_{3-7}$ branched haloalkyl, hydroxy, $C_{1-5}$ hydroxyalkyl, $C_{3-7}$ branched hydroxyalkyl, $C_{1-5}$ alkoxy, $C_{3-7}$ branched alkoxy, $C_{1-5}$ haloalkoxy, $C_{3-7}$ branched haloalkoxy, $NH_2$, $NH(C_{1-6}$ alkyl), $N(C_{1-6}$ alkyl$)_2$, COOH, $C_{1-5}(COOH)$, $NHSO_2Me$, $C_{1-5}(NHSO_2Me)$;

$R^7$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ alkoxyl, $C_{3-7}$ branched alkoxy, and hydroxyl; $R^8$ is selected from the group consisting of $C_{1-6}$ alkyl, $C_{1-6}$ haloalkyl, $C_{3-7}$ branched haloalkyl, $C_{1-6}$ hydroxyalkyl, $C_{3-7}$ branched hydroxyalkyl, $C_{1-6}$ alkoxyl, $C_{3-7}$ branched alkoxy, $CO(C_{1-6}$alkyl), $CO(C_{3-7}$ branched alkyl), $SO_2(C_{1-6}$alkyl), and $SO_2(C_{3-7}$ branched alkyl); $R^9$ is selected from the group consisting of hydrogen, $C_{1-6}$ alkyl, and aralkyl.

In more specific embodiments, the MNK inhibitors are novel pyridine-1,5-diones of formula (I), (I)

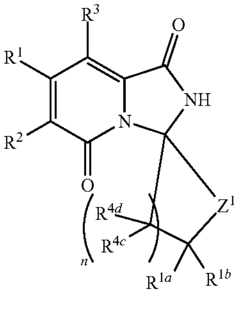

Including hydrates, solvates, pharmaceutically acceptable salts, prodrugs and complexes thereof, wherein:

$Z^1$ is selected from the groups consisting of

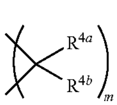
and
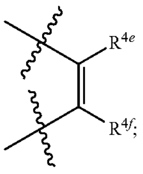
;

$R^1$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, cyano, $C_{1-6}$ alkoxyl, $C_{3-7}$ branched alkoxy, hydroxy, and $C_{3-6}$ cycloalkyl that is optionally substituted with 1 to 3 substituents selected from the groups consisting of halogen, $C_{1-6}$ alkyl, $C_{1-6}$ haloalkyl, and $C_{1-6}$ hydroxyalkyl;

$R^2$ is selected from the group consisting of

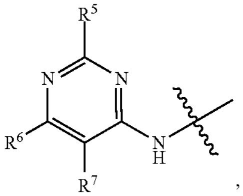
,
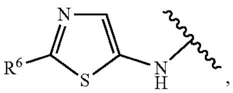
,
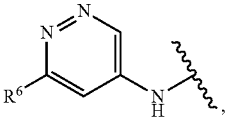
,
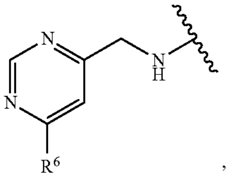
,
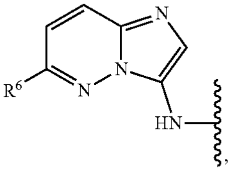
,
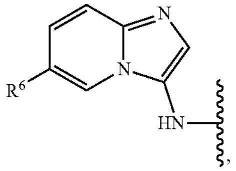
,
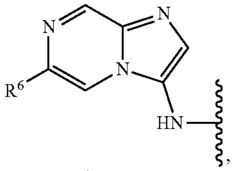
,
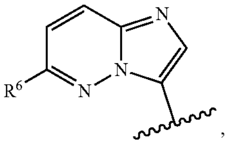
,
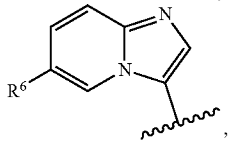
,
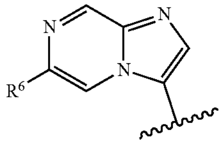
,
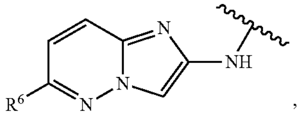
,
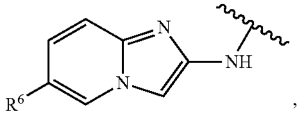
,
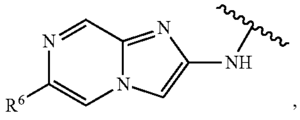
,
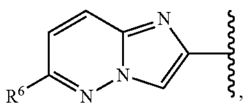
, -continued

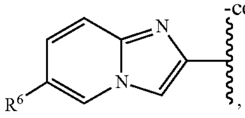

, and

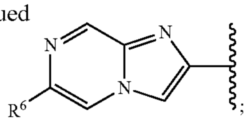

;

$R^3$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, cyano, $C_{1-6}$ alkoxyl, $C_{3-7}$ branched alkoxy, hydroxy, and $C_{3-6}$ cycloakyl that is optionally substituted with 1 to 3 substituents selected from the groups consisting of halogen, $C_{1-6}$ alkyl, $C_{1-6}$ haloalkyl, and $C_{1-6}$ hydroxyalkyl;

$R^{4a}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHCO(C_{3-7}$ cycloalkyl), $NHSO_2(C_{1-6}alkyl)$, $NHSO_2(C_{3-7}$ branched alkyl), and $NHSO_2(C_{3-7}$ cycloalkyl);

$R^{4b}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHCO(C_{3-7}$ cycloalkyl), $NHSO_2(C_{1-6}alkyl)$, $NHSO_2(C_{3-7}$ branched alkyl), and $NHSO_2(C_{3-7}$ cycloalkyl)

$R^{4c}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHCO(C_{3-7}$ cycloalkyl), $NHSO_2(C_{1-6}alkyl)$, $NHSO_2(C_{3-7}$ branched alkyl), and $NHSO_2(C_{3-7}$ cycloalkyl)

$R^{4d}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHCO(C_{3-7}$ cycloalkyl), $NHSO_2(C_{1-6}alkyl)$, $NHSO_2(C_{3-7}$ branched alkyl), and $NHSO_2(C_{3-7}$ cycloalkyl);

$R^{4e}$ is hydrogen, halogen, $C_{1-6}$ alkyl, $C_{3-7}$ branched alkyl, $C_{1-6}$ haloalkyl, and $C_{3-7}$ branched haloalkyl;

$R^{4f}$ is hydrogen, halogen, $C_{1-6}$ alkyl, $C_{3-7}$ branched alkyl, $C_{1-6}$ haloalkyl, and $C_{3-7}$ branched haloalkyl;

$R^{1a}$ and $R^{1b}$ are taken together to form an optionally substituted 3 to 7 membered ring that optionally contains an $X^1$ group;

$X^1$ is selected from the group consisting of $CF_2$, $CHCO_2R^{12}$, O, NH, NR, and $SO_2$;

m is 0, 1, or 2;

n is 1, 2, or 3;

$R^5$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ alkoxyl, $C_{3-7}$ branched alkoxy, and hydroxy; $R^6$ is selected from the group consisting of hydrogen, $NH_2$, $NHR^{6a}$, $NHCH_2CH_2OH$, $NHCH_2CH_2NHSO_2Me$, $C_{1-6}$ alkoxyl, $C_{3-7}$ branched alkoxy, and hydroxy;

$R^{6a}$ is selected from the group consisting of —(CO)$C_{1-6}$ alkyl, —(CO)$C_{3-7}$ branched alkyl, —(CO)$C_{1-6}$ hydroxyalkyl,

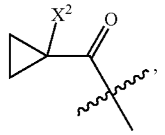

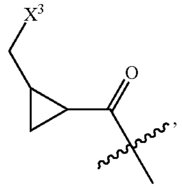

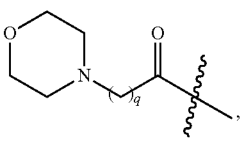

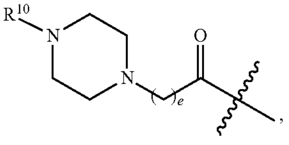

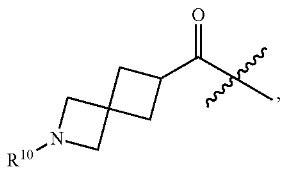

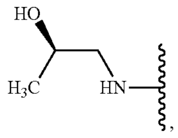

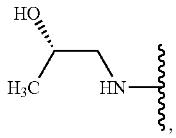

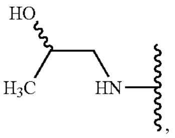

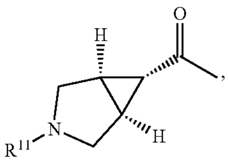

, and

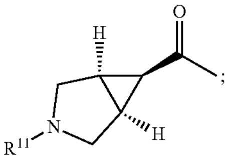

;

q is 1, 2, 3, 4, 5, or 6;

e is 1, 2, 3, 4, 5, or 6;

$X^2$ is selected from the group consisting of hydrogen, halogen, $C_{1-6}alkyl$, $C_{3-7}$ branched alkyl, $C_{1-6}haloalkyl$, $C_{3-7}$ branched haloalkyl, hydroxy, $C_{1-6}hydroxyalkyl$, $C_{3-7}$ branched hydroxyalkyl, $C_{1-6}alkoxy$, $C_{3-7}$ branched alkoxy, $C_{1-6}haloalkoxy$, $C_{3-7}$ branched haloalkoxy, $NH_2$, $NH(C_{1-6}alkyl)$, $N(C_{1-6}alkyl)_2$, $C_{1-5}(COOH)$, $C_{1-6}(NHSO_2Me)$;

$X^3$ is selected from the group consisting of hydrogen, halogen, $C_{1-5}$ alkyl, $C_{3-7}$ branched alkyl, $C_{1-5}$ haloalkyl, $C_{3-7}$ branched haloalkyl, hydroxy, $C_{1-5}$ hydroxyalkyl, $C_{3-7}$ branched hydroxyalkyl, $C_{1-5}$ alkoxy, $C_{3-7}$ branched alkoxy, $C_{1-5}$ haloalkoxy, $C_{3-7}$ branched haloalkoxy, $NH_2$, $NH(C_{1-6}$ alkyl), $N(C_{1-6}$ alkyl$)_2$, COOH, $C_{1-5}(COOH)$, $NHSO_2Me$, $C_{1-5}(NHSO_2Me)$; $R^7$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ alkoxyl, $C_{3-7}$ branched alkoxy, and hydroxy; $R^8$ is selected from the group consisting of $C_{1-6}$ alkyl, $C_{1-6}$ haloalkyl, $C_{3-7}$ branched haloalkyl, $C_{1-6}$ hydroxyalkyl, $C_{3-7}$ branched hydroxyalkyl, $C_{1-6}$ alkoxyl, $C_{3-7}$ branched alkoxy, $CO(C_{1-6}alkyl)$, $CO(C_{3-7}$ branched alkyl), $SO_2(C_{1-6}alkyl)$, and $SO_2(C_{3-7}$ branched alkyl);

$R^{10}$ is selected from the group consisting of hydrogen, $C_{1-6}$ alkyl, $C_{1-6}$ haloalkyl, $C_{3-7}$ branched haloalkyl, $C_{1-6}$ hydroxyalkyl, $C_{1-6}$ alkoxyl, $C_{3-7}$ branched alkoxy, $CO(C_{1-6}alkyl)$, $CO(C_{3-7}$ branched alkyl), $SO_2(C_{1-6}alkyl)$, and $SO_2(C_{3-7}$ branched alkyl);

$R^{11}$ is selected from the group consisting of hydrogen and $C_{1-6}$ alkyl;

$R^{12}$ is selected from the group consisting of hydrogen and $C_{1-6}$ alkyl.

The present disclosure further relates to pharmaceutical compositions comprising: a pharmaceutically acceptable excipient and an effective amount of one or more compounds according to the present invention, including Formula (I'), (I) or any one of the substructures.

The present disclosure also relates to a method for treating or preventing diseases that involve aberrant MNK activity, including, for example, neuropathic pain, Lupus, viral infection-induced pain, Covid19 related acute respiratory distress syndrome (ARDS), nonalcoholic fatty liver disease (NAFLD), high fat diet induced obesity, Alzheimer's disease, Fragile X syndrome, said method comprising administering to a subject an effective amount of a compound or composition according to the present disclosure.

The present disclosure yet further relates to a method for treating or preventing diseases that involve aberrant MNK activity, including, for example, neuropathic pain, Lupus, viral infection-induced pain, Covid19 related acute respiratory distress syndrome (ARDS), nonalcoholic fatty liver disease (NAFLD), high fat diet induced obesity, Alzhiemer's disease, and Fragile X syndrome, wherein said method comprises administering to a subject a composition comprising a pharmaceutically acceptable excipient and an effective amount of one or more compounds according to the present disclosure.

The present disclosure also relates to a method for treating or preventing disease or conditions associated with neuropathic pain, Lupus, viral infection-induced pain, Covid19 related acute respiratory distress syndrome (ARDS), nonalcoholic fatty liver disease (NAFLD), high fat diet induced obesity, Alzheimer's disease, Fragile X syndrome, and diseases that involve aberrant MNK activity. Said methods comprise administering to a subject an effective amount of a compound or composition according to the present disclosure.

The present disclosure yet further relates to a method for treating or preventing disease or conditions associated with neuropathic pain, Lupus, viral infection-induced pain, Covid19 related acute respiratory distress syndrome (ARDS), nonalcoholic fatty liver disease (NAFLD), high fat diet induced obesity, Alzhiemer's disease, Fragile X syndrome, and diseases that involve aberrant MNK activity, wherein said method comprises administering to a subject a composition comprising a pharmaceutically acceptable excipient and an effective amount of one or more compounds according to the present disclosure.

The present disclosure also relates to a method for treating or preventing disease or conditions associated with aberrant MNK activity. Said methods comprise administering to a subject an effective amount of a compound or composition according to the present disclosure.

The present disclosure yet further relates to a method for treating or preventing disease or conditions associated with aberrant MNK activity, wherein said method comprises administering to a subject a composition comprising an effective amount of one or more compounds according to the present disclosure and an excipient.

The present disclosure further relates to a process for preparing the MNK inhibitors of the present disclosure.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present disclosure.

DETAILED DESCRIPTION OF THE DISCLOSURE

Figure 1:
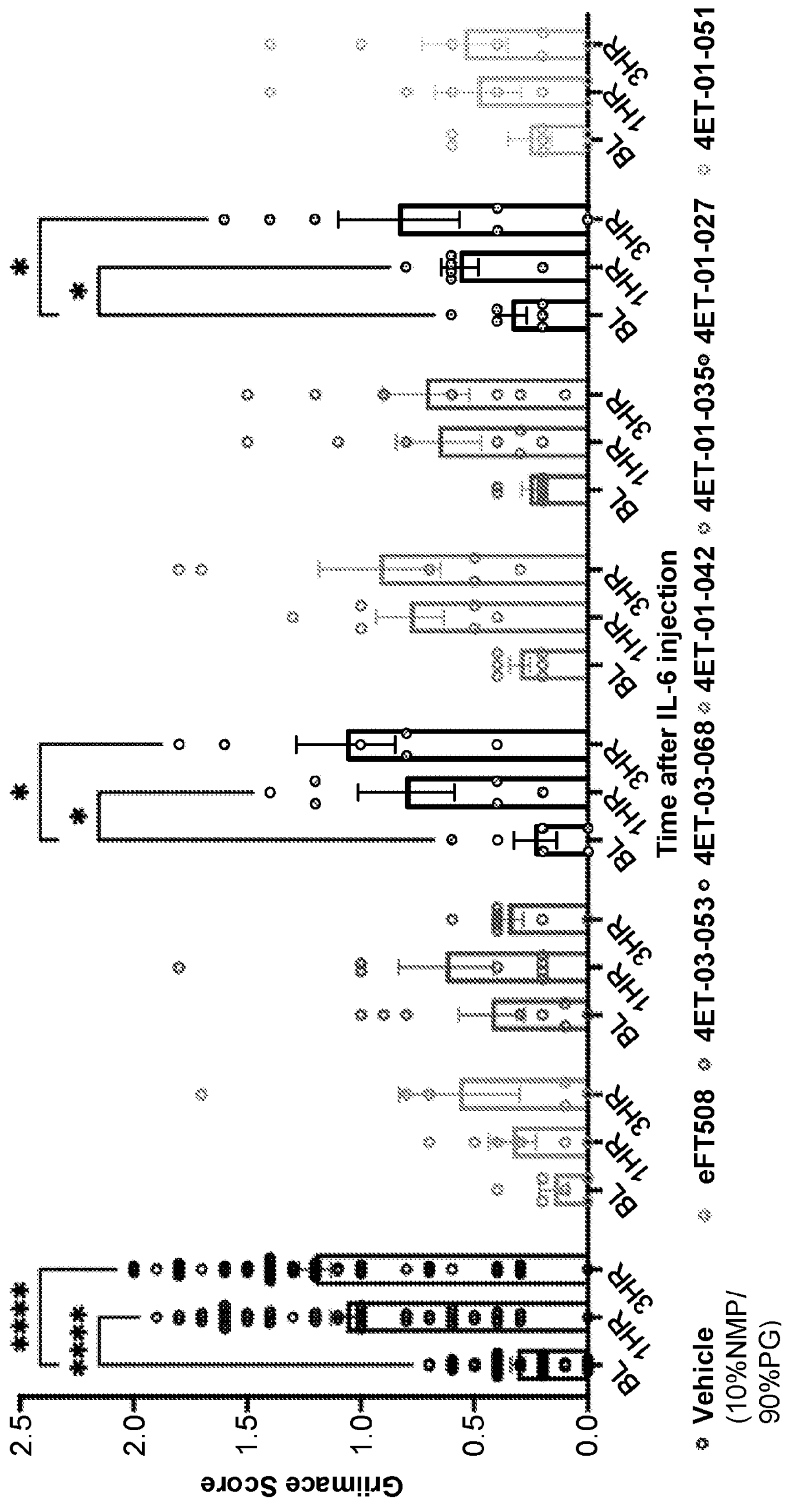
FIG. 1 shows evaluation of compounds in the IL-6 evoked grimace test.

The spirocyclic pyridine-1,5-diones of the present disclosure are capable of treating and preventing diseases associated with aberrant MNK activity, for example, neuropathic pain, Lupus, viral infection-induced pain, Covid19 related acute respiratory distress syndrome (ARDS), nonalcoholic fatty liver disease (NAFLD), high fat diet induced obesity, Alzheimer's disease, Fragile X syndrome. It has been discovered that MNK plays a key role in pain signaling. As a result, MNK is a potential drug target for the treatment of pain related disorders including neuropathic pain, as well as Lupus, viral infection-induced pain, COVID19 related acute respiratory distress syndrome (ARDS), nonalcoholic fatty liver disease (NAFLD), high fat diet induced obesity, Alzheimer's disease, Fragile X syndrome.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

Definitions

As used herein the term "MNK" shall mean mitogen-activated protein (MAP) kinases (MAPK) interacting kinases.

As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example, 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, isobutyl, tert-butyl, and the like. Alkyl groups can be optionally substituted.

Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}$ alkyl$)_2$amino, the alkyl groups may be the same or different.

As used herein, unless otherwise noted, "hydroxyalkyl" whether used alone or as part of a substituent group refers to straight and branched carbon chains having 1 to 20 carbon atoms or any number within this range, for example, 1 to 6 carbon atoms or 1 to 4 carbon atoms that also contains a hydroxyl substituent. Designated numbers of carbon atoms (e.g. $C_{1-6}$) shall refer independently to the number of carbon atoms in an alkyl moiety or to the alkyl portion of a larger alkyl-containing substituent. Non-limiting examples of hydroxyalkyl groups include hydroxymethyl, hydroxyethyl, hydroxy-n-propyl, hydroxy-iso-propyl, hydroxy-n-butyl, hydroxy-sec-butyl, hydroxy-iso-butyl and the like. Hydroxyalkyl groups can be optionally substituted. In substituent groups with multiple alkyl groups such as $(C_{2-6}$hydroxyalkyl$)_2$amino, the hydroxyalkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., $-CF_3$, $-CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group-alkyl-aryl, where the alkyl and aryl groups are as defined herein. Aralkyl groups of the present disclosure are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d] thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and R taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present disclosure fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

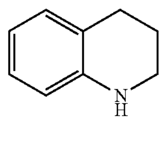

is, for the purposes of the present disclosure, considered a heterocyclic unit. 6,7-Dihydro-5H-cyclopentapyrimidine having the formula:

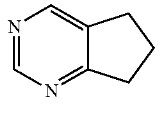

is, for the purposes of the present disclosure, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

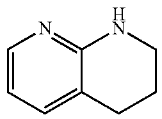

is, for the purposes of the present disclosure, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —$NO_2$, oxo (═O), —$OR^X$, —$SR^X$, —$N(R^X)_2$, —$NR^XC(O)R^X$, —$SO_2R^X$, —$SO_2OR^X$, —$SO_2N(R^X)_2$, —$C(O)R^X$, —$C(O)OR^X$, —$C(O)N(RW)_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —$NO_2$, oxo, and $R^X$; wherein $R^X$, at each occurrence, independently is hydrogen, —$OR^{x+1}$, —$SR^{x+1}$, —$C(O)R^{x+1}$, —$C(O)OR^{x+1}$, —$C(O)N(R^{x+1})_2$, —$SO_2R^{x+1}$, —$S(O)_2OR^{x+1}$, —$N(R^{x+1})_2$, —$NR^{x+1}C(O)R^{x+1}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^x$ units taken together with the atom(s) to which they are bound form an optionally substituted carbocycle or heterocycle wherein said carbocycle or heterocycle has 3 to 7 ring atoms; wherein $R^{X+1}$, at each occurrence, independently is hydrogen, $C_{1-6}$ alkyl, $C_{1-6}$ haloalkyl, $C_2$— alkenyl, $C_{2-8}$ alkynyl, cycloalkyl (e.g., $C_{3-6}$ cycloalkyl), aryl, heterocycle, or heteroaryl, or two $R^{x+1}$ units taken together with the atom(s) to which they are bound form an optionally substituted carbocycle or heterocycle wherein said carbocycle or heterocycle preferably has 3 to 7 ring atoms.

In some embodiments, the substituents are selected from i) —$OR^{x+2}$; for example, —OH, —$OCH_3$, —$OCH_2CH_3$, —$OCH_2CH_2CH_3$;
ii) —$C(O)R^{x+2}$; for example, —$COCH_3$, —$COCH_2CH_3$, —$COCH_2CH_2CH_3$;
iii) —$C(O)OR^{x+2}$; for example, —$CO_2CH_3$, —$CO_2CH_2CH_3$, —$CO_2CH_2CH_2CH_3$;
iv) —$C(O)N(R^{x+2})_2$; for example, —$CONH_2$, —$CONHCH_3$, —$CON(CH_3)_2$;
v) —$N(R^{x+2})_2$; for example, —$NH_2$, —$NHCH_3$, —$N(CH_3)_2$, —$NH(CH_2CH_3)$;
vi) halogen, —F, —Cl, —Br, and —I;
vii) —$CH_eX_g$; wherein X is halogen, m is from 0 to 2, e+g=3; for example, —$CH_2F$, —$CHF_2$, —$CF_3$, —$CCl_3$, or —$CBr_3$;
viii) —$SO_2R^{x+2}$; for example, —$SO_2H$; —$SO_2CH_3$; —$SO_2C_6H_5$;
ix) $C_1$-$C_6$ linear, branched, or cyclic alkyl;
x) Cyano
xi) Nitro;
xii) $N(R^{x+2})C(O)R^{x+2}$;
xiii) Oxo (═O);
xiv) Heterocycle; and
xv) Heteroaryl.

wherein each $R^{x+2}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two $R^{x+2}$ units can be taken together to form a ring comprising 3-7 ring atoms. In certain aspects, each $R^{x+2}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present disclosure the terms "compound," "analog," and "composition of matter" stand equally well for the MNK inhibitors described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example, sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^{x+1})_2$, each $R^{x+1}$ may be the same or different than the other). Combinations of substituents and/or variables are permissible only if such combinations result in stable compounds, The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the disclosure can be administered. In an exemplary embodiment of the present disclosure, to identify subject patients for treatment according to the methods of the disclosure, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present disclosure.

In some embodiments, "patient" or "Subject" refers to an animal including mammals (e.g., a human). The methods described herein can be useful in both human therapeutics and veterinary applications. In some embodiments, the subject is a mammal, and in some embodiments, the subject is human. Other subjects include mammals that do not tolerate opioids well or that are common pets or domesticated animals, such as dogs, cats, and horses.

The MNK Inhibitors

The MNK inhibitors of the present disclosure are pyridine-1,5-diones having the formula (I'):

Formula (I')

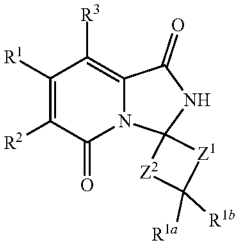

or a stereoisomer, hydrate, solvate, pharmaceutically acceptable salt, prodrugs and complexes thereof, wherein:

$R^1$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, cyano, $C_{1-6}$ alkoxyl, $C_{3-7}$ branched alkoxy, hydroxy, and $C_{3-6}$ cycloalkyl that is optionally substituted with 1 to 3 substituents selected from the groups consisting of halogen, $C_{1-6}$ alkyl, $C_{1-6}$ haloalkyl, and $C_{1-6}$ hydroxyalkyl; $R^2$ is selected from the group consisting of

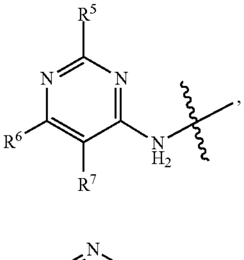
,
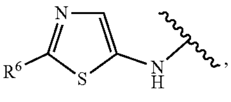
,
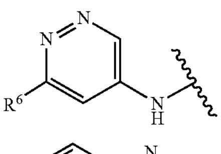
,
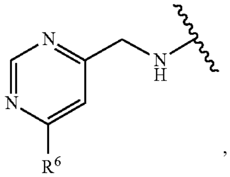
,
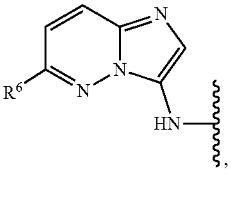
,
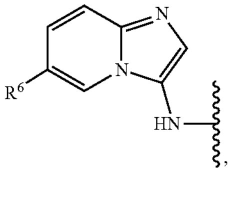
,

-continued

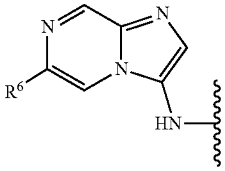,
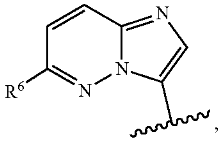,
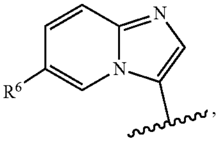,
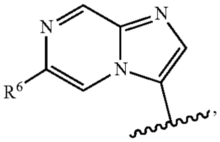,
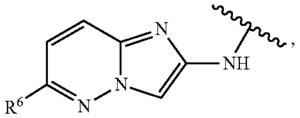,
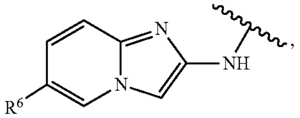,
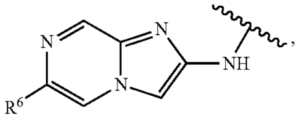,
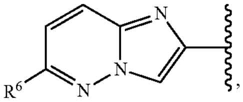,
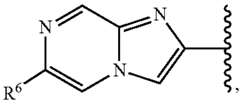, and
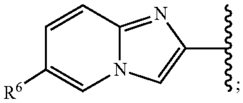;

$R^3$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, cyano, $C_{1-6}$ alkoxyl, $C_{3-7}$ branched alkoxy, hydroxy, and $C_{3-6}$ cycloakyl that is optionally substituted with 1 to 3 substituents selected from the groups consisting of halogen, $C_{1-6}$ alkyl, $C_{1-6}$ haloalkyl, and $C_{1-6}$ hydroxyalkyl;

$R^{1a}$ and $R^{1b}$ are taken together to form a 3- to 7-membered ring having 0-2 heteroatoms selected from the group consisting of N, O and S, wherein the 3- to 7-membered ring may be further optionally substituted with one or more substituents selected from the group consisting of halo, oxo, $C_{1-6}$ alkyl, $R^8$, and —C(═O)OR$^9$;

$Z^1$ and $Z^2$ are each independently a direct bond or —{C($R^{4a}$)($R^{4b}$)}$_p$—Y—; wherein p is 0, 1, 2, 3, 4, or 5, Y is a direct bond, —O—, or —N(R)—

$R^{4a}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, hydroxy, $C_{1-6}$ alkoxyl, $C_{3-7}$ branched alkoxy, NHCO($C_{1-6}$alkyl), NHCO($C_{3-7}$ branched alkyl), NHCO($C_{3-7}$ cycloalkyl), $NHSO_2$($C_{1-6}$alkyl), $NHSO_2$($C_{3-7}$ branched alkyl), and $NHSO_2$($C_{3-7}$ cycloalkyl); or two $R^{4a}$ attached to two adjacent carbons to form a direct bond;

$R^{4b}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, hydroxy, $C_{1-6}$ alkoxyl, $C_{3-7}$ branched alkoxy, NHCO($C_{1-6}$alkyl), NHCO($C_{3-7}$ branched alkyl), NHCO($C_{3-7}$ cycloalkyl), $NHSO_2$($C_{1-6}$alkyl), $NHSO_2$($C_{3-7}$ branched alkyl), and $NHSO_2$($C_{3-7}$ cycloalkyl); $R^5$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ alkoxyl, $C_{3-7}$ branched alkoxy, and hydroxy; $R^6$ is selected from the group consisting of hydrogen, $NH_2$, NHR$^{6a}$, $NHCH_2CH_2OH$, $NHCH_2CH_2NHSO_2Me$, $C_{1-6}$ alkoxyl, $C_{3-7}$ branched alkoxy, and hydroxy;

$R^{6a}$ is selected from the group consisting of —(CO)$C_{1-6}$ alkyl, —(CO)$C_{3-7}$ branched alkyl, —(CO)$C_{1-6}$ hydroxyalkyl,

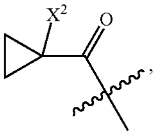,
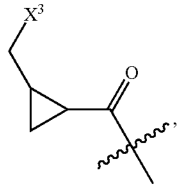,
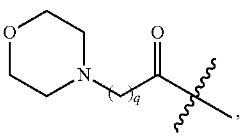,
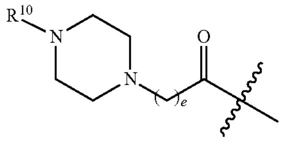,
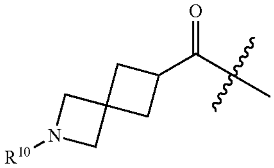,
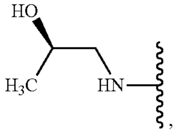,
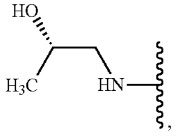,
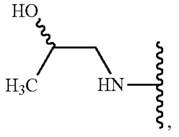,
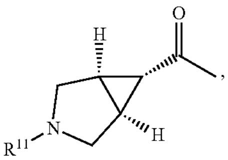, and
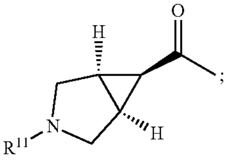;

q is 1, 2, 3, 4, 5, or 6;

e is 1, 2, 3, 4, 5, or 6;

$X^2$ is selected from the group consisting of hydrogen, halogen, $C_{1-6}$alkyl, $C_{3-7}$ branched alkyl, $C_{1-6}$haloalkyl, $C_{3-7}$ branched haloalkyl, hydroxy, $C_{1-6}$hydroxyalkyl, $C_{3-7}$ branched hydroxyalkyl, $C_{1-6}$alkoxy, $C_{3-7}$ branched alkoxy, $C_{1-6}$haloalkoxy, $C_{3-7}$ branched haloalkoxy, $NH_2$, NH($C_{1-6}$alkyl), N($C_{1-6}$alkyl)$_2$, $C_{1-5}$(COOH), $C_{1-6}$($NHSO_2Me$);

$X^3$ is selected from the group consisting of hydrogen, halogen, $C_{1-5}$ alkyl, $C_{3-7}$ branched alkyl, $C_{1-5}$ haloalkyl, $C_{3-7}$ branched haloalkyl, hydroxy, $C_{1-5}$ hydroxyalkyl, $C_{3-7}$ branched hydroxyalkyl, $C_{1-5}$ alkoxy, $C_{3-7}$ branched alkoxy, $C_{1-5}$ haloalkoxy, $C_{3-7}$ branched haloalkoxy, $NH_2$, NH($C_{1-6}$ alkyl), N($C_{1-6}$ alkyl)$_2$, COOH, $C_{1-5}$(COOH), $NHSO_2Me$, $C_{1-5}$($NHSO_2Me$); $R^7$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ alkoxyl, $C_{3-7}$ branched alkoxy, and hydroxyl; $R^8$ is selected from the group consisting of $C_{1-6}$ alkyl, $C_{1-6}$ haloalkyl, $C_{3-7}$ branched haloalkyl, $C_{1-6}$ hydroxyalkyl, $C_{3-7}$ branched hydroxyalkyl, $C_{1-6}$ alkoxyl, $C_{3-7}$ branched alkoxy, $CO(C_{1-6}alkyl)$, $CO(C_{3-7}$ branched alkyl), $SO_2(C_{1-6}alkyl)$, and $SO_2(C_{3-7}$ branched alkyl);

$R^9$ is selected from the group consisting of hydrogen, $C_{1-6}$ alkyl, and aralkyl.

In more specific embodiments, the compound exhibiting MNK inhibition has the following structure, represented by Formula (I):

(I)

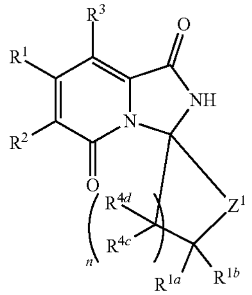

hydrates, solvates, pharmaceutically acceptable salts, prodrugs, isotopic isomers, and complexes thereof, wherein:

$Z^1$ is selected from the groups consisting of

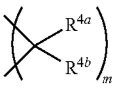 and 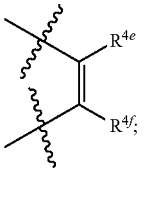

$R^1$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, cyano, $C_{1-6}$ alkoxyl, $C_{3-7}$ branched alkoxy, hydroxy, and $C_{3-6}$ cycloalkyl that is optionally substituted with 1 to 3 substituents selected from the groups consisting of halogen, $C_{1-6}$ alkyl, $C_{1-6}$ haloalkyl, and $C_{1-6}$ hydroxyalkyl;

$R^2$ is selected from the group consisting of

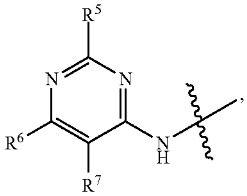
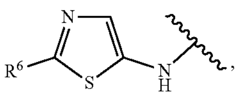
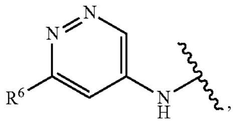
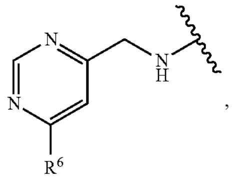

-continued

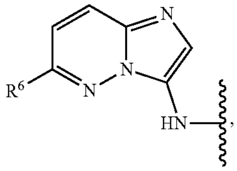
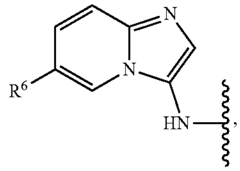
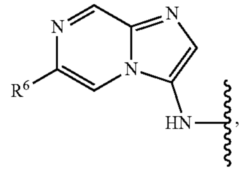
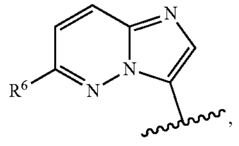
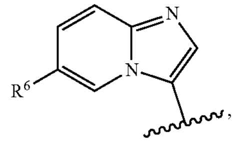
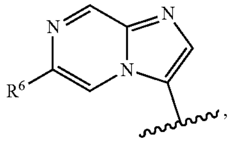
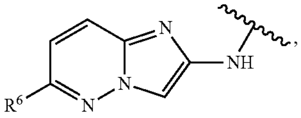
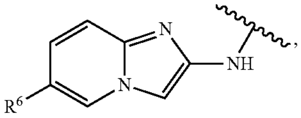
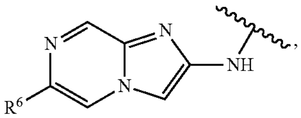
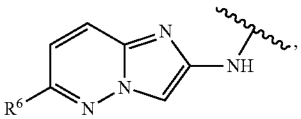
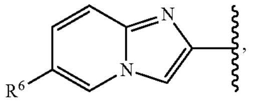 and
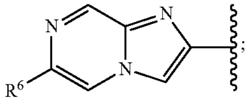

$R^3$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, cyano, $C_{1-6}$ alkoxyl, $C_{3-7}$ branched alkoxy, hydroxy, and $C_{3-6}$ cycloakyl that is optionally substituted with 1 to 3 substituents selected from the groups consisting of halogen, $C_{1-6}$ alkyl, $C_{1-6}$ haloalkyl, and $C_{1-6}$ hydroxyalkyl;

$R^{4a}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHCO(C_{3-7}$ cycloalkyl), $NHSO_2(C_{1-6}alkyl)$, $NHSO_2(C_{3-7}$ branched alkyl), and $NHSO_2(C_{3-7}$ cycloalkyl); $R^{4b}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHCO(C_{3-7}$ cycloalkyl), $NHSO_2(C_{1-6}alkyl)$, $NHSO_2(C_{3-7}$ branched alkyl), and $NHSO_2(C_{3-7}$ cycloalkyl);

$R^{4c}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), NHCO($C_{3-7}$ cycloalkyl), $NHSO_2$($C_{1-6}$alkyl), $NHSO_2$($C_{3-7}$ branched alkyl), and $NHSO_2$($C_{3-7}$ cycloalkyl);

$R^{4d}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), NHCO($C_{3-7}$ cycloalkyl), $NHSO_2$($C_{1-6}$alkyl), $NHSO_2$($C_{3-7}$ branched alkyl), and $NHSO_2$($C_{3-7}$cycloalkyl);

$R^{4e}$ is hydrogen, halogen, $C_{1-6}$ alkyl, $C_{3-7}$ branched alkyl, $C_{1-6}$ haloalkyl, and $C_{3-7}$ branched haloalkyl;

$R^{4f}$ is hydrogen, halogen, $C_{1-6}$ alkyl, $C_{3-7}$ branched alkyl, $C_{1-6}$ haloalkyl, and $C_{3-7}$ branched haloalkyl;

$R^{1a}$ and $R^{1b}$ are taken together to form an optionally substituted 3 to 7 membered ring that optionally contains an $X^1$ group forming a part of the ring;

$X^1$ is selected from the group consisting of —C(F)$_2$—, —CH($CO_2R^{12}$)—, —O—, —NH—, —N(R)—, and —S(=O)$_2$—;

m is 0, 1, or 2;

n is 1, 2, or 3;

$R^5$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ alkoxyl, $C_{3-7}$ branched alkoxy, and hydroxy;

$R^6$ is selected from the group consisting of hydrogen, $NH_2$, $NHR^{6a}$, $NHCH_2CH_2OH$, $NHCH_2CH_2NHSO_2Me$, $C_{1-6}$ alkyl, $C_{3-7}$ branched alkyl, $C_{1-6}$ alkoxyl, $C_{3-7}$ branched alkoxy, and hydroxy;

$R^{6a}$ is selected from the group consisting of —(CO)$C_{1-6}$ alkyl, —(CO)$C_{3-7}$ branched alkyl, —(CO)$C_{1-6}$ hydroxyalkyl,

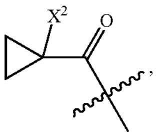
,
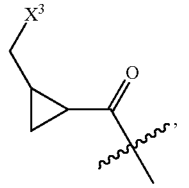
,
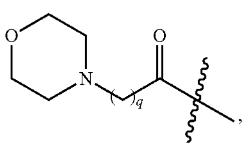
,
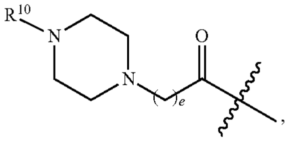
,
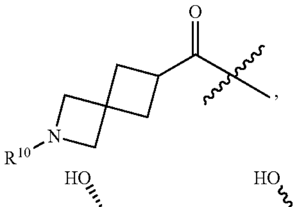
,
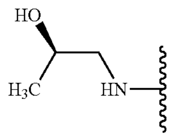

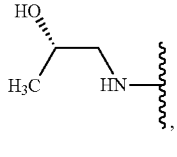
,
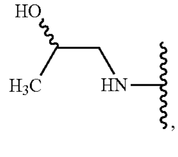
,

-continued

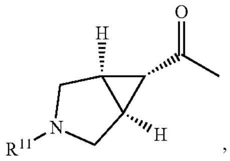
, and
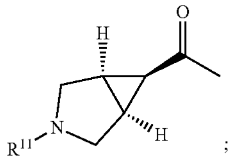
;

q is 1, 2, 3, 4, 5, or 6;

e is 1, 2, 3, 4, 5, or 6;

$X^2$ is selected from the group consisting of hydrogen, halogen, $C_{1-6}$alkyl, $C_{3-7}$ branched alkyl, $C_{1-6}$haloalkyl, $C_{3-7}$ branched haloalkyl, hydroxy, $C_{1-6}$hydroxyalkyl, $C_{3-7}$ branched hydroxyalkyl, $C_{1-6}$alkoxy, $C_{3-7}$ branched alkoxy, $C_{1-6}$haloalkoxy, $C_{3-7}$ branched haloalkoxy, $NH_2$, NH($C_{1-6}$alkyl), N($C_{1-6}$alkyl)$_2$, $C_{1-5}$(COOH), $C_{1-6}$($NHSO_2Me$);

$X^3$ is selected from the group consisting of hydrogen, halogen, $C_{1-5}$ alkyl, $C_{3-7}$ branched alkyl, $C_{1-5}$ haloalkyl, $C_{3-7}$ branched haloalkyl, hydroxy, $C_{1-5}$ hydroxyalkyl, $C_{3-7}$ branched hydroxyalkyl, $C_{1-5}$ alkoxy, $C_{3-7}$ branched alkoxy. $C_{1-5}$ haloalkoxy, $C_{3-7}$ branched haloalkoxy. $NH_2$, NH($C_{1-6}$ alkyl), N($C_{1-6}$ alkyl)$_2$, COOH, $C_{1-5}$(COOH), $NHSO_2Me$, $C_{1-5}$($NHSO_2Me$);

$R^7$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ alkoxyl, $C_{3-7}$ branched alkoxy, and hydroxy;

$R^8$ is selected from the group consisting of $C_{1-6}$ alkyl, $C_{1-6}$ haloalkyl, $C_{3-7}$ branched haloalkyl, $C_{1-6}$ hydroxyalkyl, $C_{3-7}$ branched hydroxyalkyl, $C_{1-6}$ alkoxyl, $C_{3-7}$ branched alkoxy, CO($C_{1-6}$alkyl), CO($C_{3-7}$ branched alkyl), $SO_2$($C_{1-6}$alkyl), and $SO_2$($C_{3-7}$ branched alkyl);

$R^{10}$ is selected from the group consisting of hydrogen. $C_{1-6}$ alkyl, $C_{1-6}$ haloalkyl, $C_{3-7}$ branched haloalkyl, $C_{1-6}$ hydroxyalkyl, $C_{1-6}$ alkoxyl, $C_{3-7}$ branched alkoxy, CO($C_{1-6}$alkyl), CO($C_{3-7}$ branched alkyl), $SO_2$($C_{1-6}$alkyl), and $SO_2$($C_{3-7}$branched alkyl).

$R^{11}$ is selected from the group consisting of hydrogen and $C_{1-6}$ alkyl;

$R^{12}$ is selected from the group consisting of hydrogen and $C_{1-6}$ alkyl.

In more specific embodiments, the compounds of the present disclosure include compounds having formula (II):

(II)

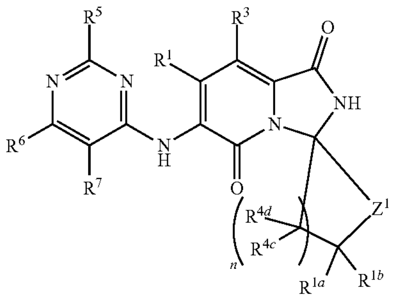

hydrates, solvates, pharmaceutically acceptable salts, prodrugs, isotopic isomers, or complexes thereof. $R^1$, $R^{1b}$, $R^1$, $R^3$, $R^{4d}$, $R^{4c}$, n, $Z^1$, R, $R^6$ and $R^7$ are as defined herein.

In more specific embodiments, the compounds of the present disclosure include compounds having formula (III):

(III)

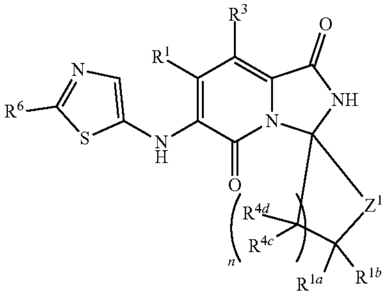

hydrates, solvates, pharmaceutically acceptable salts, prodrugs, isotopic isomers, or complexes thereof. $R^{1a}$, $R^{1b}$, $R^1$, $R^3$, $R^{4d}$, $R^{4c}$, n, $Z^1$, and $R^6$ are as defined herein.

In more specific embodiments, the compounds of the present disclosure include compounds having formula (IV):

(IV)

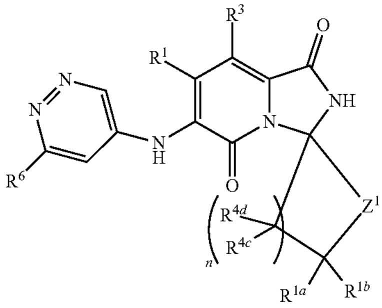

hydrates, solvates, pharmaceutically acceptable salts, prodrugs, isotopic isomers, or complexes thereof. $R^{1a}$, $R^{1b}$, $R^1$, $R^3$, $R^{4d}$, $R^{4c}$, n, $Z^1$, and $R^6$ are as defined herein.

In more specific embodiments, the compounds of the present disclosure include compounds having formula (V):

(V)

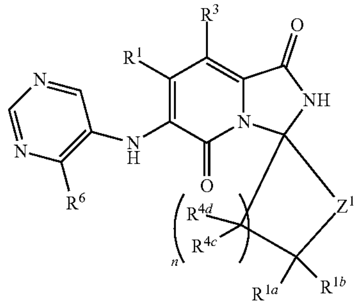

hydrates, solvates, pharmaceutically acceptable salts, prodrugs, isotopic isomers, or complexes thereof. $R^{1a}$, $R^{1b}$, $R^1$, $R^3$, $R^{4d}$, $R^{4c}$, n, $Z^1$, and $R^6$ are as defined herein.

In more specific embodiments, the compounds of the present disclosure include compounds having formula (VI):

(VI)

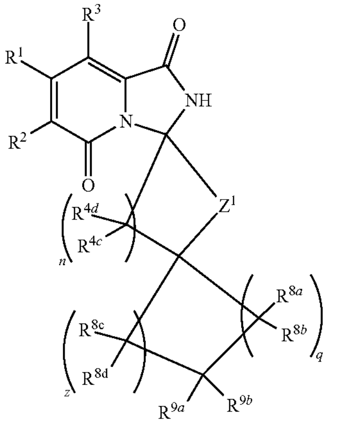

hydrates, solvates, pharmaceutically acceptable salts, prodrugs, isotopic isomers, or complexes thereof, wherein $R^1$, $R^2$, $R^3$, $R^{4d}$, $R^{4c}$, n, and $Z^1$ are as defined herein;

$R^{8a}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{8b}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{8c}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{8d}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{9a}$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, and $C_{3-7}$ branched alkoxy;

$R^{9b}$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, and $C_{3-7}$ branched alkoxy;

$R^{9a}$ and $R^{9b}$ are taken together to form an optionally substituted 3 to 7-membered ring;

q is 1, 2, or 3; and z is 0, 1, or 2.

In more specific embodiments, the compounds of the present disclosure include compounds having formula (VII):

(VII)

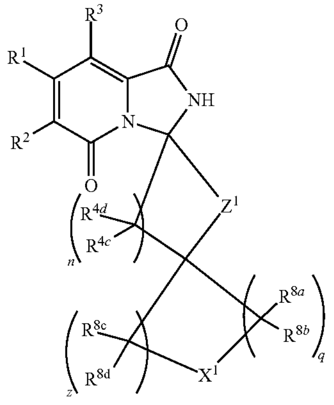

hydrates, solvates, pharmaceutically acceptable salts, prodrugs, isotopic isomers, or complexes thereof, wherein $R^1$, $R^2$, $R^3$, $R^{4d}$, $R^{4c}$, $Z^1$, $X^1$ and n are as defined herein;

$R^{8a}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{8b}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{8c}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{8d}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

q is 1, 2, or 3; and z is 0, 1, or 2.

In more specific embodiments, the compounds of the present disclosure include compounds having formula (VIII):

(VIII)

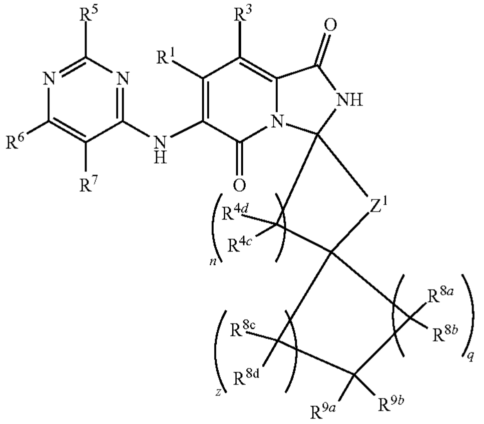

hydrates, solvates, pharmaceutically acceptable salts, prodrugs, isotopic isomers, or complexes thereof, wherein $R^1$, $R^3$, $R^{4d}$, $R^{4c}$, $Z^1$, $R^5$, $R^6$, $R^7$, and n are as defined herein;

$R^{8a}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{8b}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{8c}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{8d}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{9a}$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{9b}$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHSO_2(C_{1-6}alkyl)$, and $NHSO_2(C_{3-7}$ branched alkyl);

q is 1, 2, or 3; and z is 0, 1, or 2.

In more specific embodiments, the compounds of the present disclosure include compounds having formula (IX):

(IX)

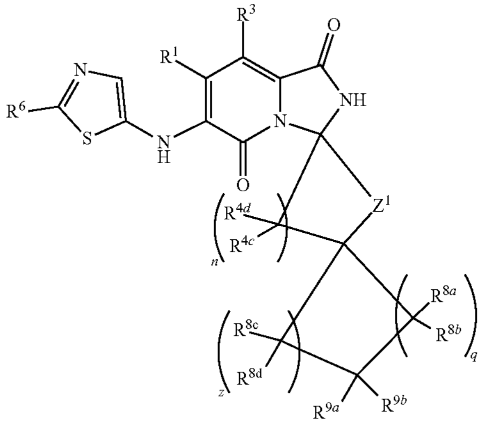

hydrates, solvates, pharmaceutically acceptable salts, prodrugs, isotopic isomers, and complexes thereof. $R^1$, $R^3$, $R^{4d}$, $R^{4c}$, $Z^1$, $R^6$, $R^{8a}$, $R^{8b}$, $R^{8c}$, $R^{8d}$, n and z are as defined herein.

In more specific embodiments, the compounds of the present disclosure include compounds having formula (X):

(X)

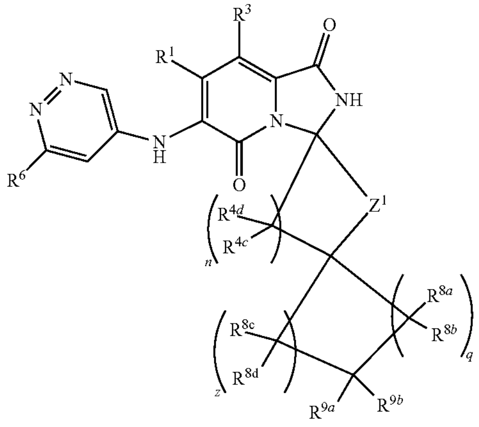

hydrates, solvates, pharmaceutically acceptable salts, prodrugs, isotopic isomers, or complexes thereof. $R^1$, $R^3$, $R^{4d}$, $R^{4c}$, $Z^1$, $R^6$, $R^{8a}$, $R^{8b}$, $R^{8c}$, $R^{8d}$, $R^{9a}$, $R^{9b}$, n and z are as defined herein.

In more specific embodiments, the compounds of the present disclosure include compounds having formula (XI):

(XI)

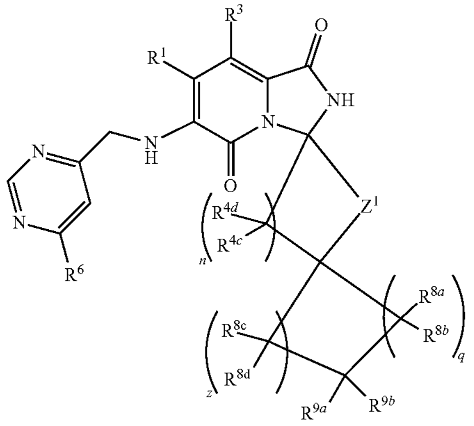

hydrates, solvates, pharmaceutically acceptable salts, prodrugs, isotopic isomers, and complexes thereof. $R^1$, $R^3$, $R^{4d}$, $R^{4c}$, $Z^1$, $R^6$, $R^{8a}$, $R^{8b}$, $R^{8c}$, $R^{8d}$, $R^{9a}$, $R^{9b}$, n and z are as defined herein.

In more specific embodiments, the compounds of the present disclosure include compounds having formula (XII):

(XII)

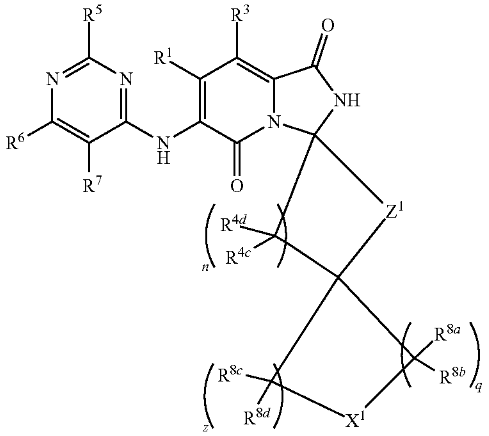

hydrates, solvates, pharmaceutically acceptable salts, prodrugs, isotopic isomers, or complexes thereof, wherein $R^1$, $R^3$, $R^{4d}$, $R^{4c}$, $Z^1$, $R^1$, $R^6$, $R^7$, $X^1$, and n are as defined herein;

$R^{8a}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHSO_2(C_{1-6}alkyl)$, and $NHSO_2(C_{3-7}$ branched alkyl);

$R^{8b}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHSO_2(C_{1-6}alkyl)$, and $NHSO_2(C_{3-7}$ branched alkyl);

$R^{8c}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branched alkyl), $NHSO_2$($C_{1-6}$alkyl), and $NHSO_2$($C_{3-7}$ branched alkyl);

$R^{8d}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, NHCO($C_{1-6}$alkyl), NHCO($C_{3-7}$ branchalkyl), $NHSO_2$($C_{1-6}$alkyl), and $NHSO_2$($C_{3-7}$ branched alkyl);

q is 1, 2, or 3; and z is 0, 1, or 2.

In more specific embodiments, the compounds of the present disclosure include compounds having formula (XIII):

(XIII)

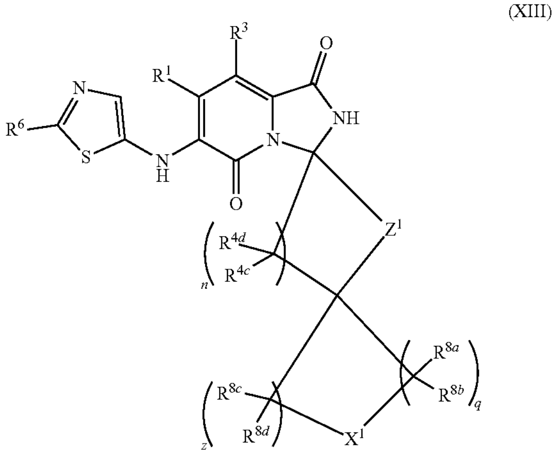

hydrates, solvates, pharmaceutically acceptable salts, prodrugs, isotopic isomers, or complexes thereof. $R^1$, $R^3$, $R^{4d}$, $R^{4c}$, $Z^1$, $R^6$, $R^{8a}$, $R^{8b}$, $R^{8c}$, $R^{8a}$, $X^1$, n and z are as defined herein.

In more specific embodiments, the compounds of the present disclosure include compounds having formula (XIV):

(XIV)

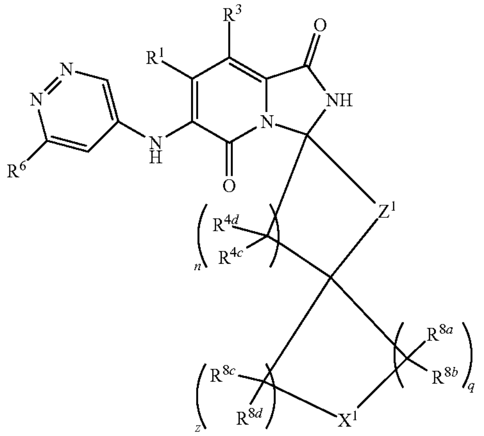

hydrates, solvates, pharmaceutically acceptable salts, prodrugs, isotopic isomers, or complexes thereof. $R^1$, $R^3$, $R^{4d}$, $R^{4c}$, $Z^1$, $R^6$, $R^{8a}$, $R^{8b}$, $R^{8c}$, $R^{8a}$, $X^1$, n and z are as defined herein.

In more specific embodiments, the compounds of the present disclosure include compounds having formula (XV):

(XV)

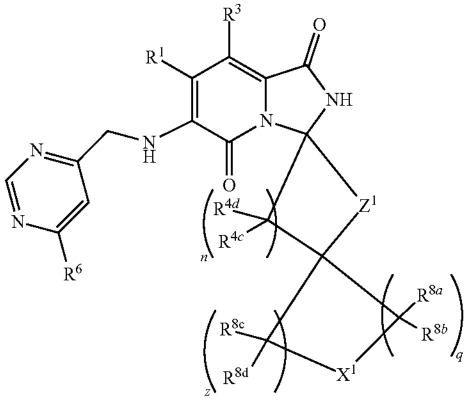

hydrates, solvates, pharmaceutically acceptable salts, prodrugs, isotopic isomers, or complexes thereof. $R^1$, $R^3$, $R^{4d}$, $R^{4c}$, $Z^1$, $R^6$, $R^{8a}$, $R^{8b}$, $R^{8c}$, $R^{8d}$, $X^1$, n and z are as defined herein.

In more specific embodiments, the compounds of the present disclosure include compounds having formula (XVI):

(XVI)

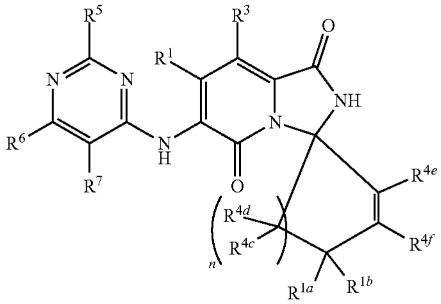

hydrates, solvates, pharmaceutically acceptable salts, prodrugs, isotopic isomers, or complexes thereof. $R^{1a}$, $R^{1b}$, $R^1$, $R^3$, $R^{4d}$, $R^{4c}$, $R^{4e}$, $R^{4f}$, $R^5$, $R^6$, $R^7$ and n are as defined herein.

The compounds of the present disclosure include compounds having formula (XV):

(XV)

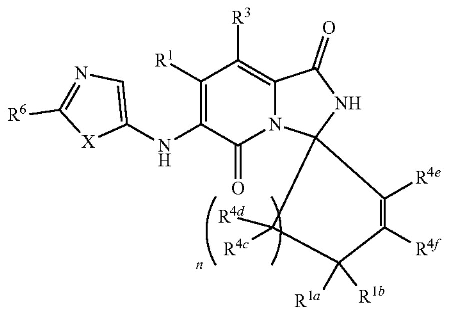

hydrates, solvates, pharmaceutically acceptable salts, prodrugs, isotopic isomers, or complexes thereof. $R^1$, $R^{1b}$, $R^1$, $R^3$, $R^{4d}$, $R^{4c}$, $R^{4e}$, $R^{4f}$, $R^6$, and n are as defined herein.

In more specific embodiments, the compounds of the present disclosure include compounds having formula (XVI):

(XVI)

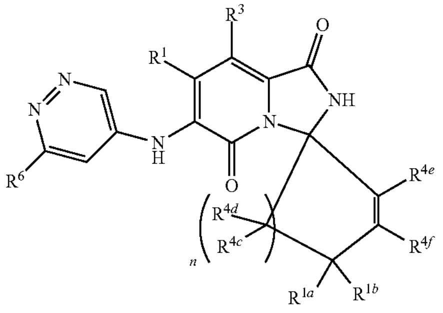

hydrates, solvates, pharmaceutically acceptable salts, prodrugs, isotopic isomers, or complexes thereof. $R^{1a}$, $R^{1b}$, $R^1$, $R^3$, $R^{4d}$, $R^{4c}$, $R^{4e}$, $R^{4f}$, $R^6$, and n are as defined herein.

In more specific embodiments, the compounds of the present disclosure include compounds having formula (XVII):

(XVII)

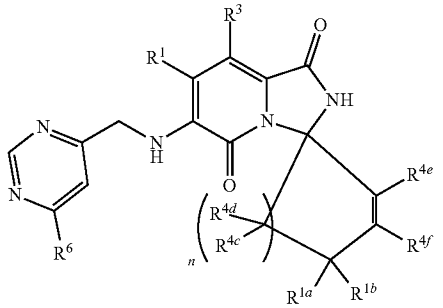

hydrates, solvates, pharmaceutically acceptable salts, prodrugs, isotopic isomers, or complexes thereof. $R^{1a}$, $R^{1b}$, $R^1$, $R^3$, $R^{4d}$, $R^{4c}$, $R^{4e}$, $R^{4f}$, $R^6$, and n are as defined herein.

In more specific embodiments, the compounds of the present disclosure include compounds having formula (XVIII):

(XVIII)

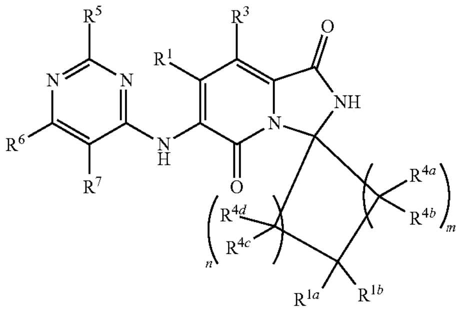

hydrates, solvates, pharmaceutically acceptable salts, prodrugs, isotopic isomers, or complexes thereof. $R^{1a}$, $R^{1b}$, $R^1$, $R^3$, $R^{4d}$, $R^{4b}$, $R^{4a}$, $R^{4c}$, $R^5$, $R^6$, $R^7$, m and n are as defined herein.

In more specific embodiments, the compounds of the present disclosure include compounds having formula (XIX):

(XIX)

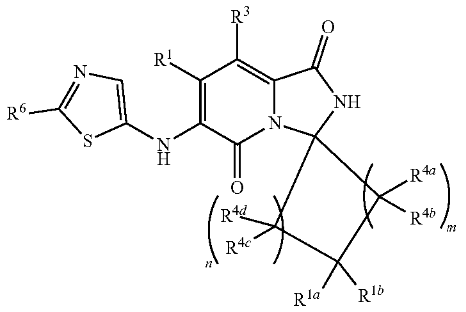

hydrates, solvates, pharmaceutically acceptable salts, prodrugs, isotopic isomers, or complexes thereof. $R^{1a}$, $R^{1b}$, $R^1$, $R^3$, $R^{4d}$, $R^{4c}$, $R^{4a}$, $R^{4b}$, R, m and n are as defined herein.

In more specific embodiments, the compounds of the present disclosure include compounds having formula (XX):

(XX)

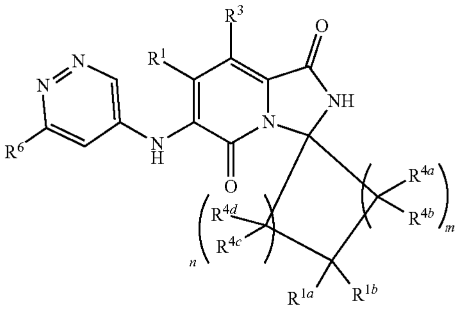

hydrates, solvates, pharmaceutically acceptable salts, prodrugs, isotopic isomers, or complexes thereof. $R^{1a}$, $R^{1b}$, $R^1$, $R^3$, $R^{46}$, $R^{4c}$, $R^{4a}$, $R^{4b}$, R, m and n are as defined herein.

In more specific embodiments, the compounds of the present disclosure include compounds having formula (XX):

(XX)

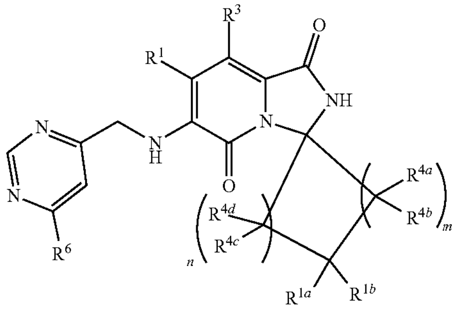

hydrates, solvates, pharmaceutically acceptable salts, prodrugs, isotopic isomers, or complexes thereof. $R^{1a}$, $R^{1b}$, $R^1$, $R^3$, $R^{4d}$, $R^{4c}$, $R^{4a}$, $R^{4b}$, R, m and n are as defined herein.

In more specific embodiments, the compounds of the present disclosure include compounds having formula (XXI):

(XXI)

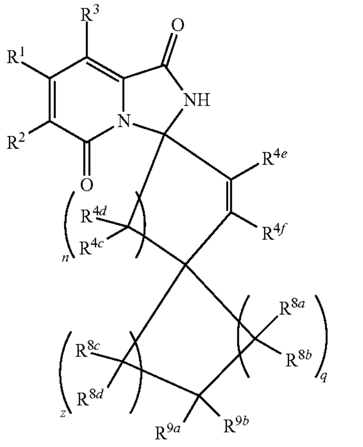

hydrates, solvates, pharmaceutically acceptable salts, prodrugs, isotopic isomers, or complexes thereof. $R^1$, $R^2$, $R^3$, $R^{4d}$, $R^{4c}$, $R^{4e}$, $R^{4f}$, $R^{8a}$, $R^{8b}$, $R^{8c}$, $R^{8d}$, $R^{9a}$, $R^{9b}$, n, q and z are as defined herein.

In more specific embodiments, the compounds of the present disclosure include compounds having formula (XXII):

(XXII)

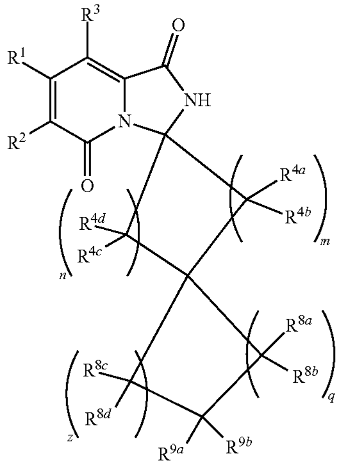

hydrates, solvates, pharmaceutically acceptable salts, prodrugs, isotopic isomers, or complexes thereof. $R^1$, $R^2$, $R^3$, $R^{4d}$, $R^{4c}$, $R^{4e}$, $R^{4f}$, $R^{8a}$, $R^{8b}$, $R^{8c}$, $R^{8d}$, $R^{9a}$, $R^{9b}$, m, n, q and z are as defined herein.

In more specific embodiments, the compounds of the present disclosure include compounds having formula (XXIII):

(XXIII)

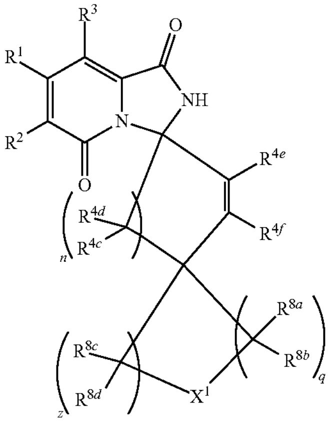

hydrates, solvates, pharmaceutically acceptable salts, prodrugs, isotopic isomers, or complexes thereof. $R^1$, $R^2$, $R^3$, $R^{4d}$, $R^{4c}$, $R^{4e}$, $R^{4f}$, $R^{8a}$, $R^{8b}$, $R^{8c}$, $R^{8d}$, $X^1$, n, q and z are as defined herein.

In more specific embodiments, the compounds of the present disclosure include compounds having formula (XXIV):

(XXIV)

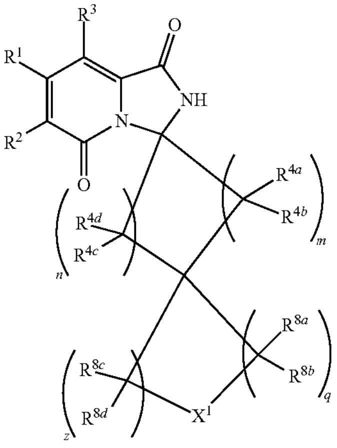

hydrates, solvates, pharmaceutically acceptable salts, prodrugs, isotopic isomers, or complexes thereof. $R^1$, $R^2$, $R^3$, $R^{4d}$, $R^{4c}$, $R^{4e}$, $R^{4f}$, $R^{8a}$, $R^{8b}$, $R^{8c}$, $R^{8a}$, $X^1$, m, n, q and z are as defined herein.

In more specific embodiments, the compounds of the present disclosure include compounds having formula (XXV):

(XXV)

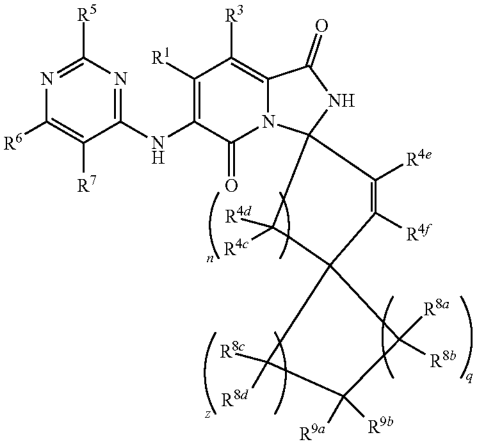

hydrates, solvates, pharmaceutically acceptable salts, prodrugs, isotopic isomers, or complexes thereof. $R^1$, $R^3$, $R^{4d}$, $R^{4c}$, $R^{4e}$, $R^{4f}$, $R^5$, $R^6$, $R^7$, $R^{8a}$, $R^{8b}$, $R^{8c}$, $R^{8d}$, $R^{9a}$, $R^{9b}$, n, q and z are as defined herein.

In more specific embodiments, the compounds of the present disclosure include compounds having formula (XXVI):

(XXVI)

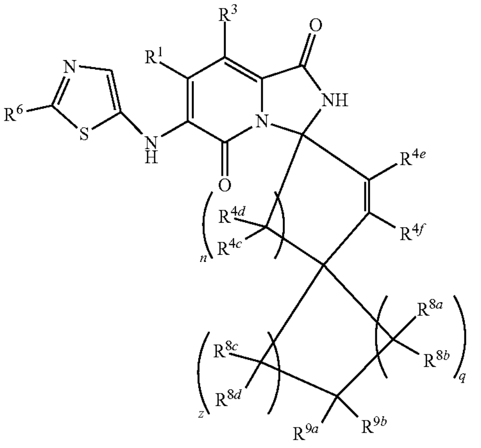

hydrates, solvates, pharmaceutically acceptable salts, prodrugs, isotopic isomers, or complexes thereof. $R^1$, $R^3$, $R^{4d}$, $R^{4c}$, $R^{4e}$, $R^{4f}$, $R^6$, $R^{8a}$, $R^{8b}$, $R^{8c}$, $R^{8d}$, $R^{9a}$, $R^{9b}$, n, q and z are as defined herein.

In more specific embodiments, the compounds of the present disclosure include compounds having formula (XXVII):

(XXVII)

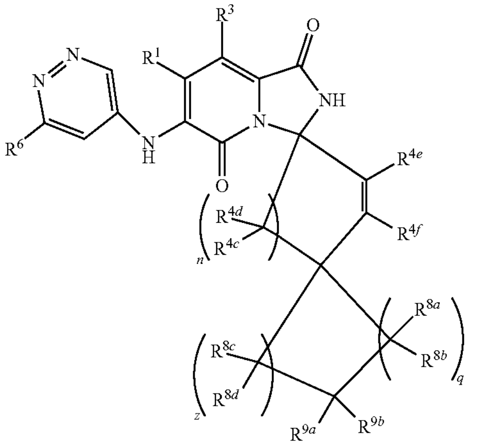

hydrates, solvates, pharmaceutically acceptable salts, prodrugs, isotopic isomers, or complexes thereof. $R^1$, $R^3$, $R^{4d}$, $R^{4c}$, $R^{4e}$, $R^{4f}$, $R^6$, $R^{8a}$, $R^{8b}$, $R^{8c}$, $R^{8d}$, $R^{9a}$, $R^{9b}$, n, q and z are as defined herein.

In more specific embodiments, the compounds of the present disclosure include compounds having formula (XXVIII):

(XXVIII)

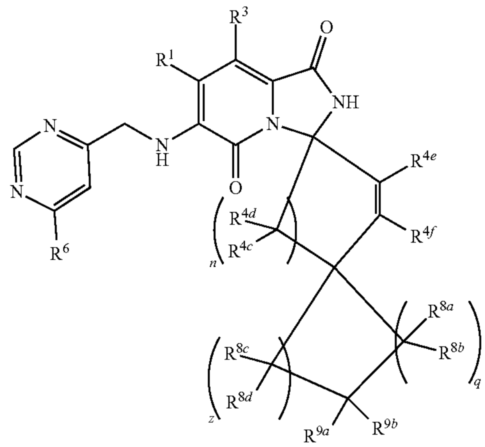

hydrates, solvates, pharmaceutically acceptable salts, prodrugs, isotopic isomers, or complexes thereof. $R^1$, $R^3$, $R^{4d}$, $R^{4c}$, $R^{4e}$, $R^{4f}$, $R^6$, $R^{8a}$, $R^{8b}$, $R^{8c}$, $R^{8d}$, $R^{9a}$, $R^{9b}$, n, q and z are as defined herein.

In more specific embodiments, the compounds of the present disclosure include compounds having formula (XXIX):

(XXIX)

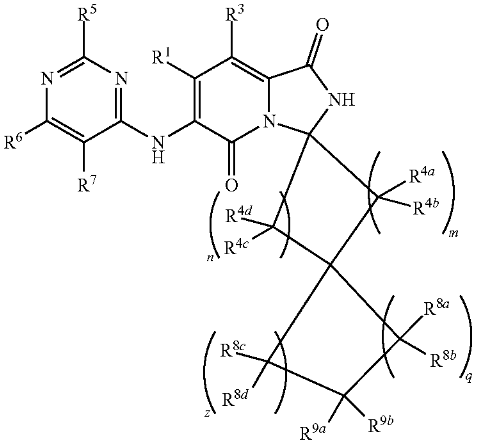

hydrates, solvates, pharmaceutically acceptable salts, prodrugs, isotopic isomers, or complexes thereof. $R^1$, $R^3$, $R^{4d}$, $R^{4b}$, $R^{4d}$, $R^{4c}$, $R^5$, $R^6$, $R^7$, $R^{8a}$, $R^{8b}$, $R^{8c}$, $R^{8d}$, $R^{9a}$, $R^{9b}$, m, n, q and z are as defined herein.

In more specific embodiments, the compounds of the present disclosure include compounds having formula (XXX):

(XXX)

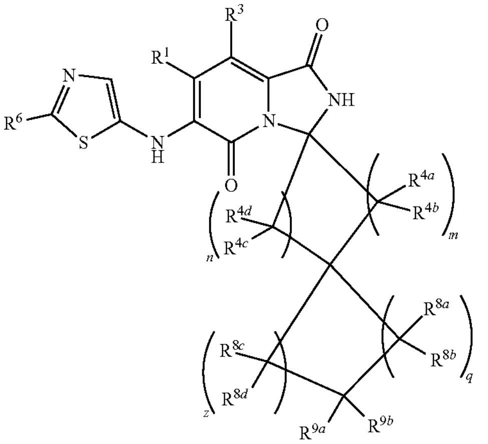

hydrates, solvates, pharmaceutically acceptable salts, prodrugs, isotopic isomers, or complexes thereof. $R^1$, $R^3$, $R^{4d}$, $R^{4b}$, $R^{4a}$, $R^{4c}$, $R^6$, $R^{8a}$, $R^{8b}$, $R^{8c}$, $R^{8d}$, $R^{9a}$, $R^{9b}$, m, n, q and z are as defined herein.

In more specific embodiments, the compounds of the present disclosure include compounds having formula (XXXI):

(XXXI)

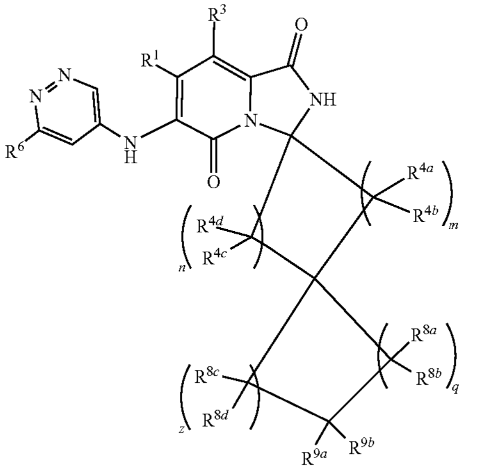

hydrates, solvates, pharmaceutically acceptable salts, prodrugs, isotopic isomers, or complexes thereof. $R^1$, $R^3$, $R^{4a}R^{4b}$, $R^4$, $R^{4c}$, $R^6$, $R^{8a}R^{88b}$, $R^{8c}$, $R^8$, $R^{9a}R^{9b}$, m, n, q and z are as defined herein.

In more specific embodiments, the compounds of the present disclosure include compounds having formula (XXXII):

(XXXII)

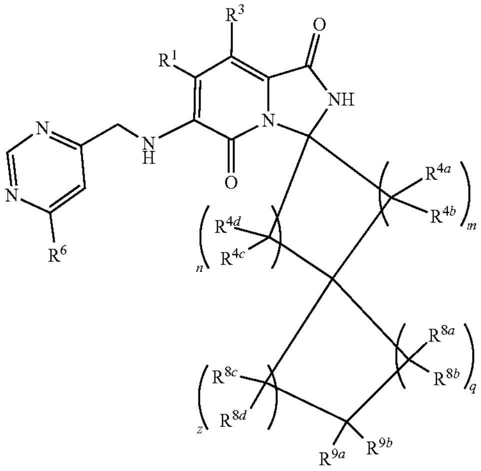

hydrates, solvates, pharmaceutically acceptable salts, prodrugs, isotopic isomers, or complexes thereof. $R^1$, $R^3$, $R^{4d}$, $R^{4b}$, $R^{4a}$, $R^{4c}$, $R^6$, $R^{8a}$, $R^{8b}$, $R^{8c}$, $R^{8d}$, $R^{9a}$, $R^{9b}$, m, n, q and z are as defined herein.

In more specific embodiments, the compounds of the present disclosure include compounds having formula (XXXIII):

(XXXIII)

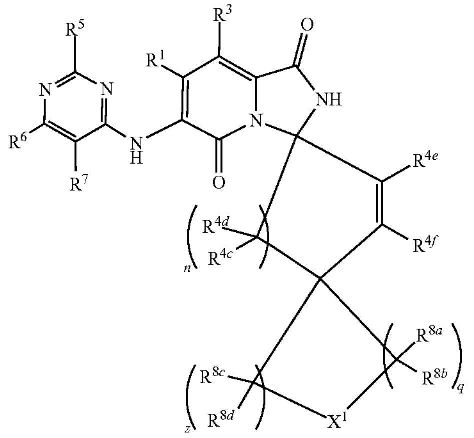

hydrates, solvates, pharmaceutically acceptable salts, prodrugs, isotopic isomers, or complexes thereof. $R^1$, $R^3$, $R^{4d}$, $R^{4c}$, $R^{4e}$, $R^{4f}$, $R^5$, $R^6$, $R^7$, $R^{8a}$, $R^{8b}$, $R^{8c}$, $R^{8d}$, $X^1$, n, q and z are as defined herein.

In more specific embodiments, the compounds of the present disclosure include compounds having formula (XXXIV):

(XXXIV)

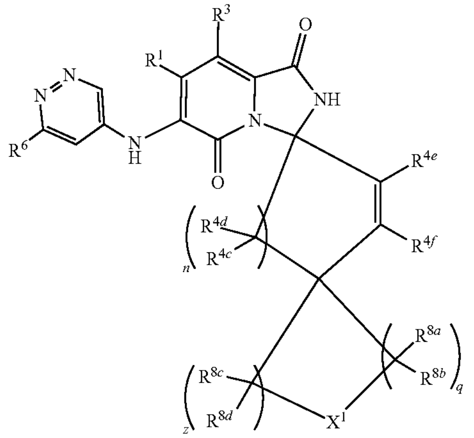

hydrates, solvates, pharmaceutically acceptable salts, prodrugs, isotopic isomers, or complexes thereof. $R^1$, $R^3$, $R^{4d}$, $R^{4c}$, $R^{4e}$, $R^{4f}$, $R^6$, $R^{8a}$, $R^{8b}$, $R^8$, $R^{8d}$, $X^1$, n, q and z are as defined herein.

In more specific embodiments, the compounds of the present disclosure include compounds having formula (XXXV):

(XXXV)

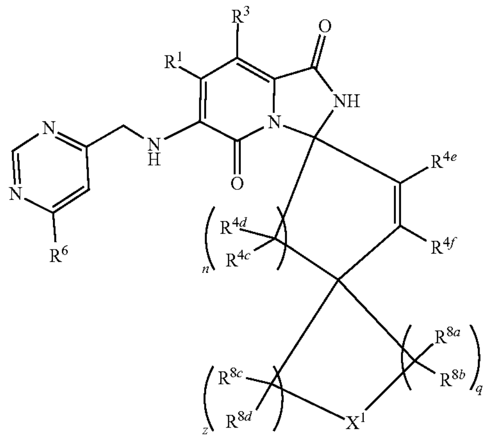

hydrates, solvates, pharmaceutically acceptable salts, prodrugs, isotopic isomers, or complexes thereof. $R^1$, $R^3$, $R^{4d}$, $R^{4c}$, $R^{4e}$, $R^{4f}$, $R^6$, $R^{8a}$, $R^{8b}$, $R^8$, $R^{8d}$, $X^1$, n, q and z are as defined herein.

In more specific embodiments, the compounds of the present disclosure include compounds having formula (XXXVI):

(XXXVI)

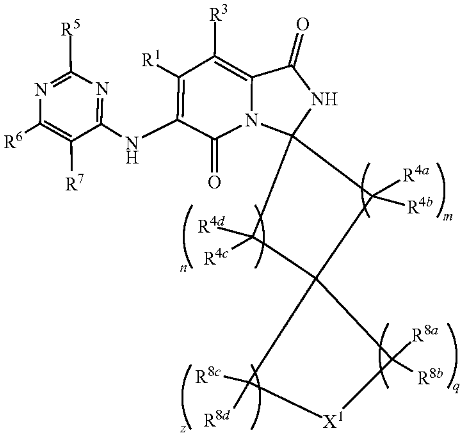

hydrates, solvates, pharmaceutically acceptable salts, prodrugs, isotopic isomers, or complexes thereof. $R^1$, $R^3$, $R^{4d}$, $R^{4c}$, $R^{4a}$, $R^{4b}$, $R^5$, $R^6$, $R^7$, $R^{8a}$, $R^{8b}$, $R^8$, $R^{8a}$, $X^1$, m, n, q and z are as defined herein.

In more specific embodiments, the compounds of the present disclosure include compounds having formula (XXXVII):

(XXXVII)

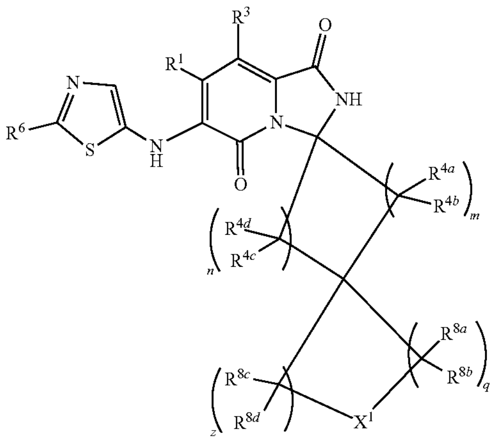

hydrates, solvates, pharmaceutically acceptable salts, prodrugs, isotopic isomers, or complexes thereof. $R^1$, $R^3$, $R^{4d}$, $R^{4c}$, $R^{4a}$, $R^{4b}$, $R^6$, $R^{8a}$, $R^{8b}$, $R^{8c}$, $R^{8a}$, $X^1$, m, n, q and z are as defined herein.

In more specific embodiments, the compounds of the present disclosure include compounds having formula (XXXVIII):

(XXXVIII)

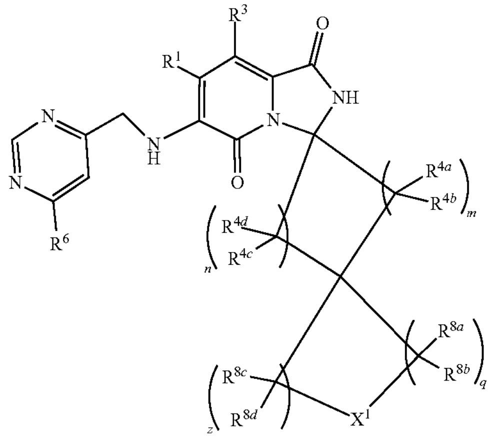

hydrates, solvates, pharmaceutically acceptable salts, prodrugs, isotopic isomers, or complexes thereof. $R^1$, $R^3$, $R^{4d}$, $R^{4c}$, $R^{4a}$, $R^{4b}$, $R^6$, $R^{8a}$, $R^{8b}$, $R^{8c}$, $R^{8d}$, $X^1$, m, n, q and z are as defined herein.

In more specific embodiments, the compounds of the present disclosure include compounds having formula (XXXVIIII) through (LI):

(XXXX)

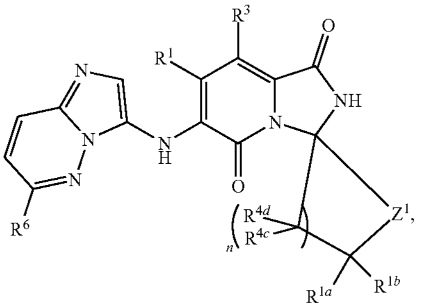

(XXXXI)

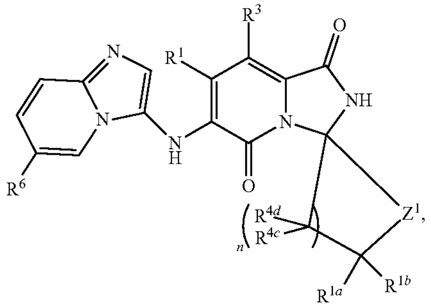

(XXXXII)

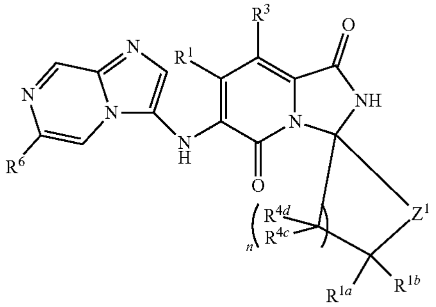

(XXXXIII)

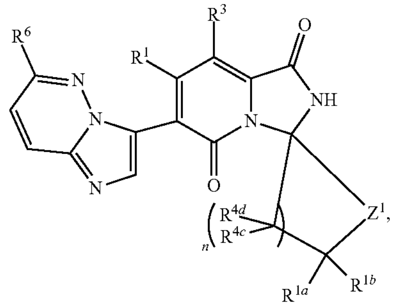

(XXXXIV)

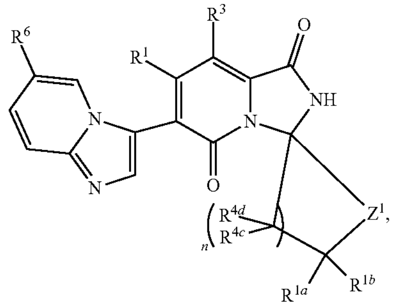

-continued (XXXXV)

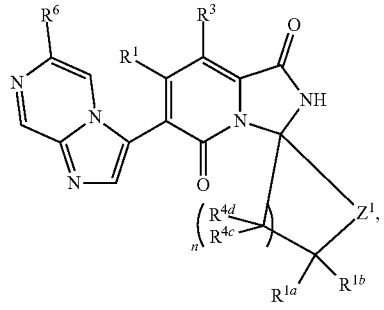

(XXXXVI)

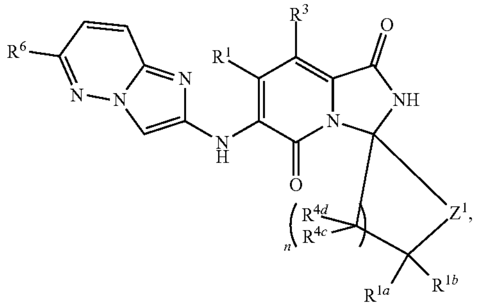

(XXXXVII)

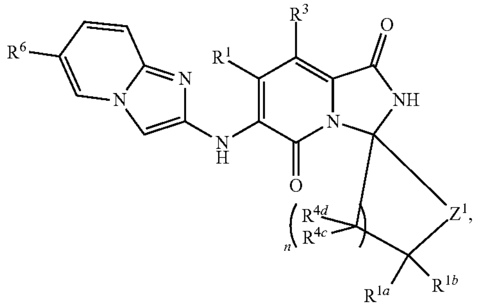

(XXXXVIII)

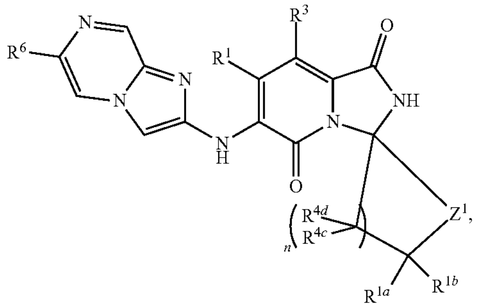

(XXXXIX)

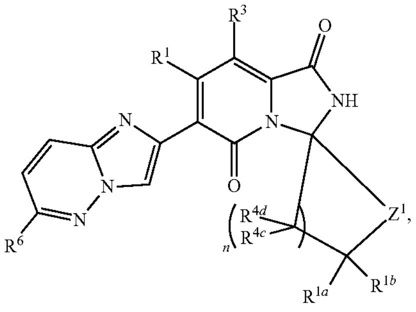

-continued (L)

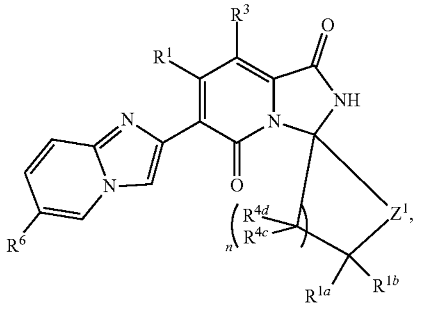

(LI)

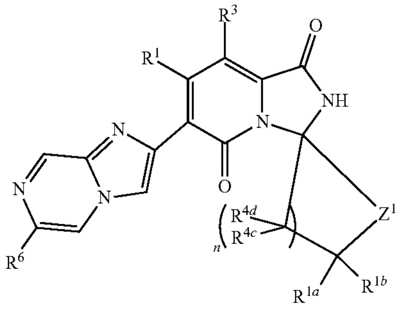

Including hydrates, solvates, pharmaceutically acceptable salts, prodrugs, isotopic isomers, and complexes thereof.

In some embodiments, $Z^1$ is

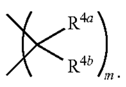

In some embodiments, $Z^1$ is

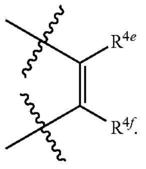

In some embodiments, $R^1$ is hydrogen.

In some embodiments, $R^1$ is halogen.

In some embodiments, $R^1$ is $C_{1-6}$ alkyl.

In some embodiments, $R^1$ is $C_{3-7}$ branched alkyl.

In some embodiments, $R^1$ is $C_{1-6}$ haloalkyl.

In some embodiments, $R^1$ is $C_{3-7}$ branched haloalkyl.

In some embodiments, $R^1$ is $C_{1-6}$ hydroxyalkyl.

In some embodiments, $R^1$ is $C_{3-7}$ branched hydroxyalkyl.

In some embodiments, $R^1$ is cyano.

In some embodiments, $R^1$ is $C_{1-6}$ alkoxyl.

In some embodiments, $R^1$ is $C_{3-7}$ branched alkoxy.

In some embodiments, $R^1$ is hydroxy

In some embodiments, $R^1$ is $C_{3-6}$ cycloalkyl.

In some embodiments, $R^1$ is $C_{3-6}$ cycloalkyl that is substituted 1 substituent selected from the groups consisting of halogen, $C_{1-6}$ alkyl, $C_{1-6}$ haloalkyl, and $C_{1-6}$ hydroxyalkyl.

In some embodiments, $R^1$ is $C_{3-6}$ cycloalkyl that is substituted 2 substituents selected from the groups consisting of halogen, $C_{1-6}$ alkyl, $C_{1-6}$ haloalkyl, and $C_{1-6}$ hydroxyalkyl.

In some embodiments, $R^1$ is $C_{3-6}$ cycloalkyl that is substituted 3 substituents selected from the groups consisting of halogen, $C_{1-6}$ alkyl, $C_{1-6}$ haloalkyl, and $C_{1-6}$ hydroxyalkyl.

In some embodiments, $R^2$ is

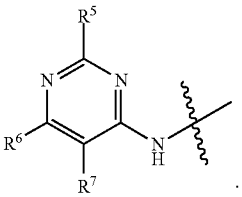

In some embodiments, $R^2$ is

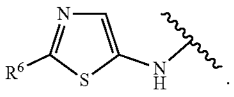

In some embodiments, $R^2$ is

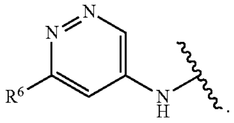

In some embodiments, $R^2$ is

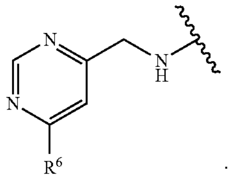

In some embodiments, $R^2$ is

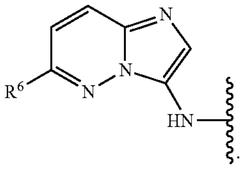

In some embodiments, $R^2$ is

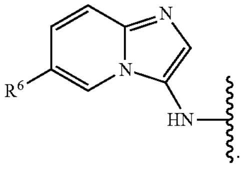

In some embodiments, $R^2$ is

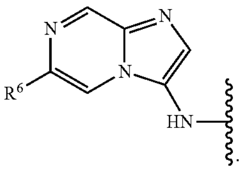

In some embodiments, $R^2$ is

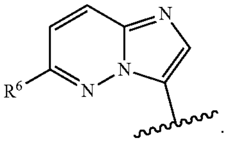

In some embodiments, $R^2$ is

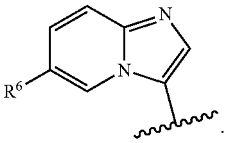

In some embodiments, $R^2$ is

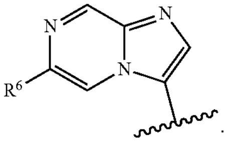

In some embodiments, $R^2$ is

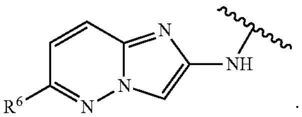

In some embodiments, $R^2$ is

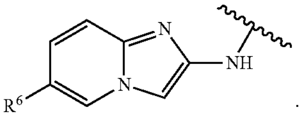

In some embodiments, $R^2$ is

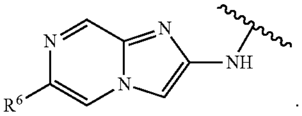

In some embodiments, $R^2$ is

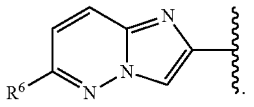

In some embodiments, $R^2$ is

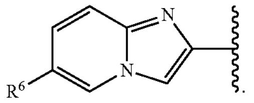

In some embodiments, $R^2$ is

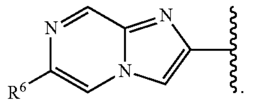

In some embodiments, $R^3$ is hydrogen.
In some embodiments, $R^3$ is halogen.
In some embodiments, $R^3$ is $C_{1-6}$ alkyl.
In some embodiments, $R^3$ is $C_{3-7}$ branched alkyl.
In some embodiments, $R^3$ is $C_{1-6}$ haloalkyl.
In some embodiments, $R^3$ is $C_{3-7}$ branched haloalkyl.
In some embodiments, $R^3$ is $C_{1-6}$ hydroxyalkyl.
In some embodiments, $R^3$ is $C_{3-7}$ branched hydroxyalkyl.
In some embodiments, $R^3$ is cyano.
In some embodiments, $R^3$ is $C_{1-6}$ alkoxyl.
In some embodiments, $R^3$ is $C_{3-7}$ branched alkoxy.
In some embodiments, $R^3$ is hydroxy.
In some embodiments, $R^3$ is $C_{3-6}$ cycloakyl.

In some embodiments, $R^3$ is $C_{3-6}$ cycloakyl that is substituted with 1 substituent selected from the groups consisting of halogen, $C_{1-6}$ alkyl, $C_{1-6}$ haloalkyl, and $C_{1-6}$ hydroxyalkyl.

In some embodiments, $R^3$ is $C_{3-6}$ cycloakyl that is substituted with 2 substituent selected from the groups consisting of halogen, $C_{1-6}$ alkyl, $C_{1-6}$ haloalkyl, and $C_{1-6}$ hydroxyalkyl.

In some embodiments, $R^3$ is $C_{3-6}$ cycloakyl that is substituted with 3 substituent selected from the groups consisting of halogen, $C_{1-6}$ alkyl, $C_{1-6}$ haloalkyl, and $C_{1-6}$ hydroxyalkyl.

In some embodiments, $R^{4a}$ is hydrogen.
In some embodiments, $R^{4a}$ is halogen.
In some embodiments, $R^{4a}$ is $C_{1-6}$ alkyl.
In some embodiments, $R^{4a}$ is $C_{3-7}$ branched alkyl.
In some embodiments, $R^{4a}$ is $C_{1-6}$ haloalkyl.
In some embodiments, $R^{4a}$ is $C_{3-7}$ branched haloalkyl.
In some embodiments, $R^{4a}$ is hydroxy.
In some embodiments, $R^{4a}$ is $C_{1-6}$ alkoxyl.
In some embodiments, $R^{4a}$ is $C_{3-7}$ branched alkoxy.
In some embodiments, $R^{4a}$ is $NHCO(C_{1-6}alkyl)$.
In some embodiments, $R^{4a}$ is $NHCO(C_{3-7}$ branched alkyl).
In some embodiments, $R^{4a}$ is $NHCO(C_{3-7}$ cycloalkyl).
In some embodiments, $R^{4a}$ is $NHSO_2(C_{1-6}alkyl)$.
In some embodiments, $R^{4a}$ is $NHSO_2(C_{3-7}$ branched alkyl).
In some embodiments, $R^{4a}$ is $NHSO_2(C_{3-7}$ cycloalkyl).
In some embodiments, $R^{4b}$ is hydrogen.
In some embodiments, $R^{4b}$ is halogen.
In some embodiments, $R^{4b}$ is $C_{1-6}$ alkyl.
In some embodiments, $R^{4b}$ is $C_{3-7}$ branched alkyl.
In some embodiments, $R^{4b}$ is $C_{1-6}$ haloalkyl.
In some embodiments, $R^{4b}$ is $C_{3-7}$ branched haloalkyl.
In some embodiments, $R^{4b}$ is hydroxy.
In some embodiments, $R^{4b}$ is $C_{1-6}$ alkoxyl.
In some embodiments, $R^{4b}$ is $C_{3-7}$ branched alkoxy.
In some embodiments, $R^{4b}$ is $NHCO(C_{1-6}alkyl)$.
In some embodiments, $R^{4b}$ is $NHCO(C_{3-7}$ branched alkyl).
In some embodiments, $R^{4b}$ is $NHCO(C_{3-7}$ cycloalkyl).
In some embodiments, $R^{4b}$ is $NHSO_2(C_{1-6}alkyl)$.
In some embodiments, $R^{4b}$ is $NHSO_2(C_{3-7}$ branched alkyl).
In some embodiments, $R^{4b}$ is $NHSO_2(C_{3-7}$ cycloalkyl).
In some embodiments, $R^{4c}$ is hydrogen.
In some embodiments, $R^{4c}$ is halogen.
In some embodiments, $R^{4c}$ is $C_{1-6}$ alkyl.
In some embodiments, $R^{4c}$ is $C_{3-7}$ branched alkyl.
In some embodiments, $R^{4c}$ is $C_{1-6}$ haloalkyl.
In some embodiments, $R^{4c}$ is $C_{3-7}$ branched haloalkyl.
In some embodiments, $R^{4c}$ is hydroxy.
In some embodiments, $R^{4c}$ is $C_{1-6}$ alkoxyl.
In some embodiments, $R^{4c}$ is $C_{3-7}$ branched alkoxy.
In some embodiments, $R^{4c}$ is $NHCO(C_{1-6}alkyl)$.
In some embodiments, $R^{4c}$ is $NHCO(C_{3-7}$ branched alkyl).
In some embodiments, $R^{4c}$ is $NHCO(C_{3-7}$ cycloalkyl).
In some embodiments, $R^{4c}$ is $NHSO_2(C_{1-6}alkyl)$.
In some embodiments, $R^{4c}$ is $NHSO_2(C_{3-7}$ branched alkyl).
In some embodiments, $R^{4c}$ is $NHSO_2(C_{3-7}$ cycloalkyl).
In some embodiments, $R^{4d}$ is hydrogen.
In some embodiments, $R^{4d}$ is halogen.
In some embodiments, $R^{4d}$ is $C_{1-6}$ alkyl.
In some embodiments, $R^{4d}$ is $C_{3-7}$ branched alkyl.
In some embodiments, $R^{4d}$ is $C_{1-6}$ haloalkyl.
In some embodiments, $R^{4d}$ is $C_{3-7}$ branched haloalkyl.
In some embodiments, $R^{4d}$ is hydroxy.
In some embodiments, $R^{4d}$ is $C_{1-6}$ alkoxyl.
In some embodiments, $R^{4d}$ is $C_{3-7}$ branched alkoxy.
In some embodiments, $R^{4d}$ is $NHCO(C_{1-6}alkyl)$.
In some embodiments, $R^{4d}$ is $NHCO(C_{3-7}$ branched alkyl).
In some embodiments, $R^{4d}$ is $NHCO(C_{3-7}$ cycloalkyl).
In some embodiments, $R^{4d}$ is $NHSO_2(C_{1-6}alkyl)$.
In some embodiments, $R^{4d}$ is $NHSO_2(C_{3-7}$ branched alkyl).
In some embodiments, $R^{4d}$ is $NHSO_2(C_{3-7}$ cycloalkyl).
In some embodiments, $R^{4c}$ is hydrogen.
In some embodiments, $R^{4c}$ is halogen.
In some embodiments, $R^{4c}$ is $C_{1-6}$ alkyl.
In some embodiments, $R^{4c}$ is $C_{3-7}$ branched alkyl.
In some embodiments, $R^{4c}$ is $C_{1-6}$ haloalkyl.
In some embodiments, $R^{4c}$ is $C_{3-7}$ branched haloalkyl.
In some embodiments, $R^{4f}$ is hydrogen.
In some embodiments, $R^{4f}$ is halogen.
In some embodiments, $R^{4f}$ is $C_{1-6}$ alkyl.
In some embodiments, $R^{4f}$ is $C_{3-7}$ branched alkyl.
In some embodiments, $R^{4f}$ is $C_{1-6}$ haloalkyl.
In some embodiments, $R^{4f}$ is $C_{3-7}$ branched haloalkyl.

In some embodiments, $R^{1a}$ and $R^{1b}$ are taken together to form an optionally substituted 3 membered ring.

In some embodiments, $R^{1a}$ and $R^{1b}$ are taken together to form an optionally substituted 4 membered ring.

In some embodiments, $R^{1a}$ and $R^{1b}$ are taken together to form an optionally substituted 5 membered ring.

In some embodiments, $R^{1a}$ and $R^{1b}$ are taken together to form an optionally substituted 6 membered ring.

In some embodiments, $R^{1a}$ and $R^{1b}$ are taken together to form an optionally substituted 7 membered ring.

In some embodiments, $R^{1a}$ and $R^{1b}$ are taken together to form an optionally substituted 3 membered ring that contains an $X^1$ group.

In some embodiments, $R^{1a}$ and $R^{1b}$ are taken together to form an optionally substituted 4 membered ring that contains an $X^1$ group.

In some embodiments, $R^{1a}$ and $R^{1b}$ are taken together to form an optionally substituted 5 membered ring that contains an $X^1$ group.

In some embodiments, $R^{1a}$ and $R^{1b}$ are taken together to form an optionally substituted 6 membered ring that contains an $X^1$ group.

In some embodiments, $R^{1a}$ and $R^{1b}$ are taken together to form an optionally substituted 7 membered ring that contains an $X^1$ group.

In some embodiments, $X^1$ is $CF_2$.

In some embodiments, $X^1$ is $CHCO_2R^{12}$.

In some embodiments, $X^1$ is O.

In some embodiments, $X^1$ is NH.

In some embodiments, $X^1$ is $NR^B$.

In some embodiments, $X^1$ is $SO_2$.

In some embodiments, m is 0.

In some embodiments, m is 1.

In some embodiments, m is 2.

In some embodiments, n is 1.

In some embodiments, n is 2.

In some embodiments, n is 3.

In some embodiments, $R^5$ is hydrogen.

In some embodiments, $R^5$ is halogen.

In some embodiments, $R^5$ is $C_{1-6}$ alkyl.

In some embodiments, $R^5$ is $C_{3-7}$ branched alkyl.

In some embodiments, $R^5$ is $C_{1-6}$ haloalkyl.

In some embodiments, $R^5$ is $C_{3-7}$ branched haloalkyl.

In some embodiments, $R^5$ is $C_{1-6}$ alkoxyl.

In some embodiments, $R^5$ is $C_{3-7}$ branched alkoxy.

In some embodiments, $R^5$ is hydroxy.

In some embodiments, $R^6$ is hydrogen.

In some embodiments, $R^6$ is $NH_2$.

In some embodiments, $R^6$ is $NHR^{6a}$

In some embodiments, $R^6$ is $NHCH_2CH_2OH$.

In some embodiments, $R^6$ is $NHCH_2CH_2NHSO_2Me$.

In some embodiments, $R^6$ is $C_{1-6}$ alkoxyl.

In some embodiments, $R^6$ is $C_{3-7}$ branched alkoxy.

In some embodiments, $R^6$ is hydroxy.

In some embodiments, $R^{6a}$ is —(CO)$C_{1-6}$ alkyl.

In some embodiments, $R^{6a}$ is —(CO)$C_{3-7}$ branched alkyl.

In some embodiments, $R^{6a}$ is —(CO)$C_{1-6}$ hydroxyalkyl.

In some embodiments, $R^{6a}$ is

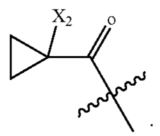

In some embodiments, $R^{6a}$ is

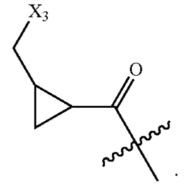

In some embodiments, $R^{6a}$ is

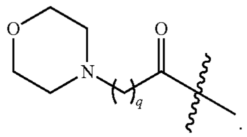

In some embodiments, $R^{6a}$ is

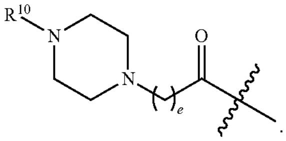

In some embodiments, $R^{6a}$ is

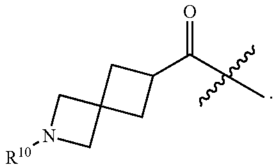

In some embodiments, $R^{6a}$ is

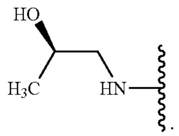

In some embodiments, $R^{6a}$ is

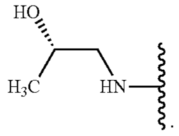

In some embodiments, $R^{6a}$ is

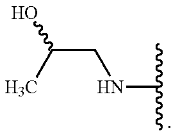

In some embodiments, $R^{6a}$ is

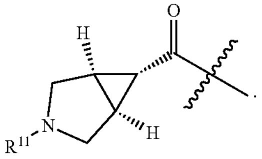

In some embodiments, q is 1.

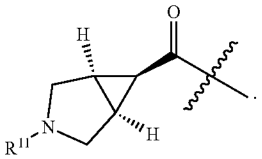

In some embodiments, q is 2.
In some embodiments, q is 3.
In some embodiments, q is 4.
In some embodiments, q is 5.
In some embodiments, q is 6.
In some embodiments, e is 1.
In some embodiments, e is 2.
In some embodiments, e is 3.
In some embodiments, e is 4.
In some embodiments, e is 5.
In some embodiments, e is 6.
In some embodiments, $X^2$ is hydrogen.
In some embodiments, $X^2$ is halogen.
In some embodiments, $X^2$ is $C_{1-6}$alkyl.
In some embodiments, $X^2$ is $C_{3-7}$ branched alkyl.
In some embodiments, $X^2$ is $C_{1-6}$haloalkyl.
In some embodiments, $X^2$ is $C_{3-7}$ branched haloalkyl.
In some embodiments, $X^2$ is hydroxy.
In some embodiments, $X^2$ is $C_{1-6}$hydroxyalkyl.
In some embodiments, $X^2$ is $C_{3-7}$ branched hydroxyalkyl.
In some embodiments, $X^2$ is $C_{1-6}$alkoxy.
In some embodiments, $X^2$ is $C_{3-7}$ branched alkoxy.
In some embodiments, $X^2$ is $C_{1-6}$haloalkoxy.
In some embodiments, $X^2$ is $C_{3-7}$ branched haloalkoxy.
In some embodiments, $X^2$ is $NH_2$.
In some embodiments, $X^2$ is $NH(C_{1-6}alkyl)$.
In some embodiments, $X^2$ is $N(C_{1-6}alkyl)_2$.
In some embodiments, $X^2$ is $C_{1-5}(COOH)$.
In some embodiments, $X^2$ is $C_{1-6}(NHSO_2Me)$.
In some embodiments, $X^3$ is hydrogen.
In some embodiments, $X^3$ is halogen.
In some embodiments, $X^3$ is $C_{1-5}$ alkyl.
In some embodiments, $X^3$ is $C_{3-7}$ branched alkyl.
In some embodiments, $X^3$ is $C_{1-5}$ haloalkyl.
In some embodiments, $X^3$ is $C_{3-7}$ branched haloalkyl.
In some embodiments, $X^3$ is hydroxy.
In some embodiments, $X^3$ is $C_{1-5}$ hydroxyalkyl.

In some embodiments, $X^3$ is $C_{3-7}$ branched hydroxyalkyl.
In some embodiments, $X^3$ is $C_{1-5}$ alkoxy.
In some embodiments, $X^3$ is $C_{3-7}$ branched alkoxy.
In some embodiments, $X^3$ is $C_{1-5}$ haloalkoxy.
In some embodiments, $X^3$ is $C_{3-7}$ branched haloalkoxy.
In some embodiments, $X^3$ is $NH_2$.
In some embodiments, $X^3$ is $NH(C_{1-6}$ alkyl).
In some embodiments, $X^3$ is $N(C_{1-6}$ alkyl$)_2$.
In some embodiments, $X^3$ is COOH.
In some embodiments, $X^3$ is $C_{1-5}(COOH)$.
In some embodiments, $X^3$ is $NHSO_2Me$.
In some embodiments, $X^3$ is $C_{1-5}(NHSO_2Me)$.
In some embodiments, $R^7$ is hydrogen.
In some embodiments, $R^7$ is halogen.
In some embodiments, $R^7$ is $C_{1-6}$ alkyl.
In some embodiments, $R^7$ is $C_{3-7}$ branched alkyl.
In some embodiments, $R^7$ is $C_{1-6}$ haloalkyl.
In some embodiments, $R^7$ is $C_{3-7}$ branched haloalkyl.
In some embodiments, $R^7$ is $C_{1-6}$ alkoxyl.
In some embodiments, $R^7$ is $C_{3-7}$ branched alkoxy.
In some embodiments, $R^7$ is hydroxy.
In some embodiments, $R^8$ is $C_{1-6}$ alkyl.
In some embodiments, $R^8$ is $C_{1-6}$ haloalkyl.
In some embodiments, $R^8$ is $C_{3-7}$ branched haloalkyl.
In some embodiments, $R^8$ is $C_{1-6}$ hydroxyalkyl.
In some embodiments, $R^8$ is $C_{3-7}$ branched hydroxyalkyl.
In some embodiments, $R^8$ is $C_{1-6}$ alkoxyl.
In some embodiments, $R^8$ is $C_{3-7}$ branched alkoxy.
In some embodiments, $R^8$ is $CO(C_{1-6}alkyl)$.
In some embodiments, $R^8$ is $CO(C_{3-7}$ branched alkyl).
In some embodiments, $R^8$ is $SO_2(C_{1-6}alkyl)$.
In some embodiments, $R^8$ is $SO_2(C_{3-7}$ branched alkyl).
In some embodiments, $R^{8a}$ is hydrogen.
In some embodiments, $R^{8a}$ is halogen.
In some embodiments, $R^{8a}$ is $C_{1-6}$ alkyl.
In some embodiments, $R^{8a}$ is $C_{3-7}$ branched alkyl.
In some embodiments, $R^{8a}$ is $C_{1-6}$ haloalkyl.
In some embodiments, $R^{8a}$ is $C_{3-7}$ branched haloalkyl.
In some embodiments, $R^{8a}$ is $C_{1-6}$ hydroxyalkyl.
In some embodiments, $R^{8a}$ is $C_{3-7}$ branched hydroxyalkyl.
In some embodiments, $R^{8a}$ is hydroxy.
In some embodiments, $R^{8a}$ is $C_{1-6}$ alkoxyl.
In some embodiments, $R^{8a}$ is $C_{3-7}$ branched alkoxy.
In some embodiments, $R^{8a}$ is $NHCO(C_{1-6}alkyl)$.
In some embodiments, $R^{8a}$ is $NHCO(C_{3-7}$ branched alkyl).
In some embodiments, $R^{8a}$ is $NHSO_2(C_{1-6}alkyl)$.
In some embodiments, $R^{8a}$ is $NHSO_2(C_{3-7}$ branched alkyl).
In some embodiments, $R^{8b}$ is hydrogen.
In some embodiments, $R^{8b}$ is halogen.
In some embodiments, $R^{8b}$ is $C_{1-6}$ alkyl.
In some embodiments, $R^{8b}$ is $C_{3-7}$ branched alkyl.
In some embodiments, $R^{8b}$ is $C_{1-6}$ haloalkyl.
In some embodiments, $R^{8b}$ is $C_{3-7}$ branched haloalkyl.
In some embodiments, $R^{8b}$ is $C_{1-6}$ hydroxyalkyl.
In some embodiments, $R^{8b}$ is $C_{3-7}$ branched hydroxyalkyl.
In some embodiments, $R^{8b}$ is hydroxy.
In some embodiments, $R^{8b}$ is $C_{1-6}$ alkoxyl.
In some embodiments, $R^{8b}$ is $C_{3-7}$ branched alkoxy.
In some embodiments, $R^{8b}$ is $NHCO(C_{1-6}alkyl)$.
In some embodiments, $R^{8b}$ is $NHCO(C_{3-7}$ branched alkyl).
In some embodiments, $R^{8b}$ is $NHSO_2(C_{1-6}alkyl)$.
In some embodiments, $R^{8b}$ is $NHSO_2(C_{3-7}$ branched alkyl).
In some embodiments, $R^{8c}$ is hydrogen.
In some embodiments, $R^{8c}$ is halogen.

In some embodiments, $R^{8c}$ is $C_{1-6}$ alkyl.

In some embodiments, $R^{8c}$ is $C_{3-7}$ branched alkyl.

In some embodiments, $R^{8c}$ is $C_{1-6}$ haloalkyl.

In some embodiments, $R^{8c}$ is $C_{3-7}$ branched haloalkyl.

In some embodiments, $R^{8c}$ is $C_{1-6}$ hydroxyalkyl.

In some embodiments, $R^{8c}$ is $C_{3-7}$ branched hydroxyalkyl.

In some embodiments, $R^{8c}$ is hydroxy.

In some embodiments, $R^{8c}$ is $C_{1-6}$ alkoxyl.

In some embodiments, $R^{8c}$ is $C_{3-7}$ branched alkoxy.

In some embodiments, $R^{8c}$ is NHCO($C_{1-6}$alkyl).

In some embodiments, $R^{8c}$ is NHCO($C_{3-7}$ branched alkyl).

In some embodiments, $R^{8c}$ is $NHSO_2$($C_{1-6}$alkyl).

In some embodiments, $R^{8c}$ is $NHSO_2$($C_{3-7}$ branched alkyl).

In some embodiments, $R^{8d}$ is hydrogen.

In some embodiments, $R^{8d}$ is halogen.

In some embodiments, $R^{8d}$ is $C_{1-6}$ alkyl.

In some embodiments, $R^{8d}$ is $C_{3-7}$ branched alkyl,

In some embodiments, $R^{8d}$ is $C_{1-6}$ haloalkyl.

In some embodiments, $R^{8d}$ is $C_{3-7}$ branched haloalkyl.

In some embodiments, $R^{8d}$ is $C_{1-6}$ hydroxyalkyl.

In some embodiments, $R^{8d}$ is $C_{3-7}$ branched hydroxyalkyl.

In some embodiments, $R^{8d}$ is hydroxy.

In some embodiments, $R^{8d}$ is $C_{1-6}$ alkoxyl.

In some embodiments, $R^{8d}$ is $C_{3-7}$ branched alkoxy

In some embodiments, $R^{8d}$ is NHCO($C_{1-6}$alkyl).

In some embodiments, $R^{8d}$ is NHCO($C_{3-7}$ branched alkyl).

In some embodiments, $R^{8d}$ is $NHSO_2$($C_{1-6}$alkyl).

In some embodiments, $R^{8d}$ is $NHSO_2$($C_{3-7}$ branched alkyl).

In some embodiments, $R^{9a}$ is hydrogen.

In some embodiments, $R^{9a}$ is halogen.

In some embodiments, $R^{9a}$ is $C_{1-6}$ alkyl.

In some embodiments, $R^{9a}$ is $C_{3-7}$ branched alkyl.

In some embodiments, $R^{9a}$ is $C_{1-6}$ haloalkyl.

In some embodiments, $R^{9a}$ is $C_{3-7}$ branched haloalkyl.

In some embodiments, $R^{9a}$ is $C_{1-6}$ hydroxyalkyl.

In some embodiments, $R^{9a}$ is $C_{3-7}$ branched hydroxyalkyl.

In some embodiments, $R^{9a}$ is hydroxy.

In some embodiments, $R^{9a}$ is $C_{1-6}$ alkoxyl.

In some embodiments, $R^{9a}$ is $C_{3-7}$ branched alkoxy.

In some embodiments, $R^{9b}$ is hydrogen.

In some embodiments, $R^{9b}$ is halogen.

In some embodiments, $R^{9b}$ is $C_{1-6}$ alkyl.

In some embodiments, $R^{9b}$ is $C_{3-7}$ branched alkyl.

In some embodiments, $R^{9b}$ is $C_{1-6}$ haloalkyl.

In some embodiments, $R^{9b}$ is $C_{3-7}$ branched haloalkyl.

In some embodiments, $R^{9b}$ is $C_{1-6}$ hydroxyalkyl.

In some embodiments, $R^{9b}$ is $C_{3-7}$ branched hydroxyalkyl.

In some embodiments, $R^{9b}$ is hydroxy.

In some embodiments, $R^{9b}$ is $C_{1-6}$ alkoxyl.

In some embodiments, $R^{9b}$ is $C_{3-7}$ branched alkoxy.

In some embodiments, $R^{9a}$ and $R^{9b}$ are taken together to form a 3 membered ring.

In some embodiments, $R^{9a}$ and $R^{9b}$ are taken together to form a 4 membered ring.

In some embodiments, $R^{9a}$ and $R^{9b}$ are taken together to form a 5 membered ring.

In some embodiments, $R^{9a}$ and $R^{9b}$ are taken together to form a 6 membered ring.

In some embodiments, $R^{9a}$ and $R^{9b}$ are taken together to form a 7 membered ring.

In some embodiments, $R^{9a}$ and $R^{9b}$ are taken together to form an optionally substituted 3 membered ring.

In some embodiments, $R^{9a}$ and $R^{9b}$ are taken together to form an optionally substituted 4 membered ring.

In some embodiments, $R^{9a}$ and $R^{9b}$ are taken together to form an optionally substituted 5 membered ring.

In some embodiments, $R^{9a}$ and $R^{9b}$ are taken together to form an optionally substituted 6 membered ring.

In some embodiments, $R^{9a}$ and $R^{9b}$ are taken together to form an optionally substituted 7 membered ring.

In some embodiments, q is 1.

In some embodiments, q is 2.

In some embodiments, q is 3.

In some embodiments, z is 0.

In some embodiments, z is 1.

In some embodiments, z is 2.

In some embodiments, $R^{10}$ is hydrogen

In some embodiments, $R^{10}$ is $C_{1-6}$ alkyl.

In some embodiments, $R^{10}$ is $C_{1-6}$ haloalkyl.

In some embodiments, $R^{10}$ is $C_{3-7}$ branched haloalkyl.

In some embodiments, $R^{10}$ is $C_{1-6}$ hydroxyalkyl.

In some embodiments, $R^{10}$ is $C_{1-6}$ alkoxyl.

In some embodiments, $R^{10}$ is $C_{3-7}$ branched alkoxy.

In some embodiments, $R^{10}$ is CO($C_{1-6}$alkyl).

In some embodiments, $R^{10}$ is CO($C_{3-7}$ branched alkyl).

In some embodiments, $R^{10}$ is $SO_2$($C_{1-6}$alkyl).

In some embodiments, $R^{10}$ is $SO_2$($C_{3-7}$ branched alkyl).

In some embodiments, $R^{11}$ is hydrogen.

In some embodiments, $R^{11}$ is $C_{1-6}$ alkyl.

In some embodiments, $R^{12}$ is hydrogen.

In some embodiments, $R^{12}$ is $C_{1-6}$ alkyl.

In some embodiments the compounds of Formula (I), (I') or substructures exclude N-(6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)cyclopropanecarboxamide; and/or 3-((6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)amino)propanoic acid.

Compounds of the present disclosure include compounds having the formula (LII) or a pharmaceutically acceptable salt form thereof:

(LII)

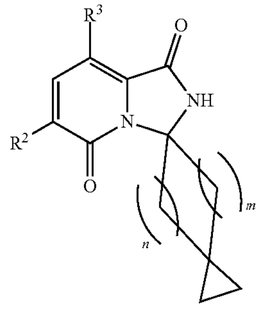

wherein m, n, $R^3$ and $R^2$ are as defined herein.

Examples of $R^2$, $R^3$, m and n, without limitation, are set forth in Table 1.

TABLE 1
| Entry | $R^2$ | $R^3$ | n | m |
|---|---|---|---|---|
| 1 | 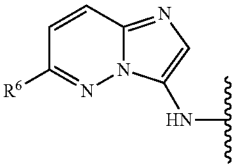 | $CH_3$ | 1 | 1 |
| 2 | 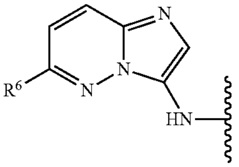 | $CH_3$ | 2 | 1 |
| 3 | 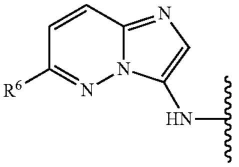 | $CH_3$ | 3 | 1 |
| 4 | 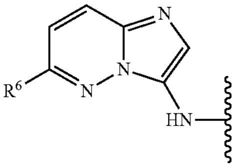 | $CH_3$ | 2 | 2 |
| 5 | 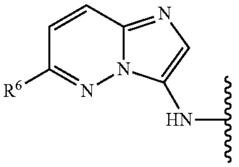 | $CH_3$ | 3 | 2 |
| 6 | 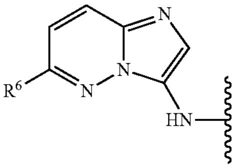 | $CH_3$ | 4 | 1 |
| 7 | 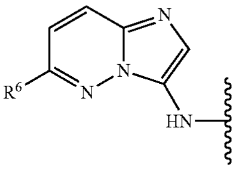 | Cl | 1 | 1 |
| 8 | 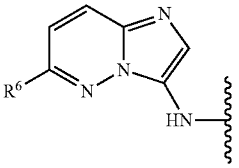 | Cl | 2 | 1 |
| 9 | 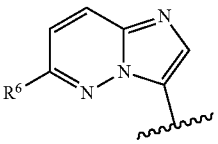 | Cl | 3 | 1 |
TABLE 1-continued
| Entry | $R^2$ | $R^3$ | n | m |
|---|---|---|---|---|
| 10 | 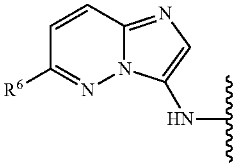 | Cl | 2 | 2 |
| 11 | 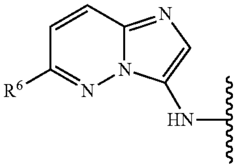 | Cl | 3 | 2 |
| 12 | 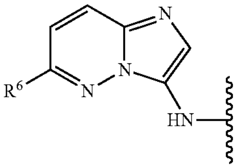 | Cl | 4 | 1 |
| 13 | 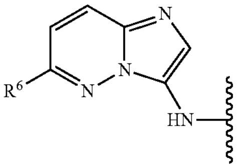 | $CH_3$ | 1 | 1 |
| 14 | 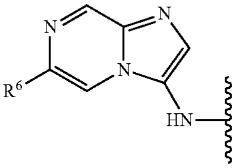 | $CH_3$ | 2 | 1 |
| 15 | 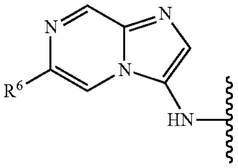 | $CH_3$ | 3 | 1 |
| 16 | 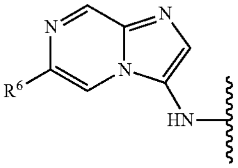 | $CH_3$ | 2 | 2 |
| 17 | 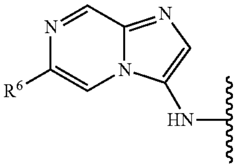 | $CH_3$ | 3 | 2 |

TABLE 1-continued
| Entry | $R^2$ | $R^3$ | n | m |
|---|---|---|---|---|
| 18 | 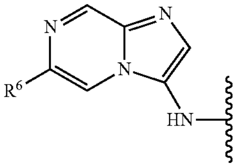 | $CH_3$ | 4 | 1 |
| 19 | 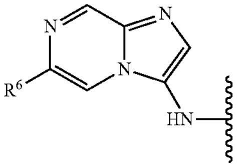 | Cl | 1 | 1 |
| 20 | 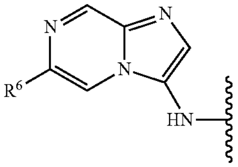 | Cl | 2 | 1 |
| 21 | 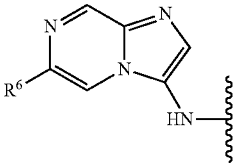 | Cl | 3 | 1 |
| 22 | 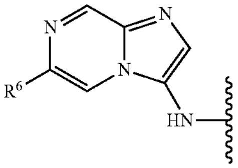 | Cl | 2 | 2 |
| 23 | 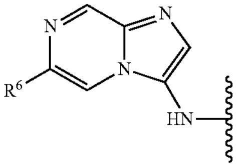 | Cl | 3 | 2 |
| 24 | 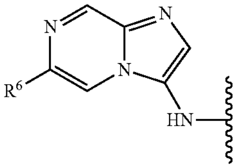 | Cl | 4 | 1 |
| 25 | 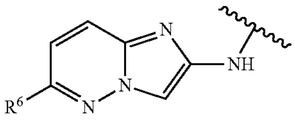 | $CH_3$ | 1 | 1 |
| 26 | 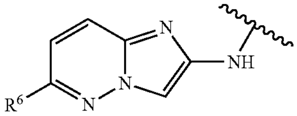 | $CH_3$ | 2 | 1 |
TABLE 1-continued
| Entry | $R^2$ | $R^3$ | n | m |
|---|---|---|---|---|
| 27 | 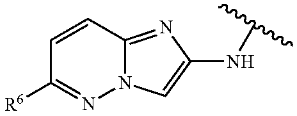 | $CH_3$ | 3 | 1 |
| 28 | 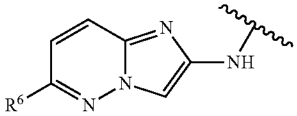 | $CH_3$ | 2 | 2 |
| 29 | 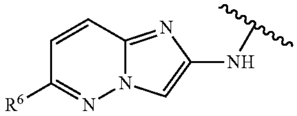 | $CH_3$ | 3 | 2 |
| 30 | 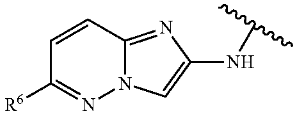 | $CH_3$ | 4 | 1 |
| 31 | 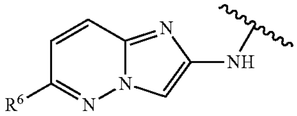 | Cl | 1 | 1 |
| 32 | 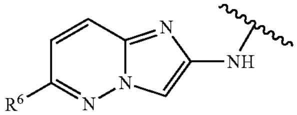 | Cl | 2 | 1 |
| 33 | 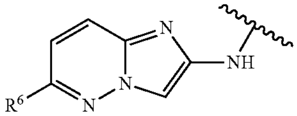 | Cl | 3 | 1 |
| 34 | 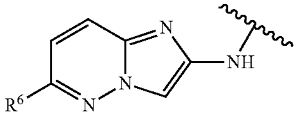 | Cl | 2 | 2 |
| 35 | 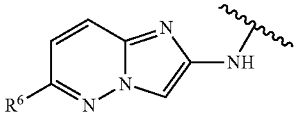 | Cl | 3 | 2 |
| 36 | 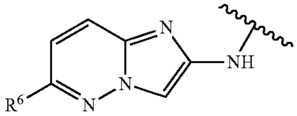 | Cl | 4 | 1 |
| 37 | 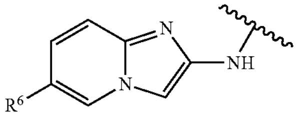 | $CH_3$ | 1 | 1 |
| 38 | 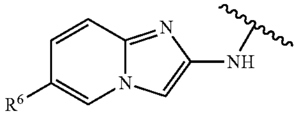 | $CH_3$ | 2 | 1 |

TABLE 1-continued
| Entry | $R^2$ | $R^3$ | n | m |
|---|---|---|---|---|
| 39 | 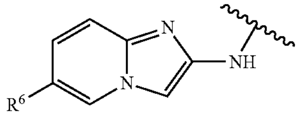 | $CH_3$ | 3 | 1 |
| 40 | 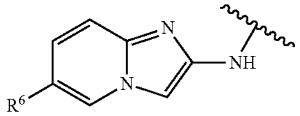 | $CH_3$ | 2 | 2 |
| 41 | 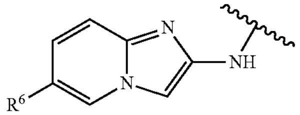 | $CH_3$ | 3 | 2 |
| 42 | 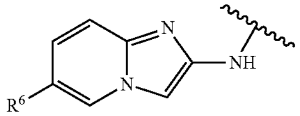 | $CH_3$ | 4 | 1 |
| 43 | 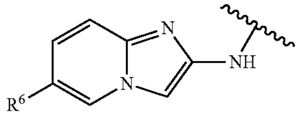 | Cl | 1 | 1 |
| 44 | 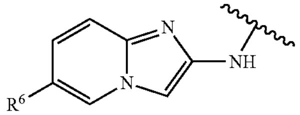 | Cl | 2 | 1 |
| 45 | 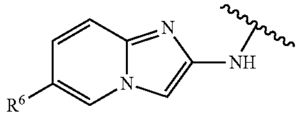 | Cl | 3 | 1 |
| 46 | 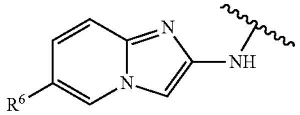 | Cl | 2 | 2 |
| 47 | 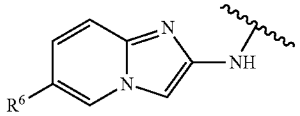 | Cl | 3 | 2 |
| 48 | 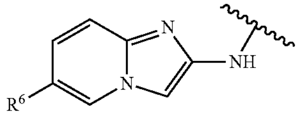 | Cl | 4 | 1 |
| 49 | 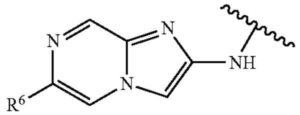 | $CH_3$ | 1 | 1 |
| 50 | 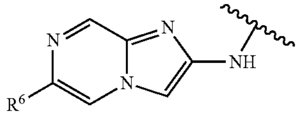 | $CH_3$ | 2 | 1 |
TABLE 1-continued
| Entry | $R^2$ | $R^3$ | n | m |
|---|---|---|---|---|
| 51 | 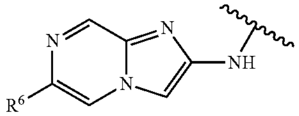 | $CH_3$ | 3 | 1 |
| 52 | 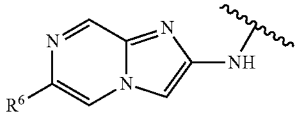 | $CH_3$ | 2 | 2 |
| 53 | 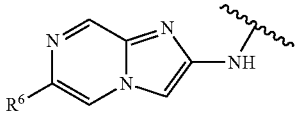 | $CH_3$ | 3 | 2 |
| 54 | 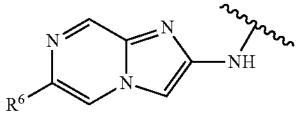 | $CH_3$ | 4 | 1 |
| 55 | 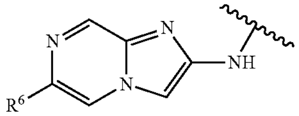 | Cl | 1 | 1 |
| 56 | 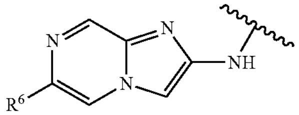 | Cl | 2 | 1 |
| 57 | 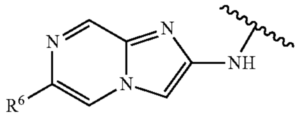 | Cl | 3 | 1 |
| 58 | 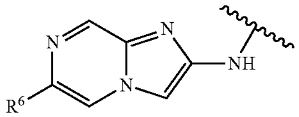 | Cl | 2 | 2 |
| 59 | 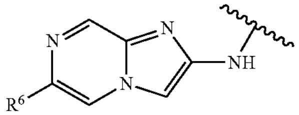 | Cl | 3 | 2 |
| 60 | 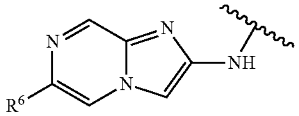 | Cl | 4 | 1 |
| 61 | 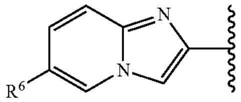 | $CH_3$ | 1 | 1 |
| 62 | 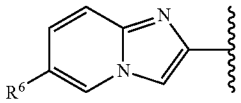 | $CH_3$ | 2 | 1 |

TABLE 1-continued
| Entry | $R^2$ | $R^3$ | n | m |
|---|---|---|---|---|
| 63 | 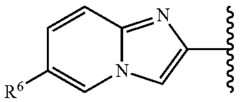 | $CH_3$ | 3 | 1 |
| 64 | 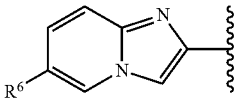 | $CH_3$ | 2 | 2 |
| 65 | 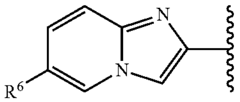 | $CH_3$ | 3 | 2 |
| 66 | 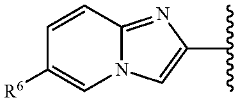 | $CH_3$ | 4 | 1 |
| 67 | 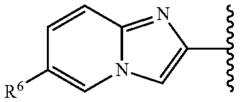 | Cl | 1 | 1 |
| 68 | 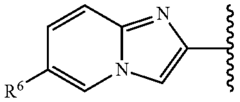 | Cl | 2 | 1 |
| 69 | 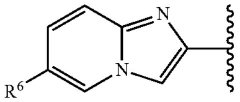 | Cl | 3 | 1 |
| 70 | 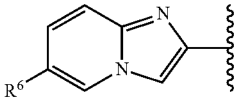 | Cl | 2 | 2 |
| 71 | 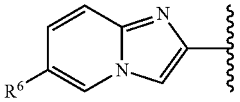 | Cl | 3 | 2 |
| 72 | 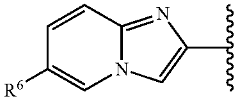 | Cl | 4 | 1 |
| 73 | 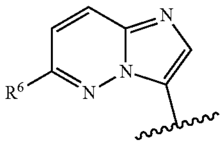 | $CH_3$ | 1 | 1 |
| 74 | 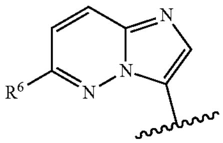 | $CH_3$ | 2 | 1 |
| 75 | 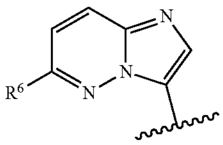 | $CH_3$ | 3 | 1 |
TABLE 1-continued
| Entry | $R^2$ | $R^3$ | n | m |
|---|---|---|---|---|
| 76 | 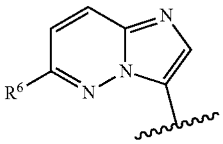 | $CH_3$ | 2 | 2 |
| 77 | 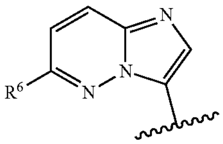 | $CH_3$ | 3 | 2 |
| 78 | 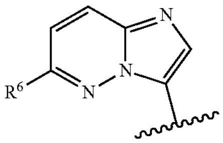 | $CH_3$ | 4 | 1 |
| 79 | 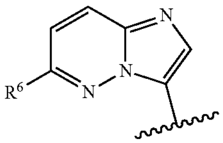 | Cl | 1 | 1 |
| 80 | 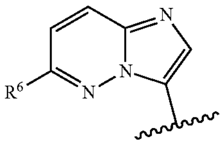 | Cl | 2 | 1 |
| 81 | 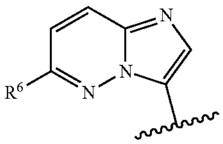 | Cl | 3 | 1 |
| 82 | 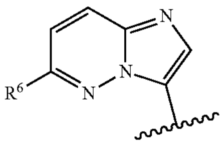 | Cl | 2 | 2 |
| 83 | 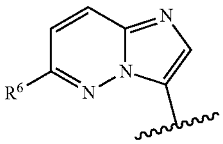 | Cl | 3 | 2 |
| 84 | 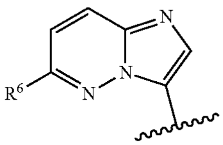 | Cl | 4 | 1 |
| 85 | 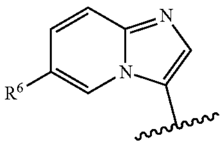 | $CH_3$ | 1 | 1 |

TABLE 1-continued
| Entry | $R^2$ | $R^3$ | n | m |
|---|---|---|---|---|
| 86 | 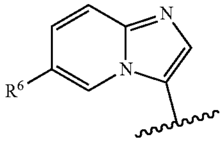 | $CH_3$ | 2 | 1 |
| 87 | 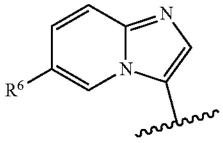 | $CH_3$ | 3 | 1 |
| 88 | 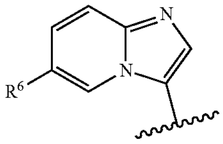 | $CH_3$ | 2 | 2 |
| 89 | 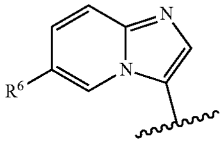 | $CH_3$ | 3 | 2 |
| 90 | 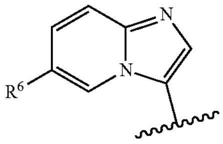 | $CH_3$ | 4 | 1 |
| 91 | 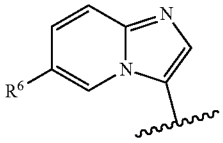 | Cl | 1 | 1 |
| 92 | 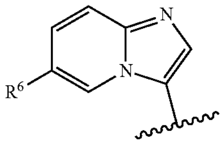 | Cl | 2 | 1 |
| 93 | 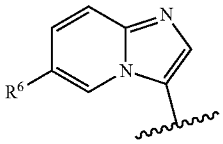 | Cl | 3 | 1 |
| 94 | 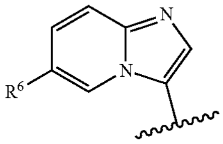 | Cl | 2 | 2 |
| 95 | 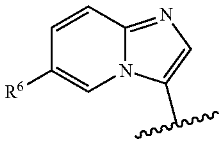 | Cl | 3 | 2 |
TABLE 1-continued
| Entry | $R^2$ | $R^3$ | n | m |
|---|---|---|---|---|
| 96 | 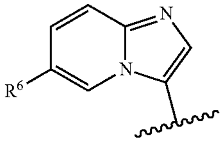 | Cl | 4 | 1 |
| 97 | 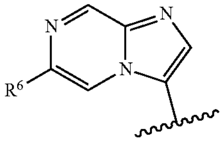 | $CH_3$ | 1 | 1 |
| 98 | 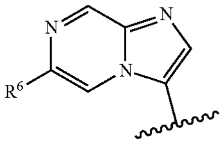 | $CH_3$ | 2 | 1 |
| 99 | 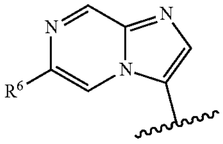 | $CH_3$ | 3 | 1 |
| 100 | 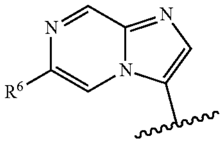 | $CH_3$ | 2 | 2 |
| 101 | 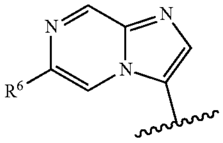 | $CH_3$ | 3 | 2 |
| 102 | 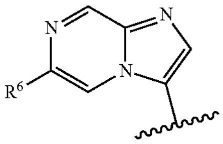 | $CH_3$ | 4 | 1 |
| 103 | 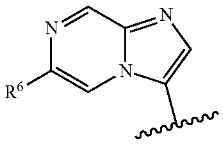 | Cl | 1 | 1 |
| 104 | 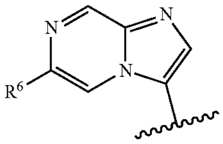 | Cl | 2 | 1 |
| 105 | 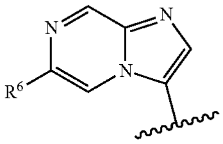 | Cl | 3 | 1 |

TABLE 1-continued
| Entry | $R^2$ | $R^3$ | n | m |
|---|---|---|---|---|
| 106 | 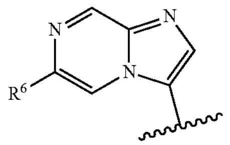 | Cl | 2 | 2 |
| 107 | 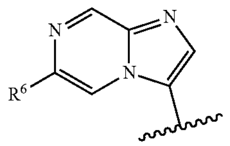 | Cl | 3 | 2 |
| 108 | 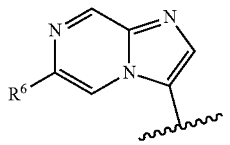 | Cl | 4 | 1 |
| 109 | 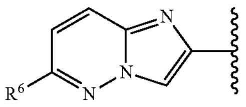 | $CH_3$ | 1 | 1 |
| 110 | 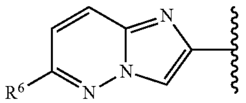 | $CH_3$ | 2 | 1 |
| 111 | 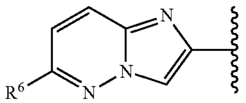 | CH | 3 | 1 |
| 112 | 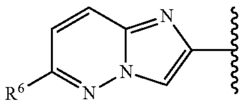 | $CH_3$ | 2 | 2 |
| 113 | 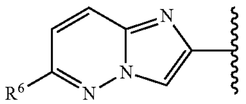 | $CH_3$ | 3 | 2 |
| 114 | 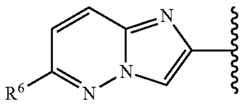 | $CH_3$ | 4 | 1 |
| 115 | 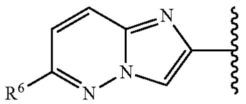 | Cl | 1 | 1 |
| 116 | 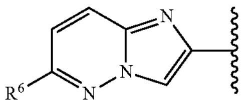 | Cl | 2 | 1 |
| 117 | 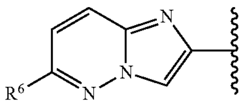 | Cl | 3 | 1 |
TABLE 1-continued
| Entry | $R^2$ | $R^3$ | n | m |
|---|---|---|---|---|
| 118 | 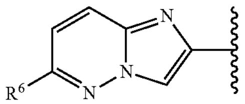 | Cl | 2 | 2 |
| 119 | 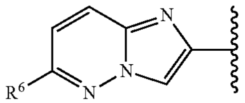 | Cl | 3 | 2 |
| 120 | 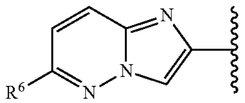 | Cl | 4 | 1 |
| 121 | 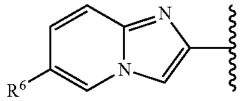 | $CH_3$ | 1 | 1 |
| 122 | 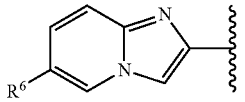 | $CH_3$ | 2 | 1 |
| 123 | 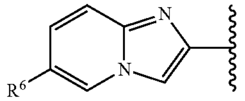 | $CH_3$ | 3 | 1 |
| 124 | 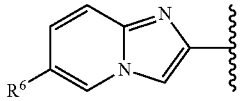 | $CH_3$ | 2 | 2 |
| 125 | 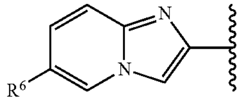 | $CH_3$ | 3 | 2 |
| 126 | 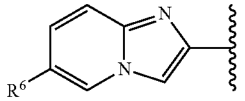 | $CH_3$ | 4 | 1 |
| 127 | 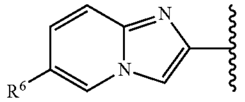 | Cl | 1 | 1 |
| 128 | 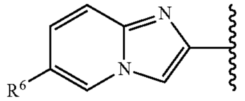 | Cl | 2 | 1 |
| 129 | 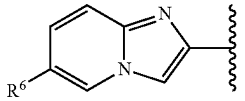 | Cl | 3 | 1 |
| 130 | 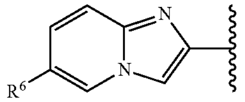 | Cl | 2 | 2 |
| 131 | 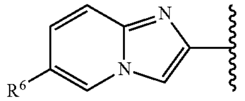 | Cl | 3 | 2 |

TABLE 1-continued
| Entry | $R^2$ | $R^3$ | n | m |
| --- | --- | --- | --- | --- |
| 132 | 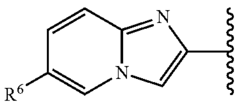 | Cl | 4 | 1 |
| 133 | 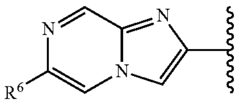 | $CH_3$ | 1 | 1 |
| 134 | 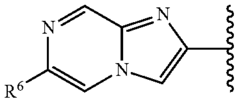 | $CH_3$ | 2 | 1 |
| 135 | 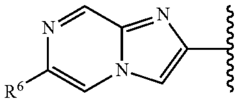 | $CH_3$ | 3 | 1 |
| 136 | 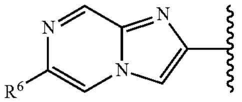 | $CH_3$ | 2 | 2 |
| 137 | 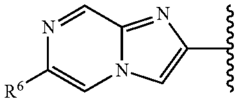 | $CH_3$ | 3 | 2 |
| 138 | 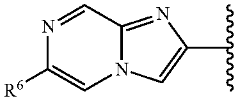 | $CH_3$ | 4 | 1 |
| 139 | 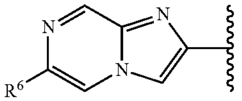 | Cl | 1 | 1 |
| 140 | 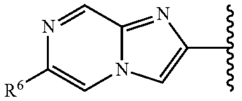 | Cl | 2 | 1 |
| 141 | 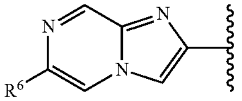 | Cl | 3 | 1 |
| 142 | 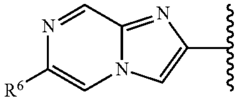 | Cl | 2 | 2 |
| 143 | 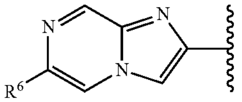 | Cl | 3 | 2 |
| 144 | 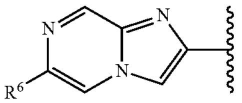 | Cl | 4 | 1 |
Compounds of the present disclosure include compounds having the formula (LIII) or a pharmaceutically acceptable salt form thereof:
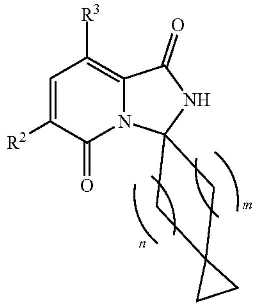
(LIII)
wherein non-limiting examples of $R^1$, $R^2$, and m are defined herein below in Table 2.
TABLE 2
| Entry | R3 | R2 | m | n |
| --- | --- | --- | --- | --- |
| 1 | $CH_3$ | 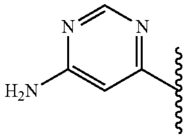 [SMILES: *c1cc(N)ncn1] | 1 | 1 |
| 2 | $CH_3$ | 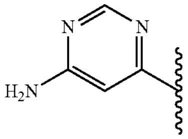 [SMILES: *c1cc(N)ncn1] | 2 | 1 |
| 3 | $CH_3$ | 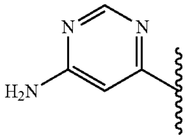 [SMILES: *c1cc(N)ncn1] | 3 | 1 |
| 4 | $CH_3$ | 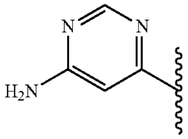 [SMILES: *c1cc(N)ncn1] | 2 | 2 |
| 5 | $CH_3$ | 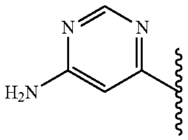 [SMILES: *c1cc(N)ncn1] | 3 | 2 |
| 6 | $CH_3$ | 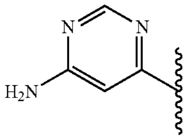 | 4 | 1 |
| 7 | $CH_3$ | 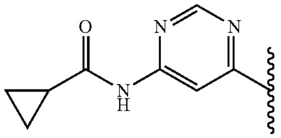 [SMILES: *c1cc(NC(=O)C2CC2)ncn1] | 1 | 1 |

TABLE 2-continued
| Entry | R3 | R2 | m | n |
|---|---|---|---|---|
| 8 | $CH_3$ | 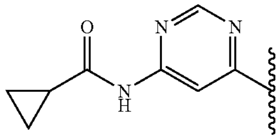 [SMILES: *c1cc(NC(=O)C2CC2)ncn1] | 2 | 1 |
| 9 | $CH_3$ | 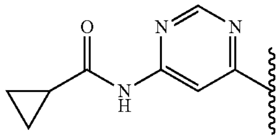 [SMILES: *c1cc(NC(=O)C2CC2)ncn1] | 3 | 1 |
| 10 | $CH_3$ | 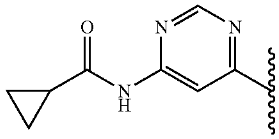 [SMILES: *c1cc(NC(=O)C2CC2)ncn1] | 2 | 2 |
| 11 | $CH_3$ | 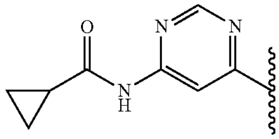 [SMILES: *c1cc(NC(=O)C2CC2)ncn1] | 3 | 2 |
| 12 | $CH_3$ | 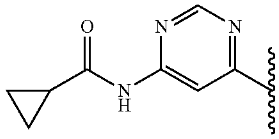 | 4 | 1 |
| 13 | Cl | 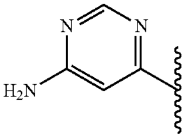 [SMILES: *c1cc(N)ncn1] | 1 | 1 |
| 14 | Cl | 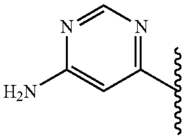 [SMILES: *c1cc(N)ncn1] | 2 | 1 |
| 15 | Cl | 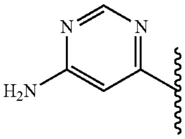 [SMILES: *c1cc(N)ncn1] | 3 | 1 |
| 16 | Cl | 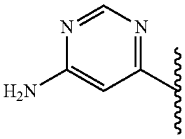 [SMILES: *c1cc(N)ncn1] | 2 | 2 |
| 17 | Cl | 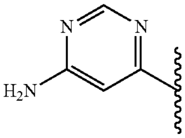 [SMILES: *c1cc(N)ncn1] | 3 | 2 |
| 18 | Cl | 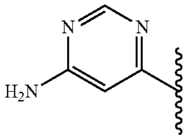 [SMILES: *c1cc(N)ncn1] | 4 | 1 |
| 19 | $CH_3$ | 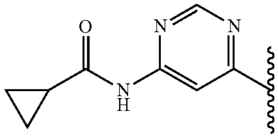 [SMILES: *c1cc(NC(=O)C2CC2)ncn1] | 1 | 1 |
| 20 | $CH_3$ | 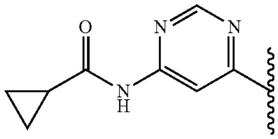 [SMILES: *c1cc(NC(=O)C2CC2)ncn1] | 2 | 1 |
| 21 | $CH_3$ | 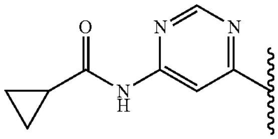 [SMILES: *c1cc(NC(=O)C2CC2)ncn1] | 3 | 1 |
| 22 | $CH_3$ | 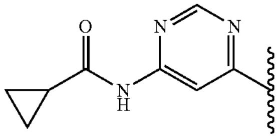 [SMILES: *c1cc(NC(=O)C2CC2)ncn1] | 2 | 2 |
| 23 | $CH_3$ | 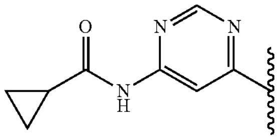 [SMILES: *c1cc(NC(=O)C2CC2)ncn1] | 3 | 2 |
| 24 | $CH_3$ | 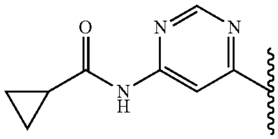 [SMILES: *c1cc(NC(=O)C2CC2)ncn1] | 4 | 1 |
| 25 | Br | 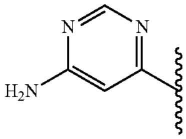 | 1 | 1 |
| 26 | Br | 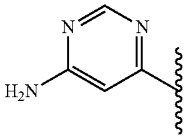 | 2 | 1 |
| 27 | $CH_2F$ | 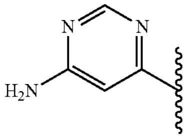 [SMILES: *c1cc(N)ncn1] | 1 | 1 |

TABLE 2-continued
| Entry | R3 | R2 | m | n |
| --- | --- | --- | --- | --- |
| 28 | $CH_2F$ | 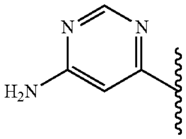 [SMILES: *c1cc(N)ncn1] | 2 | 1 |
| 29 | $CH_2F$ | 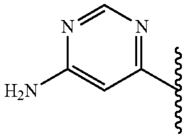 [SMILES: *c1cc(N)ncn1] | 3 | 1 |
| 30 | $CH_2F$ | 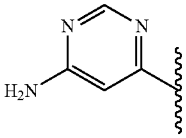 [SMILES: *c1cc(N)ncn1] | 2 | 2 |
| 31 | $CH_2F$ | 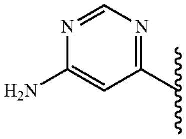 [SMILES: *c1cc(N)ncn1] | 3 | 2 |
| 32 | $CH_2F$ | 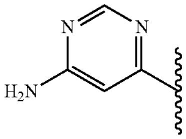 [SMILES: *c1cc(N)ncn1] | 4 | 1 |
| 33 | $CH_2CH_3$ | 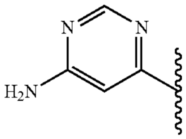 [SMILES: *c1cc(N)ncn1] | 1 | 1 |
| 34 | $CH_2CH_3$ | 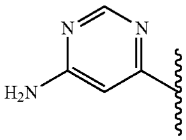 [SMILES: *c1cc(N)ncn1] | 2 | 1 |
| 35 | $CH_2CH_3$ | 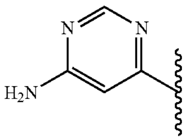 [SMILES: *c1cc(N)ncn1] | 3 | 1 |
| 36 | $CH_2CH_3$ | 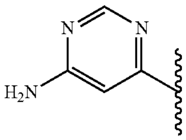 [SMILES: *c1cc(N)ncn1] | 2 | 2 |
| 37 | $CH_2CH_3$ | 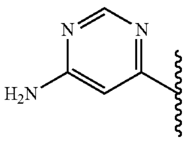 [SMILES: *c1cc(N)ncn1] | 3 | 2 |
| 38 | $CH_2CH_3$ | 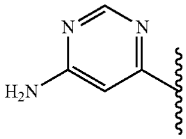 [SMILES: *c1cc(N)ncn1] | 4 | 1 |
| 39 | $CH_2CH_2F$ | 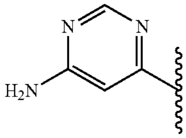 [SMILES: *c1cc(N)ncn1] | 1 | 1 |
| 40 | $CH_2CH_2F$ | 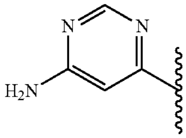 [SMILES: *c1cc(N)ncn1] | 2 | 1 |
| 41 | $CH_2CH_2F$ | 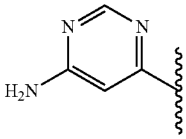 | 3 | 1 |
| 42 | $CH_2CH_2F$ | 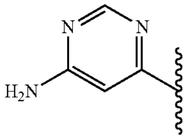 | 2 | 2 |
| 43 | $CH_2CH_2F$ | 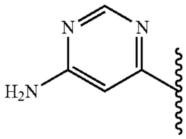 [SMILES: *c1cc(N)ncn1] | 3 | 2 |
| 44 | $CH_2CH_2F$ | 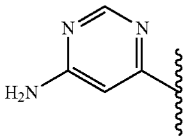 [SMILES: *c1cc(N)ncn1] | 4 | 1 |
| 45 | $CF_2CH_3$ | 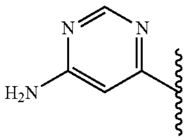 | 1 | 1 |
| 46 | $CF_2CH_3$ | 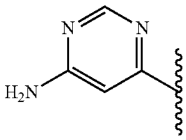 | 2 | 1 |
| 47 | $CF_2CH_3$ | 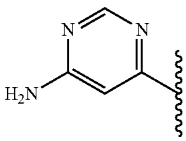 [SMILES: *c1cc(N)ncn1] | 3 | 1 |

TABLE 2-continued

| Entry | R3 | R2 | m | n |
|---|---|---|---|---|
| 48 | $CF_2CH_3$ | 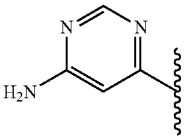 [SMILES: *c1cc(N)ncn1] | 2 | 2 |
| 49 | $CF_2CH_3$ | 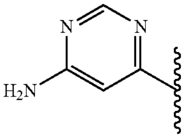 [SMILES: *c1cc(N)ncn1] | 3 | 2 |
| 50 | $CF_2CH_3$ | 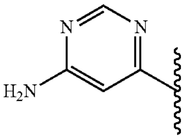 [SMILES: *c1cc(N)ncn1] | 4 | 1 |
| 51 | Br | 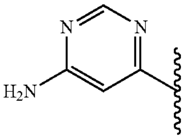 [SMILES: *c1cc(N)ncn1] | 3 | |
| 52 | Br | 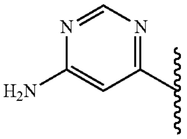 [SMILES: *c1cc(N)ncn1] | 4 | |

Compounds of the present disclosure include compounds having the formula (LIV) or a pharmaceutically acceptable salt form thereof:

(LIV)

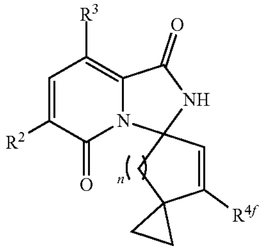

wherein non-limiting examples of $R^1$, $R^2$, and m are defined herein below in Table 3.

TABLE 3

| Entry | $R^3$ | $R^{4f}$ | n | Entry | $R^3$ | $R^{4f}$ | N |
|---|---|---|---|---|---|---|---|
| 1 | $CH_3$ | H | 1 | 19 | Cl | H | 1 |
| 2 | $CH_3$ | $CH_3$ | 1 | 20 | Cl | $CH_3$ | 1 |
| 3 | $CH_3$ | $CH_2CH_3$ | 1 | 21 | Cl | $CH_2CH_3$ | 1 |
| 4 | $CH_3$ | $CH(CH_3)_2$ | 1 | 22 | Cl | $CH(CH_3)_2$ | 1 |
| 5 | $CH_3$ | $CH_2F$ | 1 | 23 | Cl | $CH_2F$ | 1 |
| 6 | $CH_3$ | $CH_2CH_2F$ | 1 | 24 | Cl | $CH_2CH_2F$ | 1 |
| 7 | $CH_3$ | H | 2 | 25 | Cl | H | 2 |
| 8 | $CH_3$ | $CH_3$ | 2 | 29 | Cl | $CH_3$ | 2 |
| 9 | $CH_3$ | $CH_2CH_3$ | 2 | 27 | Cl | $CH_2CH_3$ | 2 |
| 10 | $CH_3$ | $CH(CH_3)_2$ | 2 | 28 | Cl | $CH(CH_3)_2$ | 2 |
| 11 | $CH_3$ | $CH_2F$ | 2 | 29 | Cl | $CH_2F$ | 2 |

TABLE 3-continued

| Entry | $R^3$ | $R^{4f}$ | n | Entry | $R^3$ | $R^{4f}$ | N |
|---|---|---|---|---|---|---|---|
| 12 | $CH_3$ | $CH_2CH_2F$ | 2 | 30 | Cl | $CH_2CH_2F$ | 2 |
| 13 | $CH_3$ | H | 3 | 31 | Cl | H | 3 |
| 14 | $CH_3$ | $CH_3$ | 3 | 32 | Cl | $CH_3$ | 3 |
| 15 | $CH_3$ | $CH_2CH_3$ | 3 | 33 | Cl | $CH_2CH_3$ | 3 |
| 16 | $CH_3$ | $CH(CH_3)_2$ | 3 | 34 | Cl | $CH(CH_3)_2$ | 3 |
| 17 | $CH_3$ | $CH_2F$ | 3 | 35 | Cl | $CH_2F$ | 3 |
| 18 | $CH_3$ | $CH_2CH_2F$ | 3 | 36 | Cl | $CH_2CH_2F$ | 3 |

For the purposes of demonstrating the manner in which the compounds of the present disclosure are named and referred to herein, the compound having the formula:

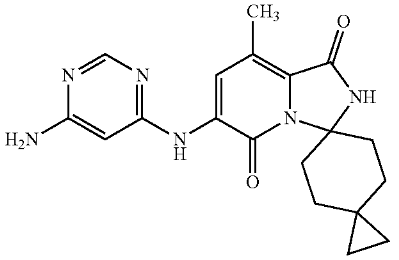 [SMILES: Cc1cc(Nc2cc(N)ncn2)c(=O)n2c1C(=O)NC21CCC2(CC2)CC1]

has the chemical name 6"-((6-aminopyrimidin-4-yl)amino)-8"-methyl-2"H-dispiro[cyclopropane-1,1'-cyclohexane-4',3"-imidazo[1,5-a]pyridine]-1",5"-dione.

For the purposes of the present disclosure, a compound depicted by the racemic formula, for example:

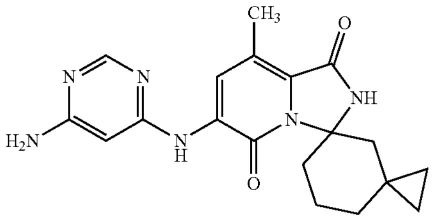 [SMILES: Cc1cc(Nc2cc(N)ncn2)c(=O)n2c1C(=O)NC21CCCC2(CC2)C1]

will stand equally well for either of the two enantiomers having the formula:

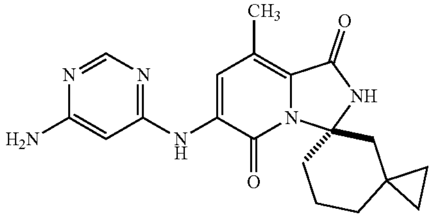

or the formula:

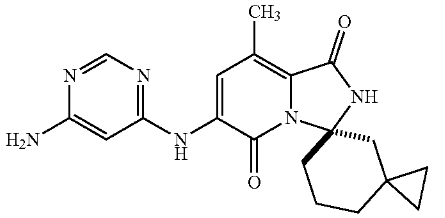

or mixtures thereof, or in the case where a second chiral center is present, all diastereomers.

For the purposes of the present disclosure, a compound depicted by the racemic formula will stand equally well for either of the two enantiomers or mixtures thereof, or in the case where a second chiral center is present, all diastereomers.

In all of the embodiments provided herein, examples of suitable optional substituents are not intended to limit the scope of the claimed disclosure. The compounds of the disclosure may contain any of the substituents, or combinations of substituents, provided herein.

Process

The present disclosure further relates to a process for preparing the MNK inhibitors of the present disclosure.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present disclosure can be prepared according to the method illustrated in the General Synthetic Schemes.

General Synthetic Schemes for Preparation of Compounds

The reagents used in the preparation of the compounds of this disclosure can be either commercially obtained or can be prepared by standard procedures described in the literature. In accordance with this disclosure, compounds in the genus may be produced by one of the following reaction schemes.

Compounds of formula (I) may be prepared according to the process outlined in Schemes 1-18.

Scheme 1

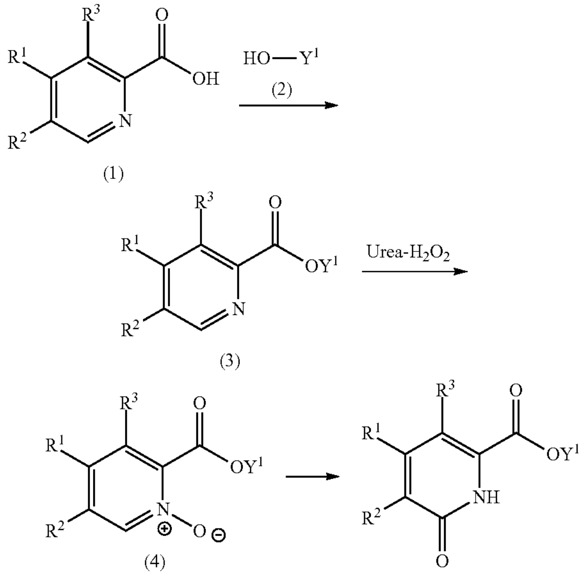

(1) (3) (4) (5)

A compound of the formula (1), a known compound or a compound prepared by known methods, is reacted with a compound of the formula (2), a known compound or a compound prepared by known methods wherein $Y^1$ is $C_{1-6}$ alkyl, in the presence of an acid such as hydrochloric acid, sulfuric acid, acetic acid, trifluoroacetic acid, and the like, in a solvent such as ethanol, methanol, tetrahydrofuran, 1,4-dioxane, methylene chloride, and the like, optionally with heating, optionally with microwave irradiation to provide a compound of the formula (3). A compound of the formula (3) is reacted with urea hydrogen peroxide in the presence of an acid anhydride such as trifluoroacetic anhydride, acetic anhydride, and the like, in a solvent such as methylene chloride, chloroform, dichloroethane, tetrahydrofuran, 1,4-dioxane, and the like, optionally with heating, optionally with microwave irradiation to provide a compound of the formula (4). A compound of the formula (4) is reacted with an acid anhydride such as trifluoroacetic anhydride, acetic anhydride, and the like, in a solvent such as N,N-dimethylformamide, N,N-dimethylacetamide, dimethyl sulfoxide, methylene chloride, chloroform, dichloroethane, tetrahydrofuran, 1,4-dioxane, and the like, optionally with heating, optionally with microwave irradiation to provide a compound of the formula (5).

Scheme 2

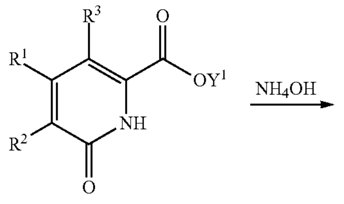

(5)

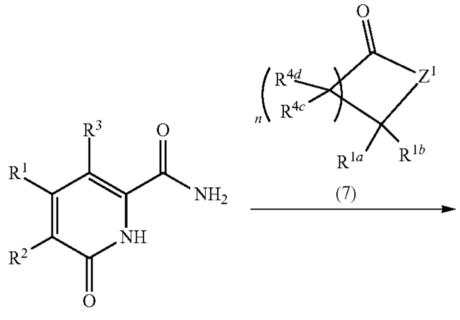

(7)

(6)

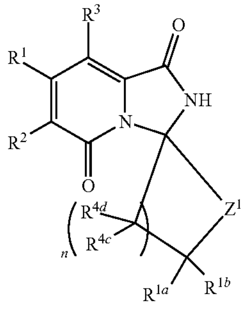

(8)

A compound of the formula (5) is reacted with ammonium hydroxide, optionally in the presence of a solvent such as methanol, ethanol, N,N-dimethylformamide, N,N-dimethylacetamide, dimethyl sulfoxide, methylene chloride, chloroform, dichloroethane, tetrahydrofuran, 1,4-dioxane, and the like, optionally with heating, optionally with microwave irradiation to provide a compound of the formula (6). A compound of the formula (6) is reacted with a compound of the formula (7), a known compound or compound prepared by known methods, in the presence of an acid such as hydrochloric acid, sulfuric acid, acetic acid, trifluoroacetic acid, and the like, in a solvent such as ethanol, methanol, tetrahydrofuran, 1,4-dioxane, methylene chloride, and the like, optionally with heating, optionally with microwave irradiation to provide a compound of the formula (8).

Scheme 3

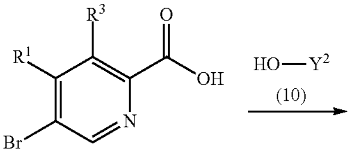

(9)

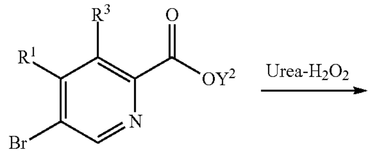

(11)

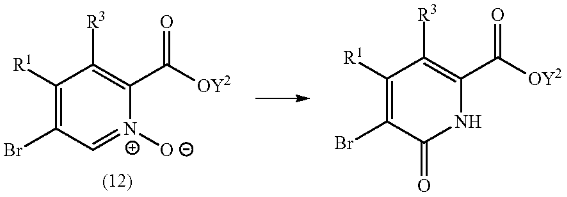

(12)

(13)

A compound of the formula (9), a known compound or a compound prepared by known methods, is reacted with a compound of the formula (10), a known compound or a compound prepared by known methods wherein $Y^2$ is $C_{1-6}$ alkyl, in the presence of an acid such as hydrochloric acid, sulfuric acid, acetic acid, trifluoroacetic acid, and the like, in a solvent such as ethanol, methanol, tetrahydrofuran, 1,4-dioxane, methylene chloride, and the like, optionally with heating, optionally with microwave irradiation to provide a compound of the formula (11). A compound of the formula (11) is reacted with urea hydrogen peroxide in the presence of an acid anhydride such as trifluoroacetic anhydride, acetic anhydride, and the like, in a solvent such as methylene chloride, chloroform, dichloroethane, tetrahydrofuran, 1,4-dioxane, and the like, optionally with heating, optionally with microwave irradiation to provide a compound of the formula (12). A compound of the formula (12) is reacted with an acid anhydride such as trifluoroacetic anhydride, acetic anhydride, and the like, in a solvent such as N,N-dimethylformamide, N,N-dimethylacetamide, dimethyl sulfoxide, methylene chloride, chloroform, dichloroethane, tetrahydrofuran, 1,4-dioxane, and the like, optionally with heating, optionally with microwave irradiation to provide a compound of the formula (13).

Scheme 4

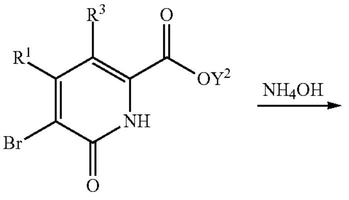

(13)

-continued

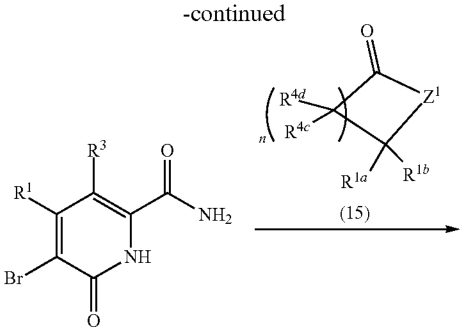

(15)

(14)

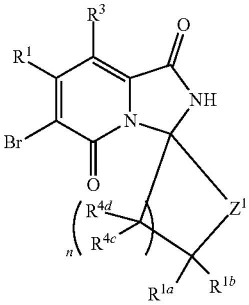

(16)

A compound of the formula (13) is reacted with ammonium hydroxide, optionally in the presence of a solvent such as methanol, ethanol, N,N-dimethylformamide, N,N-dimethylacetamide, dimethyl sulfoxide, methylene chloride, chloroform, dichloroethane, tetrahydrofuran, 1,4-dioxane, and the like, optionally with heating, optionally with microwave irradiation to provide a compound of the formula (14). A compound of the formula (14) is reacted with a compound of the formula (15), a known compound or compound prepared by known methods, in the presence of an acid such as hydrochloric acid, sulfuric acid, acetic acid, trifluoroacetic acid, and the like, in a solvent such as ethanol, methanol, tetrahydrofuran, 1,4-dioxane, methylene chloride, and the like, optionally with heating, optionally with microwave irradiation to provide a compound of the formula (16).

-continued

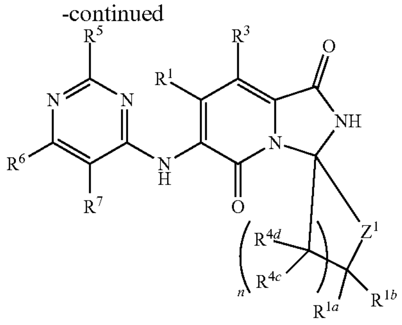

(18)

A compound of the formula (16) is reacted with a compound of the formula (17), a known compound or a compound prepared by known methods, in the presence of a palladium catalyst such as palladium (II) acetate, tetrakis (triphenylphosphine)palladium(0), dichlorobis(triphenylphosphine)palladium(II), palladium on carbon, bis(acetonitrile)dichloro palladium(II), 1,1'-bis (diphenylphosphino)ferrocene]dichloropalladium(II), bispalladium-tri(1,3-dibenzylidene)acetone, and the like, optionally in the presence of an organophosphine such as 4,5-Bis(diphenylphosphino)-9,9-dimethylxanthene, dicyclohexyl(2',6'-dimethoxybiphenyl-2-yl)phosphine, 2-dicyclo hexylphosphino-2',6'-dimethoxybiphenyl, 2-dicyclohexylphosphino-2'-(N,N-dimethylamino) biphenyl, 2-dicyclohexylphosphino-2',4',6'-triisopropylbiphenyl, 2-di-tert-butylphosphino-2',4',6'-triisopropylbiphenyl, (2-biphenyl)dicyclohexylphosphine, (2-biphenyl)di-tert-butylphosphine, 2-dicyclohexylphosphino-2',6'-diisopropoxybiphenyl, 2-di-tert-butylphosphino-3,4,5,6-tetramethyl-2',4',6'-triisopropyl-1,1'-biphenyl, Sodium 2'-dicyclohexylphosphino-2,6-dimethoxy-1,1'-biphenyl-3-sulfonate, 2-di-tert-butylphosphino-2'-methylbiphenyl, 2-dicyclohexylphosphino-2'-methylbiphenyl, 2'-(di-tert-butylphosphino)-N,N-dimethylbiphenyl-2-amine, 2'-(diphenylphosphino)-N,N'-dimethyl-(1,1'-biphenyl)-2-amine, and the like, in the presence of a base such as sodium carbonate, lithium carbonate, potassium carbonate, cesium carbonate, sodium hydroxide, lithium hydroxide, potassium hydroxide, triethylamine, N,N-diisopropylethylamine, pyridine, 2,6-dimethylpyridine, and the like, in a solvent such as tetrahydrofuran, 1,4-dioxane, acetonitrile, methylene chloride, chloroform, 1,2-dichloroethane, 1,2-dimethoxyethane, and the like, optionally in the presence of water, optionally with heating, optionally with microwave irradiation to provide a compound of the formula (18).

Scheme 5

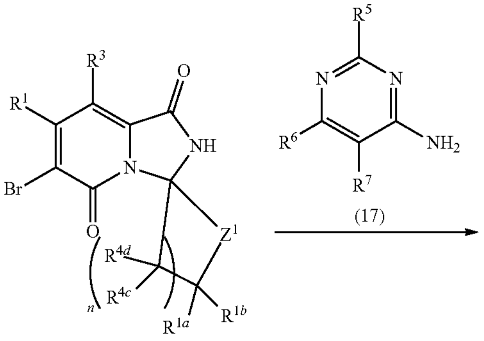

(17)

(16)

Scheme 6

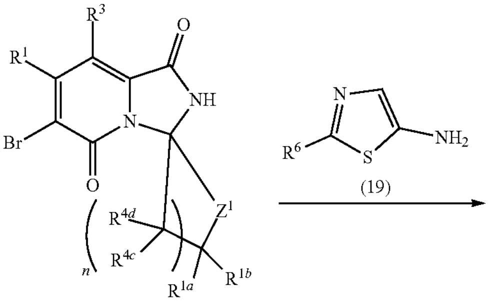

(19)

(16)

-continued

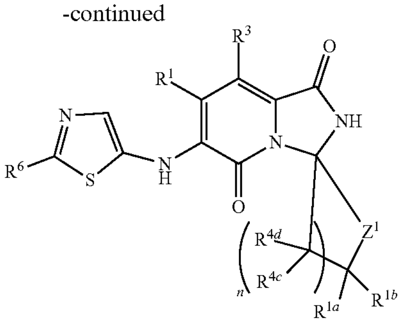

(20)

A compound of the formula (16) is reacted with a compound of the formula (19), a known compound or a compound prepared by known methods, in the presence of a palladium catalyst such as palladium (II) acetate, tetrakis (triphenylphosphine)palladium(0), dichlorobis(triphenylphosphine)palladium(II), palladium on carbon, bis(acetonitrile)dichloro palladium(II), 1,1'-bis (diphenylphosphino)ferrocene]dichloropalladium(II), bispalladium-tri(1,3-dibenzylidene)acetone, and the like, optionally in the presence of an organophosphine such as 4,5-Bis(diphenylphosphino)-9,9-dimethylxanthene, dicyclohexyl(2',6'-dimethoxybiphenyl-2-yl)phosphine, 2-dicyclo hexylphosphino-2',6'-dimethoxybiphenyl, 2-dicyclohexylphosphino-2'-(N,N-dimethylamino) biphenyl, 2-dicyclohexylphosphino-2',4',6'-triisopropylbiphenyl, 2-di-tert-butylphosphino-2',4',6'-triisopropylbiphenyl, (2-biphenyl)dicyclohexylphosphine, (2-biphenyl)di-tert-butylphosphine, 2-dicyclohexylphosphino-2',6'-diisopropoxybiphenyl, 2-di-tert-butylphosphino-3,4,5,6-tetramethyl-2',4',6'-triisopropyl-1,1'-biphenyl, Sodium 2'-dicyclohexylphosphino-2,6-dimethoxy-1,1'-biphenyl-3-sulfonate, 2-di-tert-butylphosphino-2'-methylbiphenyl, 2-dicyclohexylphosphino-2'-methylbiphenyl, 2'-(di-tert-butylphosphino)-N,N-dimethylbiphenyl-2-amine, 2'-(diphenylphosphino)-N,N'-dimethyl-(1,1'-biphenyl)-2-amine, and the like, in the presence of a base such as sodium carbonate, lithium carbonate, potassium carbonate, cesium carbonate, sodium hydroxide, lithium hydroxide, potassium hydroxide, triethylamine, N,N-diisopropylethylamine, pyridine, 2,6-dimethylpyridine, and the like, in a solvent such as tetrahydrofuran, 1,4-dioxane, acetonitrile, methylene chloride, chloroform, 1,2-dichloroethane, 1,2-dimethoxyethane, and the like, optionally in the presence of water, optionally with heating, optionally with microwave irradiation to provide a compound of the formula (20).

Scheme 7

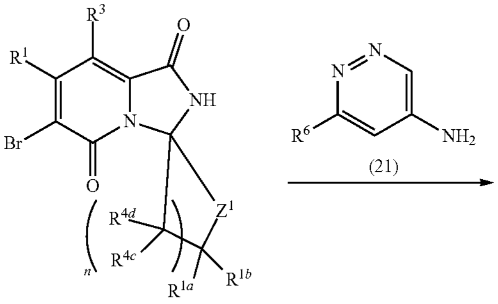

(16)

(21)

-continued

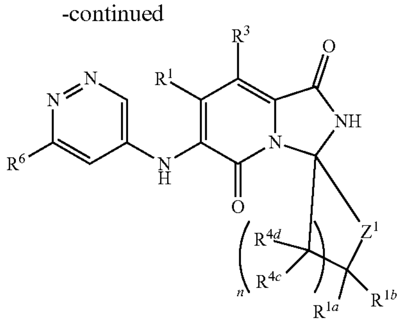

(22)

A compound of the formula (16) is reacted with a compound of the formula (21), a known compound or a compound prepared by known methods, in the presence of a palladium catalyst such as palladium (II) acetate, tetrakis (triphenylphosphine)palladium(0), dichlorobis(triphenylphosphine)palladium(II), palladium on carbon, bis(acetonitrile)dichloro palladium(II), 1,1'-bis (diphenylphosphino)ferrocene]dichloropalladium(II), bispalladium-tri(1,3-dibenzylidene)acetone, and the like, optionally in the presence of an organophosphine such as 4,5-Bis(diphenylphosphino)-9,9-dimethylxanthene, dicyclohexyl(2',6'-dimethoxybiphenyl-2-yl)phosphine, 2-dicyclo hexylphosphino-2',6'-dimethoxybiphenyl, 2-dicyclohexylphosphino-2'-(N,N-dimethylamino) biphenyl, 2-dicyclohexylphosphino-2',4',6'-triisopropylbiphenyl, 2-di-tert-butylphosphino-2',4',6'-triisopropylbiphenyl, (2-biphenyl)dicyclohexylphosphine, (2-biphenyl)di-tert-butylphosphine, 2-dicyclohexylphosphino-2',6'-diisopropoxybiphenyl, 2-di-tert-butylphosphino-3,4,5,6-tetramethyl-2',4',6'-triisopropyl-1,1'-biphenyl, Sodium 2'-dicyclohexylphosphino-2,6-dimethoxy-1,1'-biphenyl-3-sulfonate, 2-di-tert-butylphosphino-2'-methylbiphenyl, 2-dicyclohexylphosphino-2'-methylbiphenyl, 2'-(di-tert-butylphosphino)-N,N-dimethylbiphenyl-2-amine, 2'-(diphenylphosphino)-N,N'-dimethyl-(1,1'-biphenyl)-2-amine, and the like, in the presence of a base such as sodium carbonate, lithium carbonate, potassium carbonate, cesium carbonate, sodium hydroxide, lithium hydroxide, potassium hydroxide, triethylamine, N,N-diisopropylethylamine, pyridine, 2,6-dimethylpyridine, and the like, in a solvent such as tetrahydrofuran, 1,4-dioxane, acetonitrile, methylene chloride, chloroform, 1,2-dichloroethane, 1,2-dimethoxyethane, and the like, optionally in the presence of water, optionally with heating, optionally with microwave irradiation to provide a compound of the formula (22).

Scheme 8

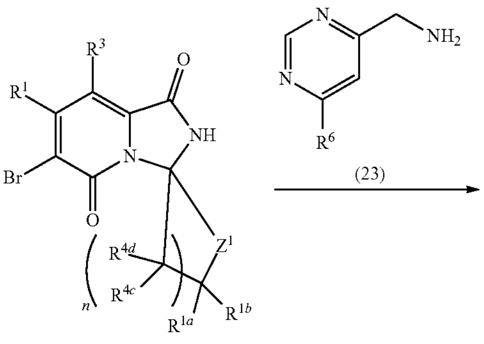

(16)

(23)

-continued

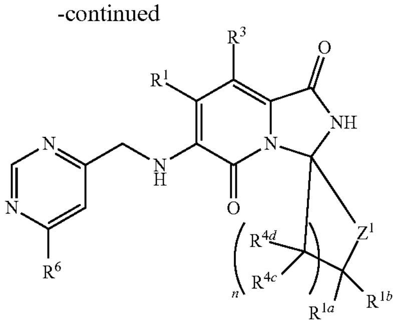

(24)

A compound of the formula (16) is reacted with a compound of the formula (23), a known compound or a compound prepared by known methods, in the presence of a palladium catalyst such as palladium (II) acetate, tetrakis (triphenylphosphine)palladium(0), dichlorobis(triphenylphosphine)palladium(II), palladium on carbon, bis(acetonitrile)dichloro palladium(II), 1,1'-bis (diphenylphosphino)ferrocene]dichloropalladium(II), bispalladium-tri(1,3-dibenzylidene)acetone, and the like, optionally in the presence of an organophosphine such as 4,5-Bis(diphenylphosphino)-9,9-dimethylxanthene, dicyclohexyl(2',6'-dimethoxybiphenyl-2-yl)phosphine, 2-dicyclo hexylphosphino-2',6'-dimethoxybiphenyl, 2-dicyclohexylphosphino-2'-(N,N-dimethylamino) biphenyl, 2-dicyclohexylphosphino-2',4',6'-triisopropylbiphenyl, 2-di-tert-butylphosphino-2',4',6'-triisopropylbiphenyl, (2-biphenyl)dicyclohexylphosphine, (2-biphenyl)di-tert-butylphosphine, 2-dicyclohexylphosphino-2',6'-diisopropoxybiphenyl, 2-di-tert-butylphosphino-3,4,5,6-tetramethyl-2',4',6'-triisopropyl-1,1'-biphenyl, Sodium 2'-dicyclohexylphosphino-2,6-dimethoxy-1,1'-biphenyl-3-sulfonate, 2-di-tert-butylphosphino-2'-methylbiphenyl, 2-dicyclohexylphosphino-2'-methylbiphenyl, 2'-(di-tert-butylphosphino)-N,N-dimethylbiphenyl-2-amine, 2'-(diphenylphosphino)-N,N'-dimethyl-(1,1'-biphenyl)-2-amine, and the like, in the presence of a base such as sodium carbonate, lithium carbonate, potassium carbonate, cesium carbonate, sodium hydroxide, lithium hydroxide, potassium hydroxide, triethylamine, N,N-diisopropylethylamine, pyridine, 2,6-dimethylpyridine, and the like, in a solvent such as tetrahydrofuran, 1,4-dioxane, acetonitrile, methylene chloride, chloroform, 1,2-dichloroethane, 1,2-dimethoxyethane, and the like, optionally in the presence of water, optionally with heating, optionally with microwave irradiation to provide a compound of the formula (24).

Scheme 9

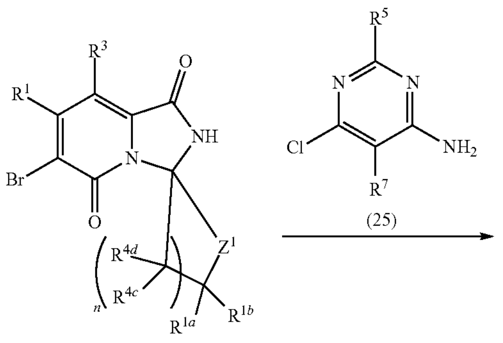

(16)

-continued

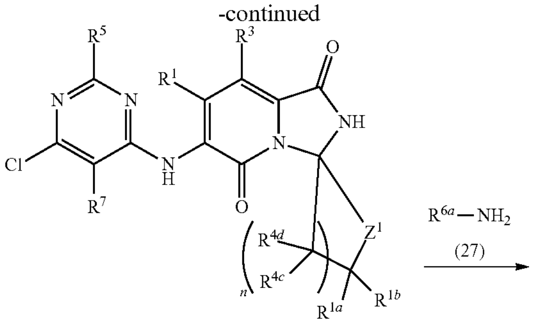

(26)

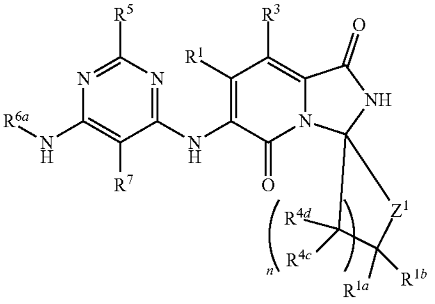

(28)

A compound of the formula (16) is reacted with a compound of the formula (25), a known compound or a compound prepared by known methods, in the presence of a palladium catalyst such as palladium (II) acetate, tetrakis (triphenylphosphine)palladium(0), dichlorobis(triphenylphosphine)palladium(II), palladium on carbon, bis(acetonitrile)dichloro palladium(II), 1,1'-bis (diphenylphosphino)ferrocene]dichloropalladium(II), bispalladium-tri(1,3-dibenzylidene)acetone, and the like, optionally in the presence of an organophosphine such as 4,5-Bis(diphenylphosphino)-9,9-dimethylxanthene, dicyclohexyl(2',6'-dimethoxybiphenyl-2-yl)phosphine, 2-dicyclo hexylphosphino-2',6'-dimethoxybiphenyl, 2-dicyclohexylphosphino-2'-(N,N-dimethylamino) biphenyl, 2-dicyclohexylphosphino-2',4',6'-triisopropylbiphenyl, 2-di-tert-butylphosphino-2',4',6'-triisopropylbiphenyl, (2-biphenyl)dicyclohexylphosphine, (2-biphenyl)di-tert-butylphosphine, 2-dicyclohexylphosphino-2',6'-diisopropoxybiphenyl, 2-di-tert-butylphosphino-3,4,5,6-tetramethyl-2',4',6'-triisopropyl-1,1'-biphenyl, Sodium 2'-dicyclohexylphosphino-2,6-dimethoxy-1,1'-biphenyl-3-sulfonate, 2-di-tert-butylphosphino-2'-methylbiphenyl, 2-dicyclohexylphosphino-2'-methylbiphenyl, 2'-(di-tert-butylphosphino)-N,N-dimethylbiphenyl-2-amine, 2'-(diphenylphosphino)-N,N'-dimethyl-(1,1'-biphenyl)-2-amine, and the like, in the presence of a base such as sodium carbonate, lithium carbonate, potassium carbonate, cesium carbonate, sodium hydroxide, lithium hydroxide, potassium hydroxide, triethylamine, N,N-diisopropylethylamine, pyridine, 2,6-dimethylpyridine, and the like, in a solvent such as tetrahydrofuran, 1,4-dioxane, acetonitrile, methylene chloride, chloroform, 1,2-dichloroethane, 1,2-dimethoxyethane, and the like, optionally in the presence of water, optionally with heating, optionally with microwave irradiation to provide a compound of the formula (26). A compound of the formula (26) is reacted with a compound of the formula (27), a known compound or a compound prepared by known methods, in the presence of a base such as triethylamine, N,N-diisopropylethylamine, pyridine, 2,6-dimethylpyridine, and the like, in a solvent such as methanol, ethanol, isopropanol, N,N-dimethylformamide, N,N-dimethylacetamide, dimethyl sulfoxide, tetrahydrofuran, 1,4-dioxane, and the like, optionally with heating, optionally with microwave irradiation to provide a compound of the formula (28).

Scheme 10

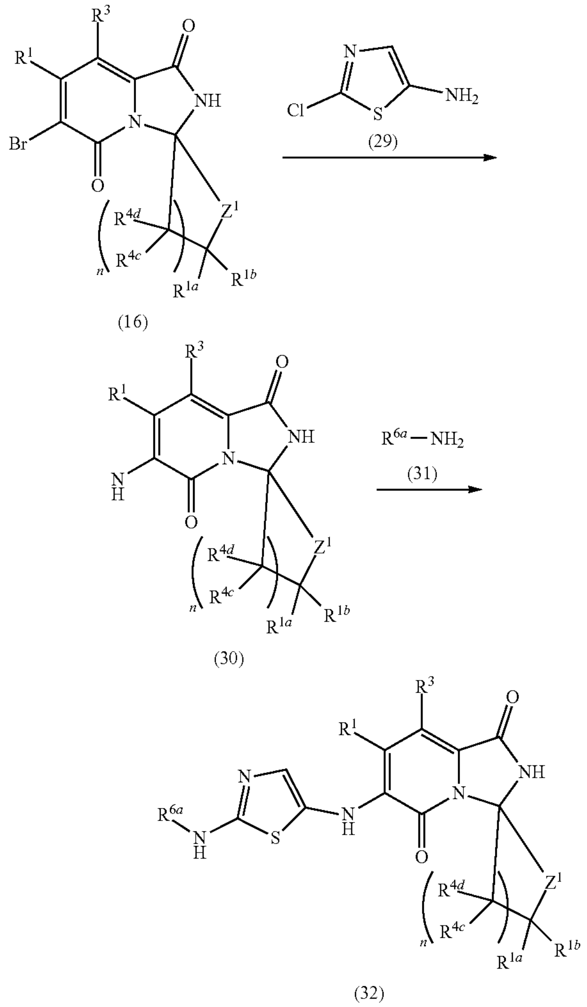

(16) (30) (32)

A compound of the formula (16) is reacted with a compound of the formula (29), a known compound or a compound prepared by known methods, in the presence of a palladium catalyst such as palladium (II) acetate, tetrakis (triphenylphosphine)palladium(0), dichlorobis(triphenylphosphine)palladium(II), palladium on carbon, bis(acetonitrile)dichloro palladium(II), 1,1'-bis (diphenylphosphino)ferrocene]dichloropalladium(II), bispalladium-tri(1,3-dibenzylidene)acetone, and the like, optionally in the presence of an organophosphine such as 4,5-Bis(diphenylphosphino)-9,9-dimethylxanthene, dicyclohexyl(2',6'-dimethoxybiphenyl-2-yl)phosphine, 2-dicyclo hexylphosphino-2',6'-dimethoxybiphenyl, 2-dicyclohexylphosphino-2'-(N,N-dimethylamino) biphenyl, 2-dicyclohexylphosphino-2',4',6'-triisopropylbiphenyl, 2-di-tert-butylphosphino-2',4',6'-triisopropylbiphenyl, (2-biphenyl)dicyclohexylphosphine, (2-biphenyl)di-tert-butylphosphine, 2-dicyclohexylphosphino-2',6'-diisopropoxybiphenyl, 2-di-tert-butylphosphino-3,4,5,6-tetramethyl-2',4',6'-triisopropyl-1,1'-biphenyl, Sodium 2'-dicyclohexylphosphino-2,6-dimethoxy-1,1'-biphenyl-3-sulfonate, 2-di-tert-butylphosphino-2'-methylbiphenyl, 2-dicyclohexylphosphino-2'-methylbiphenyl, 2'-(di-tert-butylphosphino)-N,N-dimethylbiphenyl-2-amine, 2'-(diphenylphosphino)-N,N'-dimethyl-(1,1'-biphenyl)-2-amine, and the like, in the presence of a base such as sodium carbonate, lithium carbonate, potassium carbonate, cesium carbonate, sodium hydroxide, lithium hydroxide, potassium hydroxide, triethylamine, N,N-diisopropylethylamine, pyridine, 2,6-dimethylpyridine, and the like, in a solvent such as tetrahydrofuran, 1,4-dioxane, acetonitrile, methylene chloride, chloroform, 1,2-dichloroethane, 1,2-dimethoxyethane, and the like, optionally in the presence of water, optionally with heating, optionally with microwave irradiation to provide a compound of the formula (30). A compound of the formula (30) is reacted with a compound of the formula (31), a known compound or a compound prepared by known methods, in the presence of a base such as triethylamine, N,N-diisopropylethylamine, pyridine, 2,6-dimethylpyridine, and the like, in a solvent such as methanol, ethanol, isopropanol, N,N-dimethylformamide, N,N-dimethylacetamide, dimethyl sulfoxide, tetrahydrofuran, 1,4-dioxane, and the like, optionally with heating, optionally with microwave irradiation to provide a compound of the formula (32).

Scheme 11

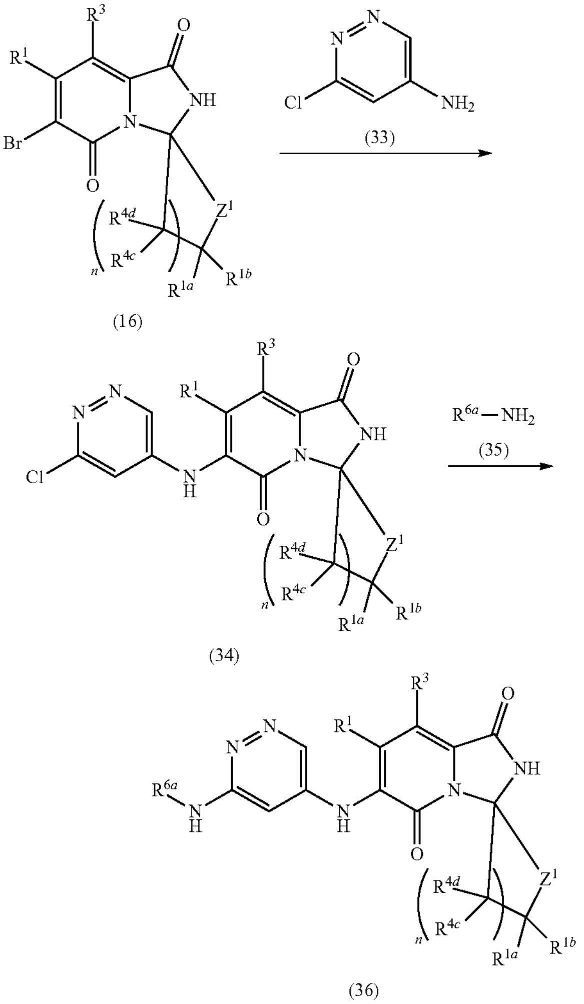

(16) (34) (36)

A compound of the formula (16) is reacted with a compound of the formula (33), a known compound or a compound prepared by known methods, in the presence of a palladium catalyst such as palladium (II) acetate, tetrakis (triphenylphosphine)palladium(0), dichlorobis(triphenylphosphine)palladium(II), palladium on carbon, bis(acetonitrile)dichloro palladium(II), 1,1'-bis (diphenylphosphino)ferrocene]dichloropalladium(II), bispalladium-tri(1,3-dibenzylidene)acetone, and the like, optionally in the presence of an organophosphine such as 4,5-Bis(diphenylphosphino)-9,9-dimethylxanthene, dicyclohexyl(2',6'-dimethoxybiphenyl-2-yl)phosphine, 2-dicyclo hexylphosphino-2',6'-dimethoxybiphenyl, 2-dicyclohexylphosphino-2'-(N,N-dimethylamino) biphenyl, 2-dicyclohexylphosphino-2',4',6'-triisopropylbiphenyl, 2-di-tert-butylphosphino-2',4',6'-triisopropylbiphenyl, (2-biphenyl)dicyclohexylphosphine, (2-biphenyl)di-tert-butylphosphine, 2-dicyclohexylphosphino-2',6'-diisopropoxybiphenyl, 2-di-tert-butylphosphino-3,4,5,6-tetramethyl-2',4',6'-triisopropyl-1,1'-biphenyl, Sodium 2'-dicyclohexylphosphino-2,6-dimethoxy-1,1'-biphenyl-3-sulfonate, 2-di-tert-butylphosphino-2'-methylbiphenyl, 2-dicyclohexylphosphino-2'-methylbiphenyl, 2'-(di-tert-butylphosphino)-N,N-dimethylbiphenyl-2-amine, 2'-(diphenylphosphino)-N,N'-dimethyl-(1,1'-biphenyl)-2-amine, and the like, in the presence of a base such as sodium carbonate, lithium carbonate, potassium carbonate, cesium carbonate, sodium hydroxide, lithium hydroxide, potassium hydroxide, triethylamine, N,N-diisopropylethylamine, pyridine, 2,6-dimethylpyridine, and the like, in a solvent such as tetrahydrofuran, 1,4-dioxane, acetonitrile, methylene chloride, chloroform, 1,2-dichloroethane, 1,2-dimethoxyethane, and the like, optionally in the presence of water, optionally with heating, optionally with microwave irradiation to provide a compound of the formula (34). A compound of the formula (34) is reacted with a compound of the formula (35), a known compound or a compound prepared by known methods, in the presence of a base such as triethylamine, N,N-diisopropylethylamine, pyridine, 2,6-dimethylpyridine, and the like, in a solvent such as methanol, ethanol, isopropanol, N,N-dimethylformamide, N,N-dimethylacetamide, dimethyl sulfoxide, tetrahydrofuran, 1,4-dioxane, and the like, optionally with heating, optionally with microwave irradiation to provide a compound of the formula (36).

Scheme 12

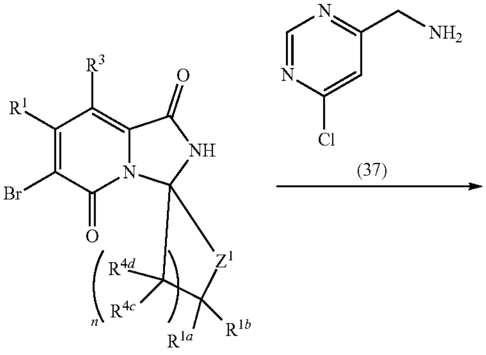

(16)

(37)

-continued

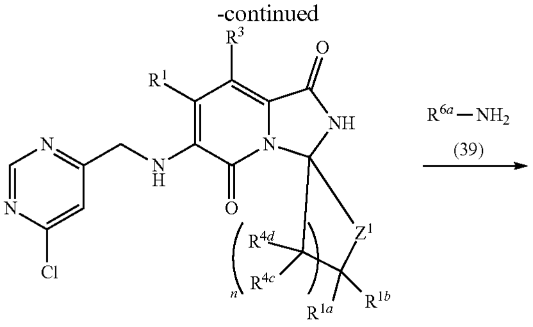

(38)

(39)

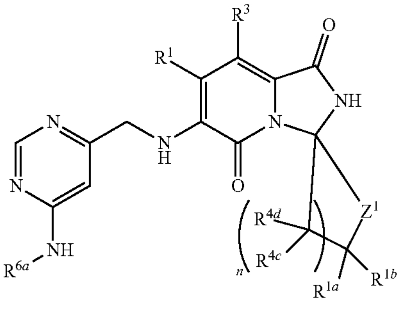

(40)

A compound of the formula (16) is reacted with a compound of the formula (37), a known compound or a compound prepared by known methods, in the presence of a palladium catalyst such as palladium (II) acetate, tetrakis (triphenylphosphine)palladium(0), dichlorobis(triphenylphosphine)palladium(II), palladium on carbon, bis(acetonitrile)dichloro palladium(II), 1,1'-bis (diphenylphosphino)ferrocene]dichloropalladium(II), bispalladium-tri(1,3-dibenzylidene)acetone, and the like, optionally in the presence of an organophosphine such as 4,5-Bis(diphenylphosphino)-9,9-dimethylxanthene, dicyclohexyl(2',6'-dimethoxybiphenyl-2-yl)phosphine, 2-dicyclo hexylphosphino-2',6'-dimethoxybiphenyl, 2-dicyclohexylphosphino-2'-(N,N-dimethylamino) biphenyl, 2-dicyclohexylphosphino-2',4',6'-triisopropylbiphenyl, 2-di-tert-butylphosphino-2',4',6'-triisopropylbiphenyl, (2-biphenyl)dicyclohexylphosphine, (2-biphenyl)di-tert-butylphosphine, 2-dicyclohexylphosphino-2',6'-diisopropoxybiphenyl, 2-di-tert-butylphosphino-3,4,5,6-tetramethyl-2',4',6'-triisopropyl-1,1'-biphenyl, Sodium 2'-dicyclohexylphosphino-2,6-dimethoxy-1,1'-biphenyl-3-sulfonate, 2-di-tert-butylphosphino-2'-methylbiphenyl, 2-dicyclohexylphosphino-2'-methylbiphenyl, 2'-(di-tert-butylphosphino)-N,N-dimethylbiphenyl-2-amine, 2'-(diphenylphosphino)-N,N'-dimethyl-(1,1'-biphenyl)-2-amine, and the like, in the presence of a base such as sodium carbonate, lithium carbonate, potassium carbonate, cesium carbonate, sodium hydroxide, lithium hydroxide, potassium hydroxide, triethylamine, N,N-diisopropylethylamine, pyridine, 2,6-dimethylpyridine, and the like, in a solvent such as tetrahydrofuran, 1,4-dioxane, acetonitrile, methylene chloride, chloroform, 1,2-dichloroethane, 1,2-dimethoxyethane, and the like, optionally in the presence of water, optionally with heating, optionally with microwave irradiation to provide a compound of the formula (38). A compound of the formula (38) is reacted with a compound of the formula (39), a known compound or a compound prepared by known methods, in the presence of a base such as triethylamine, N,N-diisopropylethylamine, pyridine, 2,6-dimethylpyridine, and the like, in a solvent such as methanol, ethanol, isopropanol, N,N-dimethylformamide, N,N-dimethylacetamide, dimethyl sulfoxide, tetrahydrofuran, 1,4-dioxane, and the like, optionally with heating, optionally with microwave irradiation to provide a compound of the formula (40).

Scheme 13

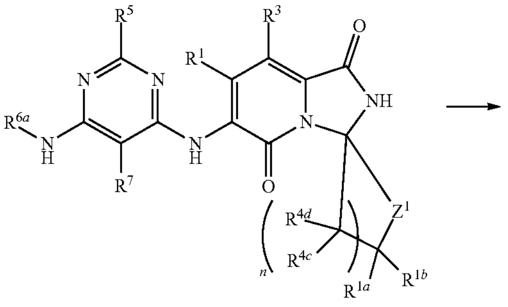

(41)

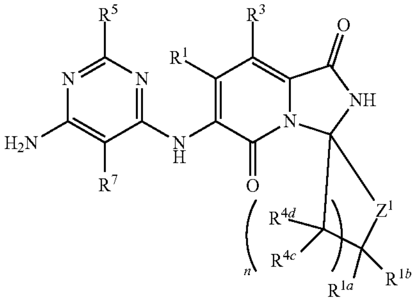

(42)

A compound of the formula (41) is reacted with a base such as sodium hydroxide, lithium hydroxide, potassium hydroxide, sodium carbonate, lithium carbonate, potassium carbonate, cesium carbonate, and the like, optionally in the presence of ethylenediamine, optionally in the presence of water, in the presence of a solvent such methanol, ethanol, isopropanol, N,N-dimethylformamide, N,N-dimethylacetamide, dimethyl sulfoxide, tetrahydrofuran, 1,4-dioxane, and the like, optionally with heating, optionally with microwave irradiation to provide a compound of the formula (42).

Scheme 14

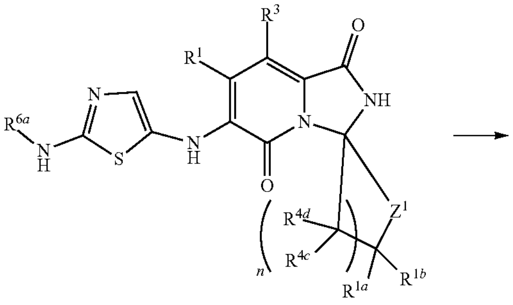

(43)

-continued

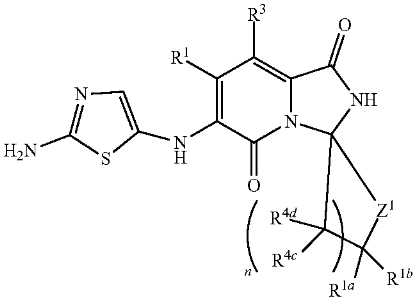

(44)

A compound of the formula (43) is reacted with a base such as sodium hydroxide, lithium hydroxide, potassium hydroxide, sodium carbonate, lithium carbonate, potassium carbonate, cesium carbonate, and the like, optionally in the presence of ethylenediamine, optionally in the presence of water, in the presence of a solvent such methanol, ethanol, isopropanol, N,N-dimethylformamide, N,N-dimethylacetamide, dimethyl sulfoxide, tetrahydrofuran, 1,4-dioxane, and the like, optionally with heating, optionally with microwave irradiation to provide a compound of the formula (44).

Scheme 15

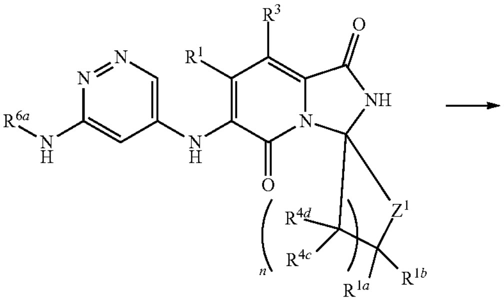

(45)

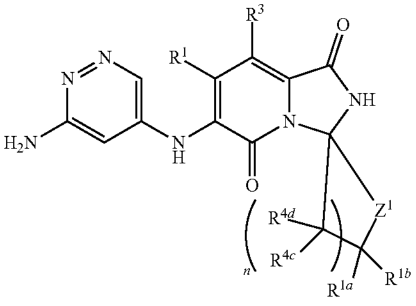

(46)

A compound of the formula (45) is reacted with a base such as sodium hydroxide, lithium hydroxide, potassium hydroxide, sodium carbonate, lithium carbonate, potassium carbonate, cesium carbonate, and the like, optionally in the presence of ethylenediamine, optionally in the presence of water, in the presence of a solvent such methanol, ethanol, isopropanol, N,N-dimethylformamide, N,N-dimethylacetamide, dimethyl sulfoxide, tetrahydrofuran, 1,4-dioxane, and the like, optionally with heating, optionally with microwave irradiation to provide a compound of the formula (46).

Scheme 16

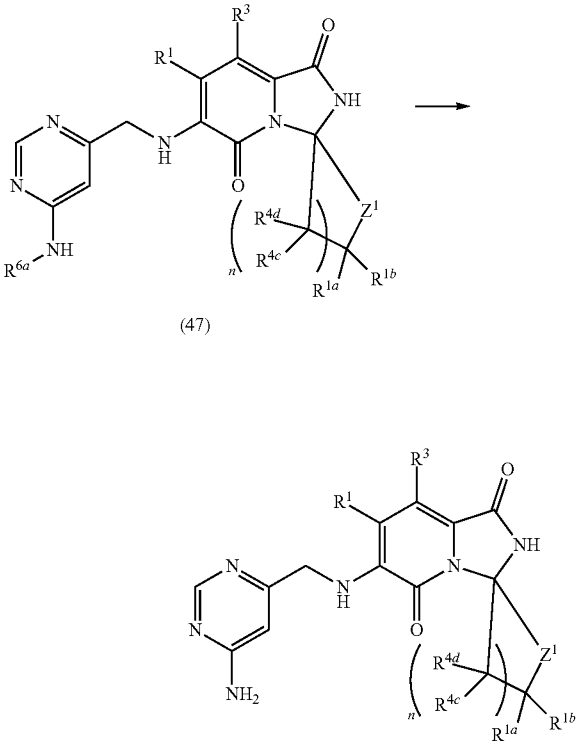

(47)

(46)

A compound of the formula (47) is reacted with a base such as sodium hydroxide, lithium hydroxide, potassium hydroxide, sodium carbonate, lithium carbonate, potassium carbonate, cesium carbonate, and the like, optionally in the presence of ethylenediamine, optionally in the presence of water, in the presence of a solvent such methanol, ethanol, isopropanol, N,N-dimethylformamide, N,N-dimethylacetamide, dimethyl sulfoxide, tetrahydrofuran, 1,4-dioxane, and the like, optionally with heating, optionally with microwave irradiation to provide a compound of the formula (48).

Scheme 17

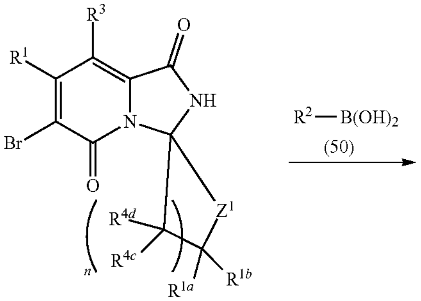

(49)

-continued

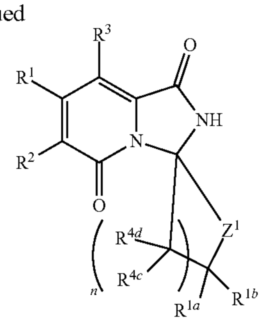

(51)

A compound of the formula (49) is reacted with a compound of the formula (50), a known compound or a compound prepared by known methods, in the presence of a palladium catalyst such as palladium (II) acetate, tetrakis (triphenylphosphine)palladium(0), dichlorobis (triphenyl phosphine)palladium(II), bis(acetonitrile)dichloropalladium (II), tris(dibenzylideneacetone) dipalladium(0), and the like, in the presence of a base such as sodium carbonate, potassium carbonate, lithium carbonate, sodium bicarbonate, potassium bicarbonate, cesium carbonate. lithium bicarbonate, triethylamine, diisopropylethylamine, pyridine, and the like, optionally in the presence of water, in a solvent such as tetrahydrofuran, 1,4-dioxane, acetonitrile, N,N-dimethyl formamide, N,N-dimethylacetamide, methylene chloride, 1,2-dichloroethane, and the like, optionally with heating, optionally with microwave irradiation to provide a compound of the formula (51).

Scheme 18

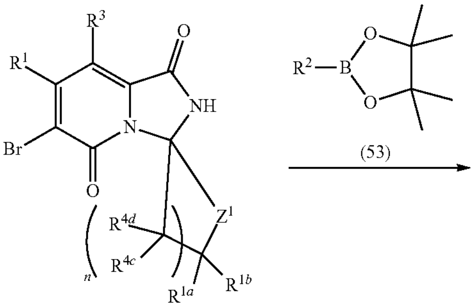

(49)

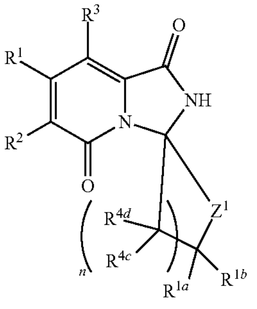

(54)

A compound of the formula (52) is reacted with a compound of the formula (53), a known compound or a compound prepared by known methods, in the presence of a palladium catalyst such as palladium (II) acetate, tetrakis (triphenylphosphine)palladium(0), dichlorobis (triphenyl phosphine)palladium(II), bis(acetonitrile)dichloropalladium (II), tris(dibenzylideneacetone) dipalladium(0), and the like, in the presence of a base such as sodium carbonate, potassium carbonate, lithium carbonate, sodium bicarbonate, potassium bicarbonate, cesium carbonate. lithium bicarbonate, triethylamine, diisopropylethylamine, pyridine, and the like, optionally in the presence of water, in a solvent such as tetrahydrofuran, 1,4-dioxane, acetonitrile, N,N-dimethyl formamide, N,N-dimethylacetamide, methylene chloride, 1,2-dichloroethane, and the like, optionally with heating, optionally with microwave irradiation to provide a compound of the formula (54).

The Examples provided below provide representative methods for preparing exemplary compounds of the present disclosure. The skilled practitioner will know how to substitute the appropriate reagents, starting materials and purification methods known to those skilled in the art, in order to prepare the compounds of the present disclosure.

Synthesis of 5-Bromo-3-methyl-6-oxo-1,6-dihydropyridine-2-carboxamide

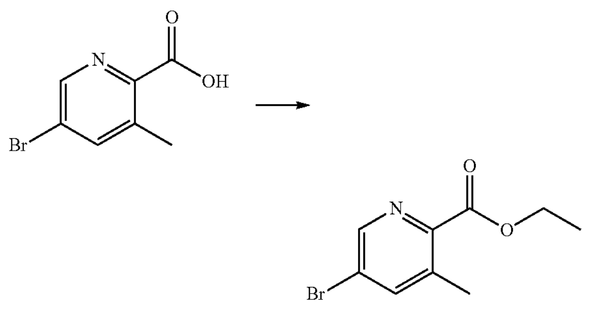

Step 1: Synthesis of ethyl 5-bromo-3-methylpicolinate. To a solution of 5-bromo-3-methylpicolinic acid (10 g, 42.3 mmol) in ethanol (37 mL) was added $H_2SO_4$ (2.3 mL, 18.4 M, 42.3 mmol) at 23° C. The reaction mixture was heated at 80° C. for 16 hours. The solvent was removed under reduced pressure and ethyl acetate (250 mL) was added. After washing with $NaHCO_3$ (200 mL×2) and water (200 mL×2), the organic phase was dried over $Na_2SO_4$, filtered, and concentrated under reduced pressure to afford ethyl 5-bromo-3-methylpicolinate (9.6 g, 39 mmol, 93%) as a colorless liquid. $^1H$ NMR (400 MHz, $CDCl_3$) δ 8.58 (s, 1H), 7.76 (s, 1H), 4.43 (q, J=7.1 Hz, 2H), 2.56 (s, 3H), 1.41 (t, J=7.1 Hz, 3H).

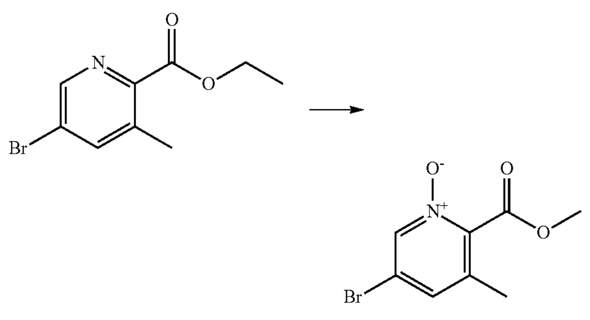

Step 2: Synthesis of 5-bromo-2-(ethoxycarbonyl)-3-methylpyridine 1-oxide. To a solution of ethyl 5-bromo-3-methylpicolinate (9.6 g, 39 mmol) in $CH_2Cl_2$ (111 mL) was added urea hydrogen peroxide (6.4 g, 68.3 mmol), followed by the addition of trifluoroacetic anhydride (9.6 mL, 68.3 mmol) at 0° C. The reaction mixture was stirred at 23° C. for 4 hours and was poured into ice/water mixture (100 mL). After extraction with $CH_2Cl_2$ (50 mL×3), the combined organic phase was washed with $NaHCO_3$ (50 mL×3) and water (50 mL×3), dried over $Na_2SO_4$, filtered, and concentrated under reduced pressure to afford 5-bromo-2-(ethoxycarbonyl)-3-methylpyridine 1-oxide (10.1 g, 39 mmol, 99%) as a colorless liquid. $^1H$ NMR (400 MHz, $CDCl_3$) δ 8.20 (s, 1H), 7.26 (s, 1H), 4.47 (q, J=7.1 Hz, 2H), 2.27 (s, 3H), 1.39 (t, J=7.1 Hz, 3H).

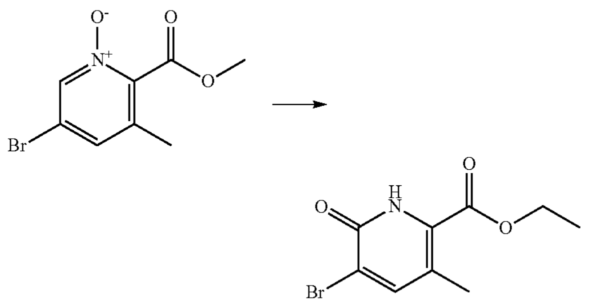

Step 3: Synthesis of ethyl 5-bromo-3-methyl-6-oxo-1,6-dihydropyridine-2-carboxylate To a solution of compound 3 (10.1 g, 39 mmol) in N,N-dimethylformamide (30.5 mL) was added trifluoroacetic anhydride (9.6 mL, 68.3 mmol) at 0° C. The reaction mixture was stirred at 40° C. for 8 hours and diluted with water (100 mL). After extraction with ethyl acetate (100 mL×3), the combined organic phase was washed with brine (100 mL×5), dried over $Na_2SO_4$, filtered, and concentrated under reduced pressure. The residue was purified by Biotage flash chromatography (silica gel, 0% to 30% ethyl acetate in hexanes) to afford ethyl 5-bromo-3-methyl-6-oxo-1,6-dihydropyridine-2-carboxylate (6.8 g, 26.1 mmol, 67%) as a white solid. $^1H$ NMR (400 MHz, $CDCl_3$) δ 7.83 (s, 1H), 4.42 (q, J=7.1 Hz, 2H), 2.45 (s, 3H), 1.41 (t, J=7.1 Hz, 3H).

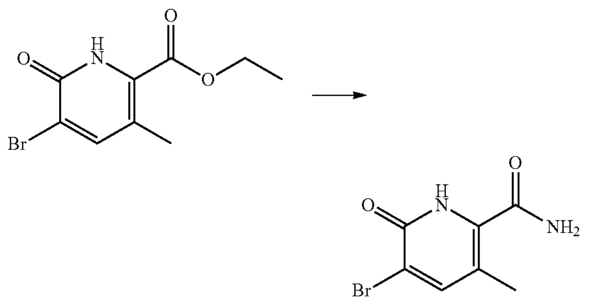

Step 4: Synthesis of 5-bromo-3-methyl-6-oxo-1,6-dihydropyridine-2-carboxamide

Ammonium hydroxide (130.5 mL, 28% in water) was added to ethyl 5-bromo-3-methyl-6-oxo-1,6-dihydropyridine-2-carboxylate (6.8 g, 26.1 mmol) at 0° C. The reaction mixture was stirred at 0° C. for 6 hours and concentrated under reduced pressure to afford 5-bromo-3-methyl-6-oxo-1,6-dihydropyridine-2-carboxamide (5, 6.0 g, 26 mmol, 99%) as a white solid. $^1$H NMR (400 MHz, DMSO-d6) δ 7.87 (s, 1H), 7.84 (s, 1H), 7.71 (s, 1H), 2.12 (s, 3H).

General Procedure A: Synthesis of spirocycloalkyl pyridones (7a-7w

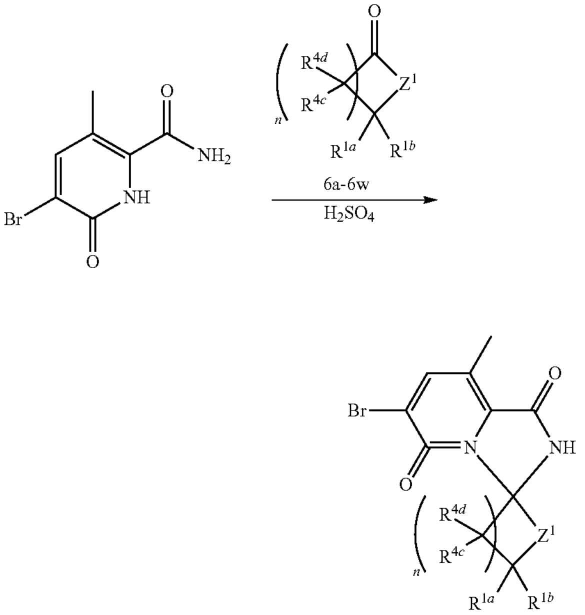

7a-7w

To a solution of compound 5-bromo-3-methyl-6-oxo-1,6-dihydropyridine-2-carboxamide (1 equiv) in 1,4-dioxane (0.2M) was added ketone 6a-6w (4 equiv), followed by the addition of $H_2SO_4$ (0.5 equiv). The reaction mixture was sealed in a pressure vessel and heated in at 100° C. for 16 hours. The reaction mixture was cooled to 23° C. and concentrated under reduced pressure. The resulting crude material was purified by Biotage flash chromatography (gradient elution, 30 to 85% ethyl acetate in hexanes or 0 to 10% MeOH in $CH_2Cl_2$) to afford compounds 7a-7w.

(7f3)

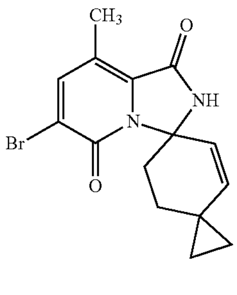

Synthesis of 6"-bromo-8"-methyl-2"H-dispiro[cyclopropane-1,1'-cyclohexane-4',3"-imidazo[1,5-a]pyridin]-2'-ene-1",5"-dione (7f3). The title compound (7f3) was prepared according to general procedure A except that 4 angstrom molecular sieves were added to the reaction using 5-bromo-3-methyl-6-oxo-1,6-dihydropyridine-2-carboxamide and spiro[2.5]oct-4-en-6-one (6u) to afford 6"-Bromo-8"-methyl-2"H-dispiro[cyclopropane-1,1'-cyclohexane-4',3"-imidazo[1,5-a]pyridin]-2'-ene-1",5"-dione (713) in 43% yield: $^1$H NMR (400 MHz, DMSO-$d_6$) δ 10.15 (s, 1H), 8.01 (s, 1H), 5.43 (d, J=9.6 Hz, 1H), 5.36 (d, J=9.3 Hz, 1H), 3.16-3.10 (m, 1H), 2.38 (s, 3H), 2.28 (t, J=14.2 Hz, 1H), 1.58 (d, J=12.5 Hz, 1H), 1.23 (d, J=12.9 Hz, 1H), 0.78-0.53 (m, 4H).

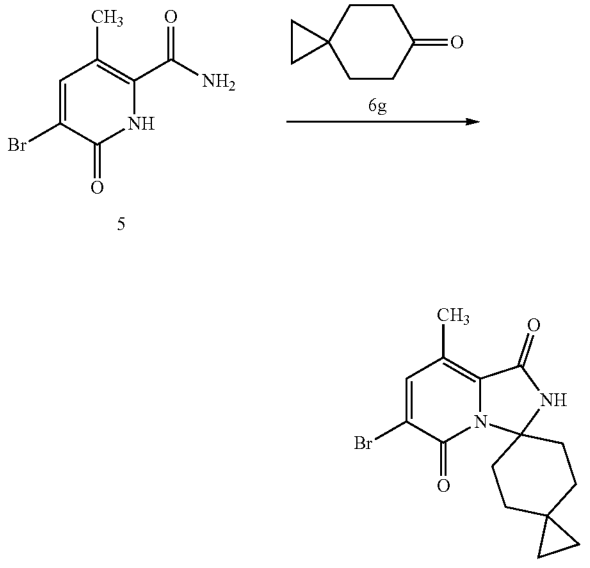

5

7g

Synthesis of 6"-bromo-8"-methyl-2"H-dispiro[cyclopropane-1,1'-cyclohexane-4',3"-imidazo[1,5-a]pyridine]-1",5"-dione (7g). The title compound (7g) was prepared according to general procedure A using 5-bromo-3-methyl-6-oxo-1,6-dihydropyridine-2-carboxamide (144 mg, 0.63 mmol), spiro[2.5]octan-6-one (6 g, 232 mg, 1.87 mmol), $H_2SO_4$ (0.017 mL, 0.31 mmol), and 1,4-dioxane (6.3 mL). 6"-Bromo-8"-methyl-2"H-dispiro[cyclopropane-1,1'-cyclohexane-4',3"-imidazo[1,5-a]pyridine]-1",5"-dione (7g) yield: (105 mg, 0.31 mmol, 50%). $^1$H NMR (400 MHz, DMSO-$d_6$) δ 10.42 (s, 1H), 8.02 (s, 1H), 3.11 (dt, J=13.3, 4.5 Hz, 2H), 2.39 (s, 3H), 2.12 (dt, J=14.6, 3.8 Hz, 2H), 1.41 (d, J=12.4 Hz, 2H), 0.88 (d, J=12.8 Hz, 2H), 0.38 (m, 2H), 0.29 (m, 2H). UHPLC-MS (ESI): Rt 0.79 min, m/z 337.1 $[M]^+$.

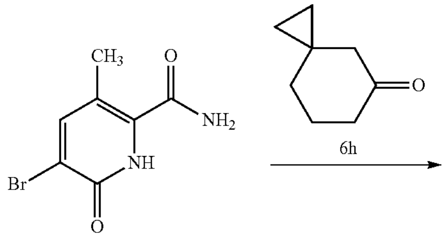

5

-continued

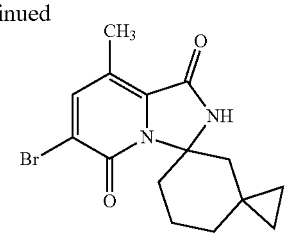

7h

Synthesis of 6"-bromo-8"-methyl-2"H-dispiro[cyclopropane-1,1'-cyclohexane-3',3"-imidazo[1,5-a]pyridine]-1",5"-dione (7h). The title compound (7h) was prepared according to general procedure A using 5-bromo-3-methyl-6-oxo-1,6-dihydropyridine-2-carboxamide (150 mg, 0.65 mmol), spiro[2.5]octan-5-one (6h, 121 mg, 0.97 mmol), $H_2SO_4$ (0.018 mL, 0.33 mmol), and 1,4-dioxane (6.0 mL). 6"-Bromo-8"-methyl-2"H-dispiro[cyclopropane-1,1'-cyclohexane-3',3"-imidazo[1,5-a]pyridine]-1",5"-dione (7h) yield: (114 mg, 0.34 mmol, 52%). $^1$H NMR (400 MHz, Chloroform-d) δ 8.00 (br, 1H), 7.73 (s, 1H), 3.73 (m, 1H), 3.20 (dt, J=4.0, 13.6 Hz, 1H), 2.48 (s, 3H), 2.00-1.90 (m, 2H), 1.65 (m, 1H), 1.58 (m, 1H), 0.93 (d, J=13.6 Hz, 1H), 0.76 (dt, J=13.0, 2.0 Hz, 1H), 0.46-0.40 (m, 3H), 0.32 (m, 1H); UHPLC-MS (ESI): m/z 339.1 $[M]^+$.

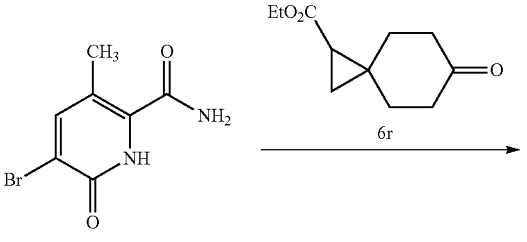

5

6r

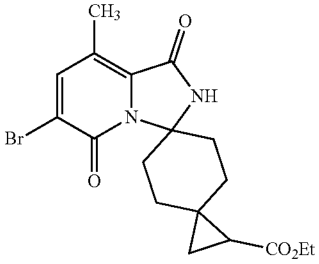

7r

Synthesis of ethyl 6"-bromo-8"-methyl-1",5"-dioxo-1",5"-dihydro-2"H-dispiro[cyclopropane-1,1'-cyclohexane-4',3"-imidazo[1,5-a]pyridine]-2-carboxylate (7r). The title compound (7r) was prepared according to general procedure A using 5-bromo-3-methyl-6-oxo-1,6-dihydropyridine-2-carboxamide (141 mg, 0.61 mmol), ethyl 6-oxospiro[2.5]octane-1-carboxylate (6r, 240 mg, 1.22 mmol), $H_2SO_4$ (0.016 mL, 0.31 mmol), and 1,4-dioxane (1.22 mL) except that the reaction was conducted for 3 hours. Ethyl 6"-bromo-8"-methyl-1",5"-dioxo-1",5"-dihydro-2"H-dispiro[cyclopropane-1,1'-cyclohexane-4',3"-imidazo[1,5-a]pyridine]-2-carboxylate (7r) yield: (123 mg, 0.30 mmol, 50%). $^1$H NMR (400 MHz, $CDCl_3$) δ 7.73 (s, 1H), 4.17 (q, J=7.1 Hz, 2H), 3.37 (m, 2H), 2.46 (s, 3H), 2.25-1.34 (m, 7H), 1.25 (t, J=7.1 Hz, 3H), 1.11-0.90 (m, 2H). UHPLC-MS (ESI): Rt 0.77 min, m/z 409.0 $[M]^+$.

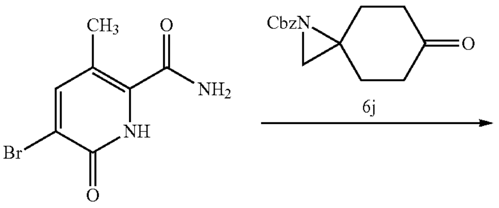

5

6j

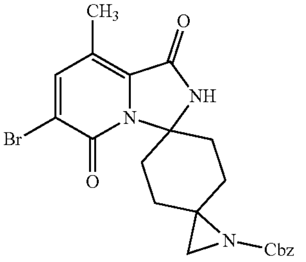

7j

Synthesis of benzyl 6"-bromo-8"-methyl-1",5"-dioxo-1",5"-dihydro-2"H-dispiro[aziridine-2,1'-cyclohexane-4',3"-imidazo[1,5-a]pyridine]-1-carboxylate (7j). The title compound (7j) was prepared according to general procedure A using 5-bromo-3-methyl-6-oxo-1,6-dihydropyridine-2-carboxamide (205 mg, 0.89 mmol), benzyl 6-oxo-1-azaspiro[2.5]octane-1-carboxylate (6j, 345 mg, 1.33 mmol), $H_2SO_4$ (0.024 mL, 0.44 mmol), and 1,4-dioxane (9.0 mL). Benzyl 6"-bromo-8"-methyl-1",5"-dioxo-1",5"-dihydro-2"H-dispiro[aziridine-2,1'-cyclohexane-4',3"-imidazo[1,5-a]pyridine]-1-carboxylate (7j) yield: (187 mg, 0.40 mmol, 46%). $^1$H NMR (400 MHz, DMSO-$d_6$) δ 10.02 (s, 1H), 8.04 (s, 1H), 7.41-7.23 (m, 5H), 5.04 (s, 2H), 3.62 (m, 2H), 3.01 (m, 2H), 2.39 (s, 3H), 2.21 (m, 2H), 1.93 (m, 1H), 1.58 (m, 1H), 1.26 (m, 1H), 0.86 (m, 1H). UHPLC-MS (ESI): Rt 0.76 min, m/z 337.1 $[M]^+$.

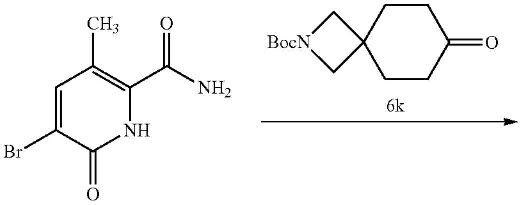

5

6k

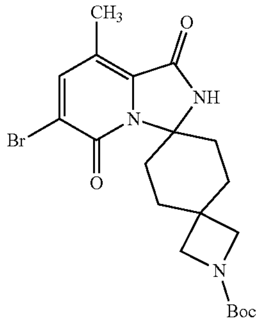

7k

Synthesis of 6"-bromo-8"-methyl-2"H-dispiro[azetidine-3,1'-cyclohexane-4',3"-imidazo[1,5-a]pyridine]-1",5"-dione (7k). The title compound (7k) was prepared according to general procedure A using 5-bromo-3-methyl-6-oxo-1,6-dihydropyridine-2-carboxamide (100 mg, 0.43 mmol), tert-butyl 7-oxo-2-azaspiro[3.5]nonane-2-carboxylate (6k, 414 mg, 1.73 mmol), $H_2SO_4$ (0.012 mL, 0.22 mmol), and 1,4-dioxane (4.0 mL). 6"-Bromo-8"-methyl-2"H-dispiro[azetidine-3,1'-cyclohexane-4',3"-imidazo[1,5-a]pyridine]-1",5"-dione (7k) yield: (101 mg, 0.29 mmol, 66%). $^1$H NMR (400 MHz, DMSO-$d_6$) δ 8.02 (s, 1H), 7.78 (s, 1H), 3.05-2.80 (m, 4H), 2.37 (s, 3H), 2.00-1.92 (m, 4H), 1.41 (dd, J=25.2, 12.9 Hz, 4H). UHPLC-MS (ESI): Rt 0.59 min, m/z 352.2 [M]$^+$.

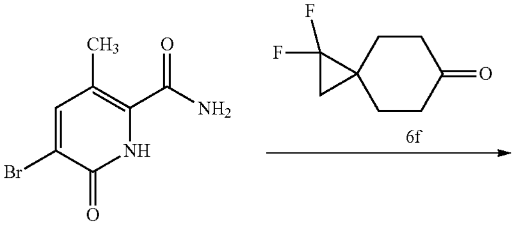

5

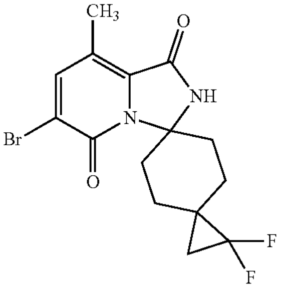

7f

Synthesis of 6"-bromo-2,2-difluoro-8"-methyl-2"H-dispiro[cyclopropane-1,1'-cyclohexane-4',3"-imidazo[1,5-a]pyridine]-1",5"-dione (7f). The title compound (7f) was prepared according to general procedure A using 5-bromo-3-methyl-6-oxo-1,6-dihydropyridine-2-carboxamide (125 mg, 0.54 mmol), 1,1-difluorospiro[2.5]octan-6-one (6f, 86 mg, 0.54 mmol), $H_2SO_4$ (0.01 mL, 0.27 mmol), and 1,4-dioxane (1.1 mL). 6"-Bromo-2,2-difluoro-8"-methyl-2"H-dispiro[cyclopropane-1,1'-cyclohexane-4',3"-imidazo[1,5-a]pyridine]-1",5"-dione (7f) yield: (39 mg, 0.10 mmol, 19%). UHPLC-MS (ESI): Rt 0.80 min, m/z 373.0 [M]$^+$.

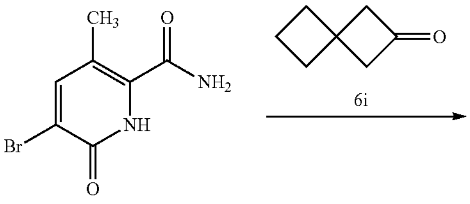

5

-continued

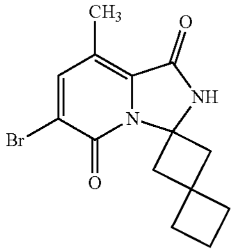

7i

Synthesis of 6"-bromo-8"-methyl-2"H-dispiro[cyclobutane-1,1'-cyclobutane-3'3"-imidazo[1,5-a]pyridine]-1",5"-dione (7i). The title compound (7i) was prepared according to general procedure A using 5-bromo-3-methyl-6-oxo-1,6-dihydropyridine-2-carboxamide (100 mg, 0.43 mmol), spiro[3.3]heptan-2-one (6i, 191 mg, 1.73 mmol), $H_2SO_4$ (0.012 mL, 0.22 mmol), and 1,4-dioxane (4.0 mL). 6"-Bromo-8"-methyl-2"H-dispiro[cyclobutane-1,1'-cyclobutane-3',3"-imidazo[1,5-a]pyridine]-1",5"-dione (7i) yield: (101 mg, 0.31 mmol, 72%). $^1$H NMR (400 MHz, DMSO-$d_6$) δ 10.26 (s, 1H), 8.02 (s, 1H), 3.56 (d, J=14.2 Hz, 2H), 2.38 (s, 3H), 2.35-2.29 (m, 2H), 2.23-2.12 (m, 4H), 1.80 (dt, J=14.7, 7.2 Hz, 2H). UHPLC-MS (ESI): Rt 0.76 min, m/z 323.1 [M]$^+$.

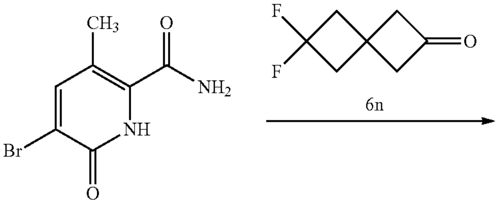

5

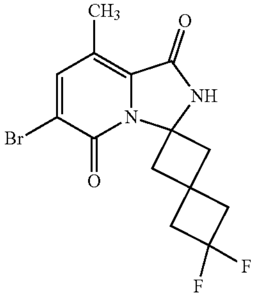

7n

Synthesis of 6"-bromo-3,3-difluoro-8"-methyl-2"H-dispiro[cyclobutane-1,1'-cyclobutane-3',3"-imidazo[1,5-a]pyridine]-1",5"-dione (7n). The title compound (7n) was prepared according to general procedure A using 5-bromo-3-methyl-6-oxo-1,6-dihydropyridine-2-carboxamide (100 mg, 0.43 mmol), 6,6-difluorospiro[3.3]heptan-2-one (6n, 108 mg, 0.74 mmol), $H_2SO_4$ (0.012 mL, 0.22 mmol), and 1,4-dioxane (4.0 mL). 6"-Bromo-3,3-difluoro-8"-methyl-2"H-dispiro[cyclobutane-1,1'-cyclobutane-3',3"-imidazo[1,5-a]pyridine]-1",5"-dione (7n) yield: (93 mg, 0.26 mmol, 60%). $^1$H NMR (400 MHz, DMSO-$d_6$) δ 10.26 (s, 1H), 8.02 (s, 1H), 3.53 (d, J=14.7 Hz, 2H), 2.78 (dt, J=33.0, 12.7 Hz, 4H), 2.52 (s, 1H), 2.49 (s, 1H), 2.34 (s, 3H). UHPLC-MS (ESI): Rt 0.77 min, m/z 358.8 [M]$^+$.

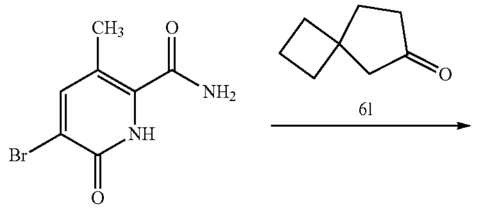

5

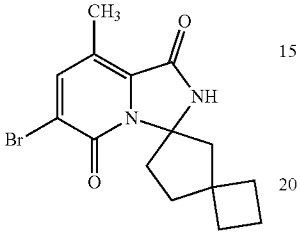

71

Synthesis of 6"-bromo-8"-methyl-2"H-dispiro[cyclobutane-1,1'-cyclopentane-3',3"-imidazo[1,5-a]pyridine]-1",5"-dione (71). The title compound (71) was prepared according to general procedure A using 5-bromo-3-methyl-6-oxo-1,6-dihydropyridine-2-carboxamide (100 mg, 0.43 mmol), spiro [3.4]octan-6-one (61, 107 mg, 0.866 mmol), $H_2SO_4$ (0.012 mL, 0.22 mmol), and 1,4-dioxane (3.0 mL). 6"-Bromo-8"-methyl-2"H-dispiro[cyclobutane-1,1'-cyclopentane-3',3"-imidazo[1,5-a]pyridine]-1",5"-dione (71) yield: (101 mg, 69%). $^1$H NMR (400 MHz, DMSO-$d_6$) δ 10.05 (s, 1H), 7.99 (s, 1H), 2.82 (d, J=13.8 Hz, 1H), 2.70 (dt, J=13.1, 8.1 Hz, 1H), 2.34 (s, 3H), 2.16-1.61 (m, 9H). UHPLC-MS (ESI): Rt 0.82 min, m/z 339.2 $[M]^+$.

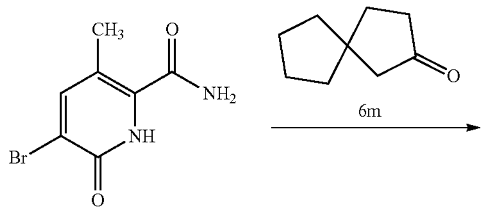

5

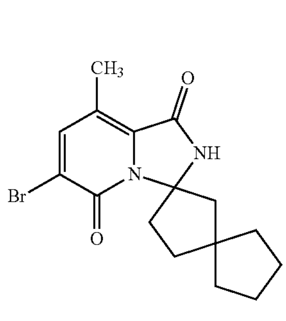

7m

Synthesis of 6"-bromo-8"-methyl-2"H-dispiro[cyclopentane-1,1'-cyclopentane-3',3"-imidazo[1,5-a]pyridine]-1",5"-dione (7m). The title compound (7m) was prepared according to general procedure A using 5-bromo-3-methyl-6-oxo-1,6-dihydropyridine-2-carboxamide (100 mg, 0.43 mmol), spiro[4.4]nonan-2-one (6m, 120 mg, 0.866 mmol), $H_2SO_4$ (0.012 mL, 0.22 mmol), and 1,4-dioxane (3.0 mL). 6"-Bromo-8"-methyl-2"H-dispiro[cyclopentane-1,1'-cyclopentane-3',3"-imidazo[1,5-a]pyridine]-1",5"-dione (7m) yield: (91 mg, 59 mg). $^1$H NMR (400 MHz, DMSO-$d_6$) δ 10.15 (s, 1H), 7.99 (s, 1H), 2.88-2.76 (m, 2H), 2.35 (s, 3H), 1.95-1.86 (m, 1H), 1.81-1.74 (m, 1H), 1.74-1.66 (m, 3H), 1.64-1.52 (m, 8H). UHPLC-MS (ESI): Rt 0.86 min, m/z 351.1 $[M]^+$.

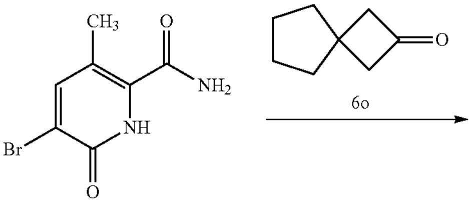

5

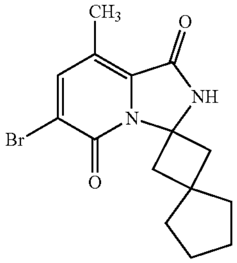

7o

Synthesis of 6"-bromo-8"-methyl-2"H-dispiro[cyclopentane-1,1'-cyclobutane-3',3"-imidazo[1,5-a]pyridine]-1",5"-dione (70). The title compound (7o) was prepared according to general procedure A using 5-bromo-3-methyl-6-oxo-1,6-dihydropyridine-2-carboxamide (100 mg, 0.43 mmol), spiro [3.4]octan-2-one (60, 215 mg, 1.73 mmol), $H_2SO_4$ (0.012 mL, 0.22 mmol), and 1,4-dioxane (4.0 mL). 6"-Bromo-8"-methyl-2"H-dispiro[cyclopentane-1,1'-cyclobutane-3',3"-imidazo[1,5-a]pyridine]-1",5"-dione (7o) yield: (100 mg, 0.3 mmol, 69%). $^1$H NMR (400 MHz, DMSO-$d_6$) δ 10.38 (s, 1H), 8.00 (s, 1H), 3.42 (d, J=13.5 Hz, 2H), 2.35 (s, 3H), 2.07 (d, J=13.6 Hz, 2H), 1.91-1.82 (m, 2H), 1.82-1.73 (m, 2H), 1.63-1.41 (m, 4H). UHPLC-MS (ESI): Rt 0.85 min, m/z 337.1 $[M]^+$.

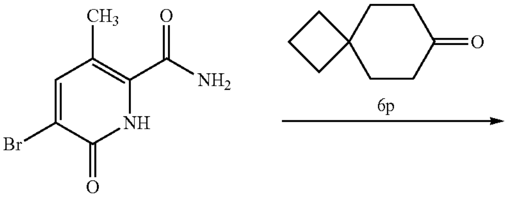

5

-continued

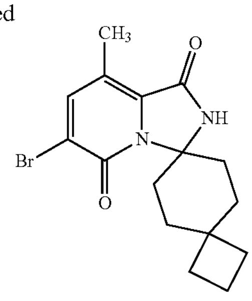

7p

Synthesis of 6"-bromo-8"-methyl-2"H-dispiro[cyclobutane-1,1'-cyclohexane-4',3"-imidazo[1,5-a]pyridine]-1",5"-dione (7p). The title compound (7p) was prepared according to general procedure A using 5-bromo-3-methyl-6-oxo-1,6-dihydropyridine-2-carboxamide (100 mg, 0.43 mmol), spiro[3.5]nonan-7-one (6p, 120 mg, 0.87 mmol), $H_2SO_4$ (0.012 mL, 0.22 mmol), and 1,4-dioxane (4.0 mL). 6"-Bromo-8"-methyl-2"H-dispiro[cyclobutane-1,1'-cyclohexane-4',3"-imidazo[1,5-a]pyridine]-1",5"-dione (7p) yield: (73 mg, 0.21 mmol, 48%). $^1H$ NMR (400 MHz, DMSO-$d_6$) δ 10.32 (s, 1H), 7.99 (s, 1H), 2.97 (t, J=11.7 Hz, 2H), 2.36 (s, 3H), 1.82 (s, 4H), 1.78-1.56 (m, 6H), 1.26 (d, J=12.3 Hz, 2H). UHPLC-MS (ESI): Rt 0.86 min, m/z 351.2 $[M]^+$.

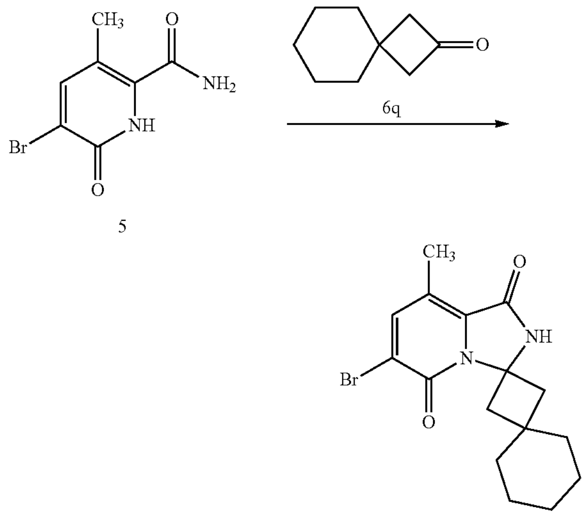

5

6q

7q

Synthesis of 6"-bromo-8"-methyl-2"H-dispiro[cyclohexane-1,1'-cyclobutane-3',3"-imidazo[1,5-a]pyridine]-1",5"-dione (7g). The title compound (7q) was prepared according to general procedure A using 5-bromo-3-methyl-6-oxo-1,6-dihydropyridine-2-carboxamide (100 mg, 0.43 mmol), spiro[3.5]nonan-2-one (6q, 120 mg, 0.87 mmol), $H_2SO_4$ (0.012 mL, 0.22 mmol), and 1,4-dioxane (4.0 mL). 6"-Bromo-8"-methyl-2"H-dispiro[cyclohexane-1,1'-cyclobutane-3',3"-imidazo[1,5-a]pyridine]-1",5"-dione (7q) yield: (95 mg, 0.27 mmol, 63%). $^1H$ NMR (400 MHz, DMSO-$d_6$) δ 10.27 (s, 1H), 8.00 (s, 1H), 3.23 (d, J=13.6 Hz, 2H), 2.35 (s, 3H), 1.95 (d, J=13.7 Hz, 2H), 1.86-1.75 (m, 2H), 1.73-1.60 (m, 2H), 1.43-1.31 (m, 6H). UHPLC-MS (ESI): Rt 0.89 min, m/z 351.1 $[M]^+$.

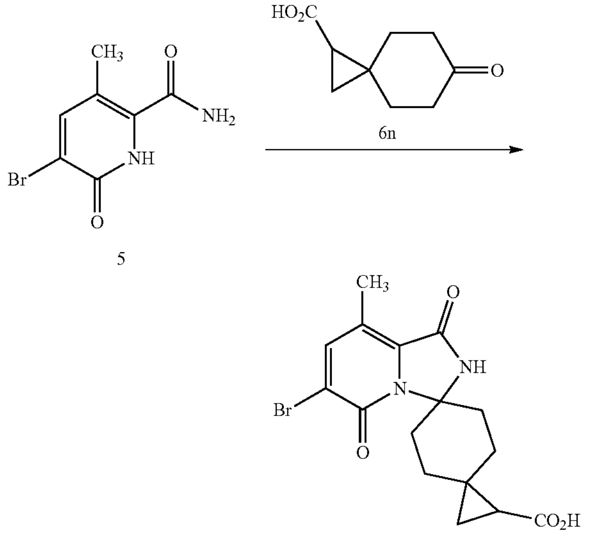

5

6n

7n

Synthesis of 6"-bromo-8"-methyl-1",5"-dioxo-1",5"-dihydro-2"H-dispiro[cyclopropane-1,1'-cyclohexane-4',3"-imidazo[1,5-a]pyridine]-2-carboxylic acid (7n). The title compound (7n) was prepared according to general procedure A using 5-bromo-3-methyl-6-oxo-1,6-dihydropyridine-2-carboxamide (460 mg, 1.99 mmol), 6-oxospiro[2.5]octane-1-carboxylic acid (6n, 668 mg, 3.97 mmol), $H_2SO_4$ (0.05 mL, 0.1 mmol), and 1,4-dioxane (4.0 mL). 6"-Bromo-8"-methyl-1",5"-dioxo-1",5"-dihydro-2"H-dispiro[cyclopropane-1,1'-cyclohexane-4',3"-imidazo[1,5-a]pyridine]-2-carboxylic acid (7n) yield: (210 mg, 0.55 mmol, 28%). $^1H$ NMR (400 MHz, $CDCl_3$) δ 7.77 (s, 1H), 3.49-3.25 (m, 2H), 2.46 (s, 3H), 2.24-1.44 (m, 7H), 1.30-1.04 (m, 2H). UHPLC-MS (ESI): Rt 0.67 min, m/z 381.0 $[M]^+$.

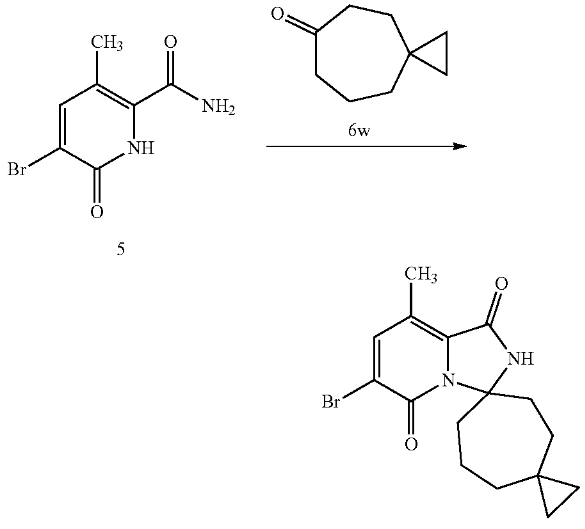

5

6w

7w

Synthesis of 6"-bromo-8"-methyl-2"H-dispiro[cyclopropane-1,1'-cycloheptane-4',3"-imidazo[1,5-a]pyridine]-1",5"-dione (7w). To a stirred solution of 5 (25 mg, 0.108 mmol) in dry isopropanol was added ketone 6w (18 mg, 0.130 mmol) followed by $Ti(iOPr)_4$ (46 mg, 0.162 mmol). The mixture was sealed and heated at 100° C. for 12 hours. Purification via flash column chromatography (gradient elution, 5% to 50% hexanes/ethyl acetate) afforded 8 mg 7w (28%): $^1H$ NMR (400 MHz, DMSO-$d_6$) δ 10.29 (s, 1H), 8.00 (s, 1H), 2.99-2.69 (m, 2H), 2.37 (s, 3H), 1.89 (s, 1H), 1.81 (dd, J=14.8, 10.8 Hz, 1H), 1.68 (dd, J=14.4, 9.2 Hz, 2H), 1.59 (dd, J=14.0, 8.0 Hz, 2H), 1.36 (dd, J=14.4, 8.0 Hz, 2H), 0.31 (d, J=7.6 Hz, 4H).

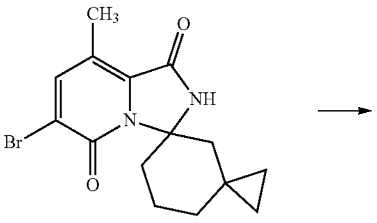

7h

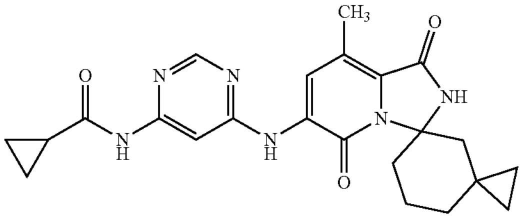

4ET-03-084

Synthesis of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropanecarboxamide (4ET-03-084): A mixture of 6"-bromo-8"-methyl-2"H-dispiro[cyclopropane-1,1'-cyclohexane-3',3"-imidazo[1,5-a]pyridine]-1",5"-dione (7h) (60 mg, 0.18 mmol), N-(6-aminopyrimidin-4-yl)cyclopropanecarboxamide (38.0 mg, 0.21 mmol), $Cs_2CO_3$, (174.0 mg, 0.53 mmol), 4,5-bis(diphenylphosphino)-9,9-dimethylxanthene (Xantphos) (21.2 mg, 0.04 mmol) and $Pd(OAc)_2$ (4.0 mg, 0.02 mmol) in 1,4-dioxane (4.0 mL) was purged with inert gas (nitrogen or argon) for 20 minutes. The reaction vessel was sealed and heated at 95° C. for 12 hours, and then cooled to 23° C. and concentrated under reduced pressure. The resulting crude material was purified through a Biotage flash chromatography (gradient elution, 0% to 10% MeOH in $CH_2Cl_2$) to afford 4ET-03-084 (48.0 mg, 0.11 mmol, 63%) as a white solid: $^1H$ NMR (400 MHz, DMSO-$d_6$) δ 10.86 (s, 1H), 9.92 (s, 1H), 9.11 (s, 1H), 8.53 (s, 1H). 8.47 (s, 1H), 7.85 (s, 1H), 3.49 (d, J=12.8 Hz, 1H), 3.03 (dt, J=4.2, 13.3 Hz, 1H), 2.44 (s, 3H), 2.02 (pent, J=6.2 Hz, 1H), 1.90 (m, 1H), 1.79-1.70 (m, 2H), 1.52 (m, 1H), 0.89 (m, 1H), 0.84 (m, 4H), 0.75 (d, J=12.2 Hz, 1H), 0.43 (m, 2H), 0.28 (m, 1H), 0.19 (m, 1H); UHPLC-MS (ESI): m/z 435.3 $[M+H]^+$

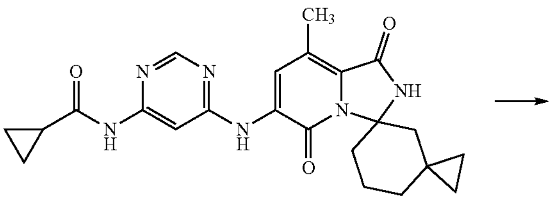

4ET-03-084

-continued

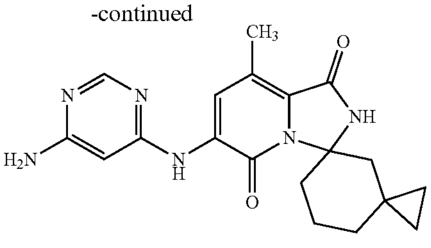

4ET-01-042

Synthesis of 6"-((6-Aminopyrimidin-4-yl)amino)-8"-methyl-2"H-dispiro[cyclopropane-1,1'-cyclohexane-3',3"-imidazo[1,5-a]pyridine]-1",5"-dione (4ET-01-042): To a suspension of 4ET-03-084 (30 mg, 0.07 mmol) in EtOH/THF/$H_2O$ (1 mL, v:v:v/2:1:1) was added 6N KOH aqueous solution (0.23 mL, 1.38 mmol). The mixture was stirred at 23° C. for 16 hours and additional 6N KOH aqueous solution (0.23 mL, 1.38 mmol) was added and stirred for another 6 hours until HPLC/MS showed the complete consumption of the starting material. The reaction was concentrated under reduced pressure and the resulting crude material was purified through a Biotage flash chromatography (gradient elution, 0% to 15% 3M $NH_3$/MeOH in $CH_2Cl_2$) to afford 4ET-01-042 (19 mg, 0.05 mmol, 75%) as a white solid: $^1H$ NMR (400 MHz, DMSO-$d_6$) δ 9.86 (s, 1H), 8.62 (s, 1H), 8.37 (s, 1H), 8.18 (s, 1H). 6.57 (br, 2H), 6.16 (s, 1H), 3.49 (d, J=12.8 Hz, 1H), 3.04 (dt, J=4.2, 13.3 Hz, 1H), 2.42 (s, 3H), 1.89 (m, 1H), 1.78-1.70 (m, 2H), 1.51 (m, 1H), 0.89 (m, 1H), 0.74 (d, J=13.0 Hz, 1H), 0.43 (m, 2H), 0.27 (m, 1H), 0.18 (m, 1H); UHPLC-MS (ESI/): m/z 367.2 $[M+H]^+$.

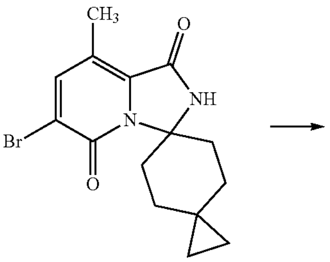

7g

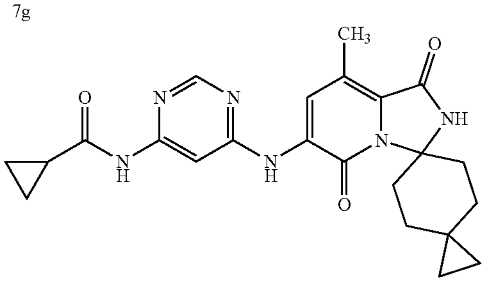

4ET-03-029

Synthesis of N-(6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)cyclopropanecarboxamide (4ET-03-029): The title compound was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropanecarboxamide except that 6"-bromo-8"-methyl-2"H-dispiro[cyclopropane-1,1'-cyclohexane-3',3"-imidazo[1,5-a]pyridine]-1",5"-dione is replaced with 6"-bromo-8"-methyl-2"H-dispiro[cyclopropane-1,1'-cyclohexane-4',3"-imidazo[1,5-a]pyridine]-1",5"-dione to provide the title compound 4ET-03-029. $^{1}$H NMR (400 MHz, DMSO-$d_6$) δ 10.86 (s, 1H), 10.12 (s, 1H), 9.17 (s, 1H), 8.54 (s, 1H), 8.48 (s, 1H), 7.84 (s, 1H), 3.22 (dt, J=13.4, 4.4 Hz, 2H), 2.45 (s, 3H), 2.15 (t, J=13.6 Hz, 2H), 2.02 (pent, J=6.4 Hz, 1H), 1.42 (d, J=12.4 Hz, 2H), 0.90 (d, J=13.4 Hz, 2H), 0.83 (m, 4H), 0.39 (m, 2H), 0.30 (m, 2H). UHPLC-MS (ESI): Rt 0.77 min, m/z 435.3 [M+H]$^+$.

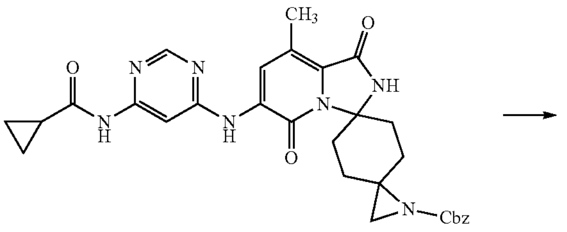

4ET-03-046

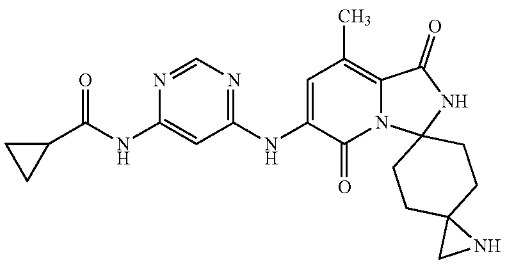

4ET-03-040

Synthesis of N-(6-((8"-methyl-1",5"-dioxo-1",5"-dihydro-2"H-dispiro[aziridine-2,1'-cyclohexane-4',3"-imidazo[1,5-a]pyridin]-6"-yl)amino)pyrimidin-4-yl)cyclopropanecarboxamide (4ET-03-040): To a solution of N-(6-((8"-methyl-1",5"-dioxo-1-(2-oxo-2-phenyl-112-ethyl)-1",5"-dihydro-2"H-dispiro[aziridine-2,1'-cyclohexane-4',3"-imidazo[1,5-a]pyridin]-6"-yl)amino)pyrimidin-4-yl) cyclopropanecarboxamide (4ET-03-046) (50 mg, 0.087 mmol) in ethanol (1 mL) was added Pd/C (10% activated on charcoal, 10 mg, 0.0087 mmol). The suspension was degassed and re-purged with hydrogen gas (this process was repeated three times). The reaction was stirred under hydrogen atmosphere at 23° C. for 16 hours. The reaction was filtered through Celite and washed with 1M $NH_3$/MeOH solution until full recovery of the desired product (TLC analysis 10% 1M $NH_3$/MeOH in $CH_2Cl_2$). The filtrate was concentrated and purified by Biotage flash chromatography (gradient elution, 0 to 25% 3M $NH_3$/MeOH in $CH_2Cl_2$) to obtain the desired compound 4ET-03-040 as white powders (11 mg, 0.025 mmol, 30%). $^{1}$H NMR (400 MHz, DMSO-$d_6$) δ 10.85 (br, 1H), 9.14 (br, 1H), 8.53 (s, 1H), 8.49 (s, 1H), 7.87 (s, 1H), 5.53 (m, 1H), 3.70 (m, 1H), 3.10 (m, 4H), 2.35-2.19 (m, 3H), 2.02 (pent, J=6.2 Hz, 1H), 1.93 (m, 1H), 1.57 (m, 1H), 0.85 (d, J=6.2 Hz, 4H). UHPLC-MS (ESI): Rt 0.61 min, m/z 436.3 [M+H]$^+$.

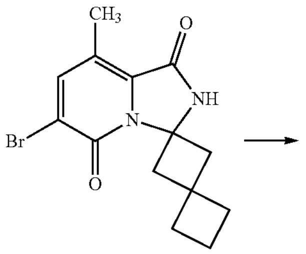

7i

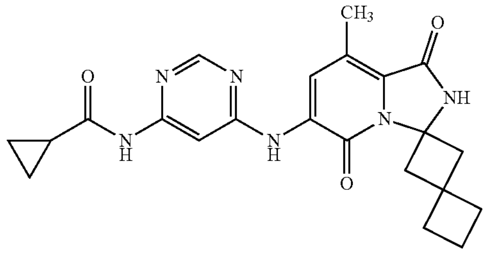

4ET-03-043

Synthesis of N-(6-((8"-methyl-1",5"-dioxo-1",5"-dihydro-2"H-dispiro[cyclobutane-1,1'-cyclobutane-3',3"-imidazo[1,5-a]pyridin]-6"-yl)amino)pyrimidin-4-yl)cyclopropanecarboxamide (4ET-03-043): The title compound was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropanecarboxamide except that 6"-bromo-8"-methyl-2"H-dispiro[cyclopropane-1,1'-cyclohexane-3',3"-imidazo[1,5-a]pyridine]-1",5"-dione is replaced with 6"-Bromo-8"-methyl-2"H-dispiro[cyclobutane-1,1'-cyclobutane-3',3"-imidazo[1,5-a]pyridine]-1",5"-dione to provide the title compound 4ET-03-043. $^{1}$H NMR (400 MHz, DMSO-$d_6$) δ 10.82 (s, 1H), 9.96 (s, 1H), 9.27 (s, 1H), 8.50 (d, J=16.6 Hz, 2H), 7.89 (s, 1H), 3.55 (d, J=13.8 Hz, 2H), 2.40 (s, 3H), 2.32 (d, J=13.6 Hz, 2H), 2.24-2.11 (m, 4H), 2.07-1.96 (m, 1H), 1.79 (dt, J=14.9, 7.6 Hz, 2H), 0.83 (d, J=6.1 Hz, 4H). UHPLC-MS (ESI): Rt 0.77 min, m/z 421.3 [M+H]$^+$.

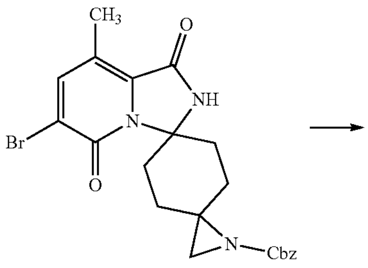

7j

-continued

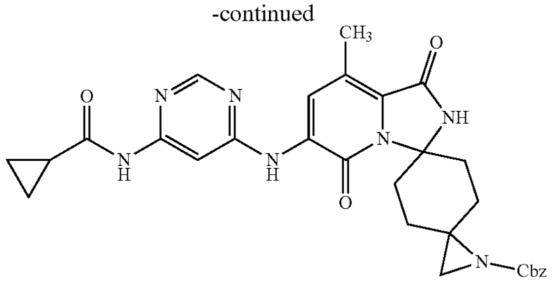

4ET-03-046

Synthesis of N-(6-((8"-methyl-1",5"-dioxo-1-(2-oxo-2-phenyl-112-ethyl)-1",5"-dihydro-2"H-dispiro[aziridine-2, 1'-cyclohexane-4',3"-imidazo[1,5-a]pyridin]-6"-yl)amino) pyrimidin-4-yl)cyclopropanecarboxamide (4ET-03-046): The title compound was prepared according to the procedure of N-(6-((8"-methyl-1",5"-dioxo-1",5"-dihydro-2"H-dispiro [cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro [cyclopropane-1,1'-cyclohexane-3',3"-imidazo[1,5-a] pyridine]-1",5"-dione is replaced with benzyl 6"-bromo-8"-methyl-1",5"-dioxo-1",5"-dihydro-2"H-dispiro[aziridine-2, 1'-cyclohexane-4',3"-imidazo[1,5-a]pyridine]-1-carboxylate to provide the title compound 4ET-03-046. $^1$H NMR (400 MHz, DMSO-$d_6$) δ 10.85 (s, 1H), 9.70 (br, 1H), 9.14 (s, 1H), 8.53 (s, 1H), 8.49 (s, 1H), 7.87 (s, 1H), 7.40-7.21 (m, 5H), 5.04 (s, 2H), 3.73-3.59 (m, 3H), 3.07 (m, 2H), 2.45 (s, 3H), 2.25 (m, 2H), 2.02 (pent, J=6.2 Hz, 1H), 1.94 (m, 1H), 1.58 (m, 2), 0.84 (d, J=6.2 Hz, 4H). UHPLC-MS (ESI): Rt 0.78 min, m/z 570.4 $[M+H]^+$.

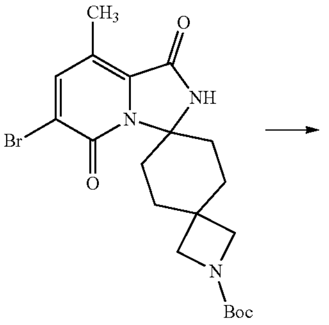

7k

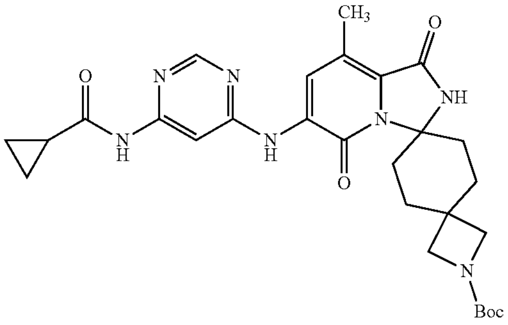

4ET-03-048

Synthesis of tert-butyl 6"-((6-(cyclopropanecarboxamido) pyrimidin-4-yl)amino)-8"-methyl-1",5"-dioxo-1",5"-dihydro-2"H-dispiro[azetidine-3,1'-cyclohexane-4',3"-imidazo[1,5-a]pyridine]-1-carboxylate (4ET-03-048): The title compound was prepared according to the procedure of N-(6-((8"-methyl-1",5"-dioxo-1",5"-dihydro-2"H-dispiro [cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro [cyclopropane-1,1'-cyclohexane-3',3"-imidazo[1,5-a] pyridine]-1",5"-dione is replaced with tert-butyl 6"-bromo-8"-methyl-1",5"-dioxo-1",5"-dihydro-2"H-dispiro [azetidine-3,1'-cyclohexane-4',3"-imidazo[1,5-a]pyridine]-1-carboxylate (7k) to provide the title compound 4ET-03-048. $^1$H NMR (400 MHz, DMSO-$d_6$) δ 10.81 (s, 1H), 10.06 (s, 1H), 9.20 (s, 1H), 8.49 (d, J=13.1 Hz, 2H), 7.84 (s, 1H), 3.73-3.57 (m, 2H), 3.57-3.41 (m, 2H), 3.09-2.97 (m, 2H), 2.41 (s, 3H), 1.93-1.73 (m, 4H), 1.45-1.31 (m, 1OH), 1.19-1.08 (m, 2H), 0.87-0.77 (m, 4H). UHPLC-MS (ESI): Rt 0.78 min, m/z 550.4 $[M+H]^+$.

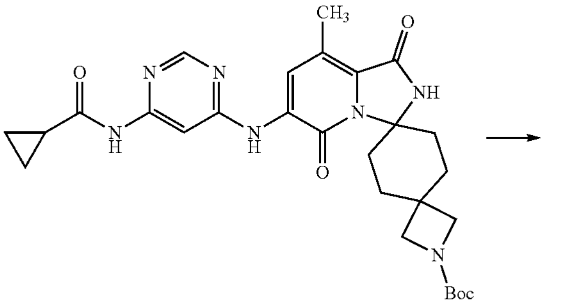

4ET-03-048

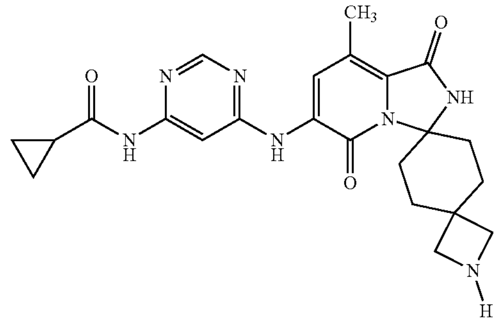

4ET-03-049

Synthesis of N-(6-((8"-methyl-1",5"-dioxo-1",5"-dihydro-2"H-dispiro[azetidine-3,1'-cyclohexane-4',3"-imidazo[1,5-a]pyridin]-6"-yl)amino)pyrimidin-4-yl)cyclopropanecarboxamide (4ET-03-049): A solution of tert-butyl 6"-((6-(cyclopropanecarboxamido)pyrimidin-4-yl)amino)-8"-methyl-1",5"-dioxo-1",5"-dihydro-2"H-dispiro[azetidine-3,1'-cyclohexane-4',3"-imidazo[1,5-a]pyridine]-1-carboxylate (4ET-03-048) (12.5 mg, 0.023 mmol) in trifluoroacetic acid/$CH_2Cl_2$ [70:30](1 mL) stirred at 23° C. for 1 hour. The reaction was concentrated and purified via strong cation exchange (SCX) flash column, eluting with $CH_2Cl_2$, MeOH, and finally 1M $NH_3$ in MeOH to generate the title compound 4ET-03-049 (8 mg, 0.018 mmol, 78%). $^1$H NMR (400 MHz, DMSO-$d_6$) δ 10.82 (s, 1H), 9.21 (s, 1H), 8.50 (d, J=15.6 Hz, 2H), 7.85 (s, 1H), 3.48-3.39 (m, 2H), 3.12-2.95 (m, 2H), 2.43 (s, 3H), 2.08-1.95 (m, J=6.7 Hz, 4H), 1.84-1.71 (m, 2H), 1.45-1.31 (m, J=12.7 Hz, 2H), 0.83 (d, J=5.8 Hz, 4H). UHPLC-MS (ESI): Rt 0.61 min, m/z 450.3 $[M+H]^+$.

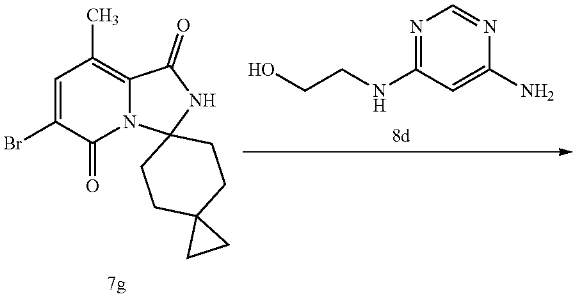

7g

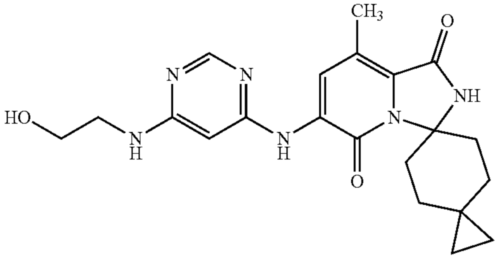

4ET-03-074

Synthesis of 6"-((6-((2-hydroxyethyl)amino)pyrimidin-4-yl)amino)-8"-methyl-2"H-dispiro[cyclopropane-1,1'-cyclohexane-4',3"-imidazo[1,5-a]pyridine]-1",5"-dione (4ET-03-074): The title compound was prepared according to the procedure of N-(6-((8"-methyl-1",5"-dioxo-1",5"-dihydro-2"H-dispiro[cyclopropane-1,1'-cyclohexane-3',3"-imidazo [1,5-a]pyridin]-6"-yl)amino)pyrimidin-4-yl)cyclopropane carboxamide except that 6"-bromo-8"-methyl-2"H-dispiro [cyclopropane-1,1'-cyclohexane-3',3"-imidazo[1,5-a]pyridine]-1",5"-dione is replaced with 6"-bromo-8"-methyl-2"H-dispiro[cyclopropane-1,1'-cyclohexane-4',3"-imidazo [1,5-a]pyridine]-1",5"-dione and N-(6-aminopyrimidin-4-yl)cyclopropanecarboxamide is replaced with 2-((6-aminopyrimidin-4-yl)amino)ethan-1-ol (8d) to provide the title compound 4ET-03-074. $^1$H NMR (400 MHz, DMSO-$d_6$) δ 10.03 (s, 1H), 8.61 (s, 1H), 8.37 (s, 1H), 8.19 (s, 1H), 6.97 (s, 1H), 6.24 (s, 1H), 4.68 (t, J=5.6 Hz, 1H), 3.53-3.43 (m, 2H), 3.24-3.11 (m, 4H), 2.41 (s, 3H), 2.18-2.05 (m, 2H), 1.39 (d, J=11.7 Hz, 2H), 0.87 (d, J=13.9 Hz, 2H), 0.37 (d, J=7.9 Hz, 2H), 0.28 (d, J=7.7 Hz, 2H). UHPLC-MS (ESI): Rt 0.66 min, m/z 411.3 [M+H]$^+$.

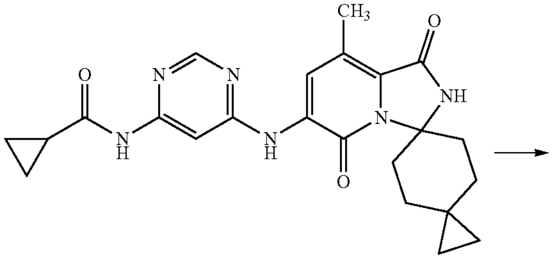

4ET-03-029

-continued

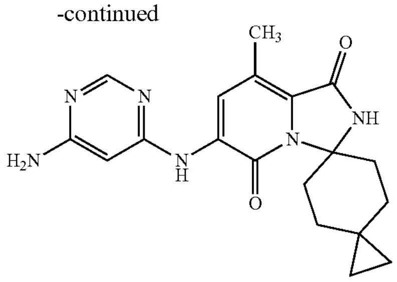

4ET-03-053

Synthesis of 6"-((6-Aminopyrimidin-4-yl)amino)-8"-methyl-2"H-dispiro[cyclopropane-1,1'-cyclohexane-4',3"-imidazo[1,5-a]pyridine]-1",5"-dione (4ET-03-053): The title compound was prepared according to the procedure of 6"-((6-Aminopyrimidin-4-yl)amino)-8"-methyl-2"H-dispiro [cyclopropane-1,1'-cyclohexane-3',3"-imidazo[1,5-a]pyridine]-1",5"-dione except that N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl) cyclopropanecarboxamide was replaced with N-(6-((8"-methyl-1",5"-dioxo-1",5"-dihydro-2"H-dispiro [cyclopropane-1,1'-cyclohexane-4',3"-imidazo[1,5-a] pyridin]-6"-yl)amino)pyrimidin-4-yl) cyclopropanecarboxamide (4ET-03-029) to provide the title compound 4ET-03-053 (12 mg, 0.033 mmol, 75%). $^1$H NMR (400 MHz, DMSO-$d_6$) δ 10.04 (s, 1H), 8.62 (s, 1H), 8.40 (s, 1H), 8.17 (s, 1H), 6.50 (br, 2H), 6.15 (s, 1H), 3.23 (dt, J=13.4, 4.4 Hz, 2H), 2.43 (s, 3H), 2.15 (t, J=13.4 Hz, 2H), 1.41 (m, 2H), 0.89 (m, 2H), 0.40 (m, 2H), 0.29 (m, 2H). UHPLC-MS (ESI): Rt 0.61 min. m/z 367.3 [M+H]$^+$.

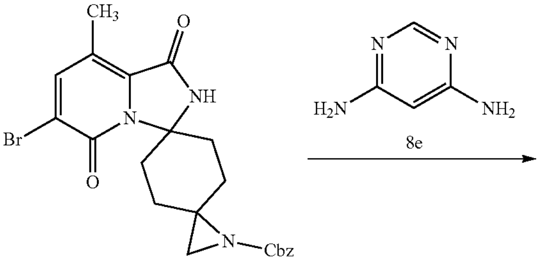

7j

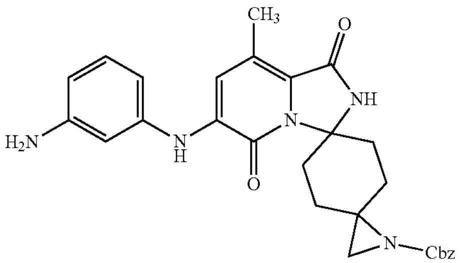

4ET-03-080

Synthesis of 6"-((6-aminopyrimidin-4-yl)amino)-8"-methyl-1-(2-oxo-2-phenyl-112-ethyl)-2"H-dispiro[aziridine-2,1'-cyclohexane-4',3"-imidazo[1,5-a]pyridine]-1",5"-dione (4ET-03-080): The title compound was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione is replaced with benzyl 6"-bromo-8"-methyl-1",5"-dioxo-1",5"-dihydro-2"H-dispiro[aziridine-2,1'-cyclohexane-4',3"-imidazo[1,5-a]pyridine]-1-carboxylate (7j) and N-(6-aminopyrimidin-4-yl)cyclopropanecarboxamide is replaced with pyrimidine-4,6-diamine (8e) to provide the title compound 4ET-03-080. $^1$H NMR (400 MHz, DMSO-$d_6$) δ 8.59 (s, 1H), 8.41 (s, 1H), 8.16 (s, 1H), 7.44-7.23 (m, 5H), 6.50 (br, 2H), 6.18 (s, 1H), 5.55 (s, 1H), 5.04 (s, 2H), 3.73-3.55 (m, 2H), 3.14-2.90 (m, 2H), 2.43 (s, 3H), 2.30 (m, 1H), 2.18 (m, 1H), 1.93 (m, 1H), 1.58 (m, 1H), 1.42 (m, 2H). UHPLC-MS (ESI): Rt 0.66 min, m/z 502.3 $[M+H]^+$.

intermediate was dissolved in $CH_2Cl_2$/Methanol (v:v/1:1, 2 mL) and added HCl (0.15 mL, 4M solution in 1,4-dioxane). The reaction was diluted with diethyl ether (30 mL) upon reaction completion as determined by monitoring by HPLC/MS. The resulting precipitates were collected through filtration and washed with diethyl ether to give the title compound 4ET-03-055 as hydrochloride salt (98 mg, 0.19 mmol, 93%). $^1$H NMR (400 MHz, DMSO-$d_6$) δ 10.15 (s, 1H), 10.02 (m, 1H), 9.36 (m, 1H), 8.58 (s, 1H), 8.49 (s, 1H), 7.96 (br s, 2H), 7.87 (s, 1H), 3.26-3.15 (m, 4H), 2.45 (s, 3H), 2.15 (m, 2H), 1.43 (m, 4H), 1.11 (m, 2H), 0.90 (m, 2H), 0.40 (m, 2H), 0.29 (m, 2H). UHPLC-MS (ESI): Rt 0.63 min, m/z 464.3 $[M+H]^+$.

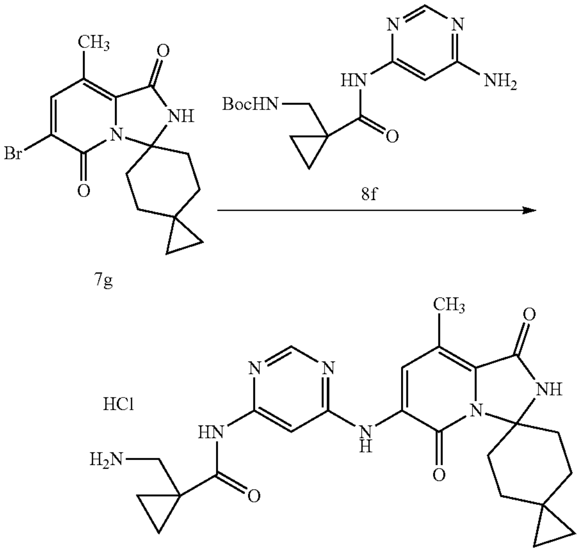

7g

8f

4ET-03-055-HCl

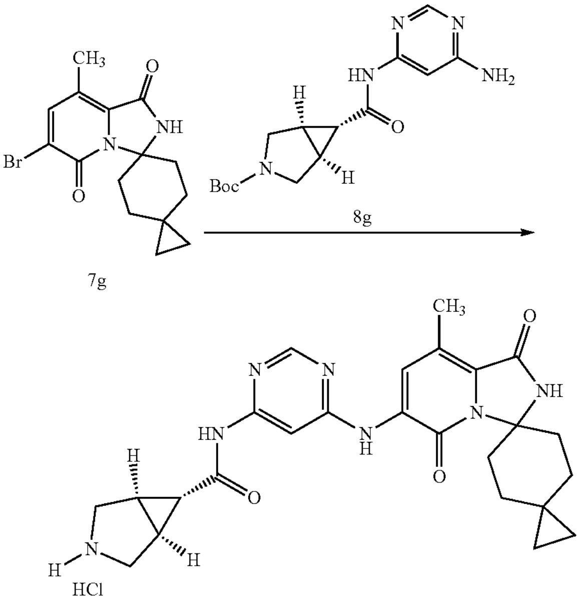

7g

8g

4ET-03-056-HCl

Synthesis of 1-(aminomethyl)-N-(6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)cyclopropane-1-carboxamide (4ET-03-055-HCl): tert-butyl ((1-((6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)carbamoyl)cyclopropyl)methyl)carbamate was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione is replaced with 6"-bromo-8"-methyl-2"H-dispiro[cyclopropane-1,1'-cyclohexane-4',3"-imidazo[1,5-a]pyridine]-1",5"-dione (7g) (70 mg, 0.21 mmol), and N-(6-aminopyrimidin-4-yl)cyclopropanecarboxamide is replaced with tert-butyl ((1-((6-aminopyrimidin-4-yl)carbamoyl)cyclopropyl)methyl)carbamate (8f) (83 mg, 0.27 mmol), $Cs_2CO_3$ (203 mg, 0.62 mmol), bis(diphenylphosphino)-9,9-dimethylxanthene (24 mg, 0.041 mmol), $Pd(OAc)_2$ (4.7 mg, 0.027 mmol), and 1,4-dioxane (2.0 mL) generated the Boc-protected intermediate tert-butyl ((1-((6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)carbamoyl)cyclopropyl)methyl) carbamate (110 mg, 0.19 mmol, 95%). The Boc-protected Synthesis of (1R,5S,6r)-N-(6-((8"-methyl-1",5"-dioxo-1",5"-dihydro-2"H-dispiro[cyclopropane-1,1'-cyclohexane-4',3"-imidazo[1,5-a]pyridin]-638-yl)amino)pyrimidin-4-yl)-3-azabicyclo[3.1.0]hexane-6-carboxamide (4ET-03-056-HCl): tert-butyl (1R,5S,6r)-6-((6-((8"-methyl-1",5"-dioxo-1",5"-dihydro-2"H-dispiro[cyclopropane-1,1'-cyclohexane-4',3"-imidazo[1,5-a]pyridin]-638-yl)amino)pyrimidin-4-yl) carbamoyl)-3-azabicyclo[3.1.0]hexane-3-carboxylate was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione is replaced with and N-(6-aminopyrimidin-4-yl)cyclopropanecarboxamide is replaced with 6"-bromo-8"-methyl-2"H-dispiro[cyclopropane-1,1'-cyclohexane-4',3"-imidazo[1,5-a]pyridine]-1",5"-dione (7g) (70 mg, 0.21 mmol), tert-butyl-(1R,5S,6r)-6-((6-aminopyrimidin-4-yl)carbamoyl)-3-azabicyclo[3.1.0]hexane-3-carboxylate (8g) (86 mg, 0.27 mmol), $Cs_2CO_3$ (203 mg, 0.62 mmol), bis(diphenylphosphino)-9,9-dimethylxanthene (24 mg, 0.041 mmol), $Pd(OAc)_2$ (4.7 mg, 0.027 mmol), and 1,4-dioxane (2.0 mL) generated the Boc-protected intermediate tert-butyl (1R,5S,6r)-6-((6-((8"-methyl-1",5"-dioxo-1",5"-dihydro-2"H-dispiro[cyclopropane-1,1'-cyclohexane-4',3"-imidazo[1,5-a]pyridin]-638-yl)amino)pyrimidin-4-yl)carbamoyl)-3-azabicyclo[3.1.0]hexane-3-carboxylate (115 mg, 0.20 mmol, 96%). The Boc-protected intermediate was dissolved in $CH_2Cl_2$/Methanol (v:v/1:1, 2 mL) and added HCl (0.15 mL, 4M solution in 1,4-dioxane). The reaction was diluted with diethyl ether (30 mL) upon reaction completion as determined by monitoring by HPLC/MS, the resulting precipitates were collected through filtration and washed with diethyl ether to give the title compound 4ET-03-056 as hydrochloride salt (95 mg, 0.19 mmol, 88%). $^1$H NMR (400 MHz, DMSO-$d_6$) δ 11.09 (s, 1H), 10.14 (s, 1H), 9.67 (br, 1H), 9.31 (s, 1H), 9.10 (br, 1H), 8.56 (s, 1H), 8.46 (s, 1H), 7.80 (s, 1H), 3.37 (m, 4H), 3.21 (dt, J=14.0, 4.4 Hz, 2H), 2.45 (s, 3H), 2.22 (m, 2H), 2.15 (t, J=14.0 Hz, 2H), 2.09 (t, J=3.2 Hz, 1H), 1.42 (d, J=12.0 Hz, 2H), 0.89 (d, J=13.2 Hz, 2H), 0.40 (m, 2H), 0.29 (m, 2H). UHPLC-MS (ESI): Rt 0.64 min, m/z 476.4 [M+H]$^+$.

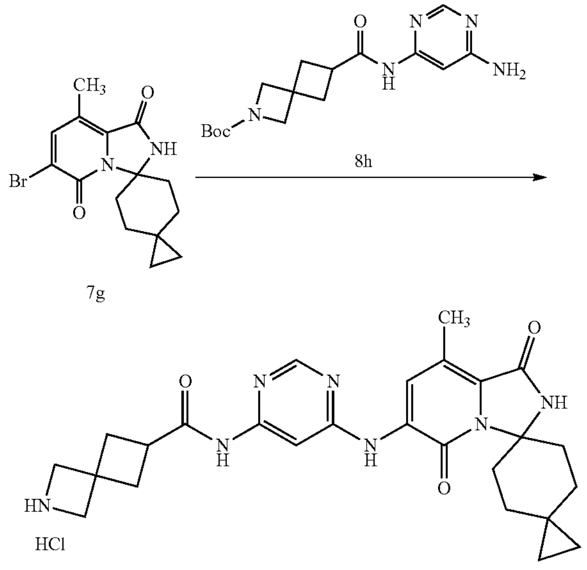

7g

4ET-03-057-HCl

Synthesis of N-(6-((8"-methyl-1",5"-dioxo-1",5"-dihydro-2"H-dispiro[cyclopropane-1,1'-cyclohexane-4',3"-imidazo[1,5-a]pyridin]-638-yl)amino)pyrimidin-4-yl)-2-azaspiro[3.3]heptane-6-carboxamide (4ET-03-057-HCl): tert-butyl 6-((6-((8"-methyl-1",5"-dioxo-1",5"-dihydro-2"H-dispiro[cyclopropane-1,1'-cyclohexane-4',3"-imidazo[1,5-a]pyridin]-638-yl)amino)pyrimidin-4-yl)carbamoyl)-2-azaspiro[3.3]heptane-2-carboxylate was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione is replaced with 6"-bromo-8"-methyl-2"H-dispiro[cyclopropane-1,1'-cyclohexane-4',3"-imidazo[1,5-a]pyridine]-1",5"-dione (7g) (70 mg, 0.21 mmol), and N-(6-aminopyrimidin-4-yl)cyclopropanecarboxamide is replaced with tert-butyl 6-((6-aminopyrimidin-4-yl)carbamoyl)-2-azaspiro[3.3]heptane-2-carboxylate 8h (90 mg, 0.27 mmol), $Cs_2CO_3$ (203 mg, 0.62 mmol), bis(diphenylphosphino)-9,9-dimethylxanthene (24 mg, 0.041 mmol), $Pd(OAc)_2$ (4.7 mg, 0.027 mmol), and 1,4-dioxane (2.0 mL) generated the Boc-protected intermediate tert-butyl 6-((6-((8"-methyl-1",5"-dioxo-1",5"-dihydro-2"H-dispiro

[cyclopropane-1,1'-cyclohexane-4',3"-imidazo[1,5-a]pyridin]-638-yl)amino)pyrimidin-4-yl)carbamoyl)-2-azaspiro[3.3]heptane-2-carboxylate (92 mg, 0.15 mmol, 75%). The Boc-protected intermediate was dissolved in $CH_2Cl_2$/Methanol (v:v/1:1, 2 mL) and added HCl (0.15 mL, 4M solution in 1,4-dioxane). The reaction was diluted with diethyl ether (30 mL) upon reaction completion as determined by monitoring by HPLC/MS, the resulting precipitates were collected through filtration and washed with diethyl ether to give the title compound 4ET-03-057 as hydrochloride salt (77 mg, 0.14 mmol, 94%). $^1$H NMR (400 MHz, DMSO-$d_6$) δ 10.59 (br, 1H), 10.14 (s, 1H), 9.33 (br, 1H), 8.92 (br, 1H), 8.54 (s, 1H), 8.46 (s, 1H), 8.12 (m, 1H), 7.86 (s, 1H), 3.93 (m, 4H), 3.21 (m, 3H), 2.45 (s, 3H), 2.41 (m, 2H), 2.21 (m, 2H), 2.15 (m, 2H), 1.42 (d, J=12.0 Hz, 2H), 0.90 (d, J=13.6 Hz, 2H), 0.40 (m, 2H), 0.30 (m, 2H). UHPLC-MS (ESI): Rt 0.65 min, m/z 490.4 [M+H]$^+$.

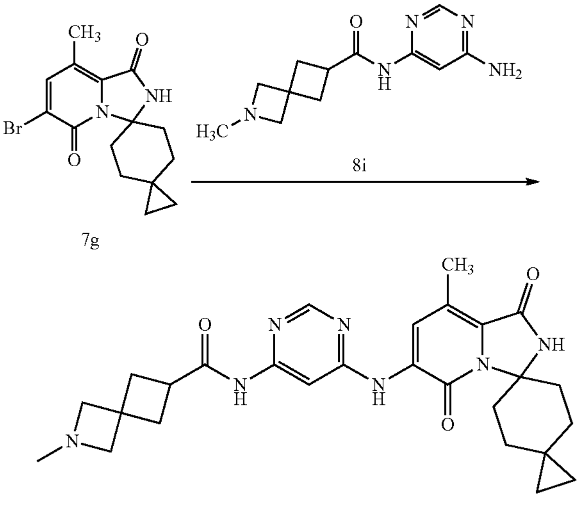

7g

4ET-03-060

Synthesis of 2-methyl-N-(6-((8"-methyl-1",5"-dioxo-1",5"-dihydro-2"H-dispiro[cyclopropane-1,1'-cyclohexane-4',3"-imidazo[1,5-a]pyridin]-638-yl)amino)pyrimidin-4-yl)-2-azaspiro[3.3]heptane-6-carboxamide (4ET-03-060): The title compound was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione is replaced with 6"-bromo-8"-methyl-2"H-dispiro[cyclopropane-1,1'-cyclohexane-4',3"-imidazo[1,5-a]pyridine]-1",5"-dione (7g) (48 mg, 0.19 mmol), and N-(6-aminopyrimidin-4-yl)cyclopropanecarboxamide is replaced with N-(6-aminopyrimidin-4-yl)-2-methyl-2-azaspiro[3.3]heptane-6-carboxamide (8i) (50 mg, 0.14 mmol), $Cs_2CO_3$ (145 mg, 0.44 mmol), bis(diphenylphosphino)-9,9-dimethylxanthene (17.1 mg, 0.029 mmol), $Pd(OAc)_2$ (3.3 mg, 0.014 mmol), and 1,4-dioxane (1.5 mL) generated the title compound 4ET-03-060 (18 mg, 0.035 mmol, 24%). $^1$H NMR (400 MHz, DMSO-$d_6$) δ 10.39 (s, 1H), 10.12 (s, 1H), 9.18 (s, 1H), 8.51 (s, 1H, 8.48 (s, 1H), 7.90 (s, 1H), 3.22 (m, 4H), 3.13 (m, 3H), 2.45 (s, 3H), 2.26 (m, 4H), 2.21 (s, 3H), 2.15 (m, 2H), 1.42 (d, J=12.0 Hz, 2H), 0.91 (d, J=13.2 Hz, 2H), 0.40 (m, 2H), 0.30 (m, 2H). UHPLC-MS (ESI): Rt 0.65 min, m/z 504.4 [M+H]$^+$.

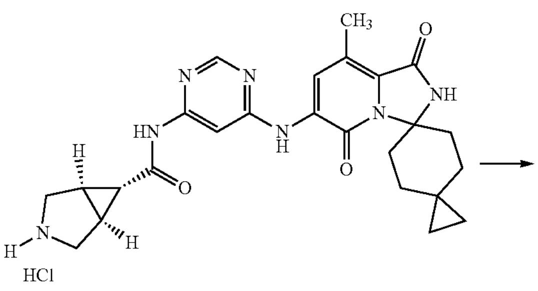

4ET-03-056-HCl

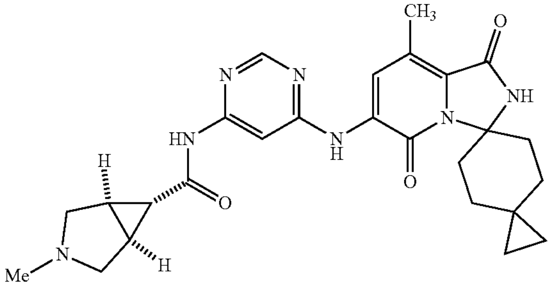

4ET-03-061

Synthesis of (1R,5S,6r)-3-methyl-N-(6-((8"-methyl-1",5"-dioxo-1",5"-dihydro-2"H-dispiro[cyclopropane-1,1'-cyclohexane-4',3"-imidazo[1,5-a]pyridin]-638-yl)amino)pyrimidin-4-yl)-3-azabicyclo[3.1.0]hexane-6-carboxamide (4ET-03-061): To a solution of (1R,5S,6r)-N-(6-((8"-methyl-1",5"-dioxo-1",5"-dihydro-2"H-dispiro[cyclopropane-1,1'-cyclohexane-4',3"-imidazo[1,5-a]pyridin]-638-yl) amino)pyrimidin-4-yl)-3-azabicyclo[3.1.0]hexane-6-carboxamide HCl (4ET-03-056-HCl) (50 mg, 0.10 mmol) in $CH_2Cl_2$/methanol (v:v/2:1, 1.5 mL) was added formaldehyde (40% aq. 0.10 mL, 1.57 mmol) and acetic acid (3.15 mg, 0.052 mmol) and the reaction was cooled to 0° C. before adding $NaCNBH_3$ (13.2 mg, 0.21 mmol). The reaction was stirred at 0° C. for 2 hours and concentrated under the reduced pressure and the resulting material was purified by Biotage flash chromatography (silica gel, 0% to 20% 3M $NH_3$/MeOH in $CH_2Cl_2$) to give the title compound 4ET-03-061 (32 mg, 0.065 mmol, 63%). $^1$H NMR (400 MHz, DMSO-$d_6$) δ 10.69 (br, 1H), 10.12 (s, 1H), 9.15 (s, 1H), 8.52 (s, 1H), 8.48 (s, 1H), 7.82 (s, 1H), 3.22 (dt, J=13.2, 4.2 Hz, 2H), 2.98 (m, 3H), 2.45 (s, 3H), 2.36 (m, 2H), 2.28 (m, 3H), 2.15 (m, 2H), 1.90 (m, 2H), 1.42 (d, J=12.0 Hz, 2H), 0.90 (d, J=13.2 Hz, 2H), 0.40 (m, 2H), 0.30 (m, 2H). UHPLC-MS (ESI): Rt 0.65 min, m/z 504.4 $[M+H]^+$.

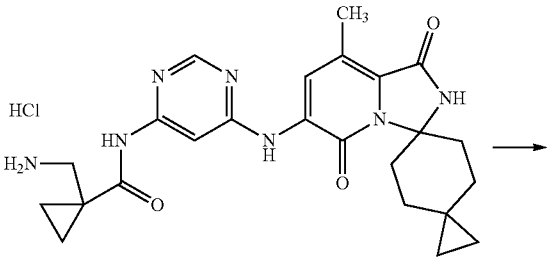

4ET-03-055-HCl

-continued

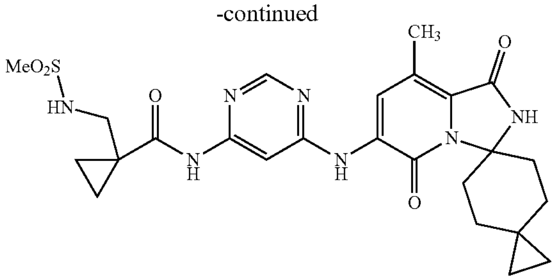

4ET-03-076

Synthesis of N-(6-((8"-methyl-1",5"-dioxo-1",5"-dihydro-2"H-dispiro[cyclopropane-1,1'-cyclohexane-4',3"-imidazo[1,5-a]pyridin]-638-yl)amino)pyrimidin-4-yl)-1-(methylsulfonamido methyl)cyclopropane-1-carboxamide (4ET-03-076): To a stirred solution of 1-(aminomethyl)-N-(6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)cyclopropane-1-carboxamide HCl (4ET-03-055-HCl) (20 mg, 0.037 mmol) in anhydrous acetonitrile (2.0 mL) under inert atmosphere at 23° C. was added trimethylamine (0.026 mL, 0.187 mmol) and methanesulfonyl chloride (0.009 mL, 0.112 mmol). After 3 hours, pyridine (0.5 mL) and additional methanesulfonyl chloride (0.010 mL). After stirring for 16 hours, the mixture was diluted with methylene chloride (3 mL) and subjected to a strong cation exchange (SCX) SPE cartridge (2 gram SCX, $CH_2Cl_2$/MeOH, then 1M $NH_3$ in MeOH). The product was in the $CH_2Cl_2$ and MeOH fractions along with pyridine. Those fractions were combined, preadsorbed onto silica and purified by flash chromatography (4g $SiO_2$, $CH_2Cl_2$:ethyl acetate 10-100% gradient) to give the title compound 4ET-03-076 (1.1 mg, 6%). $^1$H NMR (400 MHz, DMSO-$d_6$) δ 10.10 (s, 1H), 9.70 (s, 1H), 9.24 (s, 1H), 8.53 (s, 1H), 8.49 (s, 1H), 7.84 (d, J=1.1 Hz, 1H), 7.34 (t, J=6.3 Hz, 1H), 3.27 (s, 2H), 3.26-3.13 (m, 2H), 2.92 (s, 3H), 2.43 (s, 4H), 2.13 (t, J=13.4 Hz, 2H), 1.40 (d, J=12.1 Hz, 2H), 1.16 (d, J=2.9 Hz, 3H), 0.93-0.81 (m, 3H), 0.45-0.22 (m, 4H). UHPLC-MS (ESI): Rt 0.770 min, m/z 542.3 $[M+H]^+$.

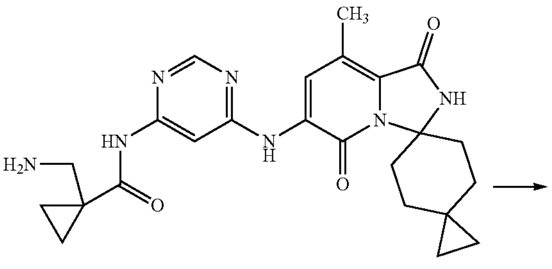

4ET-03-055

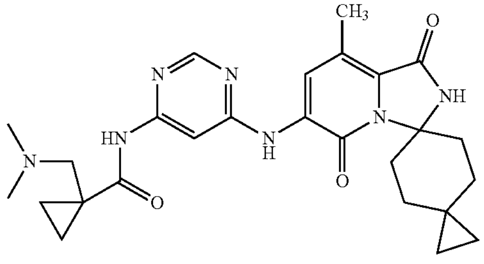

4ET-03-081

Synthesis of 1-((dimethylamino)methyl)-N-(6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)cyclopropane-1-carboxamide (4ET-03-081): To a stirred solution of 1-(aminomethyl)-N-(6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)cyclopropane-1-carboxamide (4ET-03-055) (15 mg, 0.034 mmol) in $CH_2Cl_2$ (2.0 mL) cooled to 0° C. was added acetic acid (0.010 mL, 0.172 mmol) and 40% formaldehyde (0.039 mL, 0.517 mmol). The mixture was treated with sodium triacetoxyborohydride (9 mg, 0.138 mmol) and left to gradually warm to 23° C. After stirring for 16 hours, the solvent was removed and the residue was taken up with trifluoroethanol (2.0 mL) and treated with sodium borohydride (6.4 mg, 0.170 mmol) in one portion at 23° C. After 1 hour, the mixture was diluted with MeOH (3.0 mL) and subjected to a strong cation exchange (SCX) SPE cartridge (2 gram SCX) and eluted with methanol then dichloromethane then 1M $NH_3$ in methanol to give the title compound 4ET-03-081 (4.3 mg, 27%). $^1H$ NMR (400 MHz, Chloroform-d) δ 8.58 (s, 1H), 8.55 (s, 1H), 8.22 (s, 1H), 8.02 (s, 1H), 7.64 (s, 1H), 3.34 (td, J=14.0, 12.8, 4.5 Hz, 2H), 2.57 (s, 3H), 2.51 (s, 2H), 2.41 (s, 6H), 2.02 (td, J=13.3, 12.0, 3.7 Hz, 2H), 1.55 (d, J=11.3 Hz, 2H), 1.39 (q, J=4.0 Hz, 2H), 1.07 (d, J=13.9 Hz, 2H), 0.67 (q, J=4.0 Hz, 2H), 0.45 (s, 4H). UHPLC-MS (ESI): Rt 0.65 min. m/z 492.3 $[M+H]^+$.

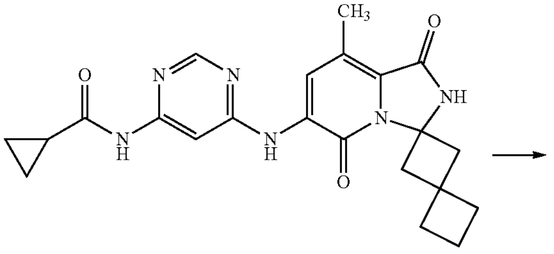

4ET-03-043

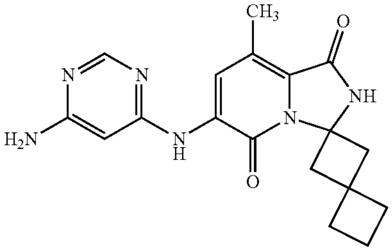

4ET-01-009

Synthesis of 6"-((6-aminopyrimidin-4-yl)amino)-8"-methyl-2"H-dispiro[cyclobutane-1,1'-cyclobutane-3',3"-imidazo[1,5-a]pyridine]-1",5"-dione (4ET-01-009): The title compound was prepared according to the procedure of 6"-((6-Aminopyrimidin-4-yl)amino)-8"-methyl-2"H-dispiro[cyclopropane-1,1'-cyclohexane-3',3"-imidazo[1,5-a]pyridine]-1",5"-dione except that N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropanecarboxamide was replaced with N-(6-((8"-methyl-1",5"-dioxo-1",5"-dihydro-2"H-dispiro[cyclobutane-1,1'-cyclobutane-3',3"-imidazo[1,5-a]pyridin]-6"-yl)amino)pyrimidin-4-yl)cyclopropanecarboxamide (4ET-03-043) to provide the title compound 4ET-01-009 (8 mg, 0.023 mmol, 87%). $^1H$ NMR (400 MHz, DMSO-$d_6$) δ 9.89 (s, 1H), 8.71 (s, 1H), 8.42 (s, 1H), 8.16 (s, 1H), 6.49 (s, 2H), 6.21 (s, 1H), 3.56 (d, J=14.2 Hz, 2H), 2.38 (s, 3H), 2.35-2.29 (m, 2H), 2.24-2.12 (m, 4H), 1.80 (dt, J=14.7, 7.2 Hz, 2H). UHPLC-MS (ESI/): Rt 0.63 min, m/z 353.3 $[M+H]^+$.

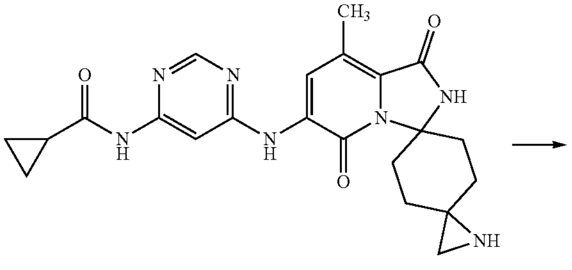

4ET-03-040

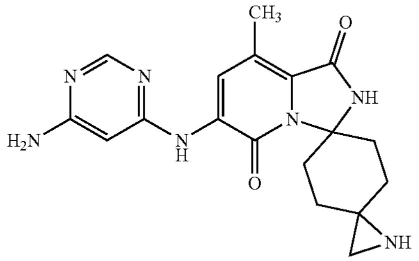

4ET-01-012

Synthesis of 6"-((6-aminopyrimidin-4-yl)amino)-8"-methyl-2"H-dispiro[aziridine-2,1'-cyclohexane-4',3"-imidazo[1,5-a]pyridine]-1",5"-dione (4ET-01-012): The title compound was prepared according to the procedure of 6"-((6-Aminopyrimidin-4-yl)amino)-8"-methyl-2"H-dispiro[cyclopropane-1,1'-cyclohexane-3',3"-imidazo[1,5-a]pyridine]-1",5"-dione except that N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropanecarboxamide was replaced with N-(6-((8"-methyl-1",5"-dioxo-1",5"-dihydro-2"H-dispiro[aziridine-2,1'-cyclohexane-4',3"-imidazo[1,5-a]pyridin]-6"-yl)amino)pyrimidin-4-yl)cyclopropanecarboxamide (4ET-03-040) to provide the title compound 4ET-01-012 (7 mg, 0.019 mmol, 38%). $^1H$ NMR (400 MHz, DMSO-$d_6$) δ 8.58 (s, 1H), 8.41 (s, 1H), 8.16 (s, 1H), 6.51 (br, 2H), 6.17 (s, 1H), 5.62 (m, 1H), 3.72 (m, 1H), 3.21 (br, 1H), 3.10 (m, 2H), 2.43 (s, 3H), 2.29 (m, 2H), 1.96 (m, 2H), 1.60 (m, 2H). UHPLC-MS (ESI/): Rt 0.55 min. m/z 368.3 $[M+H]^+$.

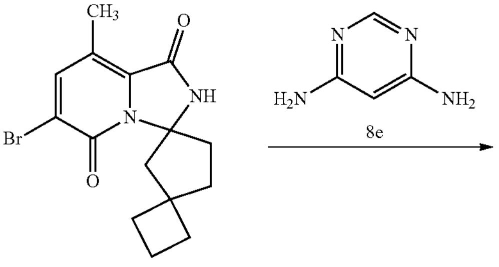

71

-continued

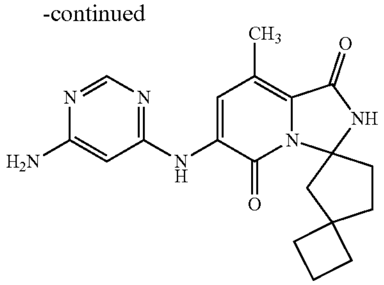

4ET-01-015

Synthesis of 6"-((6-aminopyrimidin-4-yl)amino)-8"-methyl-2"H-dispiro[cyclopropane-1,1'-cyclopentane-3',3"-imidazo[1,5-a]pyridine]-1",5"-dione (4ET-01-015): The title compound was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione is replaced with, 6"-bromo-8"-methyl-2"H-dispiro[cyclopropane-1,1'-cyclopentane-3',3"-imidazo[1,5-a]pyridine]-1",5"-dione (71) and N-(6-aminopyrimidin-4-yl)cyclopropanecarboxamide is replaced with 4,6-Diaminopyrimidine (8e) to provide the title compound 4ET-01-015 (16 mg, 37%). $^1$H NMR (400 MHz, DMSO-$d_6$) δ 9.68 (s, 1H), 8.64 (s, 1H), 8.39 (s, 1H), 8.14 (s, 1H), 6.47 (s, 2H), 6.16 (d, J=1.0 Hz, 1H), 2.90 (d, J=13.7 Hz, 1H), 2.75 (dt, J=13.1, 7.9 Hz, 1H), 2.38 (s, 3H), 2.22-2.01 (m, 2H), 1.99-1.64 (m, 5H). UHPLC-MS (ESI): Rt 0.64 min, m/z 367.3 $[M+H]^+$.

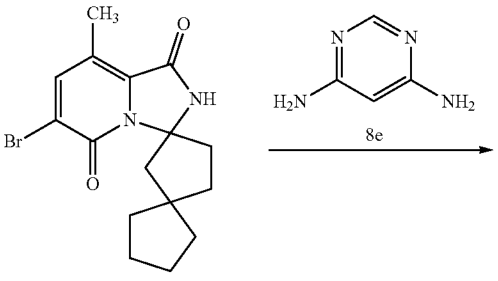

7m

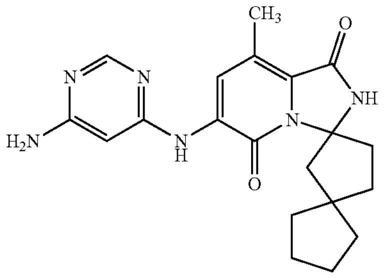

4ET-01-016

Synthesis of 6"-((6-aminopyrimidin-4-yl)amino)-8"-methyl-2"H-dispiro[cyclopentane-1,1'-cyclopentane-3',3"-imidazo[1,5-a]pyridine]-1",5"-dione (4ET-01-016): The title compound was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione is replaced with 6"-bromo-8"-methyl-2"H-dispiro[cyclopentane-1,1'-cyclopentane-3',3"-imidazo[1,5-a]pyridine]-1",5"-dione and N-(6-aminopyrimidin-4-yl)cyclopropanecarboxamide is replaced with 4,6-diaminopyrimidine (8e) to provide the title compound 4ET-01-016. $^1$H NMR (400 MHz, DMSO-$d_6$) δ 9.77 (s, 1H), 8.68 (s, 1H), 8.41 (s, 1H), 8.14 (d, J=0.9 Hz, 1H), 6.46 (s, 2H), 6.18 (d, J=1.0 Hz, 1H), 2.91 (d, J=14.0 Hz, 1H), 2.88-2.80 (m, OH), 2.39 (s, 3H), 2.03-1.91 (m, 1H), 1.86-1.68 (m, 2H), 1.60 (t, J=10.1 Hz, 9H). UHPLC-MS (ESI): Rt 0.66 min. m/z 381.3 [M+H]+.

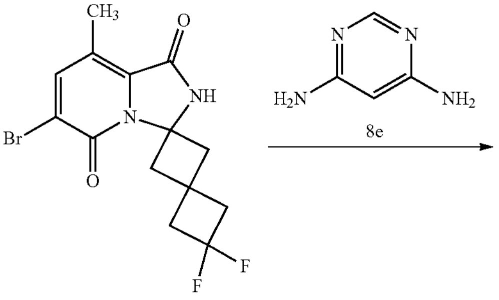

7n

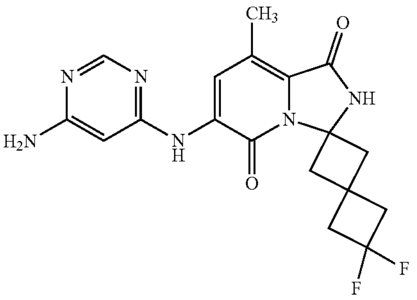

4ET-01-017

Synthesis of 6"-((6-aminopyrimidin-4-yl)amino)-3,3-difluoro-8"-methyl-2"H-dispiro[cyclobutane-1,1'-cyclobutane-3',3"-imidazo[1,5-a]pyridine]-1",5"-dione (4ET-01-017): The title compound was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione is replaced with 6"-bromo-3,3-difluoro-8"-methyl-2"H-dispiro[cyclobutane-1,1'-cyclobutane-3',3"-imidazo[1,5-a]pyridine]-1",5"-dione (7n) and N-(6-aminopyrimidin-4-yl)cyclopropanecarboxamide is replaced with 4,6-diaminopyrimidine 8e to provide the title compound 4ET-01-017. $^1$H NMR (400 MHz, DMSO-$d_6$) δ 9.91 (s, 1H), 8.71 (s, 1H), 8.41 (s, 1H), 8.14 (s, 1H), 6.48 (s, 2H), 6.20 (s, 1H), 3.61 (d, J=14.4 Hz, 2H), 2.88-2.69 (m, 4H), 2.36 (s, 3H), 2.02-1.92 (m, 2H). UHPLC-MS (ESI): Rt 0.63 min, m/z 381.3 $[M+H]^+$.

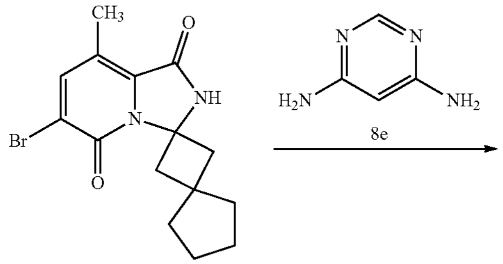

7o

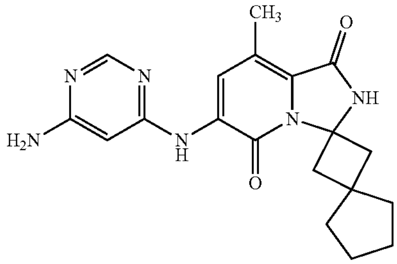

4ET-01-018

Synthesis of 6"-((6-aminopyrimidin-4-yl)amino)-8"-methyl-2"H-dispiro[cyclopentane-1,1'-cyclobutane-3',3"-imidazo[1,5-a]pyridine]-1",5"-dione (4ET-01-018): The title compound was prepared according to the procedure of N-(6-((8"-methyl-1",5"-dioxo-1",5"-dihydro-2"H-dispiro [cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro [cyclopropane-1,1'-cyclohexane-3',3"-imidazo[1,5-a] pyridine]-1",5"-dione is replaced with 6"-bromo-8"-methyl-2"H-dispiro[cyclopentane-1,1'-cyclobutane-3',3"-imidazo [1,5-a]pyridine]-1",5"-dione (7o) and N-(6-aminopyrimidin-4-yl)cyclopropanecarboxamide is replaced with 4,6-diaminopyrimidine (8e) to provide the title compound 4ET-01-018 $^1$H NMR (400 MHz, DMSO-$d_6$) δ 10.00 (s, 1H), 8.72 (s, 1H), 8.43 (s, 1H), 8.17 (s, 1H), 6.50 (s, 2H), 6.21 (s, 1H), 3.51 (d, J=13.7 Hz, 2H), 2.40 (s, 3H), 2.11 (d, J=13.6 Hz, 2H), 1.97-1.87 (m, 2H), 1.86-1.77 (m, 2H), 1.61-1.53 (m, 4H). UHPLC-MS (ESI): Rt 0.73 min. m/z 367.3 [M+H]$^+$.

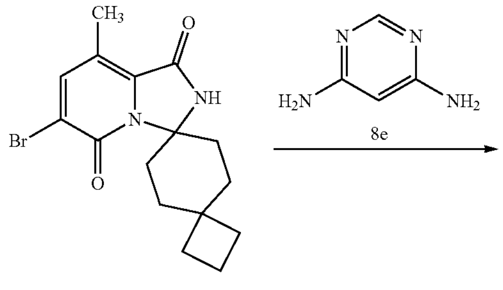

7p

-continued

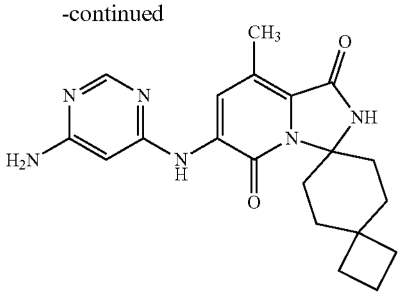

4ET-01-019

Synthesis of 6"-((6-aminopyrimidin-4-yl)amino)-8"-methyl-2"H-dispiro[cyclobutane-1,1'-cyclohexane-4',3"-imidazo[1,5-a]pyridine]-1",5"-dione (4ET-01-019): The title compound was prepared according to the procedure of N-(6-((8"-methyl-1",5"-dioxo-1",5"-dihydro-2"H-dispiro [cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro [cyclopropane-1,1'-cyclohexane-3',3"-imidazo[1,5-a] pyridine]-1",5"-dione is replaced with 6"-bromo-8"-methyl-2"H-dispiro[cyclobutane-1,1'-cyclohexane-4',3"-imidazo[1, 5-a]pyridine]-1",5"-dione (7p) and N-(6-aminopyrimidin-4-yl)cyclopropanecarboxamide is replaced with 4,6-diaminopyrimidine (8e) to provide the title compound 4ET-01-019. $^1$H NMR (400 MHz, DMSO-$d_6$) δ 9.95 (s, 1H), 8.68 (s, 1H), 8.40 (s, 1H), 8.14 (s, 1H), 6.47 (s, 2H), 6.15 (s, 1H), 3.14-3.00 (m, 2H), 2.39 (s, 3H), 1.88-1.81 (m, 3H), 1.80-1.60 (m, J=12.9 Hz, 5H), 1.32-1.19 (m, 4H). UHPLC-MS (ESI): Rt 0.66 min, m/z 381.3 [M+H]$^+$.

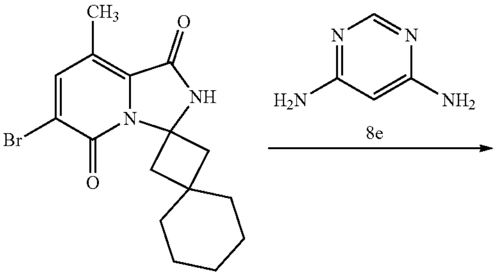

7q

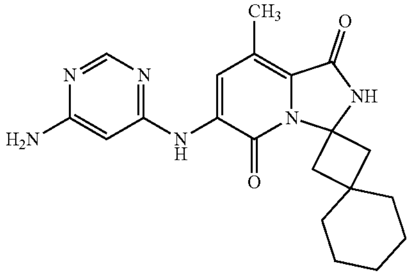

4ET-01-020

Synthesis of 6"-((6-aminopyrimidin-4-yl)amino)-8"-methyl-2"H-dispiro[cyclohexane-1,1'-cyclobutane-3',3"-imidazo[1,5-a]pyridine]-1",5"-dione (4ET-01-020): The title compound was prepared according to the procedure of N-(6-((8"-methyl-1",5"-dioxo-1",5"-dihydro-2"H-dispiro [cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione is replaced with 6"-bromo-8"-methyl-2"H-dispiro[cyclohexane-1,1'-cyclobutane-3',3"-imidazo[1,5-a]pyridine]-1",5"-dione (7q) and N-(6-aminopyrimidin-4-yl)cyclopropanecarboxamide is replaced with 4,6-diaminopyrimidine (8e) to provide the title compound 4ET-01-020 (18 mg, 0.05 mmol, 33%). $^1$H NMR (400 MHz, DMSO-$d_6$) δ 9.94-9.87 (m, 1H), 8.69 (s, 1H), 8.43 (s, 1H), 8.17 (s, 1H), 6.50 (s, 2H), 6.20 (s, 1H), 3.30-3.25 (m, 2H), 2.40 (s, 3H), 2.00 (d, J=13.7 Hz, 2H), 1.94-1.84 (m, 2H), 1.75-1.65 (m, 2H), 1.47-1.30 (m, 6H). UHPLC-MS (ESI): Rt 0.67 min, m/z 381.2 $[M+H]^+$.

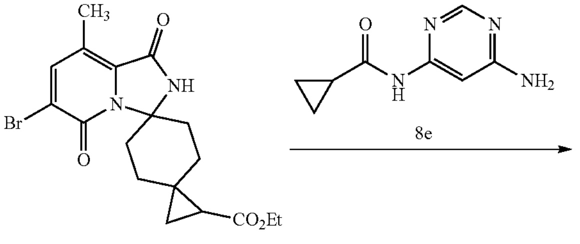

7r

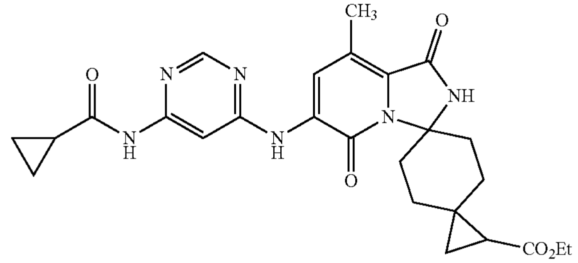

4ET-03-045

Synthesis of ethyl 6"-((6-(cyclopropanecarboxamido)pyrimidin-4-yl)amino)-8"-methyl-1",5"-dioxo-1",5"-dihydro-2"H-dispiro[cyclopropane-1,1'-cyclohexane-4',3"-imidazo[1,5-a]pyridine]-2-carboxylate (4ET-03-045): The title compound was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione is replaced with ethyl 6"-bromo-8"-methyl-1",5"-dioxo-1",5"-dihydro-2"H-dispiro[cyclopropane-1,1'-cyclohexane-4',3"-imidazo[1,5-a]pyridine]-2-carboxylate (7r) to provide the title compound 4ET-03-045 (38 mg, 0.075 mmol, 25%). $^1$H NMR (400 MHz, DMSO-$d_6$) δ 10.83 (s, 1H), 10.09 (bs, 1H), 9.12 (s, 1H), 8.50 (s, 1H), 8.44 (s, 1H), 7.82 (s, 1H), 4.07 (q, J=7.0 Hz, 2H), 3.24-3.12 (m, 2H), 2.42 (s, 3H), 2.30-2.12 (m, 2H), 1.90-1.29 (m, 6H), 1.20 (t, J=7.1 Hz, 3H), 1.08-0.92 (m, 2H), 0.82 (d, J=6.1 Hz, 4H). UHPLC-MS (ESI): Rt 0.77 min, m/z 507.3 $[M+H]^+$.

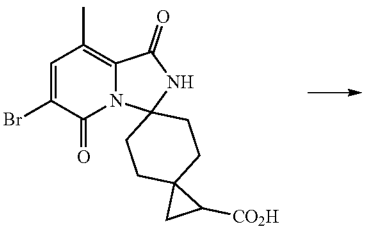

(7s)

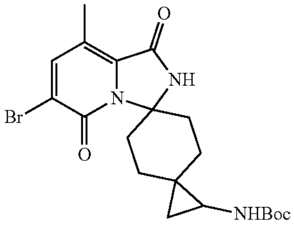

(7t)

Synthesis of tert-butyl (6"-bromo-8"-methyl-1",5"-dioxo-1",5"-dihydro-2"H-dispiro[cyclopropane-1,1'-cyclohexane-4',3"-imidazo[1,5-a]pyridin]-2-yl)carbamate: To a solution of 6"-bromo-8"-methyl-1",5"-dioxo-1",5"-dihydro-2"H-dispiro[cyclopropane-1,1'-cyclohexane-4',3"-imidazo[1,5-a]pyridine]-2-carboxylic acid (7s) (210 mg, 0.55 mmol) in toluene (1.8 mL) was added triethylamine (0.12 mL, 0.83 mmol) and diphenyl phosphoryl azide (0.18 mL, 0.83 mmol). The reaction mixture was heated to reflux for 2 h. Then, t-BuOH (0.06 mL, 0.605 mmol) was added and the reaction mixture was refluxed for 16 hours. The solvent was removed under reduced pressure and $NaHCO_3$ (50 mL) was added. After washed with ethyl acetate (50 mL×3), the organic layer was dried over $Na_2SO_4$, filtered, and concentrated under reduced pressure. The resulting material was purified by Biotage flash chromatography (gradient elution, 0-10% MeOH in $CH_2Cl_2$) to afford a tert-butyl (6"-bromo-8"-methyl-1",5"-dioxo-1",5"-dihydro-2"H-dispiro[cyclopropane-1,1'-cyclohexane-4',3"-imidazo[1,5-a]pyridin]-2-yl)carbamate (7t) (14 mg, 0.031 mmol). $^1$H NMR (400 MHz, $CDCl_3$) δ 7.73 (s, 1H), 3.23 (m, 2H), 2.51 (m, 1H), 2.48 (s, 3H), 2.10 (m, 2H), 1.53 (m, 2H), 1.30 (m, 2H), 1.11 (m, 9H), 0.81 (m, 1H), 0.42 (m, 1H). UHPLC-MS (ESI): Rt 0.74 min, m/z 451.1 $[M+H]^+$.

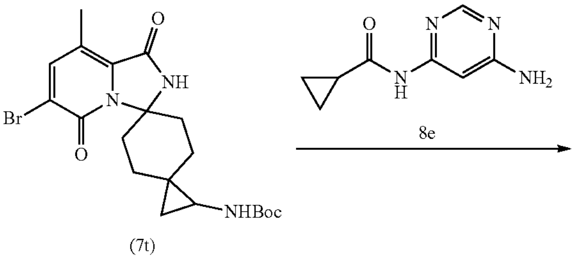

(7t)

-continued

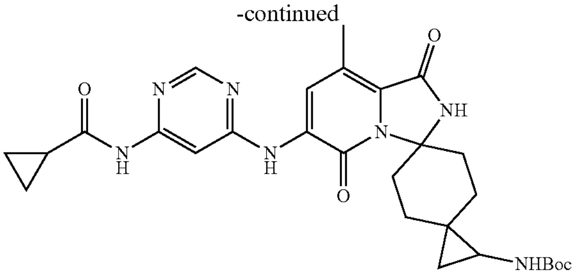

4ET-03-047

Synthesis of tert-butyl (6"-((6-(cyclopropanecarboxamido)pyrimidin-4-yl)amino)-8"-methyl-1",5"-dioxo-1",5"-dihydro-2"H-dispiro[cyclopropane-1,1'-cyclohexane-4',3"-imidazo[1,5-a]pyridin]-2-yl)carbamate (4ET-03-047): The title compound was prepared according to the procedure of N-(6-((8"-methyl-1",5"-dioxo-1",5"-dihydro-2"H-dispiro [cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro [cyclopropane-1,1'-cyclohexane-3',3"-imidazo[1,5-a] pyridine]-1",5"-dione is replaced with tert-butyl (6"-bromo-8"-methyl-1",5"-dioxo-1",5"-dihydro-2"H-dispiro [cyclopropane-1,1'-cyclohexane-4',3"-imidazo[1,5-a] pyridin]-2-yl)carbamate (7t) to provide the title compound 4ET-03-047 (2 mg, 0.004 mmol, 12%). $^1$H NMR (400 MHz, DMSO-$d_6$) δ 10.83 (s, 1H), 10.06 (bs, 1H), 9.16 (s, 1H), 8.51 (s, 1H), 8.46 (s, 1H), 7.82 (s, 1H), 3.23-3.09 (m, 2H), 2.59 (m, 1H), 2.42 (s, 3H), 2.04-1.93 (m, 2H), 1.57 (m, 1.0), 1.50-1.31 (m, 4H), 0.98-0.82 (m, 11H), 0.53 (m, 2H). UHPLC-MS (ESI): Rt 0.75 min, m/z 549.4 [M+H]$^+$.

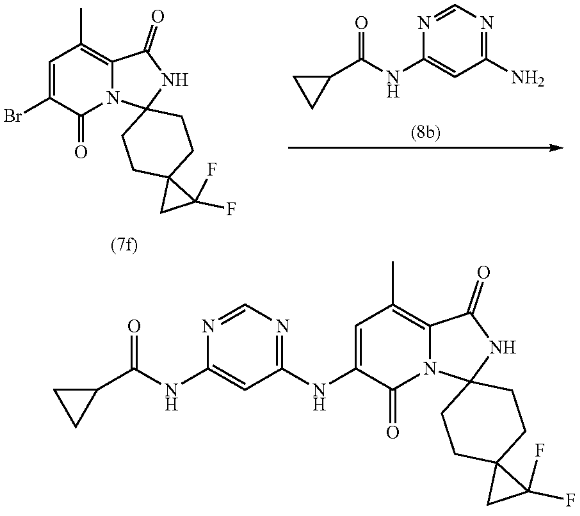

(7f)

(8b)

(7f1)

Synthesis of N-(6-((2,2-difluoro-8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl) cyclopropanecarboxamide (7f1): The title compound was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione was replaced with 6"-bromo-2,2-difluoro-8"-methyl-2"H-dispiro [cyclopropane-1,1'-cyclohexane-4',3"-imidazo[1,5-a]pyridine]-1",5"-dione (7f) to provide the title compound (7f1) (21 mg, 0.045 mmol, 43%).

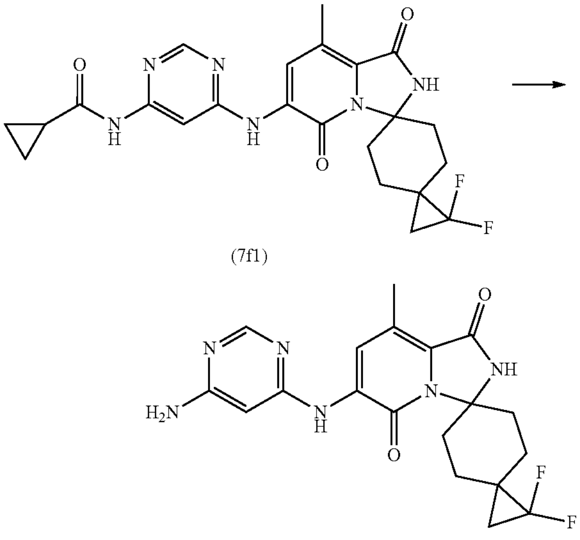

(7f1)

(4ET-03-068)

Synthesis of 6"-((6-aminopyrimidin-4-yl)amino)-2,2-difluoro-8"-methyl-2"H-dispiro[cyclopropane-1,1'-cyclohexane-4',3"-imidazo[1,5-a]pyridine]-1",5"-dione (4ET-03-068) The title compound was prepared according to the procedure of N-(6-((8"-methyl-1",5"-dioxo-1",5"-dihydro-2"H-dispiro[cyclopropane-1,1'-cyclohexane-3',3"-imidazo [1,5-a]pyridin]-6"-yl)amino)pyrimidin-4-yl)cyclopropane carboxamide except that 6"-bromo-8"-methyl-2"H-dispiro [cyclopropane-1,1'-cyclohexane-3',3"-imidazo[1,5-a]pyridine]-1",5"-dione was replaced with N-(6-((2,2-difluoro-8"-methyl-1",5"-dioxo-1",5"-dihydro-2"H-dispiro [cyclopropane-1,1'-cyclohexane-4',3"-imidazo[1,5-a] pyridin]-6"-yl)amino)pyrimidin-4-yl) cyclopropanecarboxamide (7f1) to provide the title compound 4ET-03-068 (15 mg, 0.037 mmol, 83%). $^1$H NMR (400 MHz, DMSO-$d_6$) δ 8.68 (s, 1H), 8.60 (s, 1H), 8.38 (s, 1H), 8.15 (s, 1H), 6.49 (s, 2H), 6.13 (s, 1H), 3.23-3.04 (m, 2H), 2.41 (s, 3H), 2.18-1.97 (m, 2H), 1.50 (d, J=11.5 Hz, 2H), 1.39 (d, J=12.9 Hz, 2H), 1.31 (t, J=8.3 Hz, 2H). UHPLC-MS (ESI): Rt 0.65 min, m/z 403.3 [M+H]$^+$.

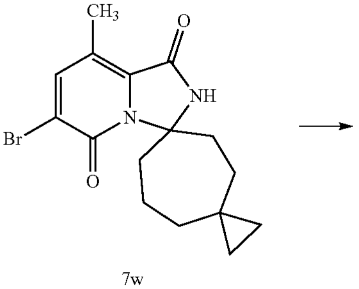

7w

-continued

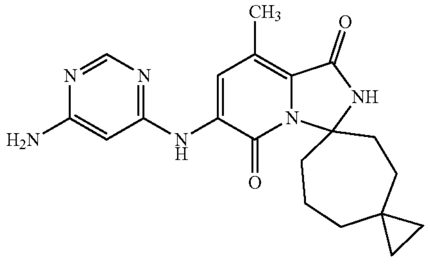

4ET-01-027

Synthesis of 6"-((6-Aminopyrimidin-4-yl)amino)-8"-methyl-2"H-dispiro[cyclopropane-1,1'-cycloheptane-4',3"-imidazo[1,5-a]pyridine]-1",5"-dione (rac-4ET-01-027): The title compound was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione is replaced with 6"-bromo-8"-methyl-2"H-dispiro[cyclopropane-1,1'-cycloheptane-4',3"-imidazo[1,5-a]pyridine]-1",5"-dione and N-(6-aminopyrimidin-4-yl)cyclopropanecarboxamide is replaced with 4,6-diaminopyrimidine: $^1H$ NMR (400 MHz, DMSO-$d_6$) δ 9.91 (s, 1H), 8.69 (s, 1H), 8.40 (s, 1H), 8.17 (s, 1H), 6.50 (br s, 2H), 6.18 (d, J=1.1 Hz, 1H), 3.04-2.94 (m, 1H), 2.88 (dd, J=14.2, 10.1 Hz, 1H), 2.41 (s, 3H), 2.0-1.97 (m, 1H), 1.90-1.80 (m, 1H), 1.71 (dd, J=14.4, 9.3 Hz, 2H), 1.59 (dd, J=14.0, 7.7 Hz, 2H), 1.35 (dt, J=15.5, 8.5 Hz, 2H), 0.32 (d, J=6.2 Hz, 4H).

Enatiomers of rac-4ET-01-027 ("Enantiomer 1 of 4ET-01-027" and "Enatiomer 2 of 4ET-01-027") were obtained via separation using chiral analytical and preparative HPLC. The separation was performed at Averica Discovery (Milford Massachusetts). Details of the analytical and preparative methods are provided below.

Analytical Super Critical Fluid (SFC) method details:

| | |
|---|---|
| Column | 4.6 x 100 mm Chiralcel OD-H from Chiral Technologies (West Chester, PA) |
| $CO_2$ Co-solvent (Solvent B) | Methanol/Acetonitrile (1:3) with 0.1% Isopropylamine |
| Gradient Method | 5-65% Co-solvent at 4 mL/min |
| System Pressure | 125 bar |
| Column Temperature | 40° C. |
| Sample Diluent | Methanol:Dichloromethane (1:1) |

Prepartive SFC method details:

| | |
|---|---|
| Column | 2.1 x 25.0 cm Chiralcel OX-H from Chiral Technologies (West Chester, PA) |
| $CO_2$ Co-solvent (Solvent B) | Methanol/Acetonitrile (1:3) with 0.25% Isopropylamine |
| Isocratic Method | 40% Co-solvent at 80 g/min |
| System Pressure | 100 bar |
| Column Temperature | 25° C. |
| Sample Diluent | Methanol:Dichloromethane (1:1) |

The structures of Enantiomer 1 of 4ET-01-027 and Enatiomer 2 of 4ET-01-027 are as follows (stereochemistry is not assigned):

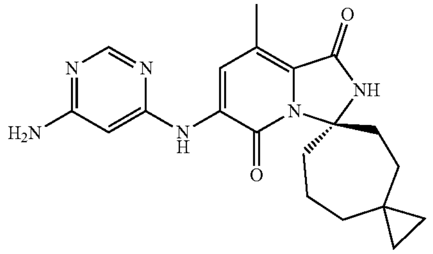

and

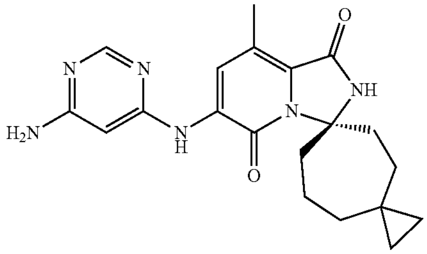

Figure 19:
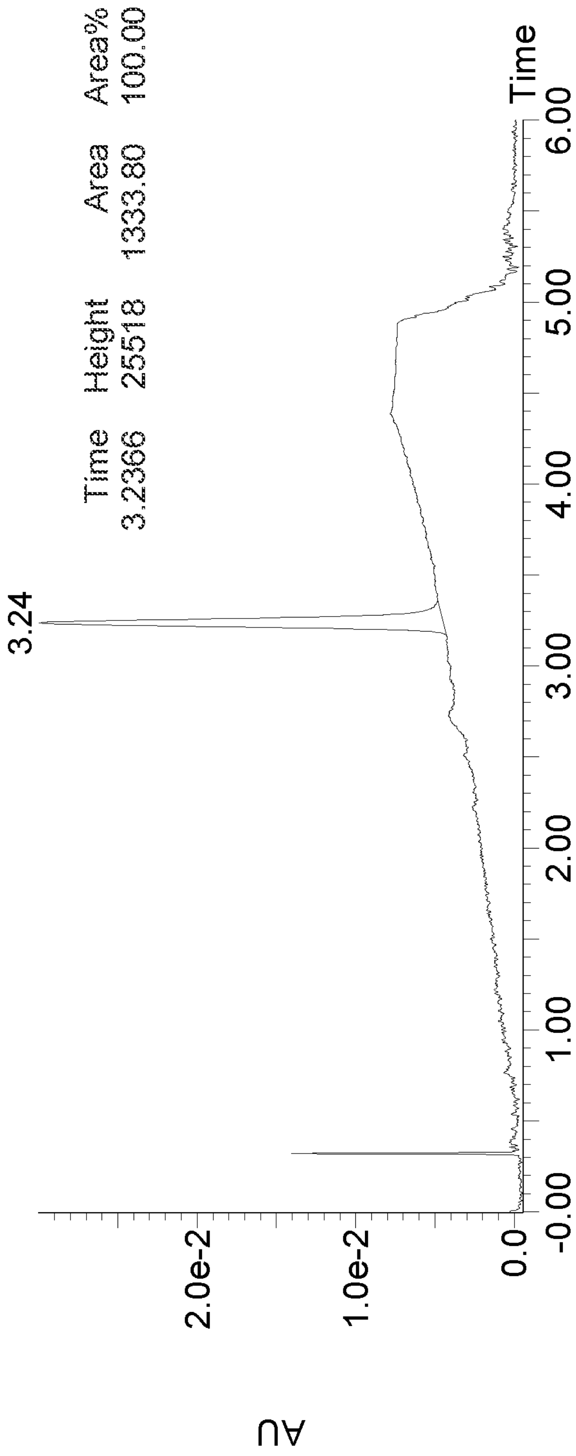
FIG. 19 shows the analytical scale chromatogram for the first eluting peak (i.e., "Enatiomer 1 of 4ET-01-027") from the separation of racemic mixture of 4ET-01-027 ("rac-4ET-01-027").
Figure 20:
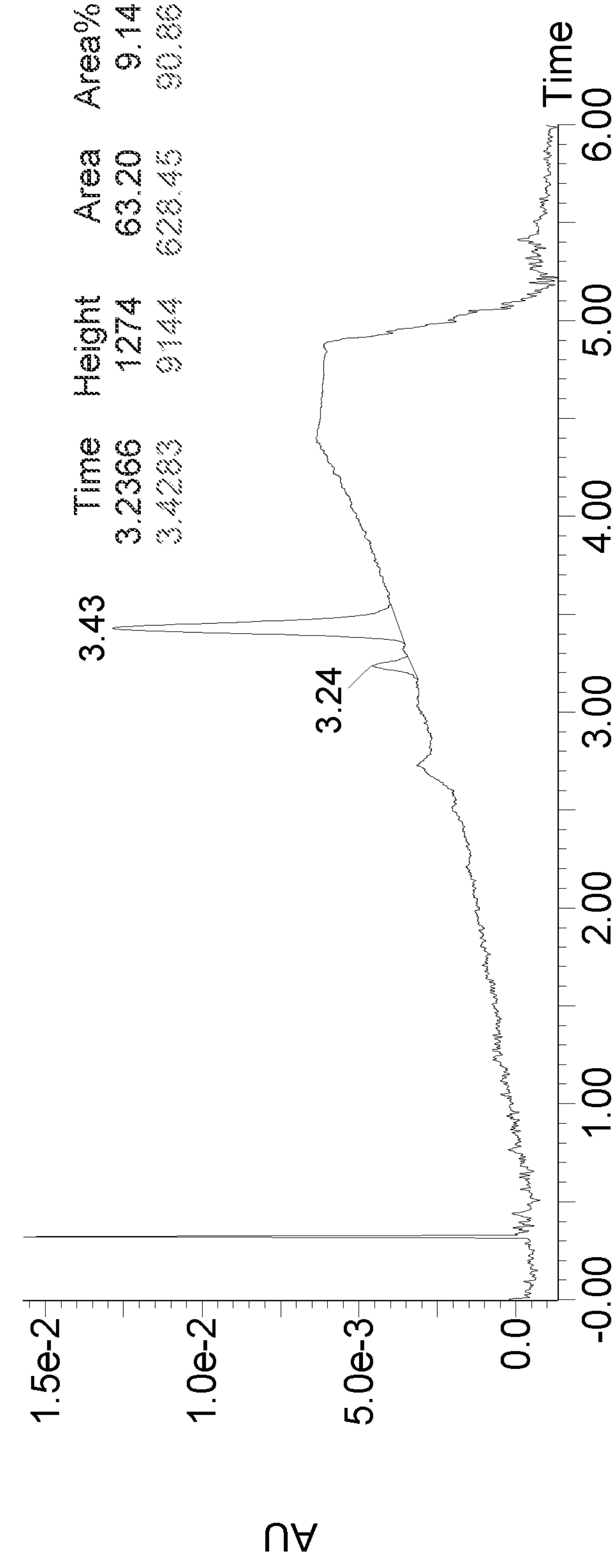
FIG. 20 shows the analytical scale chromatogram for the second eluting peak (i.e., "Enatiomer 2 of 4ET-01-027") from the separation of racemic mixture of 4ET-01-027 ("rac-4ET-01-027").

The first eluting peak had a retention time of 3.24 minutes, a peak height of 25,518, and peak area of 1333.80 using a diode array at 254 nm (see, e.g., FIG. 19). The second eluting peak had a retention time of 3.43 minutes, a peak height of 9,144, and peak area of 628.45 using a diode array at 254 nm (see, e.g., FIG. 20).

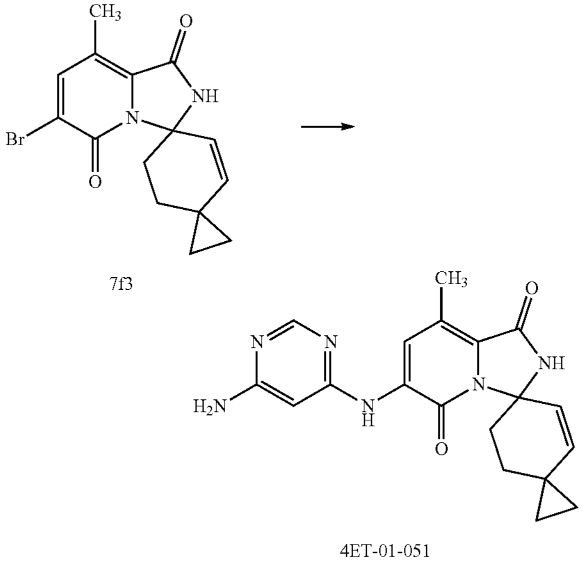

7f3

4ET-01-051

Synthesis of 6"-((6-Aminopyrimidin-4-yl)amino)-8"-methyl-2"H-dispiro[cyclopropane-1,1'-cyclohexane-4',3"-imidazo[1,5-a]pyridin]-2'-ene-1",5"-dione (4ET-01-051): The title compound was prepared according to the procedure of N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropane carboxamide except that 6"-bromo-8"-methyl-2"H-dispiro[cyclopropane-1,1'-cyclohexane-3',3"-imidazo[1,5-a]pyridine]-1",5"-dione is replaced with 6"-bromo-8"-methyl-2"H-dispiro[cyclopropane-1,1'-cyclohexane-4',3"-imidazo[1,5-a]pyridin]-2'-ene-1",5"-dione and N-(6-aminopyrimidin-4-yl)cyclopropanecarboxamide is replaced with 4,6-diaminopyrimidine; $^1H$ NMR (400 MHz, DMSO-$d_6$) δ 9.79 (s, 1H), 8.63 (s, 1H), 8.39 (s, 1H), 8.17 (s, 1H), 6.50 (s, 2H), 6.13 (s, 1H), 5.44 (d, J=9.8 Hz, 1H), 5.36 (d, J=9.8 Hz, 1H), 3.28-3.20 (m, 1H), 2.42 (s, 3H), 2.30 (t, J=13.0 Hz, 1H), 1.60 (d, J=12.4 Hz, 1H), 1.23 (d, J=11.8 Hz, 1H), 0.75-0.51 (m, 4H). UHPLC-MS (ESI): Rt 0.88 min, m/z 365.3 $[M+H]^+$.

Formulations

The present disclosure also relates to compositions or formulations which comprise the MNK inhibitors according to the present disclosure. In general, the compositions of the present disclosure comprise an effective amount of one or more spirocyclic pyridine-1,5-diones and salts thereof according to the present disclosure which are effective for providing neuropathic pain, Lupus, viral infection-induced pain, Covid19 related acute respiratory distress syndrome (ARDS), nonalcoholic fatty liver disease (NAFLD), high fat diet induced obesity, Alzhiemer's disease, Fragile X syndrome; and one or more excipients.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present disclosure have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in Remington's Pharmaceutical Sciences, 17th edition, ed. Alfonoso R. Gennaro, Mack Publishing Company, Easton, PA (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known MNK inhibitors. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and *arachis* oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present disclosure include from about 0.001 mg to about 1000 mg of one or more pyridine-1,5-dione according to the present disclosure and one or more excipients; from about 0.01 mg to about 100 mg of one or more pyridine-1,5-dione according to the present disclosure and one or more excipients; and from about 0.1 mg to about 10 mg of one or more pyridine-1,5-dione according to the present disclosure; and one or more excipients.

Pharmaceutical Use

Disease or damage causing neuropathic pain may affect the central nervous system, the peripheral nervous system, or both (as opposed to causes of nociceptive pain, which affect the peripheral nervous system only). Common causes of neuropathic pain include spinal cord injury, multiple sclerosis, central nervous system ischemia, spinal nerve disease, diabetes, other metabolic disorders, herpes zoster infection, HIV-related neuropathies, nutritional deficiencies, toxins, remote manifestations of malignancies, immune mediated disorders, physical trauma to a nerve trunk, such as during surgery, peripheral ischemia, peripheral nerve lesions, nerve compression, chemotherapy or other drug-induced nerve damage, radiation injury, arthritis, autoimmune disease, and infection, typically in an area near the affected nerves.

Neuropathic pain often involves abnormal nociceptor sensitivity. Nociceptors are specialized neurons that detect pain. Nociceptor sensitivity is not fixed; it can change over time. Some causes of neuropathic pain affect nociceptor sensitivity by inducing "peripheral sensitization." Peripheral sensitization includes spontaneous pathological activity, abnormal excitability, heightened sensitivity to chemical, stimuli, heightened sensitivity to thermal stimuli, heightened sensitivity to mechanical stimuli, and any combinations of these.

Disruption of peripheral sensitization, either by reducing or preventing such peripheral sensitization in the first place or by reducing the degree of already-developed peripheral sensitization, may therefore treat neuropathic pain. Although the disclosure is not limited to one mechanism of action, MNK inhibitors as disclosed herein may disrupt peripheral sensitization.

MNKs phosphorylate the eukaryotic translation initiation factor 4E (eIF4E) and factors that bind to AU-rich elements in the 3'-untranslated region of certain messenger RNAs (mRNAs). MNKs are a subfamily of Ser/Thr kinases, phylogenetically considered $Ca^{2+}$/calmodulin-dependent kinases (CaMKs). MNKs are activated through phosphorylation by the growth factor-stimulated Ras/extracellular signal-regulated kinase pathway and the stress-induced p38 pathway.

Nociceptor sensitization may be blocked by inhibiting activity-dependent mRNA translation through mechanistic targeting of the mitogen-activated protein kinase (MAPK) pathway. The MAPK pathway signal to the eukaryotic translation initiation factor (eIF) 4F complex to regulate the sensitization of nociceptors. MNK inhibitors disclosed herein may interrupt the MAPK pathway, thereby decreasing sensitization of nociceptors and achieving a therapeutic effect on neuropathic pain.

The present disclosure is, therefore, directed to methods of treating neuropathic pain or uses of treatments disclosed herein in treating neuropathic pain by administering an effective amount of an MNK inhibitor disclosed herein.

The present disclosure is also directed to methods of or uses of treatments disclosed herein in inhibiting an eIF4E phosphorylation site in a patient by administering an effective amount of an MNK inhibitor disclosed herein. Such methods may result in treatment of neuropathic pain.

Embodiments of the present disclosure are useful as modulators of neuropathic pain in a host species. The host species or patient can belong to any mammalian species, for example, a primate species, particularly humans. In some embodiments, the host species is a rodent (e.g., mice, rats and hamsters) a rabbit, a horse, a cow, a dog, a cat, etc. Animal models are of interest for experimental investigations, providing a model for treatment of human disease. In some embodiments, the host species is a horse. In some embodiments, the host species is a dog. In some embodiments, the host species is a cat. In some embodiments, the host species is livestock (e.g., cattle, sheep, goats, chickens, pigs, horses, donkeys, and the like).

Viral infections increase levels of Type 1 Interferons, which are known to interact directly with nociceptors to produce viral induced pain. This pain, in both acute phases of active viral infection or within one or two months after initial viral infection and in long-term or chronic phases at least two months after initial viral infection, may be decreased or alleviated by administering a MNK inhibitor of the present disclosure. In some embodiments, administration for viral induced pain may be similar to that for neuropathic pain.

Lupus, which is characterized by an autoimmune reaction to any of various bodily tissues and organs, is also characterized by excessive amounts of Type 1 Interferons and other inflammatory molecules and may, therefore, also be treated by administering a MNK inhibitor of the present disclosure.

COVID 19 related ARDS is similarly characterized by overproduction of inflammatory molecules that may be decreased by administering a MNK inhibitor of the present disclosure.

Alzheimer's disease is characterized by intracellular neurofibrillary tanges, extracellular plaques, and increased neuronal cell death, resulting in loss if neurons. Neurofibrillary tangles are typically formed from aggregaged Tau, while extraceullar plaques are typically formed from beta amyloid. Tau found in neurofibrillary tangles is hyperphosophorylated. MNK inhibitors of the present disclosure may disrupt the formation of such tangles and alleviate the symptoms of or slow the progression of Alzheimer's by disrupting Tau hyperphosphorylation. Other diseases and disorders resulting from hyperphosphorylation or inappropriate phosphorylation of Tau may be similarly treated or prevented using MNK inhibitors of the present disclosure.

Huntington's disease is characterized by an incurable breakdown of nerve cells in the brain associated with the presence of CAG repeats in the huntingtin gene. These mutations cause various abnormalities in the ERK pathway that can inappropriately activate MNK. Accordingly, MNK inhibitors of the present disclosure may combat some of the negative effects of MNK activation in Huntington's disease patients and, as a result, alleviave on or more symptoms of the disease or slow the progression of the disease.

High fat induced obesity, also sometimes referred to as diet induced obesity, is associated with phosphorylation of eIF4E. Accordingly, MNK inhibitors of the present disclosure may reduce high fat induced obesity or prevent the development of further obesity.

NAFLD is also associated with obesity and phosphorylation of eIF4E and may be prevented or treated using a MNK inhibitor of the present disclosure.

Fragile X Syndrome results from mutations that trigger epigenetic silencing of the Fmr1 gene. Silencing of Fmr1 results in increased activity of the mitogen-activated protein kinase (MAPK) pathway, including activation of MNK, which phosphorylates eIF4E. E xcessive phosphorylation of eIF4E has been directly implicated in the cognitive and behavioral deficits associated with Fragile X Syndrome. Accordingly, a MNK inhibitor of the present disclosure may improve or prevent the development of one or more of the cognitive of behavioral deficits associated with Fragile X Syndrome, particularly if administered early in the patent's life.

Embodiments of the disclosure also relate to the use of compounds according to Structure (I) or (II) and/or physiologically acceptable salts thereof for the prophylactic or therapeutic treatment and/or monitoring of diseases that are caused, mediated and/or modulated by the mitogen-activated proten kinase-interacting kinases (MNK) activity. Furthermore, embodiments of the disclosure relate to the use of compounds according to Structure (I) or (II) and/or physiologically acceptable salts thereof for the production of a medicament for the prophylactic or therapeutic treatment and/or monitoring of diseases. In certain embodiments, the use of a compound according to Structure (I) or (II) or physiologically acceptable salts thereof, for the production of a medicament for the prophylactic or therapeutic treatment.

A MNK inhibitor as disclosed herein may be administered as a single dose or multiple doses. For example, where multiple doses are administered, they may be administered at intervals of 3 times per 24 hours, 2 times per 24 hours, 1 time per 24 hours, 1 time every other day, 1 time every 3 days, 1 time every 4 days, 1 time per week, 2 times per week, or 3 times per week. The MNK inhibitor may also be delivered continuously, for example, via a continuous pump. The administration schedule may depend on dose administered, severity of disease, response to treatment, and other factors, or any combinations thereof.

The dose may be any effective amount. However, in specific examples the dose may be 25 mg, 50 mg, 100 mg, 200 mg, or 500 mg.

The initial dose may be greater than subsequent doses or all doses may be the same. The dose may depend on the administration schedule, severity of disease, response to treatment, and other factors, or any combinations thereof. The MNK inhibitor may be administered over a period of one week, two weeks, three weeks, four weeks, one month, two months, three months, four months, five months, six months, seven months, eight months, nine months, ten months, eleven months, one year, two years or three years. The duration of administration may depend on the severity of diseases, response to treatment, and other factors, or any combinations thereof For example, a less frequent administration schedule for the same dose may be adopted as the patient responds to treatment. Alternatively, the administration schedule may remain unchanged, but the dose may be decreased as the patient responds to treatment.

As another example, patients who have responded well to treatment and have little or no neuropathic pain or patients being administered the MNK inhibitor as a preventative measure to avoid the development of neuropathic pain may be administered only a low dose of MNK inhibitor and/or have a less frequent administration schedule. Alternatively, patients being administered the MNK inhibitor as a preventative measure to avoid the development of neuropathic pain may be administered a normal or high dose or have a frequent administration schedule but only for a limited duration of time, such as between one and six months, during which neuropathic pain is most likely to develop.

A MNK inhibitor according to the present disclosure may be administered in conjunction with an additional therapeutic, including another MNK inhibitor or a therapeutic that is not an MNK inhibitor, particularly another pain therapeutic, Alzheimer's therapeutic, Huntingon's disease therapeutic, Fragile X Syndrome therapeutic, lupus therapeutic, COVID 19 related ARDS therapeutic, NAFLD therapeutic, or weight loss or other obesity-related therapeutic. Suitable additional therapeutics include both small molecules and biologics. An MNK inhibitor may be administered with any combinations of additional therapeutics.

For example, a MNK inhibitor of the present disclosure may be administered with one or more opioids. Suitable opioids include Morphine, Opium, Hydromorphone, Nicomorphine, Oxycodone, Dihydrocodeine, Diamorphine, Papaveretum, Codeine, Phenylpiperidine derivatives, Ketobemidone, Pethidine, Fentanyl, Pethidine, Diphenylpropylamine derivatives, Piritramide, Dextropropoxyphene, Bezitramide, Methadone, Dextropropoxyphene, Benzomorphan derivatives, Pentazocine, Phenazocine, Oripavine derivatives, Buprenorphine, Etorphine, Oripavine derivatives, Morphinan derivatives, Butorphanol, Nalbuphine, Tilidine, Tramadol and Dezocine, and any combinations thereof.

As another example, an MNK inhibitor of the present disclosure may be administered with one or more gabapentinoids. Suitable gabapentinoids include gabapentin and pregabalin, as well as a gabapentin prodrug, gabapentin enacarbil, and any combinations thereof.

As a further example, an MNK inhibitor of the present disclosure may be administered with one or more other small molecule pain therapeutics. Suitable other small molecule pain therapeutics include salicylates, such as Aspirin (acetylsalicylic acid), Diflunisal and Salsalate, Propionic acid derivatives (Ibuprofen, Dexibuprofen, Naproxen, Fenoprofen, Ketoprofen, Dexketoprofen, Flurbiprofen, Oxaprozin, Loxoprofen), Acetic acid derivatives, (Indomethacin, Tolmetin, Sulindac, Etodolac, Ketorolac, Diclofenac, Nabumetone), Enolic acid (Oxicam) derivatives (Piroxicam, Meloxicam, Tenoxicam, Droxicam, Lomoxicam, Isoxicam), Fenamic acid derivatives or "Fenamates" (Mefenamic acid, Meclofenamic acid, Flufenamic acid, Tolfenamic acid), Selective COX-2 inhibitors (Celecoxib, Rofecoxib, Valdecoxib, Parecoxib, Lumiracoxib, Etoricoxib, Firocoxib), Sulphonanilides such as Nimesulide, and a range of other compounds (Licofelone, Lysine clonixinate, Hyperforin, Figwort), and any combinations thereof.

When administered with another pain therapeutic, an MNK inhibitor according to the present disclosure may allow a reduction in the dose or administration frequency of the other pain therapeutic, or a decrease in the total duration of time the other therapeutic is administered. Such an administration schedule may be particularly beneficial when the additional pain therapeutic is addictive, such as an opioid.

As another example, a MNK inhibitor according to the present disclosure may be administered with an anti-viral therapeutic or an anti-Type 1 Interferon therapeutic, such as Abacavir, Acyclovir (Aciclovir), Adefovir, Amantadine, Ampligen, Amprenavir (Agenerase), Umifenovir (Arbidol), Atazanavir, Atripla, Baloxavir marboxil (Xofluza), Biktarvy, Boceprevir, Bulevirtide, Cidofovir, Cobicistat (Tybost), Combivir, Daclatasvir (Daklinza), Darunavir, Delavirdine, Descovy, Didanosine, Docosanol, Dolutegravir, Doravirine (Pifeltro), Edoxudine, Efavirenz, Elvitegravir, Emtricitabine, Enfuvirtide, Entecavir, Etravirine (Intelence), Famciclovir, Fomivirsen, Fosamprenavir, Foscarnet, Ganciclovir (Cytovene), Ibacitabine, Ibalizumab (Trogarzo), Idoxuridine, Imiquimod, Imunovir, Indinavir, Lamivudine, Letermovir (Prevymis), Lopinavir, Loviride, Maraviroc, Methisazone, Moroxydine, Nelfinavir, Nevirapine, Nexavir formerly (Kutapressin), Norvir, Oseltamivir (Tamiflu), Penciclovir, Peramivir, Penciclovir, Peramivir (Rapivab), Pleconaril, Podophyllotoxin, Raltegravir, Remdesivir, Ribavirin, Rilpivirine (Edurant), Rilpivirine, Rimantadine, Ritonavir, Saquinavir, Simeprevir (Olysio), Sofosbuvir, Stavudine, Taribavirin (Viramidine), Telaprevir, Telbivudine (Tyzeka), Tenofovir alafenamide, Tenofovir disoproxil, Tipranavir, Trifluridine, Trizivir, Tromantadine, Truvad, Umifenovir, Valaciclovir (Valtrex), Valganciclovir (Valcyte), Vicriviroc, Vidarabine, Zalcitabine, Zanamivir (Relenza), or Zidovudine.

As another example, a MNK inhibitor of the present disclosure may be administered with an Alzheimer's or other tau-related diseases therapeutic, such as Aducanumab (Aduhelm), Donepezil (Aricept), Rivastigmine (Exelon), Galantamine (Razadyne), Memantine (Namenda), Donepezil and Memantine combination (Namzaric), or Suvorexant (Belsomra).

An yet another example, a MNK inhibitor of the present disclosure may be administered with a weight loss or other obesity-related therapeutic or a NAFLD therapeutic, such as Metformin, Orlistat (Xenical or Alli), Phentermine-topiramate (Qsymia), Naltrexone-Bupropion (Contrave), Liraglutide (Saxenda), Semaglutide (Wegovy), Phentermine, Benzphetamine, Diethylpropion, or Phendimetrazine.

As another example, a MNK inhibitor of the present disclosure may be administered with a Huntington's disease therapeutic, such as Tetrabenazine (Xenazine), Deutetrabenazine (Austedo), Aloperidol (Haldol), Fluphenazine, Risperidone (Risperdal), Olanzapine (Zyprexa), Quetiapine (Seroquel), Amantadine (Gocovri ER, Osmolex ER), Levetiracetam (Keppra, Elepsia XR, Spritam), Clonazepam (Klonopin), Citalopram (Celexa), Escitalopram (Lexapro), Fluoxetine (Prozac, Sarafem), Sertraline (Zoloft), Divalproex (Depakote), Carbamazepine (Carbatrol, Epitol), or Lamotrigine (Lamictal).

As another example, a MNK inhibitor of the present disclosure may be administered with a Fragile X Syndrome therapeutic, such as Sertraline (Zoloft), Metformin, cannabidiols, Acamprosate, Lovastatin, Minocycline, other mood stabilizers, other antianxiety medications, or other antidepressants.

As another example, a MNK inhibitor of the present disclosure may be administered with a COVID 19 ARDS therapeutic, such as an antiviral medication, a steroid, an anti-inflammatory medication, or an antibody that specifically binds a SARS-CoV-2 antigen.

The agents disclosed herein or other suitable agents are administered depending on the condition being treated. Hence, in some embodiments the one or more compounds of the disclosure will be co-administered with other agents. When used in combination therapy, the compounds described herein are administered with the second agent simultaneously or separately. This administration in combination can include simultaneous administration of the two or more agents in the same dosage form, simultaneous administration in separate dosage forms, and separate administration. That is, a compound described herein and any additional agent (e.g., an anti-inflammatory agent, a pain management agent, etc.) can be formulated together in the same dosage form and administered simultaneously. Alternatively, a compound of the disclosure and additional agent can be simultaneously administered, wherein both the agents are present in separate formulations. In another alternative, a compound of the present disclosure can be administered just followed by an additional agent, or vice versa. In some embodiments of the separate administration protocol, a compound of the disclosure and additional agent are administered a few minutes apart, or a few hours apart, or a few days apart. In some embodiments, the compounds of Structure (I) or (II) are administered as a mono-therapy.

The methods of embodiments of embodiments of the disclosure can be performed either in vitro or in vivo. The susceptibility of a particular patient, subject, or cell to treatment with the compounds of Structure (I) or (II) can be particularly determined by in vitro tests, whether in the course of research or clinical application.

EXAMPLES

The following procedures can be utilized in evaluating and selecting compounds as MNK inhibitors.

The ability of MNK inhibitors described herein to inhibit activity of MNK1 was tested using the recombinant full-length human kinase MNK1 that is expressed in insect cells. In the radiometric activity assay, the test compound is incubated with MNK1 kinase, substrate, cofactors, and radioisotope-labeled ATP, and % kinase activity determined based upon the extent of substrate phosphorylation. $IC_{50}$ data is provided in Table 4.

The ability of MNK inhibitors described herein to inhibit activity of MNK2 was tested using the recombinant full length human kinase MNK2 that is expressed in insect cells. Additional details are provided in the above paragraph.

The ability of MNK inhibitors described herein to inhibit eIF4E phosphorylation at Serine 209 in the human embryonic kidney (HEK) 293 cell line was tested by exposing the cells to compound for 2 hours and then measuring eIF4E phosphorylation with a phosphorylation-specific antibody in a fluorescent plate reader. $IC_{50}$ data is provided in Table 4. These experiments were done with HEK-293 cells plated on 96 well plates. Following treatment, cells were fixed with ice cold methanol for 10 min and then washed in 1× phosphate buffered saline (PBS) and the permeabilized with 0.02% Triton X-100 in 10% normal goat serum made up in PBS. Primary antibody was applied overnight at a concentration dilution of 1:2000 (p-eIF4E antibody from Cell Signaling ab76256). Following washing, cells were then exposed to secondary antibody conjugated to alexa-fluor 488 and then visualized on a Syngergy HTX plate reader. Fluorescence for p-eIF4E was measured and normalized to total DAPI fluorescence to determine the percentage of eIF4E phosphorylation in each well. Data were plotted in Graphpad Prism V8 to determine concentration-response effects and calculate $IC_{50}$ values. $IC_{50}$ data is provided in Table 4.

Biological Data

TABLE 4

| Compound | MNK1 (nM) | MNK2 (nM) | HEK 293 cell (nM) |
|---|---|---|---|
| 4ET-01-009 | 13.1 | 0.8 | 3.6 |
| 4ET-01-012 | 27.9 | 3.0 | 57.1 |
| 4ET-01-015 | 30.9 | 2.6 | 3.9 |
| 4ET-01-016 | 33.0 | 3.5 | 8.9 |
| 4ET-01-017 | 69.2 | 7.9 | 41.6 |
| 4ET-01-018 | 41.8 | 4.1 | 4.1 |
| 4ET-01-019 | 43.9 | 4.2 | 4.9 |
| 4ET-01-020 | 36.0 | 3.0 | 4.3 |
| 4ET-01-023 | 63.8 | 3.0 | 36.7 |
| 4ET-01-025 | 73.3 | 5.5 | 4.4 |
| rac-4ET-01-027 | 35.2 | 1.6 | 12.6 |
| Enatiomer 1 of 4ET-01-027 | 73.4 | 2.4 | 11.6 |
| Enatiomer 2 of 4ET-01-027 | 177.0 | 9.7 | 25.4 |
| 4ET-01-030 | 48.0 | 2.3 | 9.9 |
| 4ET-01-036 | 48.4 | 3.5 | 52.2 |
| 4ET-01-039 | 96.6 | 4.4 | 9.7 |
| 4ET-01-035 | 22.7 | 1.8 | 0.9 |
| 4ET-01-038 | 66.2 | 4.2 | 6.0 |
| 4ET-01-042 | 16.5 | 2.0 | 0.8 |
| 4ET-01-051 | 58.6 | 3.1 | 7.3 |
| 4ET-03-040 | 38.6 | 2.0 | 27.4 |
| 4ET-03-043 | 44.9 | 1.7 | 0.9 |
| 4ET-03-045 | 130.8 | 12.1 | 17.7 |
| 4ET-03-046 | 49.8 | 1.7 | 6.4 |
| 4ET-03-047 | ND | ND | ND |
| 4ET-03-048 | 144.9 | 5.2 | 6.1 |
| 4ET-03-049 | 80.0 | 2.8 | 110.5 |
| 4ET-03-053 | 214.9 | 20.9 | 10.1 |
| 4ET-03-055 | 126.7 | 29.5 | 44.0 |
| 4ET-03-056 | 51.8 | 3.5 | 11.1 |
| 4ET-03-057 | 61.6 | 3.4 | 8.7 |
| 4ET-03-060 | 31.0 | 1.7 | 6.5 |

TABLE 4-continued

| Compound | MNK1 (nM) | MNK2 (nM) | HEK 293 cell (nM) |
|---|---|---|---|
| 4ET-03-061 | 36.2 | 1.7 | 5.2 |
| 4ET-03-068 | 25.3 | 1.5 | 3.4 |
| 4ET-03-074 | 45.9 | 3.1 | 11.3 |
| 4ET-03-076 | 37.5 | 12.2 | ND |
| 4ET-03-081 | 30.3 | 10.1 | ND |

ND: not determined

Example 1: Blood-Brain Barrier Permeability

Permeability of the blood-brain barrier to various MNK inhibitors of the present disclosure and eFT508 as a comparison was evaluated using an in vitro drug and metabolism pharmacokinetic (DMPK) study. In particular, the study was conducted in Madin Darby Canine Kidney (MDCK) cells that express the MDR1 gene (ABCB1) that encodes for the efflux protein, P-gp. MDCK-MDR1 is a stable-transfected cell line originating from MDCK cells, with over-expression of human MDR1 gene. Because MDCK-MDR1 permeability correlates well with brain exposure it is often utilized as predictor of blood-brain-barrier penetration. In the assay, test compounds were evaluated at 5 uM and the average of two experiments reported for Papp A-B and Papp B-A. Analysis was performed using LC-MS/MS. Apparent permeability (Papp) values are calculated using the following equation: Papp=(dQ/dt)/A/Co where dQ/dt is the initial rate of amount of test compound transported across cell monolayer, A is the surface area of the filter membrane, and $C_0$ is the initial concentration of the test compound, calculated for each direction using a 4-point calibration curve by LC-MS/MS. Net flux ratio between the two directional transports was calculated by the following equation: Ratio=Papp, B-A/Papp, A-B, where Papp, B-A and Papp, A-B represent the apparent permeability of test compound from the basal to apical and apical to basal side of the cellular monolayer, respectively. Results are presented in Table 5.

TABLE 5

| Compound | $P_{app}$ A-B × $^{10-6}$ cm/s[#] | $P_{app}$ B-A × $^{10-6}$ cm/s[*#] | Efflux ratio (ratio B-A/A-B) |
|---|---|---|---|
| 4ET-01-015 | 49.2 | 51.4 | 1.0 |
| 4ET-01-016 | 48.6 | 46.5 | 1.0 |
| 4ET-01-017 | 29.0 | 47.2 | 1.6 |
| 4ET-01-018 | 50.8 | 66.7 | 1.3 |
| 4ET-01-019 | 43.9 | 71.9 | 1.6 |
| 4ET-01-020 | 46.7 | 70.7 | 1.5 |
| 4ET-01-022 | 45.5 | 52.0 | 1.1 |
| 4ET-01-023 | 1.6 | 7.5 | 4.7 |
| 4ET-01-025 | 28.3 | 73.9 | 2.6 |
| rac-4ET-01-027 | 52.9 | 62.1 | 1.2 |
| 4ET-01-030 | 52.6 | 52.1 | 1.0 |
| 4ET-01-035 | 52.0 | 59.1 | 1.1 |
| 4ET-01-036 | 12.5 | 55.0 | 4.4 |
| 4ET-01-038 | 46.5 | 54.9 | 1.2 |
| 4ET-01-039 | 26.4 | 44.7 | 1.7 |
| 4ET-01-042 | 50.4 | 68.9 | 1.4 |
| 4ET-01-051 | 22.7 | 52.4 | 2.3 |
| 4ET-03-040 | 0.6 | 1.6 | 2.4 |
| 4ET-03-043 | 27.4 | 56.3 | 2.1 |
| 4ET-03-049 | 0.3 | 0.7 | 2.1 |
| 4ET-03-053 | 63.3 | 68.1 | 1.1 |
| 4ET-03-055 | 3.0 | 57.6 | 19.0 |
| 4ET-03-056 | 0.5 | 15.9 | 31.8 |
| 4ET-03-057 | 0.3 | 1.1 | 4.2 |
| 4ET-03-068 | 18.7 | 71.0 | 3.8 |
| 4ET-03-074 | 7.6 | 58.1 | 7.6 |
| 4ET-03-081 | 17.1 | 23.4 | 1.4 |

[#]Apical to basolateral transport;

[*#]Basolateral to apical transport.

Example 2: Liver Microsome Stability

Liver microsome stability of NMNK inhibitors of the present disclosure and eFT508 as a comparison was tested to assess half-life ($Ti_2$) and intrinsic clearance ($CL_{int}$) in both rodent and human liver microsomes. $T_{1/2}$ and $CL_{int}$ from in vitro liver microsomal assays are used to predict rate of metabolism in the liver. Compounds that are rapidly metabolized by liver microsomes are predicted to have limited systemic exposure and poor oral bioavailability. Results are presented in Table 6.

TABLE 6

| Compound | Mouse liver microsomes $t_{1/2}$ (min) |
|---|---|
| 4ET-01-015 | 311 |
| 4ET-01-016 | 679 |
| 4ET-01-017 | 261 |
| 4ET-01-018 | 51.2 |
| 4ET-01-019 | 252 |
| 4ET-01-020 | 47.6 |
| 4ET-01-022 | 20.0 |
| 4ET-01-023 | 99.0 |
| 4ET-01-025 | 52.8 |
| 4ET-01-027 | 66.4 |
| 4ET-01-030 | 449 |
| 4ET-01-035 | 81.9 |
| 4ET-01-036 | 168 |
| 4ET-01-038 | 198 |
| 4ET-01-039 | 227 |
| 4ET-01-042 | 113 |
| 4ET-01-051 | 835 |
| 4ET-03-040 | 77 |
| 4ET-03-043 | 201 |
| 4ET-03-044 | 163 |
| 4ET-03-049 | 146 |
| 4ET-03-053 | 228 |
| 4ET-03-056 | 177 |
| 4ET-03-057 | 219 |
| 4ET-03-068 | 296 |
| 4ET-03-074 | 112 |
| 4ET-03-081 | 74.2 |

$t_{1/2}$ = the half-life, where $t_{1/2}$ is equal to 0.693/slope; $CL_{int}$ = the intrinsic hepatic clearance (uL/min/mg), where $CL_{int}$ is equal to 0.693/($t_{1/2}$ × $C_{mp}$); $C_{mp}$ = microsomal protein concentration (mg/mL).

Example 3: PK Study of 4ET-03-053 in CD-1 Male Mice with IV and PO Dosing

In mice, following IV administration with 1.5 mg/kg, plasma concentrations declined in a multiphasic manner with an initial concentration (Co) of 708 ng/mL and a last measurable concentration (Clast) of 5.29 ng/mL at 24 h post dose. The compound displayed a low systemic clearance (CLp) of 19.3 mL/min/kg and a high steady-state volume of distribution (Vss) of 5.63 L/kg, suggesting modest metabolism and extensive tissue distribution. The total systemic exposure (AUCinf) was 1.324 h*ug/mL with a terminal half-life (t1/2) of 6.17 h.

Following oral administration to mice at 10 mg/kg, the compound displayed its mean peak plasma concentration (Cmax) of 807 ng/mL within 30 min. After that, its plasma concentrations declined in an approximately monophasic manner with a last measurable concentration of 33.2 ng/mL at 24 h and a terminal half-life (t1/2) of 5.14 h. The total systemic exposure (AUCinf) was 6.62 h*ug/mL with an oral bioavailability of 75%. Results are presented in Tables 7 and 8. Regarding results presented in Table 7, the first animal died immediately after a slow IV injection at 3 mg/kg. The dose level was subsequently reduced to 1.5 mg/kg. Immediately after dosing, all animals were lying on side and immobile with heavy breathing for about 1 min. After that, all displayed difficulty walking around cage for about 2 min and appeared normal 15 min later.

TABLE 7

1.5 mg/mL IV administration of 4ET-03-053 in 10% DMI: 15% EtOH: 35% PG: 40% N5*

| Animal # | $t_{1/2}$ (hr) | $C_o$ (ng/mL) | $T_{last}$ (hr) | $C_{last}$ (ng/mL) | $AUC_{last}$ (hr* ng/mL) |
|---|---|---|---|---|---|
| 1 | 5.99 | 820 | 24.0 | 6.17 | 1482 |
| 2 | 6.26 | 713 | 24.0 | 5.21 | 1304 |
| 3 | 6.27 | 591 | 24.0 | 4.50 | 1049 |
| Mean (n = 3) | 6.17 | 708 | 24.0 | 5.29 | 1278 |
| SD | 0.160 | 114 | 0 | 0.838 | 218 |
| % CV | 2.59 | 16.2 | 0 | 15.8 | 17.0 |

| Animal # | $AUC_{inf}$ (hr* ng/mL) | Vss (L/kg) | $AUC_{inf}$/D (hr* mg/mL) | $MRT_{inf}$ (hours) | CLp (mL/min/kg) |
|---|---|---|---|---|---|
| 1 | 1534 | 4.82 | 1023 | 4.93 | 16.3 |
| 2 | 1350 | 5.21 | 900 | 4.69 | 18.5 |
| 3 | 1089 | 6.85 | 726 | 4.97 | 23.0 |
| Mean (n = 3) | 1324 | 5.63 | 883 | 4.87 | 19.3 |
| SD | 224 | 1.08 | 149 | 0.153 | 3.39 |
| % CV | 16.9 | 19.1 | 16.9 | 4.93 | 17.6 |

*DMI: dimethylisosorbide; EtOH: ethanol; PG: propylene glycol; NS: normal saline.

Regarding results presented in Table 8, no abnormal clinical symptoms immediately after dosing. Animals were found lying ventrally in cage with increased respiration and squinty eyes from about 30 min to 2 hours after dosing. All displayed normal behavior about 4 hours after dosing.

TABLE 8

10 mg/mL PO administration of 4ET-03-053 in 10% DMA/PG*

| Animal # | $t_{1/2}$ (hr) | $T_{max}$ (hr) | $C_{max}$ (ng/mL) | $C_{max/D}$ (kg/kL) | $T_{last}$ (hr) | $C_{last}$ (ng/mL) |
|---|---|---|---|---|---|---|
| 1 | 5.24 | 0.500 | 934 | 93.4 | 24.0 | 33.4 |
| 2 | 5.07 | 0.500 | 854 | 85.4 | 24.0 | 37.6 |
| 3 | 5.11 | 0.500 | 632 | 63.2 | 24.0 | 28.7 |
| Mean (n = 3) | 5.14 | 0.500 | 807 | 80.7 | 24.0 | 33.2 |
| SD | 0.092 | 0.00 | 156 | 15.6 | 0.00 | 4.45 |
| % CV | 1.80 | 0.00 | 19.4 | 19.4 | 0.00 | 13.4 |

| Animal # | $AUC_{last}$(hr* ng/mL) | $AUC_{inf}$ (hr*ng/mL) | $AUC_{inf}$/D (hr*kg/kL) | $MRT_{inf}$ (hr) | F (%) |
|---|---|---|---|---|---|
| 1 | 6422 | 6674 | 667 | 6.70 | 75.6 |
| 2 | 7266 | 7539 | 754 | 6.81 | 85.4 |
| 3 | 5433 | 5644 | 564 | 6.86 | 63.9 |
| Mean (n = 3) | 6374 | 6619 | 662 | 6.79 | 75.0 |
| SD | 917 | 949 | 94.9 | 0.080 | 10.7 |
| % CV | 14.4 | 14.3 | 14.3 | 1.18 | 14.3 |

*DMA: dimethylacetamide; PG: propylene glycol.

In mice, 4ET-03-053 has a brain to plasma ratio of 0.039 (B:P ratio=0.039) at 2 h post dosing shown in Table 9 below.

TABLE 9

| Male CD1 mice plasma and brain tissues. | | | | | | | | |
|---|---|---|---|---|---|---|---|---|
| Matrix | Plasma or Tissue Homogenate Conc. (ng/mL) n = 3 | | | Mean (ng/mL) | Mean Tissue (ng/g) | SD (ng/mL) | CV (%) | Mean Tissue/ Plasma Conc. Ratio |
| Plasma | 488 | 584 | 661 | 578 | N/A | 86.7 | 15.0 | N/A |
| Brain | 4.61 | 5.89 | 6.41 | 5.64 | 22.5 | 0.926 | 16.4 | 0.039 |

N/A=not applicable

Example 4: PK Study of 4ET-03-053 in Male Sprague Dawley (SD) Rats with IV and PO Dosing In rats, with 1 mg/kg IV dosing, plasma concentrations declined in a multiphasic manner with a high initial concentration (Co) of 7.73 ug/mL and a last measurable concentration (Clast) of 350 ng/mL at 24 h post dose. The compound displayed a low systemic clearance (CLp) of 0.33 mL/min/kg and a low steady-state volume of distribution (Vss) of 0.15 L/kg, suggesting insignificant metabolism and minor tissue distribution. The total systemic exposure (AUCinf) was 51.5 h*ug/mL with a terminal half-life (t1/2) of 6.36 h. Results are presented in Table 10. The second animal died right after a slow IV injection. A replacement rat was dosed. Immediately after dosing, all animals were lying on side and immobile with heavy breathing for about 10 min. After that, all were still lying laterally/ventrally for 1 hr. exploring cage with periodic lying down between 1 and 8 hr. All appeared normal after 8 hr.

TABLE 10

1 mg/mL IV administration of 4ET-03-053 in 10% DMI: 15% EtOH: 35% PG: 40% N5

| Animal # | $t_{1/2}$ (hr) | $C_o$ (ng/mL) | $T_{last}$ (hr) | $C_{last}$ (ng/mL) | $AUC_{last}$ (hr* ng/mL) |
|---|---|---|---|---|---|
| 1 | 6.19 | 7726 | 24.0 | 336 | 50110 |
| 2 | 6.63 | 8106 | 24.0 | 411 | 51112 |
| 3 | 6.19 | 7353 | 24.0 | 302 | 43568 |
| Mean (n = 3) | 6.36 | 7728 | 24.0 | 350 | 48263 |
| SD | 0.281 | 377 | 0.00 | 55.8 | 4097 |
| % CV | 4.43 | 437 | 0.00 | 15.9 | 8.49 |

| Animal # | AUCinf (hr* ng/mL) | Vss (L/kg) | AUCinf/ D(hr* kg/kL) | MRTinf(hr) | CLp (mL/ min/kg) |
|---|---|---|---|---|---|
| 1 | 53103 | 0.136 | 53103 | 7.24 | 0.314 |
| 2 | 55049 | 0.145 | 55049 | 7.97 | 0.303 |
| 3 | 46264 | 0.161 | 46264 | 7.44 | 0.360 |
| Mean (n = 3) | 51472 | 0.147 | 51472 | 7.55 | 0.326 |
| SD | 4614 | 0.0124 | 4614 | 0.376 | 0.0305 |
| % CV | 8.96 | 8.42 | 8.96 | 4.98 | 9.37 |

Following oral administration to rats at 10 mg/kg, the compound rapidly reached its high peak plasma concentration (Cmax) of 17.5 ug/mL within 30 m. After that, its plasma concentrations declined in an approximately monophasic manner with a last measurable concentration of 2.62 ug/mL at 24 h and a terminal half-life (t1/2) of 9.10 h. The total systemic exposure (AUCinf) was 221 h*ug/mL with an oral bioavailability of 42.9%. Results are presented in Table 11. No abnormal clinical symptoms immediately after dosing. Animals were found lying ventrally in cage with increased respiration and squinty eyes from about 30 min to 4 hours after dosing. All animals began exploration of cage between 4 and 8 hr and appeared normal about 8 hr after dosing.

TABLE 11

10 mg/mL PO administration of 4ET-03-053 to SD rats in 10% DMA/PG

| Animal # | $t_{1/2}$ (hr) | $T_{max}$ (hr) | $C_{max}$ (ng/mL) | $C_{max/D}$ (kg/kL) | $T_{last}$ (hr) | $C_{last}$ (ng/mL) |
|---|---|---|---|---|---|---|
| 1 | 9.22 | 0.500 | 19600 | 1960 | 24.0 | 2710 |
| 2 | 9.01 | 0.500 | 18400 | 1840 | 24.0 | 2950 |
| 3 | 9.07 | 0.500 | 14400 | 1440 | 24.0 | 2210 |
| Mean (n = 3) | 9.10 | 0.500 | 17467 | 1747 | 24.0 | 2623 |
| SD | 0.108 | 0.00 | 2723 | 272 | 0.00 | 378 |
| % CV | 1.19 | 0.00 | 15.6 | 15.6 | 0000 | 14.4 |

| Animal # | AUClast (hr* ng/mL) | AUCinf (hr* ng/mL) | AUCinf/ D(hr* kg/kL) | MRTinf(hr) | F (%) |
|---|---|---|---|---|---|
| 1 | 193960 | 229999 | 23000 | 12.1 | 44.7 |
| 2 | 206657 | 245044 | 24504 | 123 | 47.6 |
| 3 | 158552 | 187510 | 18751 | 12.1 | 36.4 |
| Mean (n = 3) | 186390 | 2208151 | 22085 | 12.2 | 42.9 |
| SD | 24930 | 29838 | 2983.8 | 0.0989 | 5.80 |
| % CV | 13.4 | 13.5 | 13.5 | 0.810 | 13.5 |

A brain to plasma ratio of 0.096 (BP=0.096) in SD rats is observed at 2 hr following a single 10 mg/kg dose of 4ET-03-053. Results are presented in Table 12.

TABLE 12

| SD rats plasma and brain tissues 2 hr post single PO dose 10 mg/kg. | | | | | | | | |
|---|---|---|---|---|---|---|---|---|
| Matrix | Plasma or Tissue Homogenate Conc. (ng/mL) n = 3 | | | Mean (ng/mL) | Mean Tissue (ng/g) | SD (ng/mL) | CV (%) | Mean Tissue/ Plasma Conc. Ratio |
| Plasma | 12200 | 16900 | 14400 | 14500 | N/A | 2352 | 16.2 | N/A |
| Brain | 319 | 406 | 323 | 349 | 1397 | 49.1 | 14.1 | 0.096 |

Figure 10:
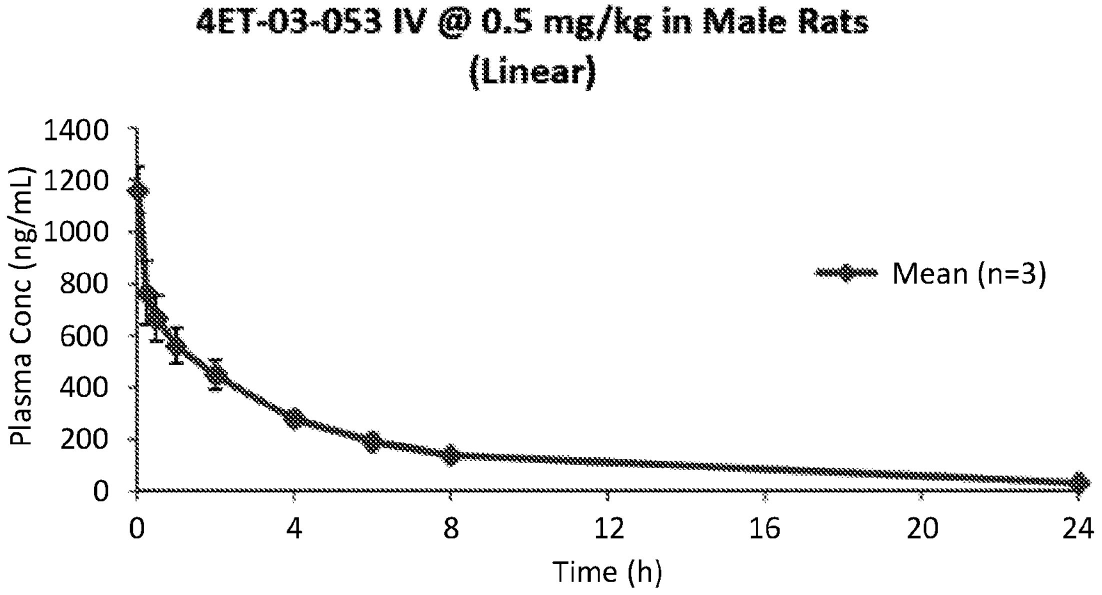
FIG. 10 shows plasma concentrations of 4ET-03-053 following a single 1 mg/kg IV administration to rats.

Example 5: PK Study of 4ET-03-053 in Male Sprague-Dawley Rats with IV (0.5 mg/kg; 10% DMI 15% EtOH 35% PG 40% NS) and PO (1 mg Kg; 10% DMA PG) Dosing In male Sprague-Dawley rats, following IV administration with 0.5 mg/kg 4ET-03-053, plasma concentrations declined in a multiphasic manner with an initial concentration (Co) of 1.24 ug/mL and a last measurable concentration (Clast) of 33.2 ng/mL at 24 h post dose. The compound displayed a low systemic clearance (CLp) of 1.87 mL/min/kg and a moderate steady-state volume of distribution (Vss) of 0.87 L/kg, suggesting insignificant metabolism and approximately even distribution between plasma and tissues. The total systemic exposure (AUCinf) was 4.50 h*ug/mL with a terminal half-life (t1/2) of 7.33 hr. FIG. 10 shows a graph of concentration vs. time and Table 13 provides the pharmacokinetic data.

TABLE 13

PK data from 0.5 mg/mL IV dosing 4ET-03-053 (10% DMI: 15% EtOH: 35% PG: 40% N5)

| Animal # | $t_{1/2}$ (hr) | $C_o$ (ng/mL) | $T_{last}$ (hr) | $C_{last}$ (ng/mL) | AUClast (hr* ng/mL) |
|---|---|---|---|---|---|
| 1 | 7.44 | 1256 | 24.0 | 29.7 | 3767 |
| 2 | 7.26 | 1141 | 24.0 | 33.1 | 4033 |
| 3 | 7.29 | 1313 | 24.0 | 36.7 | 4654 |
| Mean (n = 3) | 7.33 | 1237 | 24.0 | 33.2 | 4151 |
| SD | 0.095 | 87.6 | 0 | 3.50 | 455 |
| % CV | 1.29 | 7.09 | 0 | 10.6 | 11.0 |

| Animal # | AUCinf (hr* ng/mL) | Vss (L/kg) | AUCinf/ D(hr* kg/kL) | MRTinf(hr) | CLp (mL/ min/kg) |
|---|---|---|---|---|---|
| 1 | 4084 | 0.942 | 8167 | 7.69 | 2.04 |
| 2 | 4377 | 0.905 | 8753 | 7.92 | 1.90 |
| 3 | 5036 | 0.761 | 10073 | 7.67 | 1.65 |
| Mean (n = 3) | 4499 | 0.870 | 8998 | 7.76 | 1.87 |

TABLE 13-continued

PK data from 0.5 mg/mL IV dosing 4ET-03-053 (10% DMI: 15% EtOH: 35% PG: 40% N5)

| | | | | | |
|---|---|---|---|---|---|
| SD | 488 | 0.095 | 976 | 0.139 | 0.196 |
| % CV | 10.8 | 11.0 | 10.8 | 1.79 | 10.5 |

Figure 11:
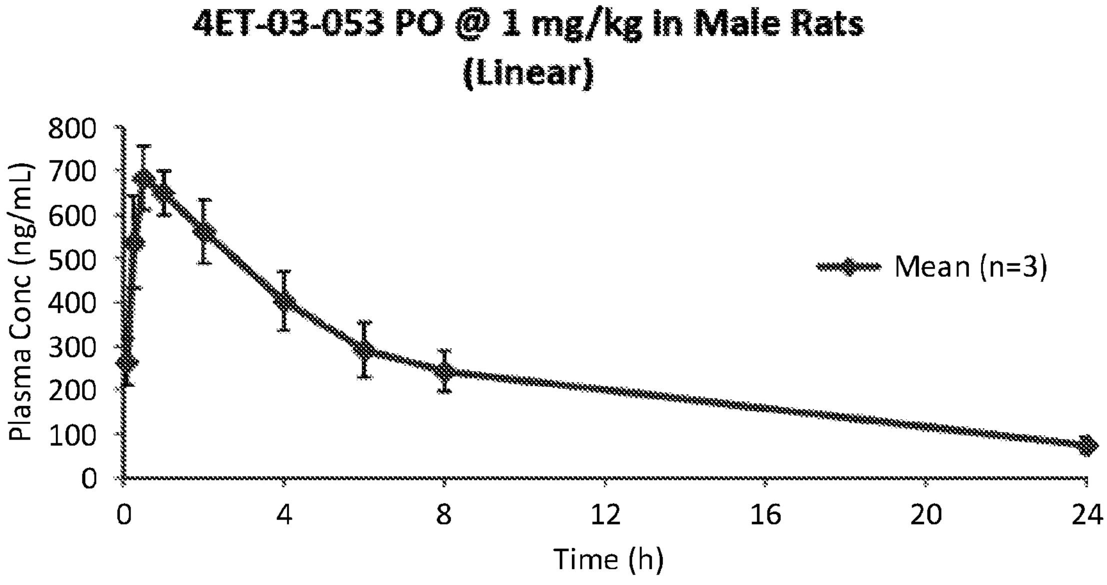
FIG. 11 shows the oral absorption curve for 4ET-03-053 following a single 1 mg/kg PO administration to rats (vehicle: 10% DMA/PG).

In Sprague-Dawley rats, following a single PO administration of 1 mg/kg 4ET-03-053, plasma concentrations reached its high peak plasma concentrations ($C_{max}$) of 683 ng/mL within 30 min. After that, its plasma concentration declined in a multiphasic manner with a last measurable concentration of 74.6 ng/mL at 24 hr with a terminal half-life (t1/2) of 9.23 hr. The total systemic exposure (AUCinf) was 6.90 h*ug/mL with an oral bioavailability of 76.7%. FIG. 11 shows a graph of concentration vs. time and Table 14 provides pharmacokinetic data. Table 15 provides plasma and brain concentrations at 2 hr after a single P0 dose of 1 mg/kg. The brain:plasma ratio is 0.083, indicating that 4ET-03-053 is a non-brain penetrant compound.

TABLE 14

PK data from 1 mg/mL PO dosing of 4ET-03-053 (10% DMA/PG)

| Animal # | $t_{1/2}$ (hr) | $T_{max}$ (hr) | $C_{max}$ (ng/mL) | $C_{max/D}$ (kg/kL) | $T_{last}$ (hr) | $C_{last}$ (ng/mL) |
|---|---|---|---|---|---|---|
| 1 | 8.89 | 0.500 | 765 | 765 | 24.0 | 71.2 |
| 2 | 9.21 | 0.500 | 628 | 628 | 24.0 | 58.6 |
| 3 | 9.58 | 0.500 | 656 | 656 | 24.0 | 94.1 |
| Mean (n = 3) | 9.23 | 0.500 | 683 | 683 | 24.0 | 74.6 |
| SD | 0.344 | 0.00 | 72.4 | 72.4 | 0.00 | 18.0 |
| % CV | 3.73 | 0.00 | 10.6 | 10.6 | 0.00 | 24.1 |

| Animal # | $AUC_{last}$ (hr* ng/mL) | $AUC_{inf}$ (hr* ng/mL) | $AUC_{inf}$/ D(hr* kg/kL) | $MRT_{inf}$(hr) | F (%) |
|---|---|---|---|---|---|
| 1 | 6112 | 7023 | 7023 | 10.6 | 78.1 |
| 2 | 4934 | 5713 | 5713 | 10.8 | 63.5 |
| 3 | 6652 | 7949 | 7949 | 12.4 | 88.3 |
| Mean (n = 3) | 5899 | 6895 | 6895 | 11.2 | 76.6 |
| SD | 879 | 1124 | 1124 | 0.969 | 12.5 |
| % CV | 14.9 | 16.3 | 16.3 | 8.62 | 16.3 |

TABLE 15

Plasma and brain tissue concentrations and brain to plasma ratio of 4ET-03-053.

| Matrix | Plasma or Tissue Homogenate Conc. (ng/mL) n = 3 | | | Mean (ng/mL) | Mean Tissue (ng/g) | SD (ng/mL) | CV (%) | Mean Tissue/ Plasma Conc. Ratio |
|---|---|---|---|---|---|---|---|---|
| Plasma | 506 | 539 | 652 | 566 | N/A | 76.6 | 13.5 | N/A |
| Brain | 9.82 | 11.4 | 14.2 | 11.8 | 47.2 | 2.22 | 18.4 | 0.083 |

Example 6: PK Study of 4ET-03-053 in Male Sprague-Dawley Rats Dosed Once Per Day for Five Days (PO; 1 mg/kg; 0.500 HPMC Aqueous Suspension)

Figure 12:
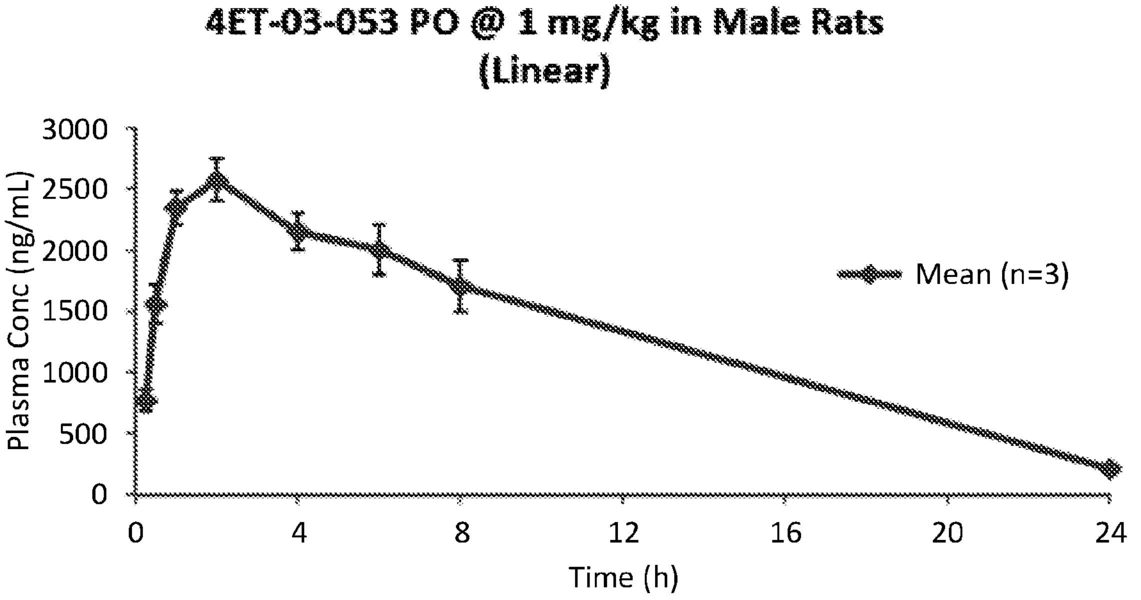
FIG. 12 shows the oral absorption curve for 4ET-03-053 following a single 1 mg/kg PO administration to rats (vehicle: 0.5% HPMC).

In male Sprague-Dawley rats, following a single P0 administration of 1 mg/kg 4ET-03-053 as a 0.50% aqueous hydroxypropyl methylcellulose suspension, plasma concentrations reached its high peak plasma concentrations ($C_{max}$) of 2.58 ug/mL within 2 hr. After that, its plasma concentration declined to a last measurable concentration of 213 ng/mL at 24 hr with a terminal half-life (t1/2) of 5.73 hr. The total systemic exposure (AUCinf) was 33.6 h*ug/mL with an oral bioavailability of 65.4%. FIG. 12 shows a graph of 4ET-03-053 concentration vs. time and Table 16 provides pharmacokinetic data.

TABLE 16

PK data from 1 mg/mL PO dosing of 4ET-03-053 (0.5% HPMC suspension).

| Animal # | $t_{1/2}$ (hr) | $T_{max}$ (hr) | $C_{max}$ (ng/mL) | $C_{max/D}$ (kg/kL) | $T_{last}$ (hr) | $C_{last}$ (ng/mL) |
|---|---|---|---|---|---|---|
| 1 | 5.77 | 2.00 | 2750 | 2750 | 24.0 | 237 |
| 2 | 5.92 | 2.00 | 2580 | 2580 | 24.0 | 224 |
| 3 | 5.51 | 2.00 | 2400 | 2400 | 24.0 | 179 |
| Mean (n = 3) | 5.73 | 2.00 | 2577 | 2577 | 24.0 | 213 |
| SD | 0.208 | 0.00 | 175 | 175 | 0.00 | 30.4 |
| % CV | 3.64 | 0.00 | 6.79 | 6.79 | 0.00 | 14.3 |

| Animal # | $AUC_{last}$ (hr* ng/mL) | $AUC_{inf}$ (hr* ng/mL) | $AUC_{inf}$/ D(hr* kg/kL) | $MRT_{inf}$(hr) | F (%) |
|---|---|---|---|---|---|
| 1 | 35139 | 37178 | 37178 | 8.25 | 72.2 |
| 2 | 31340 | 33302 | 33302 | 8.31 | 64.7 |
| 3 | 28992 | 30451 | 30451 | 7.83 | 59.2 |
| Mean (n = 3) | 31824 | 33644 | 33644 | 8.13 | 65.4 |
| SD | 3102 | 3376 | 3376 | 0.261 | 6.56 |
| % CV | 9.75 | 10.0 | 10.0 | 3.21 | 10.0 |

Figure 13:
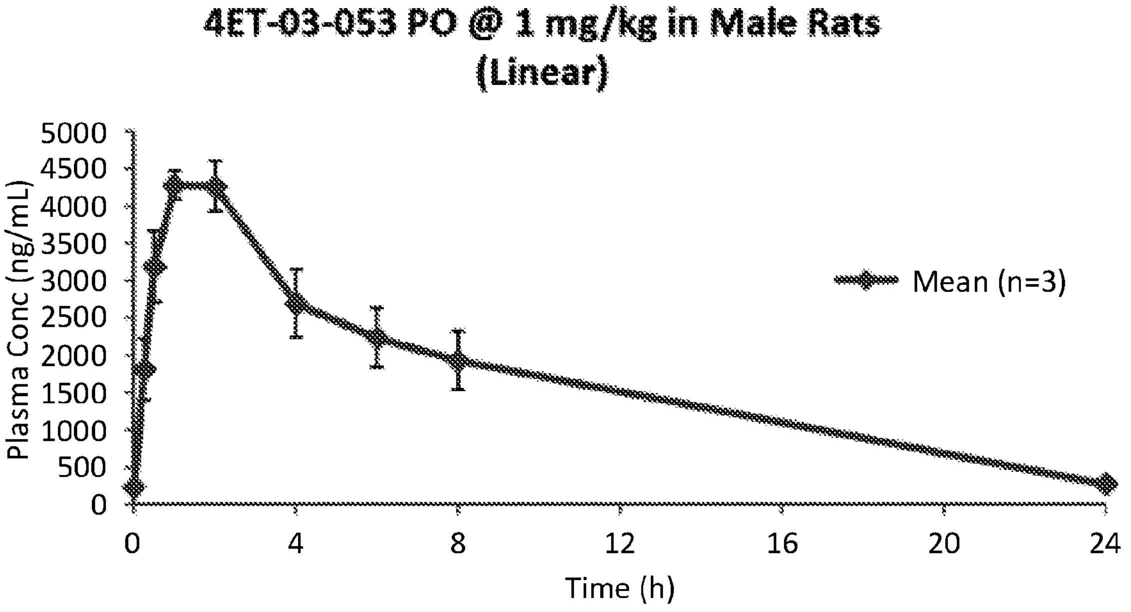
FIG. 13 shows the oral absorption curve for 4ET-03-053 following the fifth dose of five daily 1 mg/kg PO doses to rats (vehicle: 0.5% HPMC).

In Sprague-Dawley rats, after five daily P0 doses of 1 mg/kg 4ET-03-053 as a 0.5% aqueous hydroxypropyl methylcellulose suspension, plasma concentrations reached its high peak plasma concentrations ($C_{max}$) of 4.40 ug/mL within 2 hr. After that, its plasma concentration declined to a last measurable concentration of 278 ng/mL at 24 hr with a terminal half-life (t1/2) of 6.01 hr. The total systemic exposure (AUCinf) was 43.2 h*ug/mL with an oral bioavailability of 84.0%. FIG. 13 shows a graph of 4ET-03-053 concentration vs. time and Table 17 provides pharmacokinetic data. Table 18 provides plasma and brain concentrations of 4ET-03-0053 at 24 hr after the last dose of five daily P0 doses. The brain:plasma ratio is 0.086, indicating that 4ET-03-053 is a non-brain penetrant compound.

TABLE 17

PK data on day 5 of 1 mg/mL PO dosing of 4ET-03-053 (0.5% HPMC suspension)

| Animal # | $t_{1/2}$ (hr) | $T_{max}$ (hr) | $C_{max}$ (ng/mL) | $C_{max/D}$ (kg/kL) | $T_{last}$ (hr) | $C_{last}$ (ng/mL) |
|---|---|---|---|---|---|---|
| 1 | 5.90 | 2.00 | 4550 | 4550 | 24.0 | 318 |
| 2 | 6.21 | 1.00 | 4500 | 4500 | 24.0 | 291 |
| 3 | 5.91 | 1.00 | 4150 | 4150 | 24.0 | 226 |
| Mean (n = 3) | 6.01 | 1.33 | 4400 | 4400 | 24.0 | 278 |
| SD | 0.179 | 0.577 | 218 | 218 | 0.00 | 47.3 |
| % CV | 2.97 | 43.3 | 4.95 | 4.95 | 0.00 | 17.0 |

| Animal # | $AUC_{last}$ (hr* ng/mL) | $AUC_{inf}$ (hr* ng/mL) | $AUC_{inf}$/ D(hr* kg/kL) | $MRT_{inf}$(hr) | F (%) |
|---|---|---|---|---|---|
| 1 | 47073 | 49825 | 49825 | 7.89 | 96.8 |
| 2 | 40882 | 43537 | 43537 | 7.96 | 84.6 |
| 3 | 34335 | 36277 | 36277 | 7.55 | 70.5 |
| Mean (n = 3) | 40763 | 43213 | 43213 | 7.80 | 84.0 |
| SD | 6370 | 6780 | 6780 | 0.221 | 13.2 |
| % CV | 15.6 | 15.7 | 15.7 | 2.83 | 15.7 |

TABLE 18

Plasma and brain tissue concentrations and brain to plasma ratio of 4ET-03-053 24 hr after the last 1 mg/kg PO dose on day 5.

| Matrix | Plasma or Tissue Homogenate Conc. (ng/mL) n = 3 | | | Mean (ng/mL) | Mean Tissue (ng/g) | SD (ng/mL) | CV (%) | Mean Tissue/ Plasma Conc. Ratio |
|---|---|---|---|---|---|---|---|---|
| Plasma | 318 | 291 | 226 | 278 | N/A | 47.3 | 17.0 | N/A |
| Brain | 7.22 | 5.79 | 5.04 | 6.02 | 24.1 | 1.11 | 18.4 | 0.086 |

Example 7. PK Study of 4ET-03-053 in Male Sprague-Dawley Rats Dosed Once Per Day For Five Days (P0; 10 mg/kg; 0.5%0 HPMC Aqueous Suspension)

Figure 14:
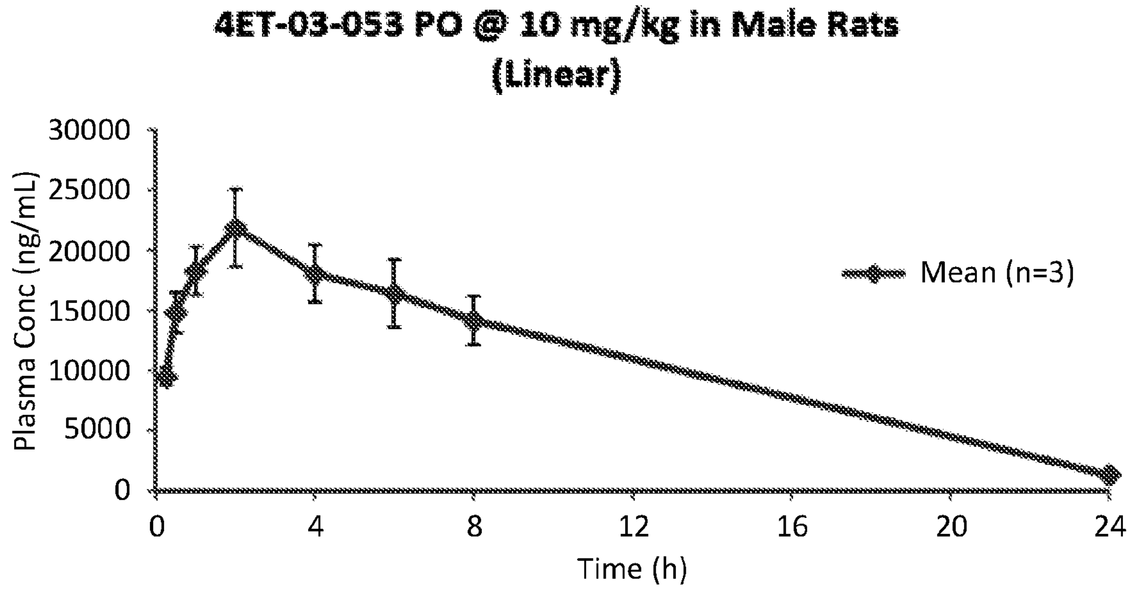
FIG. 14 shows the oral absorption curve for 4ET-03-053 following a single 10 mg/kg PO administration to rats (vehicle: 0.5% HPMC).

In male Sprague-Dawley rats, following a single PO administration of 10 mg/kg 4ET-03-053 as a 0.500 aqueous hydroxypropyl methylcellulose suspension, plasma concentrations reached its high peak plasma concentrations ($C_{max}$) of 22.3 ug/mL within 2 hr. After that, its plasma concentration declined to a last measurable concentration of 1.34 ug/mL at 24 hr with a terminal half-life (t1/2) of 5.11 hr. The total systemic exposure (AUCinf) was 272 h*ug/mL with an oral bioavailability of 52.80. FIG. 14 shows a graph of 4ET-03-053 concentration vs. time and Table 19 provides pharmacokinetic data.

Figure 15:
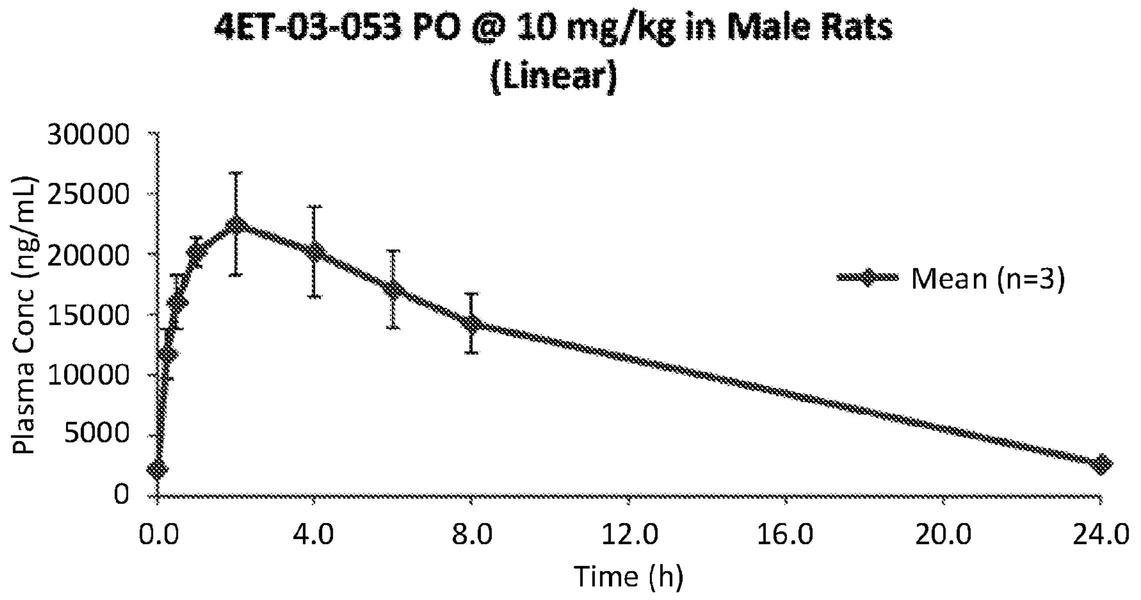
FIG. 15 shows the oral absorption curve for 4ET-03-053 following the fifth dose of five daily 10 mg/kg PO doses to rats (vehicle: 0.5% HPMC).

In Sprague-Dawley rats, following five daily doses of P0 administration of 10 mg/kg 4ET-03-053 as a 0.5% aqueous hydroxypropyl methylcellulose suspension, plasma concentrations reached its high peak plasma concentrations ($C_{max}$) of 22.8 ug/mL within 2 hr. After that, its plasma concentration declined to a last measurable concentration of 2.67 ug/mL at 24 hr with a terminal half-life (t/2) of 6.82 hr. The total systemic exposure (AUCinf) was 308 h*ug/mL with an oral bioavailability of 59.9%. FIG. 15 shows a graph of 4ET-03-053 concentration vs. time and Table 20 provides pharmacokinetic data for 4ET-03-053. Table 21 provides plasma and brain concentrations at 24 hr after the last dose of five daily P0 doses of 4ET-03-053.

TABLE 19

PK data from a single 10 mg/mL PO dose of 4ET-03-053 (0.5% HPMC suspension)

| Animal # | $t_{1/2}$ (hours) | $T_{max}$ (hours) | $C_{max}$ (ng/mL) | $C_{max/D}$ (kg/kL) | $T_{last}$ (hours) | $C_{last}$ (ng/mL) |
|---|---|---|---|---|---|---|
| 1 | 4.83 | 1.00 | 19900 | 1990 | 24.0 | 1120 |
| 2 | 5.11 | 2.00 | 21800 | 2180 | 24.0 | 1560 |
| 3 | 5.38 | 2.00 | 25100 | 2510 | 24.0 | 1330 |
| Mean(n = 3) | 5.11 | 1.67 | 22267 | 2227 | 24.0 | 1337 |
| SD | 0.277 | 0.577 | 2631 | 263 | 0.00 | 220 |
| % CV | 5.42 | 34.6 | 11.8 | 11.8 | 0.00 | 16.5 |

| Animal # | $AUC_{last}$ (hr* ng/mL) | $AUC_{inf}$ (hr* ng/mL) | $AUC_{inf}$/D(hr* kg/kL) | $MRT_{inf}$(hr) | F (%) |
|---|---|---|---|---|---|
| 1 | 247198 | 255254 | 25525 | 7.18 | 49.6 |
| 2 | 296855 | 308776 | 30878 | 7.59 | 60.0 |
| 3 | 240643 | 251304 | 25130 | 7.51 | 48.8 |
| Mean (n = 3) | 261565 | 271778 | 27178 | 7.43 | 52.8 |
| SD | 30737 | 32102 | 3210.2 | 0.216 | 6.24 |
| % CV | 11.8 | 11.8 | 11.8 | 2.91 | 11.8 |

TABLE 20

PK data on day five of 10 mg/mL PO dosing of 4ET-03-053 (0.5% HPMC suspension)

| Animal # | $t_{1/2}$ (hr) | $T_{max}$ (hr) | $C_{max}$ (ng/mL) | $C_{max/D}$ (kg/kL) | $T_{last}$ (hr) | $C_{last}$ (ng/mL) |
|---|---|---|---|---|---|---|
| 1 | 7.19 | 1.00 | 18800 | 1880 | 24.0 | 2390 |
| 2 | 6.73 | 2.00 | 25100 | 2510 | 24.0 | 2740 |
| 3 | 6.54 | 2.00 | 24600 | 2460 | 24.0 | 2880 |
| Mean (n = 3) | 6.82 | 1.67 | 22833 | 2283 | 24.0 | 2670 |
| SD | 0.335 | 0.577 | 3502 | 350 | 0.00 | 252 |
| % CV | 4.91 | 34.6 | 15.3 | 15.3 | 0.00 | 9.45 |

| Animal # | $AUC_{last}$ (hr* ng/mL) | $AUC_{inf}$ (hr* ng/mL) | $AUC_{inf}$/ D(hr* kg/kL) | $MRT_{inf}$(hr) | F (%) |
|---|---|---|---|---|---|
| 1 | 233589 | 258620 | 25862 | 9.79 | 50.2 |
| 2 | 291659 | 318204 | 31820 | 9.17 | 61.8 |
| 3 | 320410 | 347920 | 34792 | 9.18 | 67.6 |
| Mean (n = 3) | 281886 | 308248 | 30825 | 9.38 | 59.9 |
| SD | 44228 | 45475 | 4548 | 0.355 | 8.83 |
| % CV | 15.7 | 14.8 | 14.8 | 3.78 | 14.8 |

TABLE 21

Plasma and brain tissue concentrations and brain to plasma ratio of 4ET-03-053 24 hr after the last of five 10 mg/kg PO doses.

| Matrix | Plasma or Tissue Homogenate Conc. (ng/mL) n = 3 | | | Mean (ng/mL) | Mean Tissue (ng/g) | SD (ng/mL) | CV (%) | Mean Tissue/ Plasma Conc. Ratio |
|---|---|---|---|---|---|---|---|---|
| Plasma | 2390 | 2740 | 2880 | 2670 | N/A | 252 | 9.45 | N/A |
| Brain | 75.6 | 88.2 | 93.0 | 85.6 | 342 | 8.99 | 10.5 | 0.128 |

Example 8. PK Study of 4ET-03-053 in Male Sprague-Dawley Rats Dosed Once Per Day for Five Days (P0; 25 mg/kg; 0.5 HPMC Aqueous Suspension)

Figure 16:
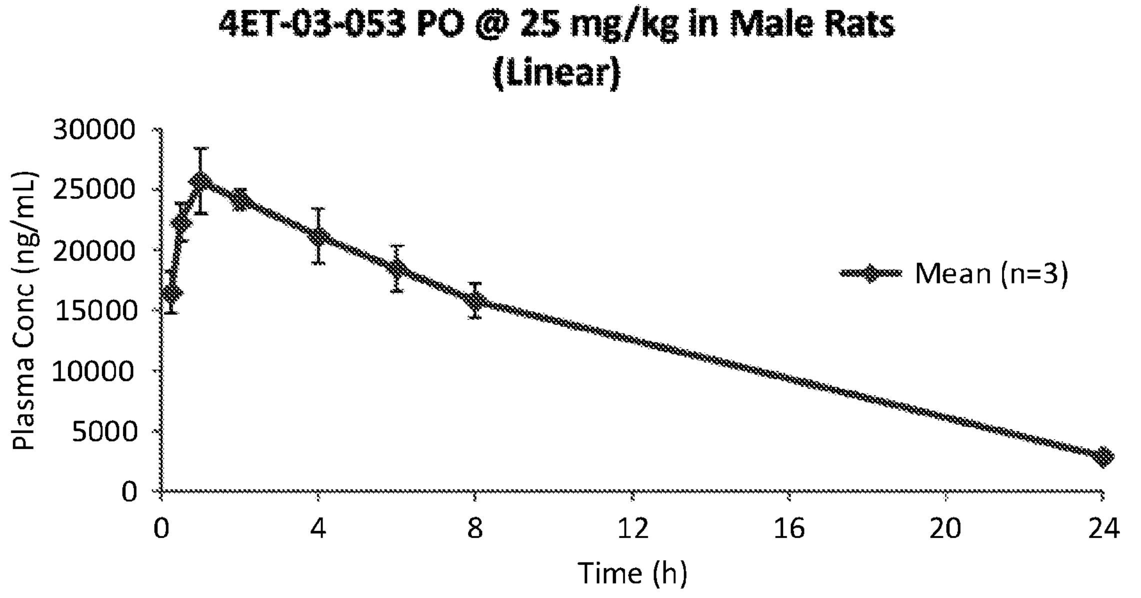
FIG. 16 shows the oral absorption curve for 4ET-03-053 following a single 25 mg/kg PO administration to rats (vehicle: 0.5% HPMC).

In Sprague-Dawley rats, following a single PO administration of 25 mg/kg 4ET-03-053 as a 0.50 aqueous hydroxypropyl methylcellulose suspension, plasma concentrations reached its high peak plasma concentrations ($C_{max}$) of 25.9 ug/mL within 2 hr. After that, its plasma concentration declined to a last measurable concentration of 2.89 ug/mL at 24 hr with a terminal half-life (t1/2) of 6.82 hr. The total systemic exposure (AUCinf) was 341 h*ug/mL with an oral bioavailability of 826.5%. FIG. 16 shows a graph of 4ET-03-053 concentration vs. time and Table 22 provides pharmacokinetic data.

Figure 17:
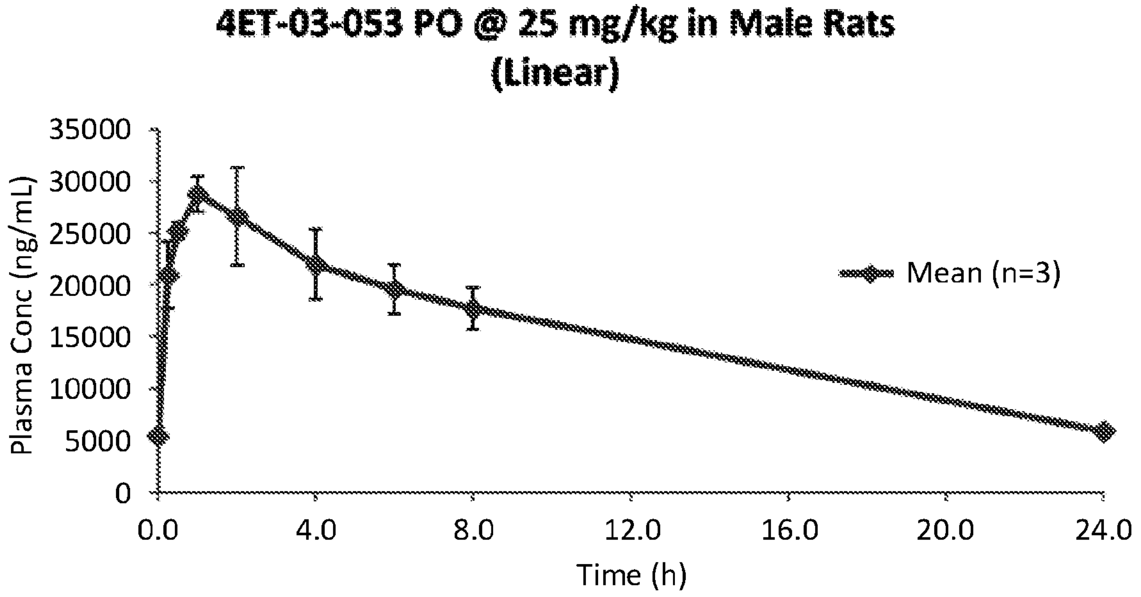
FIG. 17 shows the oral absorption curve for 4ET-03-053 following the fifth dose of five daily 25 mg/kg PO doses to rats (vehicle: 0.5% HPMC).
Figure 18:
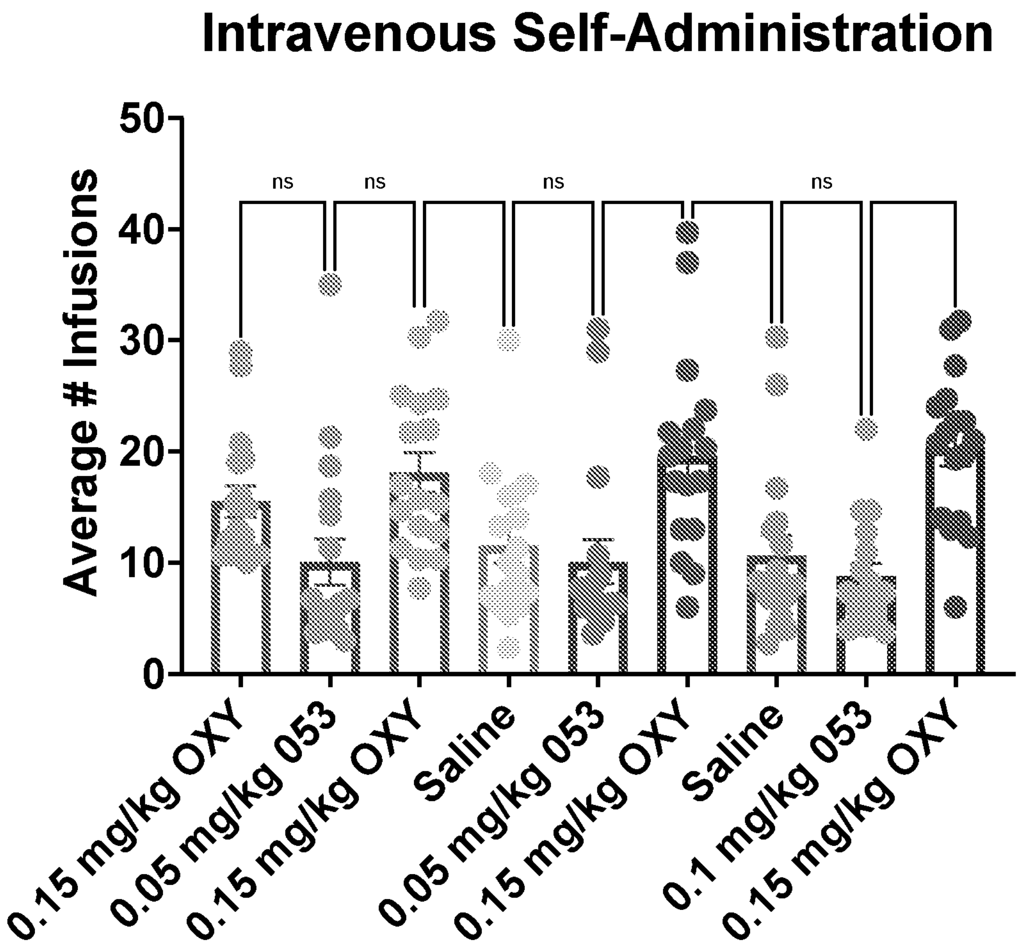
FIG. 18 shows average number of infusions for intravenous self-administration for oxycondone ("OXY"), 4ET-03-053 ("053"), and saline, respectively.

In Sprague-Dawley rats, after the last of five daily 25 mg/kg PO doses of 4ET-03-053 as a 0.5% aqueous hydroxypropyl methylcellulose suspension, plasma concentrations reached its high peak plasma concentrations ($C_{max}$) of 28.8 ug/mL within 1 hr. After that, its plasma concentration declined to a last measurable concentration of 5.89 ug/mL at 24 hr with a terminal half-life (t1/2) of 10.5 hr. The total systemic exposure (AUCinf) was 456 h*ug/mL with an oral bioavailability of 35.5%. FIG. 17 shows a graph of 4ET-03-053 concentration vs. time and Table 23 provides pharmacokinetic data for 4ET-03-053. Table 24 provides plasma and brain concentrations at 24 hr after the last dose of five daily PO doses of 4ET-03-053.

TABLE 22

PK data from a single 25 mg/mL PO dose of 4ET-03-053 (0.5% HPMC suspension)

| Animal # | $t_{1/2}$ (hours) | $T_{max}$ (hours) | $C_{max}$ (ng/mL) | $C_{max/D}$ (kg/kL) | $T_{last}$ (hours) | $C_{last}$ (ng/mL) |
|---|---|---|---|---|---|---|
| 1 | 6.94 | 2.00 | 24600 | 984 | 24.0 | 2660 |
| 2 | 6.50 | 1.00 | 28800 | 1152 | 24.0 | 2870 |
| 3 | 7.03 | 1.00 | 24400 | 976 | 24.0 | 3130 |
| Mean (n = 3) | 6.82 | 1.33 | 25933 | 1037 | 24.0 | 2887 |
| SD | 0.284 | 0.58 | 2485 | 99.4 | 0.00 | 235 |
| % CV | 4.16 | 43.3 | 9.58 | 9.58 | 0.00 | 8.16 |

| Animal # | $AUC_{last}$ (hr* ng/mL) | $AUC_{inf}$ (hr* ng/mL) | $AUC_{inf}$/D(hr* kg/kL) | $MRT_{inf}$(hr) | F (%) |
|---|---|---|---|---|---|
| 1 | 287918 | 314979 | 12599 | 9.26 | 24.5 |
| 2 | 336460 | 363793 | 14552 | 8.89 | 28.3 |
| 3 | 313078 | 345084 | 13803 | 9.60 | 26.8 |
| Mean (n = 3) | 312485 | 341285 | 13651 | 9.25 | 26.5 |
| SD | 24277 | 24628 | 985 | 0.357 | 1.91 |
| % CV | 7.77 | 7.22 | 7.22 | 3.86 | 7.22 |

TABLE 23

PK data on day five of 25 mg/mL PO dosing of 4ET-03-053 (0.5% HPMC suspension)

| Animal # | $t_{1/2}$ (hours) | $T_{max}$ (hours) | $C_{max}$ (ng/mL) | $C_{max/D}$ (kg/kL) | $T_{last}$ (hours) | $C_{last}$ (ng/mL) |
|---|---|---|---|---|---|---|
| 1 | 10.7 | 1.00 | 26800 | 1072 | 24.0 | 5340 |
| 2 | 9.67 | 1.00 | 29900 | 1196 | 24.0 | 6120 |
| 3 | 11.0 | 1.00 | 29600 | 1184 | 24.0 | 6220 |
| Mean (n = 3) | 10.5 | 1.00 | 28767 | 1151 | 24.0 | 5893 |
| SD | 0.718 | 0.00 | 1710 | 68.4 | 0.00 | 482 |
| % CV | 6.85 | 0.00 | 5.94 | 5.94 | 0.00 | 8.18 |

| Animal # | $AUC_{last}$ (hr* ng/mL) | $AUC_{inf}$ (hr* ng/mL) | $AUC_{inf}$/D(hr* kg/kL) | $MRT_{inf}$(hr) | F (%) |
|---|---|---|---|---|---|
| 1 | 324395 | 407906 | 16316 | 14.5 | 31.7 |
| 2 | 403575 | 489224 | 19569 | 13.2 | 38.0 |
| 3 | 371995 | 471587 | 18863 | 14.8 | 36.6 |
| Mean (n = 3) | 366655 | 456239 | 18250 | 14.1 | 35.5 |
| SD | 39859 | 42776 | 1711 | 0.856 | 3.32 |
| % CV | 10.9 | 9.38 | 9.38 | 6.06 | 9.38 |

TABLE 24

Plasma and brain tissue concentrations and brain to plasma ratio of 4ET-03-053 24 hr after the last of five 25 mg/kg PO doses.

| Matrix | Plasma or Tissue Homogenate Conc. (ng/mL) n = 3 | | | Mean (ng/mL) | Mean Tissue (ng/g) | SD (ng/mL) | CV (%) | Mean Tissue/ Plasma Conc. Ratio |
|---|---|---|---|---|---|---|---|---|
| Plasma | 5340 | 6120 | 6220 | 5893 | N/A | 482 | 8.18 | N/A |
| Brain | 104 | 127 | 136 | 122 | 489 | 16.5 | 13.5 | 0.183 |

Example 9: In Vivo Efficacy Testing; IL-6 Evoked Grimace Test

FIG. 1 shows evaluation of compounds in the IL-6 evoked grimace test. Male and female Institute for Cancer Research (ICR) mice were used in these experiments. Mice were bred in house at University of Texas at Dallas and used at between 12 and 24 weeks of age. Mice were habituated to plexiglass boxes of approximately 4×6 inches in size with openable tops. Habituation took place over 2 days with animals exposed to the boxes for at least 30 min. A blinded observer scored baseline grimacing using the method previously described by Mogil and colleagues (Langford D J, et al. "Coding of facial expressions of pain in the laboratory mouse" *Nat Methods* 7:447-449 (2010)). On test day, mice were given test compounds 1 hr prior to injection of interleukin 6 (human recombinant IL-6, R&D Systems) which was given at a dose of 0.1 ng in saline via an intraplantar injection as described previously (Moy J K, et al. "The MNK-eIF4E Signaling Axis Contributes to Injury-Induced Nociceptive Plasticity and the Development of Chronic Pain" *J Neurosci.* 37:7481-7499 (2017)). Test compounds were given orally (PO) via a flexible oral gavage canula built for mice. 4ET-03-053 is efficacious in the IL-6 evoked grimace test in mice (PO; 10 mg/kg). In addition, 4ET-01-035, 4ET-01-027, and 4ET-01-051 are efficacious in the IL-6 evoked grimace assay.

Figure 2:
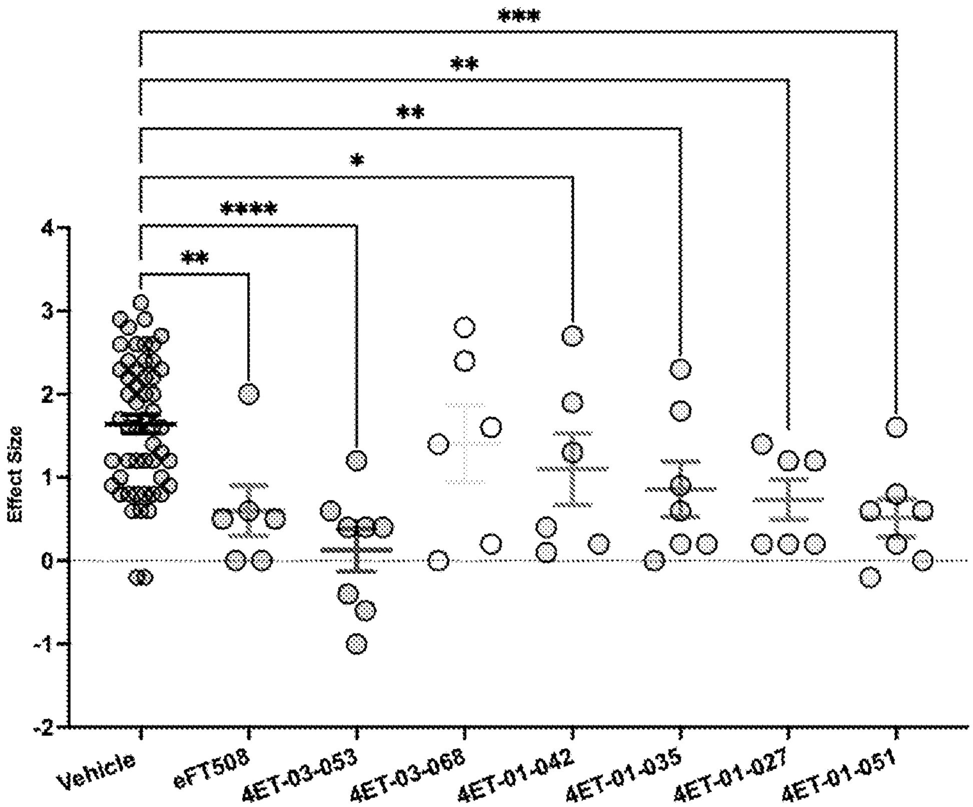
FIG. 2 shows comparison of effect size in the IL-6 evoked grimace test.

FIG. 2 shows comparison of effect size in the IL-6 evoked grimace test. Effect sizes were calculated per mouse by subtracting the baseline grimace score from the sum of the grimace scores for 1 and 3 hr time points. 4ET-03-053 has a statistically significant effect sizes in the IL-6 evoked grimace test (one-way anova).

Figure 3:
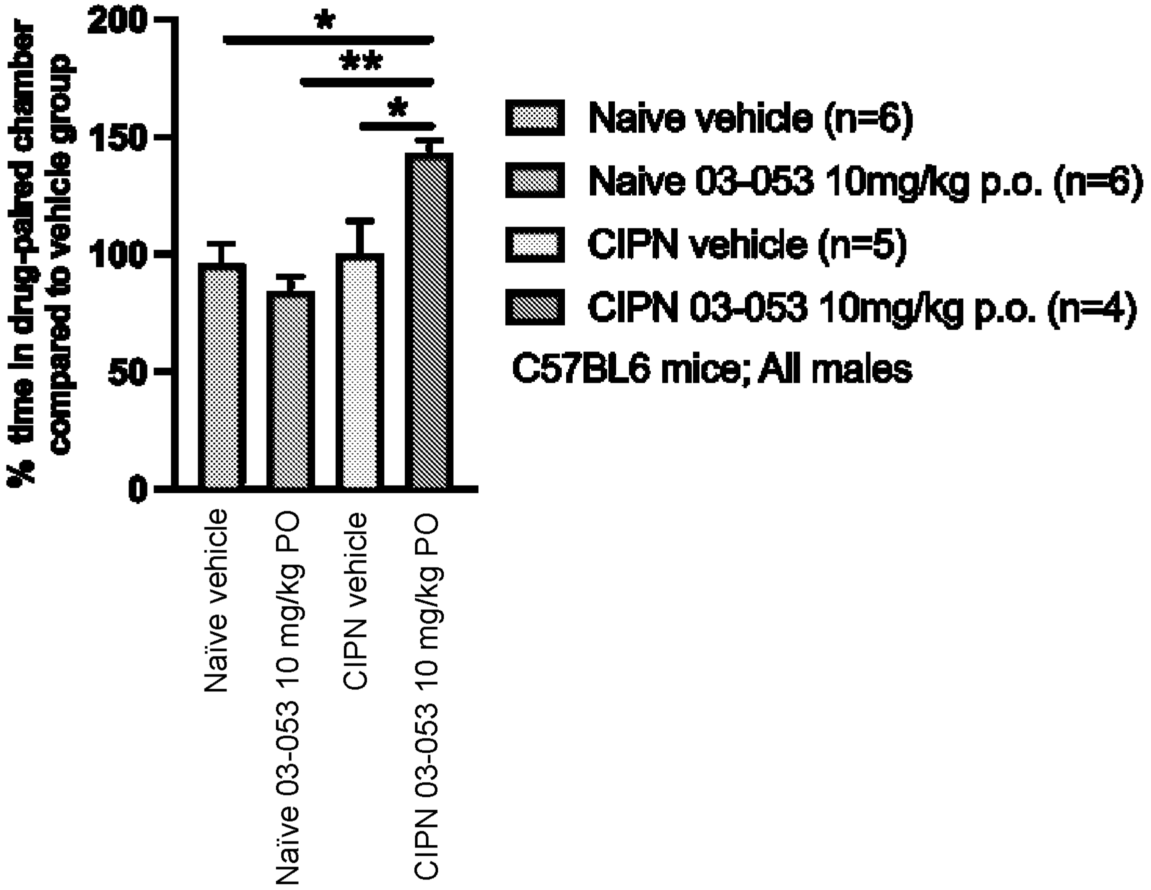
FIG. 3 shows CPP with CIPN mice treated with 4ET-03-053.

Example 10: In Vivo Efficacy Testing; Conditioned Place Preference (CPP) Test with Chemotherapy Induced Peripheral Neuropathy (CIPN) Mice (CPP CIPN FIG. 3 shows CPP with CIPN mice treated with 4ET-03-053. Mice were treated over a period of 8 days with 4 injections of paclitaxel, made in ethanol and kollipher vehicle, each at 4 mg/kg for a cumulative dose of 16 mg/kg. Mice were habituated to CPP boxes at least 14 days after the first paclitaxel treatment and the CPP experiment was done with a single drug-pairing paradigm as described previously (Megat S, et al. "Nociceptor Translational Profiling Reveals the Ragulator-Rag GTPase Complex as a Critical Generator of Neuropathic Pain" *J Neurosci.* 39:393-411 (2019)). 4ET-03-053 was given with pairing with the white chamber in the CPP box with the idea that pain relief in the white chamber will counteract the natural aversion mice have to areas with bright light. CIPN mice treated with 4ET-03-053 (10 mg/kg) spent more time in the white chamber vs. dark chambers, indicating that the compound is efficacious in alleviating neuropathic pain. There was no effect of 4ET-03-053 in the mice that did not have CIPN showing that the compound is not rewarding on its own.

Example 11 Cultured Human Dorsal Root Ganglion Cells (hDRGs)

Figure 4:
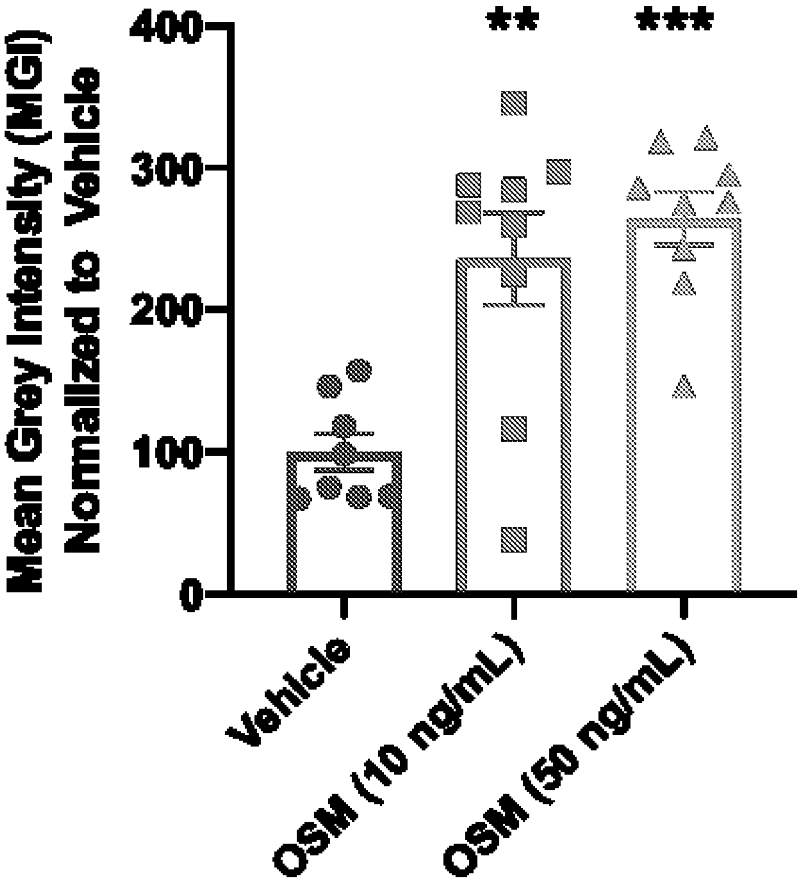
FIG. 4 shows OSM (10 and 50 ng/ml) increases phosphorylation of eIF4E.

FIG. 4 shows OSM (10 and 50 ng/ml) increases phosphorylation of eIF4E. Treatment of hDRGs with oncostatin M (OSM) increased phosphorylation of eIF4E as determined by immunoflourescence determination of p-eIF4E using a validated phospho-specific antibody (Cell Signaling ab76256). For all human DRG experiments, DRGs were recovered from organ donors at the Southwest Transplant Alliance under an IRB approved protocol at University of Texas at Dallas. DRGs were recovered within 3 hrs of cross clamp. DRGs were recovered and taken back to the University of Texas lab where they were cultured using the protocol described previously. Cultures were grown on glass coverslips for microscopy. Coverslips were coated with poly-D-lysine and laminin to improve neuronal adherence to the coverslips. Cultures of human DRG neurons were grown for 4-7 days prior to treatment with OSM. OSM treatment was done in culture media for a period of 30 min. Cells were stained with antibodies using the same protocol as described above for HEK293 cells. Imaging was done on an Olympus FV1200 microscope and image analysis was done with CellSens software. Statistical analysis was done with Graphpad Prism V8.

Figure 5:
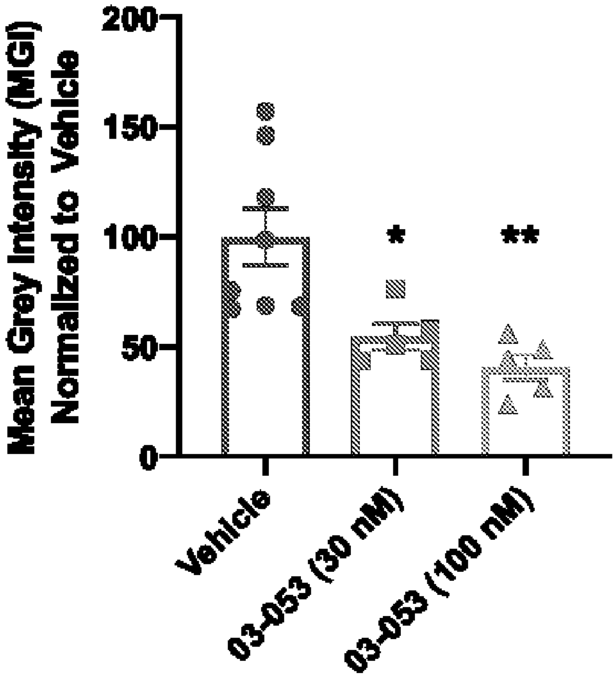
FIG. 5 shows treatment of hDRGs with 4ET-03-053 at the indicated concentrations for 30 min.

FIG. 5 shows treatment of hDRGs with 4ET-03-053 at the indicated concentrations for 30 min. Treatment of hDRGs with 4ET-03-053 reduces phosphorylation of eIF4E as determined by immunoflourescence determination of p-eIF4E using a validated phospho-specific antibody (Cell Signaling ab76256). Human DRG recovery and other experimental protocols were the same as described herein.

Figure 6:
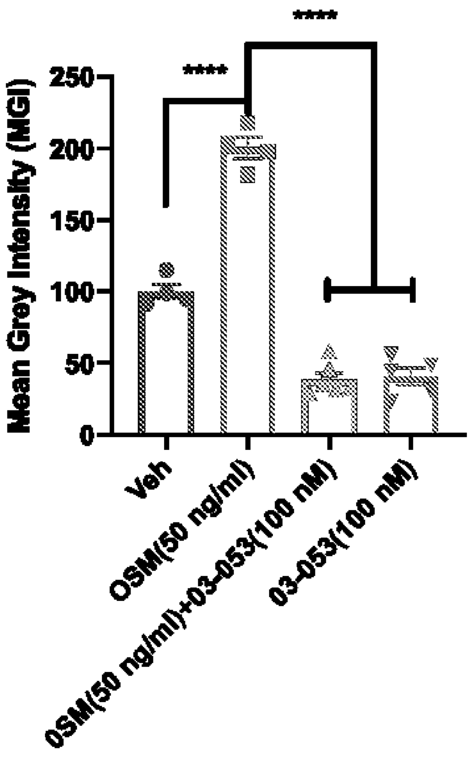
FIG. 6 shows treatment of hDRGs with 4ET-03-053 in presence of OSM.

FIG. 6 shows treatment of hDRGs with 4ET-03-053 in presence of OSM. Treatment of hDRGs with 4ET-03-053 in the presence of OSM reduces phosphorylation of eIF4E as determined by immunoflourescence determination of p-eIF4E using a validated phospho-specific antibody. Human DRG recovery and other experimental protocols were the same as described herein.

Example 12: In Vivo Biochemical Assay in Mice to Determine Levels of eIF4E Phosphorylation in Different Tissues 2 Hours after Dosing with 4ET-03-053

Figure 7:
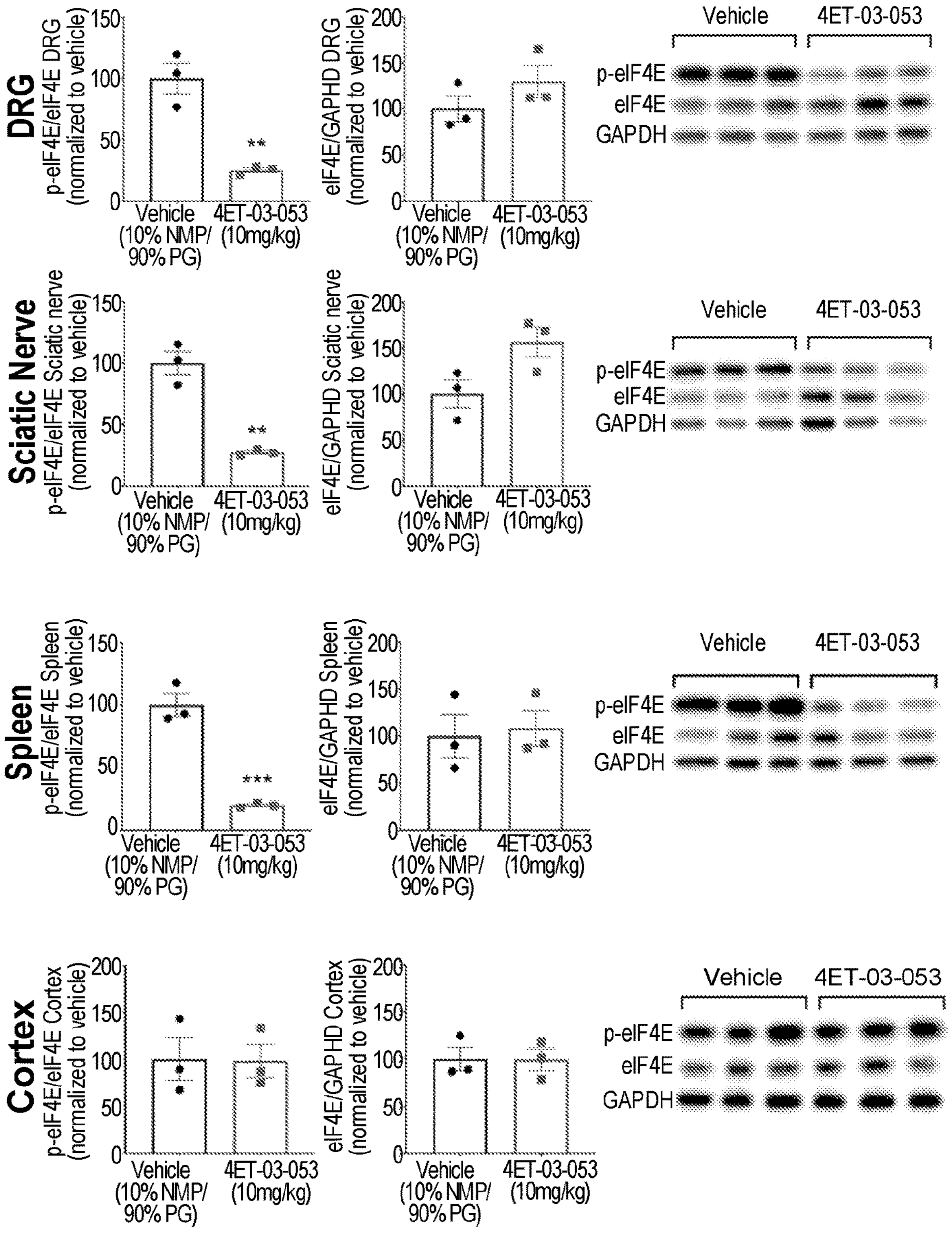
FIG. 7 shows Western blot analysis in tissues from mice dosed with 4ET-03-053.
Figure 8:
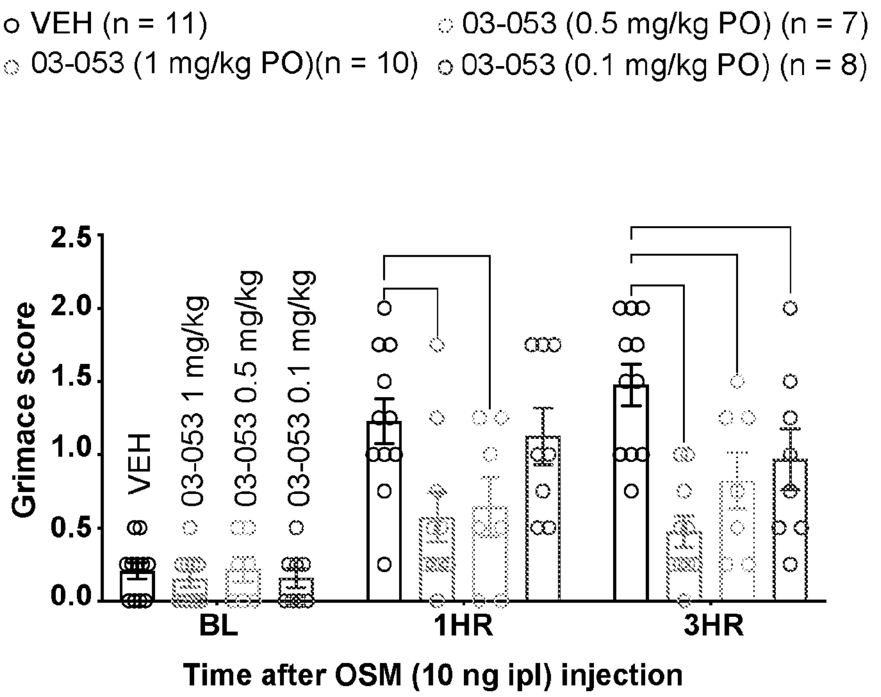
FIG. 8 shows evaluation of 4ET-03-053 in OSM rat grimace test.
Figure 9:
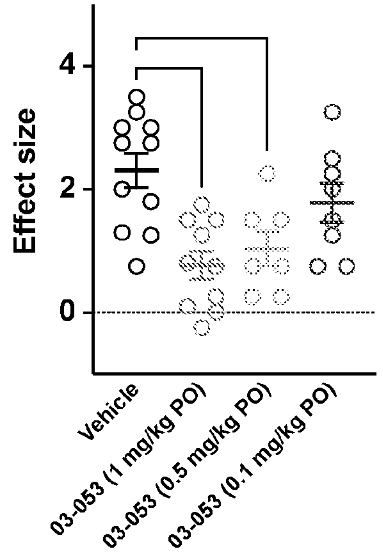
FIG. 9 shows comparison of effect size at different doses of 4ET-03-053.

FIG. 7 shows Western blot analysis in tissues from mice dosed with 4ET-03-053. Mice received PO injections via oral gavage and then were sacrificed by cervical dislocation under gas anesthesia 4 hrs later. Tissues were acutely dissected and immediately frozen. Frozen samples were later bead homogenized with protease and phosphatase inhibitor cocktails present in the homogenization buffer and then protein was quantified by Bradford assay. 20 μg of protein was run per lane on standard SDS-PAGE. Blots were probed with antibodies against p-eIF4E and total-eIF4E and imaged on a BioRad imaging system. Mice treated with 4ET-03-053 (PO; 10 mg/kg) showed significant inhibition of eIF4E phosphorylation, 2 hours post dose, in DRGs, sciatic nerve, and spleen. However, inhibition of phosphorylation of eIF4E in the brain was not observed, as determined by Western blot analysis of brain tissue from the cortex.

Example 13: Assessment of 4ET-03-053 when Dosed in Combination of Self-Administered Oxycodone and Saline Regimen Animals Ten male and eleven female Wistar rats (Charles River, Hollister, CA) were used in this study. Rats were housed in groups of 2-3 per cage prior to surgery, and then individually housed to protect their catheters, in a temperature-controlled (22° C.) vivarium on a 12/12 h light/dark cycle (lights off at 8:00 AM) with ad libitum access to food and water. The rats acclimated to the animal facility for at least 7 days before surgery. All procedures adhered to the National Institutes of Health Guide for the Care and Use of Laboratory Animals and were approved by the Institutional Animal Care and Use Committee of The Scripps Research Institute.

Surgical Procedure

For surgery, rats were anesthetized with 2 to 3% isoflurane. They were implanted with a silastic catheter (0.3 mm i.d.×0.64 mm o.d.; Dow Corning Co. Midland, MI) into the right external jugular vein under aseptic conditions. The distal end of the catheter was subcutaneously threaded to the back of the rat where it exited via a metal guide cannula (22G; Plastics One Inc., Roanoke, VA) that was anchored at the back of the rat and closed with a small plastic cap and metal cover cap to keep the inside part of the catheter clean and protected (Caine S B, et al. "Effects of dopamine D-1 and D-2 antagonists on cocaine self-administration under different schedules of reinforcement in the rat" J Pharmacol Exp Ther. 270(1):209-18 (1994); Wee S, et al. "Effects of dose and session duration on cocaine self-administration in rats" *J Pharmacol Exp Ther.* 320(3):1134-43 (2007); Zorrilla E P, et al. "Extended access cocaine self-administration differentially activates dorsal raphe and amygdala corticotropin-releasing factor systems in rats" *Addict Biol.* 17(2): 300-8 (2012); Valtcheva M V, et al. "Surgical extraction of human dorsal root ganglia from organ donors and preparation of primary sensory neuron cultures" *Nat Protoc.* 11:1877-1888 (2016)). All incisions were closed using veterinary tissue adhesive. After surgery, rats were given analgesic (Flunixin, 2.5 mg/kg s.c.). Rats were allowed 5-7 days for recovery prior to self-administration. They were monitored and flushed daily during the recovery period and then after each self-administration session with heparinized saline (10 U/mL of heparin sodium; American Pharmaceutical Partners, Schaumberg, IL, United States) in 0.9% bacteriostatic sodium chloride (Hospira, Lake Forest, IL, United States) that contained 52.4 mg/0.2 mL of the antibiotic cefazolin.

The patency of catheters in the rats was tested using an ultra-short-acting barbiturate methohexital sodium (Brevital, Eli Lilly, Indianapolis, 1N, 10 mg/mL, 2 mg/rat) every 10-12 days during the study. Generally, a total loss of muscle tone within 3 s after a methohexital sodium injection indicates the patency of a catheter. Any animal that failed the test was excluded from the study.

Experimental Procedure

During experimental sessions, each rat was placed in a standard operant chamber, which was placed in a light- and sound-attenuating cubicle (28×26×20 cm; Med Associates Inc., St. Albans, VT). The front door and the back wall of the chamber were made of transparent plastic, and the other walls were opaque metal. The chamber had two retractable response levers mounted on one side of the opaque walls. A stimulus light was mounted above each lever. A drug injection was delivered by a syringe pump (Razel Scientific Instruments, Georgia, VT) located on top of the cubicle. Experimental sessions were controlled and recorded by a PC computer with custom interface and software in the experimental room.

Experimental sessions were conducted once a day, 5-7 days a week during the dark (active) cycle. After being flushed with 0.9% saline, a rat's indwelling catheter was connected to a tube that exited the chamber through a metal spring and a swivel and was connected to a syringe pump. After the drug delivery system was connected to the rat, the chamber was closed, and the 2 hr session was started immediately. The start of a session was signaled by the presentation of two response levers into the chamber. Responding on the right lever resulted in the delivery of 0.1 mL of a drug injection over 4 s. During an injection, stimulus lights above both levers were illuminated and lasted throughout a time-out period (20 s) that followed each injection. Pressing the left lever was counted but had no other programmed consequences. One to two priming injections were given for up to 3 days if rats did not spontaneously press the active lever within 30 min of the start of the session. After the session, the catheter was filled with 0.9% saline containing 52.4 mg/0.2 mL of the antibiotic cefazolin, and the rat was returned to the home cage.

All rats first received 0.15 mg/kg oxycodone (made up freshly every week and separately for males and females based on their average body weights). This dose was chosen based on published literature (Kimbrough A, et al. "Oxycodone self-administration and withdrawal behaviors in male and female Wistar rats" Psychopharmacology (Berl); 237 (5):1545-1555 (2020); Blackwood C A, et al. "Escalated Oxycodone Self-Administration and Punishment: Differential Expression of Opioid Receptors and Immediate Early Genes in the Rat Dorsal Striatum and Prefrontal Cortex" Front Neurosci. 13:1392 (2020); Blackwood C A, et al. "Oxycodone self-administration activates the mitogen-activated protein kinase/mitogen- and stress-activated protein kinase (MAPK-MSK) signaling pathway in the rat dorsal striatum" Sci Rep. 11(1):2567 (2021)). Oxycodone sessions continued until a rat achieved the criterion of 3 consecutive days having less than 20% variability in infusions across these days. Once this criterion was achieved, rats received 0.05 mg/kg 4ET-03-053 until this same criterion was achieved. The rats then were moved through the following sequence of solutions: 0.15 mg/kg oxycodone, saline, 0.05 mg/kg 4ET-03-053, 0.15 mg/kg oxycodone, saline, 0.1 mg/kg 4ET-03-053, and finally back to 0.15 mg/kg oxycodone (see summary timeline below). In this way, rats experienced 4ET-03-053 both after oxycodone and saline to assess contrast effects. Note that it wasn't always possible to use this acquisition criterion with saline, as 20% of a low number is very low and also there tended to be more variability in responding for saline.

Results

Twenty-one rats (10 males, 11 females) received intravenous catheterization surgery, and of these, 17 rats (9 males, 8 females) completed the study. One male had a good catheter but did not meet acquisition criteria and 3 females failed a catheter check.

The averages of the last three days (i.e., the days used to assess the acquisition criterion) on each drug were used for statistical analyses (Prism 9 for macOS). A repeated measures ANOVA with the between subject sex and the within subject drug revealed overall non-significant effects of sex ($F(1,15)=3.35$, $p=0.08$) and sex by drug ($F(8,120)=0.938$, $p=0.49$), despite females generally taking more oxycodone than males (consistent with the literature, i.e., Kimbrough A, et al. "Oxycodone self-administration and withdrawal behaviors in male and female Wistar rats" Psychopharmacology (Berl); 237(5):1545-1555 (2020)). However, the effect of drug on numbers of infusions was highly significant ($F(8,120)=10.11$, $p<0.0001$). Due to the lack of a significant impact of sex, data from males and females were collapsed for further analyses. SidCk's multiple comparisons tests (see Table 25 below) of consecutive drug challenges revealed significant differences between oxycodone and subsequent saline (both times this occurred), 0.05 mg/kg 4ET-03-053 and subsequent oxycodone, and 0.1 mg/kg 4ET-03-053 and the final oxycodone test.

TABLE 25

Statistical results and comparisons for various dosing strategies according to Example 13.

| Šidák's multiple comparisons test | Mean Difference | 95.00% Confidence Interval of Difference | Below Threshold? | Summary | Adjusted P-value |
|---|---|---|---|---|---|
| 0.15 mg/kg oxycodone vs. 0.05 4ET-03-053 | 5.441 | −1.536 to 12.42 | No | ns | 0.1930 |
| 0.05 mg/kg 4ET-03-053 vs. 0.15 oxycodone | −8.041 | −16.19 to 0.1062 | No | ns | 0.0544 |
| 0.15 mg/kg oxycodone vs. saline | 6.547 | 1.157 to 11.94 | Yes | * | 0.0123 |
| saline vs. 0.05 4ET-03-053 | 1.500 | −2.437 to 5.437 | No | ns | 0.8995 |
| 0.05 mg/kg 4ET-03-053 vs. 0.15 mg/kg oxycodone | −9.588 | −17.13 to −2.051 | Yes | ** | 0.0084 |
| 0.15 mg/kg oxycodone vs. saline | 9.006 | 1.748 to 16.26 | Yes | * | 0.0104 |
| Saline vs. 0.1 mg/kg 4ET-03-053 | 1.871 | −4.133 to 7.875 | No | ns | 0.9654 |
| 0.1 mg/kg 4ET-03-053 vs. 0.15 mg/kg oxycodone | −11.56 | −17.61 to −5.516 | Yes | *** | 0.0001 |

CONCLUSION

4ET-03-053 at two doses did not support intravenous self-administration in male and female Wistar rats. Intake levels were not significantly different from those associated with saline availability and were significantly lower than those associated with oxycodone availability were. Importantly, this was true whether the rats had just experienced oxycodone or saline. In other words, they appeared to find 4ET-03-053 less rewarding than oxycodone and not more rewarding than saline. The results of this study suggest that 4ET-03-053, under the experimental conditions employed, has negligible addictive potential.

This application claims the benefit of priority to U.S. Provisional Application No. 63/217,264, filed Jun. 30, 2021, which application is hereby incorporated by reference in its entirety.

What is claimed is:

1. A compound having formula (I):

(I)

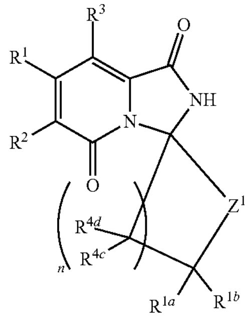

or a pharmaceutically acceptable salt thereof, wherein:

$Z^1$ is selected from the group consisting of

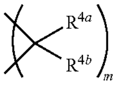

and

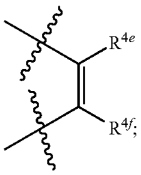

$R^1$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, cyano, $C_{1-6}$ alkoxyl, $C_{3-7}$ branched alkoxy, hydroxy, and $C_{3-6}$ cycloalkyl that is optionally substituted with 1 to 3 substituents selected from the group consisting of halogen, $C_{1-6}$ alkyl, $C_{1-6}$ haloalkyl, and $C_{1-6}$ hydroxyalkyl;

$R^2$ is selected from the group consisting of

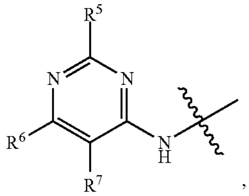

,

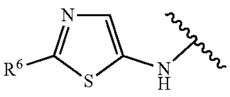

,

-continued

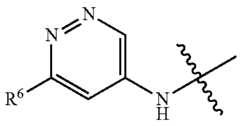, 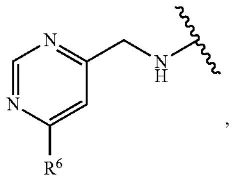,

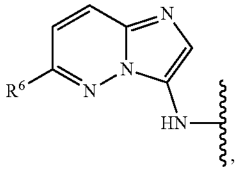 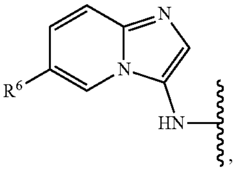,

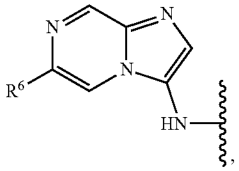, 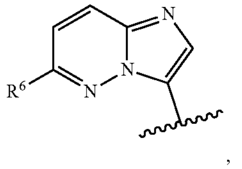,

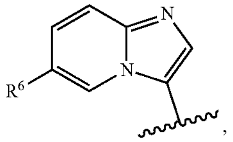, 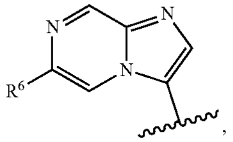,

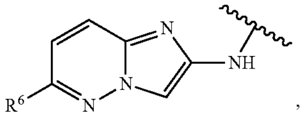,

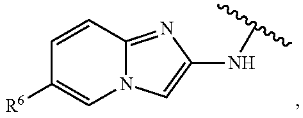,

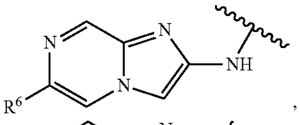, 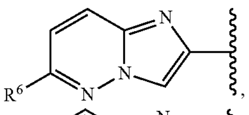,

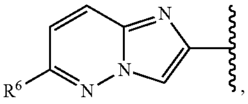, and 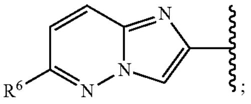;

$R^3$ is selected from the group consisting of hydrogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, cyano, $C_{1-6}$ alkoxyl, $C_{3-7}$ branched alkoxy, hydroxy, and $C_{3-6}$ cycloalkyl that is optionally substituted with 1 to 3 substituents selected from the group consisting of halogen, $C_{1-6}$ alkyl, $C_{1-6}$ haloalkyl, and $C_{1-6}$ hydroxyalkyl;

$R^{4a}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHCO(C_{3-7}$ cycloalkyl), $NHSO_2(C_{1-6}alkyl)$, $NHSO_2(C_{3-7}$ branched alkyl), and $NHSO_2(C_{3-7}$ cycloalkyl);

$R^{4b}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHCO(C_{3-7}$ cycloalkyl), $NHSO_2(C_{1-6}alkyl)$, $NHSO_2(C_{3-7}$ branched alkyl), and $NHSO_2(C_{3-7}$ cycloalkyl);

$R^{4c}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHCO(C_{3-7}$ cycloalkyl), $NHSO_2(C_1$-6alkyl), $NHSO_2(C_{3-7}$ branched alkyl), and $NHSO_2(C_{3-7}$ cycloalkyl);

$R^{4d}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHCO(C_{3-7}$ cycloalkyl), $NHSO_2(C_{1-6}alkyl)$, $NHSO_2(C_{3-7}$ branched alkyl), and $NHSO_2(C_{3-7}$ cycloalkyl);

$R^{4e}$ is hydrogen, halogen, $C_{1-6}$ alkyl, $C_{3-7}$ branched alkyl, $C_{1-6}$ haloalkyl, and $C_{3-7}$ branched haloalkyl;

$R^{4f}$ is hydrogen, halogen, $C_{1-6}$ alkyl, $C_{3-7}$ branched alkyl, $C_{1-6}$ haloalkyl, and $C_{3-7}$ branched haloalkyl;

$R^{1a}$ and $R^{1b}$ are taken together to form an optionally substituted 3 to 7 membered ring that optionally contains an $X^1$ group;

$X^1$ is selected from the group consisting of $CF_2$, $CHCO_2R^{12}$, O, NH, $NR^8$, and $SO_2$;

m is 0, 1, or 2;

n is 1, 2, or 3;

$R^5$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ alkoxyl, $C_{3-7}$ branched alkoxy, and hydroxy;

$R^6$ is selected from the group consisting of hydrogen, $NH_2$, $NHR^{6a}$, $NHCH_2CH_2OH$, $NHCH_2CH_2NHSO_2Me$, $C_{1-6}$ alkoxyl, $C_{3-7}$ branched alkoxy, and hydroxy;

$R^{6a}$ is selected from the group consisting of —(CO)$C_{1-6}$ alkyl, —(CO)$C_{3-7}$ branched alkyl, —(CO)$C_{1-6}$ hydroxyalkyl,

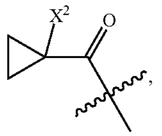, 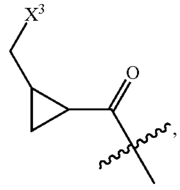,

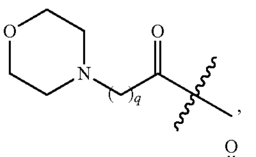, 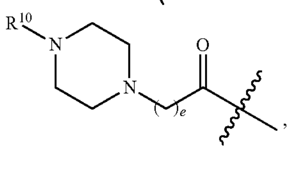,

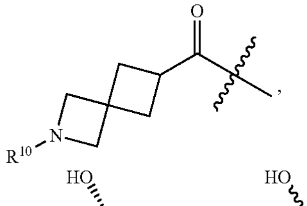, 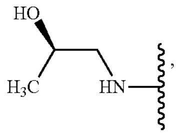,

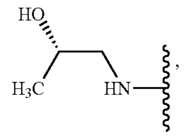, 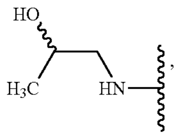,

-continued

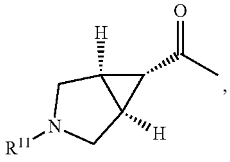

, and

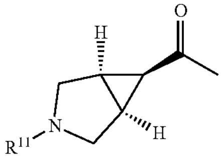

;

q is 1, 2, 3, 4, 5, or 6;

e is 1, 2, 3, 4, 5, or 6;

$X^2$ is selected from the group consisting of hydrogen, halogen, $C_{1-6}$alkyl, $C_{3-7}$ branched alkyl, $C_{1-6}$haloalkyl, $C_{3-7}$ branched haloalkyl, hydroxy, $C_{1-6}$hydroxyalkyl, $C_{3-7}$ branched hydroxyalkyl, $C_{1-6}$alkoxy, $C_{3-7}$ branched alkoxy, $C_{1-6}$haloalkoxy, $C_{3-7}$ branched haloalkoxy, $NH_2$, NH($C_{1-6}$alkyl), and N($C_{1-6}$alkyl) 2;

$X^3$ is selected from the group consisting of hydrogen, halogen, $C_{1-5}$ alkyl, $C_{3-7}$ branched alkyl, $C_{1-5}$ haloalkyl, $C_{3-7}$ branched haloalkyl, hydroxy, $C_{1-5}$ hydroxyalkyl, $C_{3-7}$ branched hydroxyalkyl, $C_{1-5}$ alkoxy, $C_{3-7}$ branched alkoxy, $C_{1-5}$ haloalkoxy, $C_{3-7}$ branched haloalkoxy, $NH_2$, NH($C_{1-6}$ alkyl), N($C_{1-6}$ alkyl) 2, COOH, and $NHSO_2Me$;

$R^7$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ alkoxyl, $C_{3-7}$ branched alkoxy, and hydroxy;

$R^8$ is selected from the group consisting of $C_{1-6}$ alkyl, $C_{1-6}$ haloalkyl, $C_{3-7}$ branched haloalkyl, $C_{1-6}$ hydroxyalkyl, $C_{3-7}$ branched hydroxyalkyl, $C_{1-6}$ alkoxyl, $C_{3-7}$ branched alkoxy, CO($C_{1-6}$alkyl), CO($C_{3-7}$ branched alkyl), $SO_2$($C_{1-6}$alkyl), and $SO_2$($C_{3-7}$ branched alkyl);

$R^{10}$ is selected from the group consisting of hydrogen, $C_{1-6}$ alkyl, $C_{1-6}$ haloalkyl, $C_{3-7}$ branched haloalkyl, $C_{1-6}$ hydroxyalkyl, $C_{1-6}$ alkoxyl, $C_{3-7}$ branched alkoxy, CO($C_{1-6}$alkyl), CO($C_{3-7}$ branched alkyl), $SO_2$($C_{1-6}$alkyl), and $SO_2$($C_{3-7}$ branched alkyl);

$R^{11}$ is selected from the group consisting of hydrogen and $C_{1-6}$ alkyl; and $R^{12}$ is selected from the group consisting of hydrogen and $C_{1-6}$ alkyl.

2. The compound of claim 1 having the formula (II)

(II)

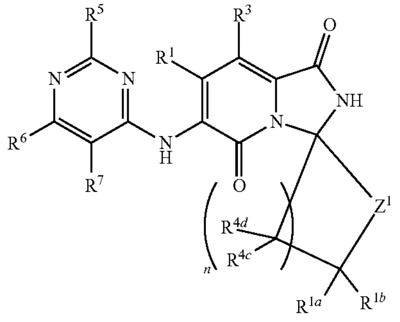

or a pharmaceutically acceptable salt thereof.

3. The compound of claim 1 having the formula (III)

(III)

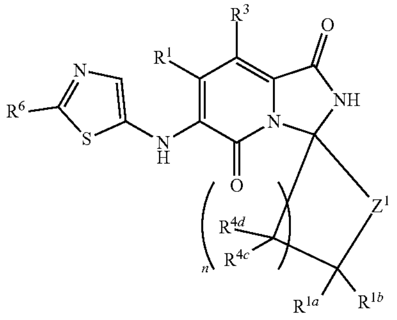

or a pharmaceutically acceptable salt thereof.

4. The compound of claim 1 having the formula (IV)

(IV)

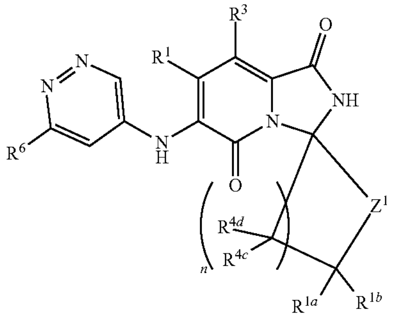

or a pharmaceutically acceptable salt thereof.

5. The compound of claim 1 having the formula (V)

(V)

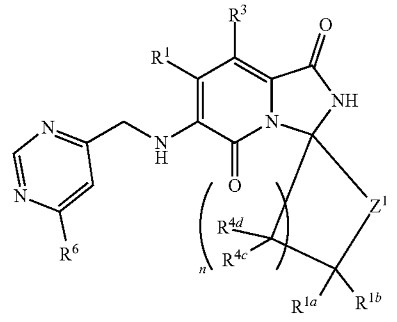

or a pharmaceutically acceptable salt thereof.

6. The compound of claim 1 having the formula (VI)

(VI)

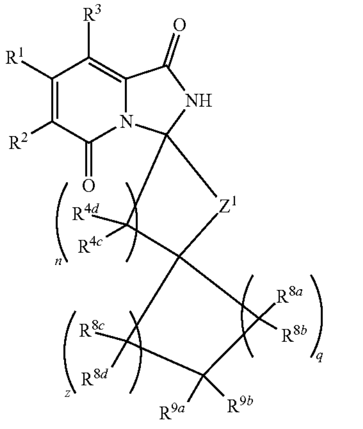

or a pharmaceutically acceptable salt thereof, wherein $R^{8a}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHSO_2(C_{1-6}alkyl)$, and $NHSO_2$ ($C_{3-7}$ branched alkyl);

$R^{8b}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHSO_2(C_{1-6}alkyl)$, and $NHSO_2$ ($C_{3-7}$ branched alkyl);

$R^{8c}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHSO_2(C_{1-6}alkyl)$, and $NHSO_2$ ($C_{3-7}$ branched alkyl);

$R^{8d}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHSO_2(C_{1-6}alkyl)$, and $NHSO_2$ ($C_{3-7}$ branched alkyl);

$R^{9a}$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, and $C_{3-7}$ branched alkoxy;

$R^{9b}$ is selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, and $C_{3-7}$ branched alkoxy;

or $R^{9a}$ and $R^{9b}$ are taken together to form an optionally substituted 3 to 7-membered ring;

q is 1, 2, or 3; and z is 0, 1, or 2.

7. The compound of claim 1 having the formula (VII)

(VII)

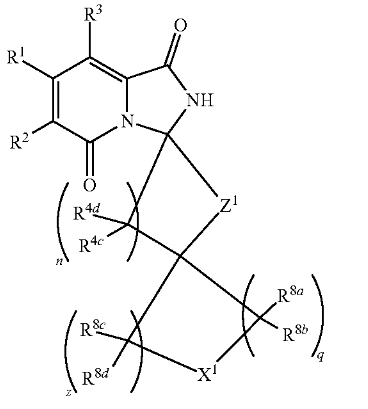

or a pharmaceutically acceptable salt thereof, wherein $R^{8a}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHSO_2(C_{1-6}alkyl)$, and $NHSO_2$ ($C_{3-7}$ branched alkyl);

$R^{8b}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHSO_2(C_{1-6}alkyl)$, and $NHSO_2$ ($C_{3-7}$ branched alkyl);

$R^{8c}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHSO_2(C_{1-6}alkyl)$, and $NHSO_2$ ($C_{3-7}$ branched alkyl);

$R^{8d}$ is at each occurrence independently selected from the group consisting of hydrogen, halogen, $C_{1-6}$ alkyl, $C_{3-7}$ branched alkyl, $C_{1-6}$ haloalkyl, $C_{3-7}$ branched haloalkyl, $C_{1-6}$ hydroxyalkyl, $C_{3-7}$ branched hydroxyalkyl, hydroxy, $C_{1-6}$ alkoxyl, $C_{3-7}$ branched alkoxy, $NHCO(C_{1-6}alkyl)$, $NHCO(C_{3-7}$ branched alkyl), $NHSO_2(C_{1-6}alkyl)$, and $NHSO_2$ ($C_{3-7}$ branched alkyl);

q is 1, 2, or 3; and z is 0, 1, or 2.

8. A compound selected from the group consisting of:

N-(6-((8"-methyl-1",5"-dioxo-1",5"-dihydro-2"H-dispiro[cyclopropane-1,1'-cyclohexane-3',3"-imidazo[1,5-a]pyridin]-6"-yl)amino)pyrimidin-4-yl)cyclopropanecarboxamide;

6"-((6-Aminopyrimidin-4-yl)amino)-8"-methyl-2"H-dispiro[cyclopropane-1,1'-cyclohexane-3',3"-imidazo[1,5-a]pyridine]-1",5"-dione;

N-(6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)cyclopropanecarboxamide;

N-(6-((8"-methyl-1",5"-dioxo-1",5"-dihydro-2"H-dispiro[aziridine-2,l'-cyclohexane-4',3"-imidazo[1,5-a]pyridin]-6"-yl)amino)pyrimidin-4-yl)cyclopropanecarboxamide;

N-(6-((8"-methyl-1",5"-dioxo-1",5"-dihydro-2"H-dispiro[cyclobutane-1,1'-cyclobutane-3',3"-imidazo[1,5-a]pyridin]-6"-yl)amino)pyrimidin-4-yl)cyclopropanecarboxamide;

tert-butyl 6"-((6-(cyclopropanecarboxamido)pyrimidin-4-yl)amino)-8"-methyl-1",5"-dioxo-1",5"-dihydro-2"H-dispiro[azetidine-3,l'-cyclohexane-4',3"-imidazo[1,5-a]pyridine]-1-carboxylate;

N-(6-((8"-methyl-1",5"-dioxo-1",5"-dihydro-2"H-dispiro[azetidine-3,l'-cyclohexane-4',3"-imidazo[1,5-a]pyridin]-6"-yl)amino)pyrimidin-4-yl)cyclopropanecarboxamide;

6"-((6-((2-hydroxyethyl)amino)pyrimidin-4-yl)amino)-8"-methyl-2"H-dispiro[cyclopropane-1,l'-cyclohexane-4',3"-imidazo[1,5-a]pyridine]-1",5"-dione;

6"-((6-Aminopyrimidin-4-yl)amino)-8"-methyl-2"H-dispiro[cyclopropane-1,1'-cyclohexane-4',3"-imidazo[1,5-a]pyridine]-1",5"-dione;

1-(aminomethyl)-N-(6-((8"-methyl-1",5"-dioxo-1",5"-dihydro-2"H-dispiro[cyclopropane-1,l'-cyclohexane-4',3"-imidazo[1,5-a]pyridin]-6"-yl)amino)pyrimidin-4-yl)cyclopropane-1-carboxamide;

(1R,5S,6r)-N-(6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)-3-azabicyclo[3.1.0]hexane-6-carboxamide;

N-(6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)-2-azaspiro[3.3]heptane-6-carboxamide;

2-methyl-N-(6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)-2-azaspiro[3.3]heptane-6-carboxamide;

(1R,5S,6r)-3-methyl-N-(6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)-3-azabicyclo[3.1.0]hexane-6-carboxamide;

N-(6-((8"-methyl-1",5"-dioxo-1",5"-dihydro-2"H-dispiro[cyclopropane-1,1'-cyclohexane-4',3"-imidazo[1,5-a]pyridin]-6"-yl)amino)pyrimidin-4-yl)-1-(methylsulfonamido methyl)cyclopropane-1-carboxamide;

1-((dimethylamino)methyl)-N-(6-((8"-methyl-1",5"-dioxo-1",5"-dihydro-2"H-dispiro[cyclopropane-1,l'-cyclohexane-4',3"-imidazo[1,5-a]pyridin]-6"-yl)amino)pyrimidin-4-yl)cyclopropane-1-carboxamide;

6"-((6-aminopyrimidin-4-yl)amino)-8"-methyl-2"H-dispiro[cyclobutane-1,1'-cyclobutane-3',3"-imidazo[1,5-a]pyridine]-1",5"-dione;

6"-((6-aminopyrimidin-4-yl)amino)-8"-methyl-2"H-dispiro[aziridine-2,1'-cyclohexane-4',3"-imidazo[1,5-a]pyridine]-1",5"-dione;

6"-((6-aminopyrimidin-4-yl)amino)-8"-methyl-2"H-dispiro[cyclopropane-1,1'-cyclopentane-3',3"-imidazo[1,5-a]pyridine]-1",5"-dione;

6"-((6-aminopyrimidin-4-yl)amino)-8"-methyl-2"H-dispiro[cyclopentane-1,1'-cyclopentane-3',3"-imidazo[1,5-a]pyridine]-1",5"-dione;

6"-((6-aminopyrimidin-4-yl)amino)-3,3-difluoro-8"-methyl-2"H-dispiro[cyclobutane-1,l'-cyclobutane-3',3"-imidazo[1,5-a]pyridine]-1",5"-dione;

6"-((6-aminopyrimidin-4-yl)amino)-8"-methyl-2"H-dispiro[cyclopentane-1,1'-cyclobutane-3',3"-imidazo[1,5-a]pyridine]-1",5"-dione;

6"-((6-aminopyrimidin-4-yl)amino)-8"-methyl-2"H-dispiro[cyclobutane-1,1'-cyclohexane-4',3"-imidazo[1,5-a]pyridine]-1",5"-dione;

6"-((6-aminopyrimidin-4-yl)amino)-8"-methyl-2"H-dispiro[cyclohexane-1,1'-cyclobutane-3',3"-imidazo[1,5-a]pyridine]-1",5"-dione;

ethyl 6"-((6-(cyclopropanecarboxamido)pyrimidin-4-yl)amino)-8"-methyl-1",5"-dioxo-1",5"-dihydro-2"H-dispiro[cyclopropane-1,l'-cyclohexane-4',3'"-imidazo[1,5-a]pyridine]-2-carboxylate;

tert-butyl (6"-((6-(cyclopropanecarboxamido)pyrimidin-4-yl)amino)-8"-methyl-1",5"-dioxo-1",5"-dihydro-2"H-dispiro[cyclopropane-1,l'-cyclohexane-4',3"-imidazo[1,5-a]pyridin]-2-yl) carbamate;

N-(6-((2,2-difluoro-8"-methyl-1",5"-dioxo-1",5"-dihydro-2"H-dispiro[cyclopropane-1, l'-cyclohexane-4',3"-imidazo[1,5-a]pyridin]-6"-yl)amino)pyrimidin-4-yl)cyclopropanecarboxamide;

6"-((6-aminopyrimidin-4-yl)amino)-2,2-difluoro-8"-methyl-2"H-dispiro[cyclopropane-1,l'-cyclohexane-4',3"-imidazo[1,5-a]pyridine]-1",5"-dione;

6"-((6-Aminopyrimidin-4-yl)amino)-8"-methyl-2"H-dispiro[cyclopropane-1,1'-cycloheptane-4',3"-imidazo[1,5-a]pyridine]-1",5"-dione;

6"-((6-Aminopyrimidin-4-yl)amino)-8"-methyl-2"H-dispiro[cyclopropane-1,1'-cyclohexane-4',3"-imidazo[1,5-a]pyridin]-2'-ene-1",5"-dione;

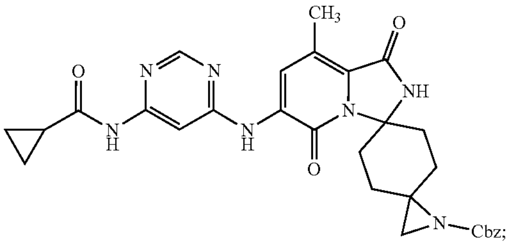 and

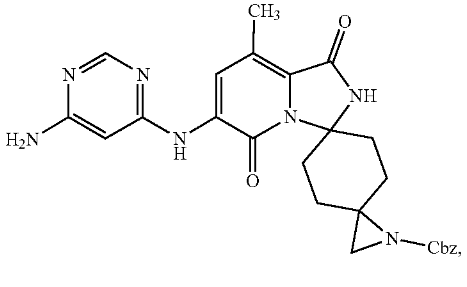

or a pharmaceutically acceptable salt thereof.

9. The compound of claim 2, wherein:

$R^1$ is hydrogen;

$R^3$ is $C_{1-6}$ alkyl;

each $R^{4a}$, $R^{4b}$, $R^{4c}$, $R^{4d}$, $R^{4e}$, and $R^{4f}$ is hydrogen;

$R^5$ is hydrogen;

$R^6$ is —$NH_2$, —$NHR^{6a}$, —$NHCH_2CH_2OH$, or —$NHCH_2CH_2NHSO_2Me$; and $R^7$ is hydrogen.

10. The compound of claim 9, wherein $R^6$ is —$NH_2$.

11. The compound of claim 1, wherein the compound is a compound of formula (LII):

(LII)

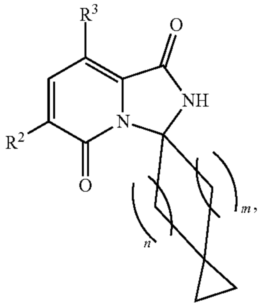

or a pharmaceutically acceptable salt thereof.

12. The compound of claim 11, wherein $R^2$ is

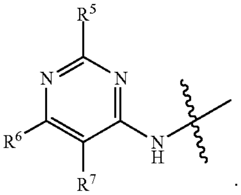

13. The compound of claim 11, wherein $R^3$ is $C_{1-6}$ alkyl.

14. The compound of claim 12, wherein $R^5$ is hydrogen.

15. The compound of claim 12, wherein $R^6$ is —$NH_2$, —$NHR^{6a}$, —$NHCH_2CH_2OH$, or —$NHCH_2CH_2NHSO_2Me$.

16. The compound of claim 15, wherein $R^6$ is —$NH_2$.

17. The compound of claim 15, wherein $R^6$ is —$NHR^{6a}$.

18. The compound of claim 12, wherein $R^7$ is hydrogen.

19. The compound of claim 11, wherein:

$R^2$ is

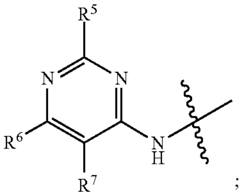

$R^3$ is $C_{1-6}$ alkyl;

$R^5$ is hydrogen;

$R^6$ is —$NH_2$, —$NHR^{6a}$, —$NHCH_2CH_2OH$, or —$NHCH_2CH_2NHSO_2Me$; and $R^7$ is hydrogen.

20. The compound of claim 19, wherein $R^6$ is —$NH_2$.

21. The compound of claim 19, wherein n is 2 and m is 2.

22. The compound of claim 19, wherein n is 3 and m is 1.

23. The compound of claim 19, wherein n is 3 and m is 2.

24. The compound of claim 1, wherein the compound is:

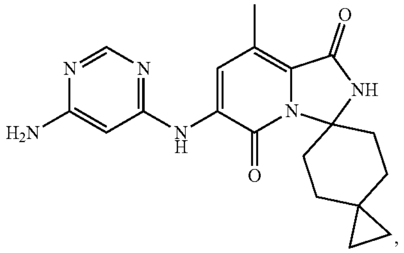 [SMILES: Cc1cc(Nc2cc(N)ncn2)c(=O)n2c1C(=O)NC21CCC2(CC2)CC1]

or a pharmaceutically acceptable salt thereof.

25. A pharmaceutical composition comprising the compound of claim 1, or a pharmaceutically acceptable salt thereof, and one or more pharmaceutically acceptable carriers, excipients, or diluents.

26. A pharmaceutical composition comprising the compound of claim 24, or a pharmaceutically acceptable salt thereof, and one or more pharmaceutically acceptable carriers, excipients, or diluents.

27. The compound of claim 24, wherein the compound is:

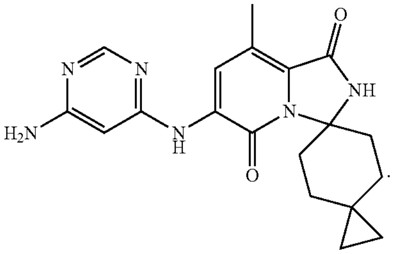 [SMILES: Cc1cc(Nc2cc(N)ncn2)c(=O)n2c1C(=O)NC21CCC2(CC2)CC1]

* * * * *